(12) United States Patent
Campbell et al.

(10) Patent No.: US 6,878,722 B2
(45) Date of Patent: Apr. 12, 2005

(54) SUBSTITUTED CYCLOALKYL P1' HEPATITIS C VIRUS INHIBITORS

(75) Inventors: Jeffrey Allen Campbell, Cheshire, CT (US); Stanley D'Andrea, Meriden, CT (US); Andrew Good, Wallingford, CT (US); Jianqing Li, Guilford, CT (US); Fiona Mcphee, Wallingford, CT (US); Amy Ripka, Cambridge, MA (US); Paul Michael Scola, Glastonbury, CT (US); Yong Tu, Cheshire, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/441,428

(22) Filed: May 20, 2003

(65) Prior Publication Data

US 2004/0077551 A1 Apr. 22, 2004

Related U.S. Application Data

(60) Provisional application No. 60/382,149, filed on May 20, 2002.

(51) Int. Cl.$^7$ .................. C07D 401/02; A61K 31/47
(52) U.S. Cl. ................................. 514/312; 546/154
(58) Field of Search .................... 546/154; 514/312

(56) References Cited

U.S. PATENT DOCUMENTS

| | | | |
|---|---|---|---|
| 5,633,388 A | 5/1997 | Diana et al. |
| 5,866,684 A | 2/1999 | Attwood et al. |
| 5,869,253 A | 2/1999 | Draper |
| 6,018,020 A | 1/2000 | Attwood et al. |
| 6,225,284 B1 | 5/2001 | Albert et al. |
| 6,265,380 B1 | 7/2001 | Tung et al. |
| 6,268,207 B1 | 7/2001 | Bailey |
| 6,323,180 B1 | 11/2001 | Linas-Brunet et al. |
| 6,410,531 B1 | 6/2002 | Linas-Brunet et al. |
| 6,420,380 B2 | 7/2002 | Linas-Brunet et al. |
| 6,534,523 B1 | 3/2003 | Linas-Brunet et al. |
| 2002/0111313 A1 | 8/2002 | Campbell et al. |

FOREIGN PATENT DOCUMENTS

| | | |
|---|---|---|
| WO | WO 95/33764 | 12/1995 |
| WO | WO 97/06804 | 2/1997 |
| WO | WO 97/43310 | 11/1997 |
| WO | WO 98/17679 | 4/1998 |
| WO | WO 98/22496 | 5/1998 |
| WO | WO 98/46597 | 10/1998 |
| WO | WO 98/46630 | 10/1998 |
| WO | WO 99/07733 | 2/1999 |
| WO | WO 99/07734 | 2/1999 |
| WO | WO 99/38888 | 8/1999 |
| WO | WO 99/50230 | 10/1999 |
| WO | WO 99/64442 | 12/1999 |
| WO | WO 00/06529 | 2/2000 |
| WO | WO 00/09543 | 2/2000 |
| WO | WO 00/09558 | 2/2000 |
| WO | WO 00/10573 | 3/2000 |
| WO | WO 00/13708 | 3/2000 |
| WO | WO 00/18231 | 4/2000 |
| WO | WO 00/59929 | 10/2000 |
| WO | 1162196 A1 | 12/2000 |
| WO | WO 01/32153 A2 | 5/2001 |
| WO | WO 01/85172 A1 | 11/2001 |
| WO | WO 02/04425 A2 | 1/2002 |
| WO | WO 02/06246 A1 | 1/2002 |
| WO | WO 02/060926 A2 | 8/2002 |
| WO | WO 03/064416 A1 | 8/2003 |
| WO | WO 03/064455 A2 | 8/2003 |
| WO | WO 03/064456 A1 | 8/2003 |
| WO | WO 03/066103 A1 | 8/2003 |

OTHER PUBLICATIONS

Lauer et al. (2001) New England Journal of Medicine, vol. 345 No. 1, pp. 41–52.
Zeuzem et al. (2000) The New England Journal of Medicine, vol. 343 No. 23, pp. 1666–1672.
Poynard et al. (1998) The Lancet, vol. 352, pp. 1426–1432.
Poupart et al. (2001) The Journal of Organic Chemistry, vol. 66 No. 14, pp. 4743–4751.
Steinkuhler et al. (1998) Biochemistry, vol. 37, pp. 8899–8905.
Ingallinella et al. (1998) Biochemistry, vol. 37, pp. 8906–8914.
Chu et al. (1996) Tetrahedron Letters, vol. 37 No. 40, pp. 7229–7232.
Matsumoto et al. (1996) Antiviral Research, vol. 30 No. 1, p. A23, Abstract 19.

Primary Examiner—Zinna Northington Davis
(74) Attorney, Agent, or Firm—Warren K. Volles

(57) ABSTRACT

The present invention relates to tripeptide compounds, compositions and methods for the treatment of hepatitis C virus (HCV) infection. In particular, the present invention provides novel tripeptide analogs, pharmaceutical compositions containing such analogs and methods for using these analogs in the treatment of HCV infection.

31 Claims, No Drawings

SUBSTITUTED CYCLOALKYL P1' HEPATITIS C VIRUS INHIBITORS

CROSS REFERENCE TO RELATED APPLICATION

The non-provisional application claims priority from the provisional application U.S. Ser. No. 60/382,149 filed May 20, 2002.

FIELD OF THE INVENTION

The present invention is generally directed to antiviral compounds, and more specifically directed to compounds which inhibit the functioning of the NS3 protease encoded by Hepatitis C virus (HCV), compositions comprising such compounds and methods for inhibiting the functioning of the, NS3 protease.

BACKGROUND OF THE INVENTION

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma. (Lauer, G. M.; Walker, B. D. N. Engl. J. Med. (2001), 345, 41–52).

Presently, the most effective HCV therapy employs a combination of alpha-interferon and ribavirin, leading to sustained efficacy in 40% of patients. (Poynard, T. et al. Lancet (1998), 352, 1426–1432). Recent clinical results demonstrate that pegylated alpha-interferon is superior to unmodified alpha-interferon as monotherapy (Zeuzem, S. et al. N. Engl. J. Med. (2000), 343, 1666–1672). However, even with experimental therapeutic regimens involving combinations of pegylated alpha-interferon and ribavirin, a substantial fraction of patients do not have a sustained reduction in viral load. Thus, there is a clear and long-felt need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one, as yet poorly characterized, cleaves at the NS2–NS3 junction; the second one is a serine protease contained within the N-terminal region of NS3 (henceforth referred to as NS3 protease) and mediates all the subsequent cleavages downstream of NS3, both in cis, at the NS3-NS4A cleavage site, and in trans, for the remaining NS4A–NS4B, NS4B–NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B is a RNA-dependent RNA polymerase that is involved in the replication of HCV.

Among the compounds that have demonstrated efficacy in inhibiting HCV replication, as selective HCV serine protease inhibitors, are the peptide compounds disclosed in U.S. Pat. No. 6,323,180.

SUMMARY OF THE INVENTION

The present invention provides compounds, or pharmaceutically acceptable salts, solvates or prodrugs thereof, having the structure of formula I:

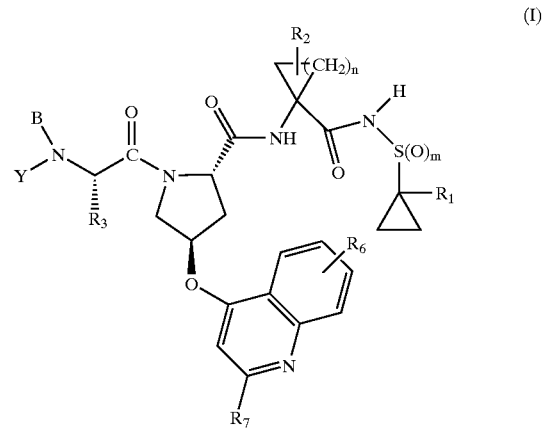

(I)

wherein:

(a) $R_1$ is trialkylsilane; halo; $C_{3-7}$ cycloalkyl, $C_{4-7}$ cycloalkenyl; $C_{6-10}$ aryl; $C_{7-14}$ alkylaryl; $C_{6-10}$ aryloxy; $C_{7-14}$ alkylaryloxy; $C_{8-15}$ alkylarylester;

Het; or $C_{1-8}$ alkyl optionally substituted with $C_{1-6}$ alkoxy, hydroxy, halo, $C_{2-10}$ alkenyl, $C_{2-10}$ alkynyl, $C_{3-7}$ cycloalkyl, $C_{4-7}$ cycloalkenyl, $C_{6-10}$ aryl, $C_{7-14}$ alkylaryl, $C_{6-10}$ aryloxy, $C_{7-14}$ alkylaryloxy, $C_{8-15}$ alkylarylester or Het;

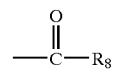

wherein $R_8$ is $C_{3-7}$ cycloalkyl, $C_{4-7}$ cycloalkenyl; $C_{6-10}$ aryl; $C_{7-14}$ alkylaryl; $C_{6-10}$ aryloxy; $C_{7-14}$ alkylaryloxy; $C_{8-15}$ alkylarylester; Het; or $C_{1-8}$ alkyl optionally substituted with $C_{1-6}$ alkoxy, hydroxy, halo, $C_{2-10}$ alkenyl, $C_{2-10}$ alkynyl, $C_{3-7}$ cycloalkyl, $C_{4-7}$ cycloalkenyl, $C_{6-10}$ aryl, $C_{7-14}$ alkylaryl, $C_{6-10}$ aryloxy, $C_{7-14}$ alkylaryloxy, $C_{8-15}$ alkylarylester or Het;

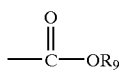

wherein $R_9$ is $C_{3-7}$ cycloalkyl, $C_{4-7}$ cycloalkenyl; $C_{6-10}$ aryl; $C_{7-14}$ alkylaryl; $C_{6-10}$ aryloxy; $C_{7-14}$ alkylaryloxy; $C_{8-15}$ alkylarylester; Het; or $C_{1-8}$ alkyl optionally substituted with $C_{1-6}$ alkoxy, hydroxy, halo, $C_{2-10}$ alkenyl, $C_{2-10}$ alkynyl, $C_{3-7}$ cycloalkyl, $C_{4-7}$ cycloalkenyl, $C_{6-10}$ aryl, $C_{7-14}$ alkylaryl, $C_{6-10}$ aryloxy, $C_{7-14}$ alkylaryloxy, $C_{8-15}$ alkylarylester or Het;

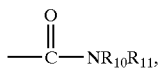

wherein $R_{10}$ and $R_{11}$, are each independently $C_{3-7}$ cycloalkyl, $C_{4-7}$ cycloalkenyl; $C_{6-10}$ aryl; $C_{7-14}$ alkylaryl; $C_{6-10}$ aryloxy; $C_{7-14}$ alkylaryloxy; $C_{8-15}$ alkylarylester; Het; or $C_{1-8}$ alkyl optionally substituted with $C_{1-6}$ alkoxy, hydroxy, halo, $C_{2-10}$ alkenyl, $C_{2-10}$ alkynyl, $C_{3-7}$ cycloalkyl, $C_{4-7}$ cycloalkenyl, $C_{6-10}$ aryl, $C_{7-14}$ alkylaryl, $C_{6-10}$ aryloxy, $C_{7-14}$ alkylaryloxy, $C_{8-15}$ alkylarylester or Het; —$SO_2R_{12}$ wherein $R_{12}$ is $C_{3-7}$ cycloalkyl, $C_{4-7}$ cycloalkenyl; $C_{6-10}$ aryl; $C_{7-14}$ alkylaryl; $C_{6-10}$ aryloxy; $C_{7-14}$ alkylaryloxy; $C_{8-15}$ alkylarylester; Het; or $C_{1-8}$ alkyl optionally substituted with $C_{1-6}$ alkoxy, hydroxy, halo, $C_{2-10}$ alkenyl, $C_{2-10}$ alkynyl, $C_{3-7}$ cycloalkyl, $C_{4-7}$ cycloalkenyl, $C_{6-10}$ aryl, $C_{7-14}$ alkylaryl, $C_{6-10}$ aryloxy, $C_{7-14}$ alkylaryloxy, $C_{8-15}$ alkylarylester or Het;

or

wherein $R_{13}$ is $C_{3-7}$ cycloalkyl, $C_{4-7}$ cycloalkenyl; $C_{6-10}$ aryl; $C_{7-14}$ alkylaryl; $C_{6-10}$ aryloxy; $C_{7-14}$ alkylaryloxy; $C_{8-15}$ alkylarylester; Het; or $C_{1-8}$ alkyl optionally substituted with $C_{1-6}$ alkoxy, hydroxy, halo, $C_{2-10}$ alkenyl, $C_{2-10}$ alkynyl, $C_{3-7}$ cycloalkyl, $C_{4-7}$ cycloalkenyl, $C_{6-10}$ aryl, $C_{7-14}$ alkylaryl, $C_{6-10}$ aryloxy, $C_{7-14}$ alkylaryloxy, $C_{8-15}$ alkylarylester or Het;

(b) $R_2$ is $C_{1-6}$ alkyl, $C_{2-6}$ alkenyl or $C_{3-7}$ cycloalkyl, each optionally substituted from one to three times with halogen; or $R_2$ is H; or $R_2$ together with the carbon to which it is attached forms a 3, 4 or 5 membered ring;

(c) $R_3$ is $C_{1-8}$ alkyl optionally substituted with halo, cyano, amino, $C_{1-6}$ dialkylamino, $C_{6-10}$ aryl, $C_{7-14}$ alkylaryl, $C_{1-6}$ alkoxy, carboxy, hydroxy, aryloxy, $C_{7-14}$alkylaryloxy, $C_{2-6}$ alkylester, $C_{8-15}$ alkylarylester; $C_{3-12}$ alkenyl, $C_{3-7}$ cycloalkyl, or $C_{4-10}$ alkylcycloalkyl, wherein the cycloalkyl or alkylcycloalkyl are optionally substituted with hydroxy, $C_{1-6}$ alkyl, $C_{2-6}$ alkenyl or $C_{1-6}$ alkoxy; or $R_3$ together with the carbon atom to which it is attached forms a $C_{3-7}$ cycloalkyl group optionally substituted with $C_{2-6}$ alkenyl;

(d) $R_6$ is H, $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono-or di-halo-$C_{1-6}$ alkoxy, cyano, halo, thioalkyl, hydroxy, alkanoyl, $NO_2$, SH, amino, $C_{1-6}$ alkylamino, di ($C_{1-6}$)alkylamino, di ($C_{1-6}$)alkylamide, carboxyl, ($C_{1-6}$)carboxyester, $C_{1-6}$ alkylsulfone, $C_{1-6}$ alkylsulfoxide, $C_{1-6}$ alkylsulfonamide or di ($C_{1-6}$)alkyl(alkoxy)amine;

(e) $R_7$ is H, $C_{1-6}$ alkyl, $C_{3-7}$ cycloalkyl, $C_{6-10}$ aryl, $C_{7-14}$ alkylaryl; $C_{6-10}$ aryloxy; $C_{7-14}$ alkylaryloxy; $C_{8-15}$ alkylarylester or Het;

(f) m is 1 or 2;

(g) n is 1 or 2;

(h) p is 1, 2 or 3;

(i) Y is H, phenyl substituted with nitro, pyridyl substituted with nitro, or $C_{1-6}$ alkyl optionally substituted with cyano, OH or $C_{3-7}$ cycloalkyl; provided that if $R_4$ or $R_5$ is H then Y is H;

(j) B is H, $C_{1-6}$ alkyl, $R_4$—(C=O)—, $R_4O(C=O)$—, $R_4$—N($R_5$)—C(=O)—, $R_4$—N($R_5$)—C(=S)—, $R_4SO_2$—, or $R_4$—N($R_5$)—$SO_2$—;

(k) $R_4$ is (i) $C_{1-10}$ alkyl optionally substituted with phenyl, carboxyl, $C_{1-6}$ alkanoyl, 1–3 halogen, hydroxy, —OC(O)$C_{1-6}$ alkyl, $C_{1-6}$ alkoxy, amino optionally substituted with $C_{1-6}$ alkyl, amido, or (lower alkyl) amido; (ii) $C_{3-7}$ cycloalkyl, $C_{3-7}$ cycloalkoxy, or $C_{4-10}$ alkylcycloalklyl, each optionally substituted with hydroxy, carboxyl, ($C_{1-6}$ alkoxy)carbonyl, amino optionally substituted with $C_{1-6}$ alkyl, amido, or (lower alkyl) amido; (iii) $C_{6-10}$ aryl or $C_{7-16}$ arylalkyl, each optionally substituted with $C_{1-6}$ alkyl, halogen, nitro, hydroxy, amido, (lower alkyl) amido, or amino optionally substituted with $C_{1-6}$ alkyl; (iv) Het; (v) bicyclo (1.1.1)pentane; or (vi) —C(O)O$C_{1-6}$ alkyl, $C_{2-6}$alkenyl or $C_{2-6}$ alkynyl; and.

(l) $R_5$ is H; $C_{1-6}$ alkyl optionally substituted with 1–3 halogens; or $C_{1-6}$ alkoxy provided $R_4$ is $C_{1-10}$ alkyl;

or a pharmaceutically acceptable salt, solvate or prodrug thereof.

The present invention also provides compositions comprising the compounds or pharmaceutically acceptable salts, solvates or prodrugs thereof and a pharmaceutically acceptable carrier. In particular, the present invention provides pharmaceutical compositions useful for inhibiting HCV NS3 comprising a therapeutically effective amount of a compound of the present invention, or a pharmaceutically acceptable salt, solvate or prodrug thereof, and a pharmaceutically acceptable carrier.

The present invention further provides methods for treating patients infected with HCV, comprising administering to the patient a therapeutically effective amount of a compound of the present invention, or a pharmaceutically acceptable salt, solvate or prodrug thereof. Additionally, the present invention provides methods of inhibiting HCV NS3 protease by administering to a patient an effective amount of a compound of the present invention.

By virute of the present invention, it is now possible to provide improved drugs comprising the compounds of the invention which can be effective in the treatment of patients infected with HCV. Specifically, the present invention provides peptide compounds that can inhibit the functioning of the NS3 protease, e.g., in combination with the NS4A protease.

DETAILED DESCRIPTION OF THE INVENTION

Stereochemical definitions and conventions used herein generally follow McGraw-Hill Dictionary of Chemical Terms, S. P. Parker, Ed., McGraw-Hill Book Company, New York (1984) and Stereochemistry of Organic Compounds, Eliel, E. and Wilen, S., John Wiley & Sons, Inc., New York (1994). Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory and (+) or d, meaning the compound, is dextrorotatory. For a given chemical structure, these compounds, called stereoisomers, are identical except that they are mirror images of one another. A specific stereoisomer of a mirror image pair may also be referred to as an enantiomer, and a mixture of such isomers is often called an enantiomeric mixture.

The nomenclature used to describe organic radicals, e.g., hydrocarbons and substituted hydrocarbons, generally follows standard nomenclature known in the art, unless otherwise specifically defined. Combinations of groups, e.g., alkylalkoxyamine, include all possible stable configurations, unless otherwise specifically stated. Certain radicals and combinations are defined below for purposes of illustration.

The terms "racemic mixture" and "racemate" refer to an equimolar mixture of two enantiomeric species, devoid of optical activity.

The term "chiral" refers to molecules which have the property of non-superimposability of the mirror image partner, while the term "achiral" refers to molecules which are superimposable on their mirror image partner.

The term "stereoisomers" refers to compounds which have identical chemical composition, but differ with regard to the arrangement of the atoms or groups in space.

The term "diastereomer" refers to a stereoisomer which is not an enantiomer, e.g., a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

The term "enantiomers" refers to two stereoisomers of a compound which are non-superimposable mirror images of one another.

The term "pharmaceutically acceptable salt" is intended to include nontoxic salts synthesized from a compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p. 1445. The compounds of the present invention are useful in the form of the free base or acid or in the form of a pharmaceutically acceptable salt thereof. All forms are within the scope of the invention.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The term "compounds of the invention", and equivalent expressions, are meant to embrace compounds of Formula I, and pharmaceutically acceptable salts, and solvates, e.g. hydrates. Similarly, reference to intermediates, is meant to embrace their salts, and solvates, where the context so permits. References to the compound of the invention also include the preferred compounds of Formula II and III.

The term "derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, and the like.

The term "prodrug" as used herein means derivatives of the compounds of the invention which have chemically or metabolically cleavable groups and become, by solvolysis or under physiological conditions, the compounds of the invention which are pharmaceutically active in vivo. A prodrug of a compound may be formed in a conventional manner with a functional group of the compounds such as with an amino, hydroxy or carboxy group when present. The prodrug derivative form often offers advantages of solubility, tissue compatibility, or delayed release in a mammalian organism (see, Bundgard, H., Design of Prodrugs, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine.

The term "patient" includes both human and other mammals.

The term "pharmaceutical composition" means a composition comprising a compound of the invention in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18$^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and (iii) relieving the disease, disorder or condition, i.e., causing regression of the disease, disorder and/or condition.

The term "substituted" as used herein includes substitution at from one to the maximum number of possible binding sites on the core, e.g., organic radical, to which the subsitutent is bonded, e.g., mono-, di-, tri- or tetra-substituted, unless otherwise specifically stated.

The term "halo" as used herein means a halogen substituent selected from bromo, chloro, fluoro or iodo. The term "haloalkyl" means an alkyl group that in substituted with one or more halo substituents.

The term "alkyl" as used herein means acyclic, straight or branched chain alkyl substituents and includes, for example, methyl, ethyl, propyl, butyl, tert-butyl, hexyl, 1-methylethyl, 1-methylpropyl, 2-methypropyl, 1,1-dimethylethyl. Thus, $C_{1-6}$ alkyl refers to an alkyl group having from one to six carbon atoms. The term "lower alkyl" means an alkyl group having from one to six, preferably from one to four carbon atoms. The term "alkylester" means an alkyl group additionally containing on ester group. Generally, a stated carbon number range, e.g., $C_{2-6}$ alkylester, includes all of the carbon atoms in the radical.

The term "alkenyl" as used herein means an alkyl radical containing at least one double bond, e.g., ethenyl (vinyl) and alkyl.

The term "alkoxy" as used herein means an alkyl group with the indicated number of carbon atoms attached to an oxygen atom. Alkoxy includes, for example, methoxy, ethoxy, propoxy, 1-methylethoxy, butoxy and 1,1-dimethylethoxy. The latter radical is referred to in the art as tert-butoxy. The term "alkoxycarbonyl" means an alkoxy group additionally containing a carbonyl group.

The term "cycloalkyl" as used herein means a cycloalkyl substituent containing the indicated number of carbon atoms and includes, for example, cyclopropyl, cyclobutyl, cyclopentyl, cyclohexyl, cycloheptyl and spiro cyclic groups such as spirocyclopropyl as spirocyclobutyl. The term "cycloalkoxy" as used herein means a cycloalkyl group linked to an oxygen atom, such as, for example, cyclobutyloxy or cyclopropyloxy. The term "alkylcycloalkyl" means a cycloalkyl group linked to an alkyl group. The stated carbon number range includes the total number of carbons in the radical, unless otherwise specfically stated. This a $C_{4-10}$ alkylcycloalkyl may contain from 1-7 carbon atoms in the alkyl group and from 3–9 carbon atoms in the ring, e.g., cyclopropylmethyl or cyclohexylethyl.

The term "aryl" as used herein means an aromatic moiety containing the indicated number of carbon atoms, such as, but not limited to phenyl, indanyl or naphthyl. For example, $C_{6-10}$ aryl refers to an aromatic moiety having from six to ten carbon atoms which may be in the form of a monocyclic or bicyclic structure. The term "haloaryl" as used herein refers to an aryl mono, di or tri substituted with one or more halogen atoms. The terms "alkylaryl", "arylalkyl" and "aralalkyl" mean an aryl group substituted with one or more alkyl groups. Thus, a $C_{7-14}$ alkylaryl group many have from 1–8 carbon atoms in the alkyl group for a monocyclic aromatic and from 1–4 carbon atoms in the alkyl group for a fused aromatic. The aryl radicals include those substituted with typical substituents known to those skilled in the art, e.g., halo, hydroxy, carboxy, carbonyl, nitro, sulfo, amino, cyano, dialkylamino'haloalkyl, $CF_3$, haloalkoxy, thioalkyl, alkanoyl, SH, alkylamino, alkylamide, dialkylamide, carboxyester, alkylsulfone, alkylsulfonamide and alkyl (alkoxy)amine. Examples of alkylaryl groups include benzyl, butylphenyl and 1-naphthylmethyl. The terms "alkylaryloxy" and "alkylarylester" mean alkylaryl groups containing an oxygen atom and ester group, respectively.

The term "carboxyalkyl" as used herein means a carboxyl group (COOH) linked through an alkyl group as defined above and includes, for example, butyric acid.

The term "alkanoyl" as used herein means straight or branched 1-oxoalkyl radicals containing the indicated number of carbon atoms and includes, for example, formyl, acetyl, 1-oxopropyl (propionyl), 2-methyl-1-oxopropyl, 1-oxohexyl and the like.

The term "amino aralkyl" as used herein means an amino group substituted with an aralkyl group, such as the following amino aralkyl

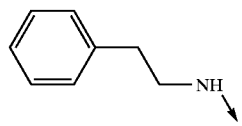

The term "alkylamide" as used herein means an amide mono-substituted with an alkyl, such as

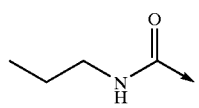

The term "carboxyalkyl" as used herein means a carboxyl group (COOH) linked through a alkyl group as defined above and includes, for example, butyric acid.

The term "heterocycle", as used herein means a monovalent radical derived by removal of a hydrogen from a five-, six-, or seven-membered saturated or unsaturated (including aromatic) heterocycle containing from one to four heteroatoms selected from nitrogen, oxygen and sulfur. Furthermore, the term heterocycle includes heterocycles, as defined above, that are fused to one or more other ring structure. The heterocycles of the present invention include those substituted with typical substituents known to those skilled in the art on any of the ring carbon atoms, e.g., one to three substituents. Examples of such substituents include $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono-or di-halo-$C_{1-6}$ alkoxy, cyano, halo, thioalkyl, hydroxy, alkanoyl, $NO_2$, SH, amino, $C_{1-6}$ alkylamino, di ($C_{1-6}$)alkylamino, di ($C_{1-6}$)alkylamide, carboxyl, ($C_{1-6}$)carboxyester, $C_{1-6}$ alkylsulfone, $C_{1-6}$ alkylsulfonamide, $C_{1-6}$ alkylsulfoxide, di ($C_{1-6}$)alkyl (alkoxy)amine, $C_{6-10}$ aryl, $C_{7-14}$ alkylaryl, and a 5–7 membered monocyclic heterocycle. Examples of suitable heterocycles include, but are not limited to, pyrrolidine, tetrahydrofuran, thiazolidine, pyrrole, thiophene, diazepine, 1H-imidazole, isoxazole, thiazole, tetrazole, piperidine, 1,4-dioxane, 4-morpholine, pyridine, pyrimidine, thiazolo[4,5-b]-pyridine, quinoline, or indole, or the following heterocycles:

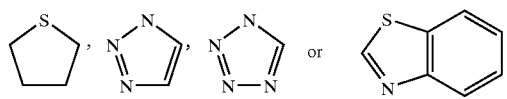

The term "alkyl-heterocycle" as used herein, means a heterocyclic radical as defined above linked through a chain or branched alkyl group, wherein alkyl as defined above containing the indicated number of carbon atoms. Examples of $C_{1-6}$ alkyl-Het include:

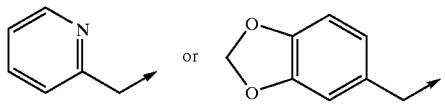

The term "heteroaryl" as used herein means an aromatic five- or six-membered cyclic organic group having at least one O, S and/or N atom. Furthermore, the term "heteroaryl" includes heteroaryl groups as defined about that fused to one or more other ring structures. Examples of heteroaryl groups include pyridyl, thienyl, thiazolyl, imidazolyl, isoxazolyl, isothiazolyl, furyl, pyrimidinyl, pyrazinyl, or pyridazinyl.

Where used in naming compounds of the present invention, the designations "P1', P1, P2, P3 and P4", as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend towards the C-terminus. For example, P1' refers to the first position away from the right hand end of the C-terminus of the cleavage site (ie. N-terminus first position); whereas P1 starts the numbering from the left hand side of the C-terminus cleavage site, P2: second position from the C-terminus, etc.)(see Berger A. & Schechter I., Transactions of the Royal Society London series (1970), B257, 249–264].

Thus in the compounds of formula I, the "P1' to P4" portions of the molecule are indicated below:

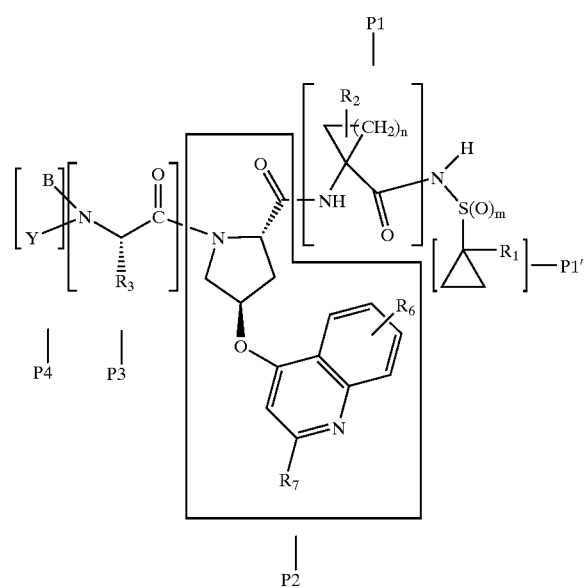

As used herein the term "1-aminocyclopropyl-carboxylic acid" (Acca) refers to a compound of formula:

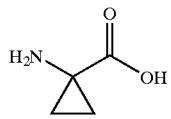

As used herein the term "tert-butylglycine" refers to a compound of the formula:

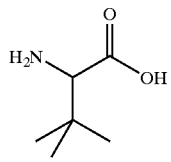

The term "residue" with reference to an amino acid or amino acid derivative means a radical derived from the corresponding α-amino acid by eliminating the hydroxyl of the carboxy group and one hydrogen of the α-amino acid group. For instance, the terms Gln, Ala, Gly, Ile, Arg, Asp, Phe, Ser, Leu, Cys, Asn, Sar and Tyr represent the "residues" of L-glutamine, L-alanine, glycine, L-isoleucine, L-arginine, L-aspartic acid, L-phenylalanine, L-serine, L-leucine, L-cysteine, L-asparagine, sarcosine and L-tyrosine, respectively.

The term "side chain" with reference to an amino acid or amino acid residue means a group attached to the α-carbon atom of the α-amino acid. For example, the R-group side chain for glycine is hydrogen, for alanine it is methyl, for valine it is isopropyl. For the specific R-groups or side chains of the α-amino acids reference is made to A. L. Lehninger's text on Biochemistry (see chapter 4).

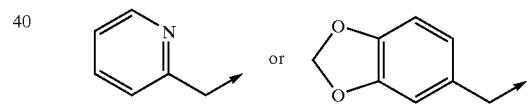

For compounds of the present invention, it is preferred that m is 2. It is also preferred that n is 1. It is additionally preferred that $R_2$ is ethyl or ethenyl.

In accordance with one aspect of the present invention, $R_1$ may be trialkylsilane; halo; $C_{3-7}$ cycloalkyl, $C_{4-7}$ cycloalkenyl; $C_{6-10}$ aryl; $C_{7-14}$ alkylaryl; $C_{6-10}$ aryloxy; $C_{7-14}$ alkylaryloxy; $C_{8-15}$ alkylarylester; Het; or $C_{1-8}$ alkyl optionally substituted with $C_{1-6}$ alkoxy, hydroxy, halo, $C_{2-10}$ alkenyl, $C_{2-10}$ alkynyl, $C_{3-7}$ cycloalkyl, $C_{4-7}$ cycloalkenyl, $C_{6-10}$ aryl, $C_{7-14}$ alkylaryl, $C_{6-10}$ aryloxy, $C_{7-14}$ alkylaryloxy, $C_{8-15}$ alkylarylester or Het.

In accordance with another aspect of the present invention, $R_1$ may be

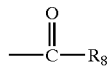

wherein $R_8$ is $C_{3-7}$ cycloalkyl, $C_{4-7}$ cycloalkenyl; $C_{6-10}$ aryl; $C_{7-14}$ alkylaryl; $C_{6-10}$ aryloxy; $C_{7-14}$ alkylaryloxy; $C_{8-15}$ alkylarylester; Het; or $C_{1-8}$ alkyl optionally substituted with $C_{1-6}$ alkoxy, hydroxy, halo, $C_{2-10}$ alkenyl, $C_{2-10}$ alkynyl, $C_{3-7}$ cycloalkyl, $C_{4-7}$ cycloalkenyl, $C_{6-10}$ aryl, $C_{7-14}$ alkylaryl, $C_{6-10}$ aryloxy, $C_{7-14}$ alkylaryloxy, $C_{8-15}$ alkylarylester or Het.

In accordance with another aspect of the present invention, $R_1$ may be

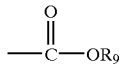

wherein $R_9$ is $C_{3-7}$ cycloalkyl, $C_{4-7}$ cycloalkenyl; $C_{6-10}$ aryl; $C_{7-14}$ alkylaryl; $C_{6-10}$ aryloxy; $C_{7-14}$ alkylaryloxy; $C_{8-15}$ alkylarylester; Het; or $C_{1-8}$ alkyl optionally substituted with $C_{1-6}$ alkoxy, hydroxy, halo, $C_{2-10}$ alkenyl, $C_{2-10}$ alkynyl, $C_{3-7}$ cycloalkyl, $C_{4-7}$ cycloalkenyl, $C_{6-10}$ aryl, $C_{7-14}$ alkylaryl, $C_{6-10}$ aryloxy, $C_{7-14}$ alkylaryloxy, $C_{8-15}$ alkylarylester or Het.

In accordance with another aspect of the present invention, $R_1$ may be

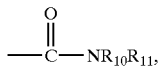

wherein $R_{10}$ and $R_1$ are each independently $C_{3-7}$ cycloalkyl, $C_{4-7}$ cycloalkenyl; $C_{6-10}$ aryl; $C_{7-14}$ alkylaryl; $C_{6-10}$ aryloxy; $C_{7-14}$ alkylaryloxy; $C_{8-15}$ alkylarylester; Het; or $C_{1-8}$ alkyl optionally substituted with $C_{1-6}$ alkoxy, hydroxy, halo, $C_{2-10}$ alkenyl, $C_{2-10}$ alkynyl, $C_{3-7}$ cycloalkyl, $C_{4-7}$ cycloalkenyl, $C_{6-10}$ aryl, $C_{7-14}$ alkylaryl, $C_{6-10}$ aryloxy, $C_{7-14}$ alkylaryloxy, $C_{8-15}$ alkylarylester or Het.

In accordance with another aspect of the present invention, $R_1$ may be $-SO_2R_{12}$ wherein $R_{12}$ is $C_{3-7}$ cycloalkyl, $C_{4-7}$ cycloalkenyl; $C_{6-10}$ aryl; $C_{7-14}$ alkylaryl; $C_{6-10}$ aryloxy; $C_{7-14}$ alkylaryloxy; $C_{8-15}$ alkylarylester; Het; or $C_{1-8}$ alkyl optionally substituted with $C_{1-6}$ alkoxy, hydroxy, halo, $C_{2-10}$ alkenyl, $C_{2-10}$ alkynyl, $C_{3-7}$ cycloalkyl, $C_{4-7}$ cycloalkenyl, $C_{6-10}$ aryl, $C_{7-14}$ alkylaryl, $C_{6-10}$ aryloxy, $C_{7-14}$ alkylaryloxy, $C_{8-15}$ alkylarylester or Het.

In accordance with another aspect of the present invention, $R_1$ may be

wherein $R_{13}$ is $C_{3-7}$ cycloalkyl, $C_{4-7}$ cycloalkenyl; $C_{6-10}$ aryl; $C_{7-14}$ alkylaryl; $C_{6-10}$ aryloxy; $C_{7-14}$ alkylaryloxy; $C_{8-15}$ alkylarylester; Het; or $C_{1-8}$ alkyl optionally substituted with $C_{1-6}$ alkoxy, hydroxy, halo, $C_{2-10}$ alkenyl, $C_{2-10}$ alkynyl, $C_{3-7}$ cycloalkyl, $C_{4-7}$ cycloalkenyl, $C_{6-10}$ aryl, $C_{7-4}$ alkylaryl, $C_{6-10}$ aryloxy, $C_{7-14}$ alkylaryloxy, $C_{8-15}$ alkylarylester or Het.

Preferably, $R_1$ is $C_{1-8}$ alkyl optionally substituted with $C_{1-6}$ alkoxy, hydroxy, halo, $C_{2-10}$ alkenyl, $C_{2-10}$ alkynyl, $C_{3-6}$ cycloalkyl, $C_{4-7}$ cycloalkenyl, $C_{6-10}$ aryl, $C_{7-14}$ alkylaryl, $C_{6-10}$ aryloxy, $C_{7-14}$ alkylaryloxy, $C_{8-15}$ alkylarylester or Het. More preferably, $R_1$ is $C_{1-8}$ alkyl optionally substituted with $C_{1-6}$ alkoxy, hydroxy, halo, $C_{2-10}$ alkenyl, $C_{2-10}$ alkynyl, $C_{3-6}$ cycloalkyl, $C_{4-7}$ cycloalkenyl, $C_{6-10}$ aryl, $C_{7-14}$ alkylaryl, $C_{6-10}$ aryloxy, $C_{7-14}$ alkylaryloxy, or $C_{8-15}$ alkylarylester.

In accordance with the present invention, $R_2$ may be $C_{1-16}$ alkyl, $C_{2-6}$ alkenyl or $C_{3-7}$ cycloalkyl, each optionally substituted from one to three times with halogen; or $R_2$ is H; or $R_2$ together with the carbon to which it is attached forms a 3, 4 or 5 membered ring. Preferably, $R_2$ is $C_{1-6}$ alkyl, $C_{2-6}$ alkenyl or $C_{3-7}$ cycloalkyl. More preferably, $R_2$ is $C_{2-6}$ alkenyl. Most preferably, $R_2$ is vinyl In accordance with the present invention, $R_3$ may be $C_{1-8}$ alkyl optionally substituted with halo, cyano, amino, $C_{1-6}$ dialkylamino, $C_{6-10}$ aryl, $C_{7-14}$ alkylaryl, $C_{1-6}$ alkoxy, carboxy, hydroxy, aryloxy, $C_{7-14}$ alkylaryloxy, $C_{2-6}$ alkylester, $C_{8-15}$ alkylarylester; $C_{3-12}$ alkenyl, $C_{3-7}$ cycloalkyl, or $C_{4-10}$ alkylcycloalkyl, wherein the cycloalkyl or alkylcycloalkyl are optionally substituted with hydroxy, $C_{1-6}$ alkyl, $C_{2-6}$ alkenyl or $C_{1-6}$ alkoxy; or $R_3$ together with the carbon atom to which it is attached forms a $C_{3-7}$ cycloalkyl group optionally substituted with $C_{2-6}$ alkenyl. Preferably, $R_3$ is $C_{1-8}$ alkyl optionally substituted with $C_6$ aryl, $C_{1-6}$ alkoxy, carboxy, hydroxy, aryloxy, $C_{7-14}$ alkylaryloxy, $C_{2-6}$ alkylester, $C_{8-15}$ alkylarylester; $C_{3-12}$ alkenyl, $C_{3-7}$ cycloalkyl, or $C_{4-10}$ alkylcycloalkyl. More preferably, $R_3$ is $C_{1-8}$ alkyl optionally substituted with $C_{1-6}$ alkoxy; or $C_{3-7}$ cycloalkyl. Most preferably, $R_3$ is t-butyl.

In accordance with the present invention, Y may be H, phenyl substituted with nitro, pyridyl substituted with nitro, or $C_{1-6}$ alkyl optionally substituted with cyano, OH or $C_{3-7}$ cycloalkyl; provided that if $R_4$ or $R_5$ is H then Y is H. Preferably, Y is H.

In accordance with the present invention, B may be H, $C_{1-6}$ alkyl, $R_4-(C=O)-$, $R_4O(C=O)-$, $R_4-N(R_5)-C(=O)-$, $R_4-N(R_5)-C(=S)-$, $R_4SO_2-$, or $R_4-N(R_5)-SO_2-$, Preferably, B is H, $C_{1-6}$ alkyl, $R_4-(C=O)-$, $R_4O(C=O)-$, $R_4-N(R_5)-C(=O)-$, $R_4-N(R_5)-C(=S)-$, $R_4SO_2-$, or $R_4-N(R_5)-SO_2-$. More preferably, B is $R_4-(C=O)-$, $R_4O(C=O)-$, or $R_4-N(R_5)-C(=O)-$. Most preferably, B is $R_4O(C=O)-$.

In accordance with the present invention, $R_4$ may be (i) $C_{1-10}$ alkyl optionally substituted with phenyl, carboxyl, $C_{1-6}$ alkanoyl, 1-3 halogen, hydroxy, $-OC(O)C_{1-6}$ alkyl, $C_{1-6}$ alkoxy, amino optionally substituted with $C_{1-6}$ alkyl, amido, or (lower alkyl) amido; (ii) $C_{3-7}$ cycloalkyl, $C_{3-7}$ cycloalkoxy, or $C_{4-10}$ alkylcycloalklyl, each optionally substituted with hydroxy, carboxyl, ($C_{1-6}$ alkoxy)carbonyl, amino optionally substituted with $C_{1-6}$ alkyl, amido, or (lower alkyl) amido; (iii) $C_{6-10}$ aryl or $C_{7-16}$ arylalkyl, each optionally substituted with $C_{1-6}$ alkyl, halogen, nitro, hydroxy, amido, (lower alkyl) amido, or amino optionally substituted with $C_{1-6}$ alkyl; (iv) Het; (v) bicyclo(1.1.1) pentane; or (vi) $-C(O)OC_{1-6}$ alkyl, $C_{2-6}$alkenyl or $C_{2-6}$ alkynyl. Preferably, $R_4$ is (i) $C_{1-10}$ alkyl optionally substituted with phenyl, carboxyl, $C_{1-6}$ alkanoyl, 1–3 halogen, hydroxy, $C_{1-6}$ alkoxy; (ii) $C_{3-7}$ cycloalkyl, $C_{3-7}$ cycloalkoxy, or $C_{4-10}$ alkylcycloalklyl; or (iii) $C_{6-10}$ aryl or $C_{7-16}$ arylalkyl, each optionally substituted with $C_{1-6}$alkyl or halogen. More preferably, $R_4$ is (i) $C_{1-10}$ alkyl optionally substituted with 1–3 halogen or $C_{1-6}$ alkoxy; or (ii) $C_{3-7}$ cycloalkyl or $C_{4-10}$ alkylcycloalkyl. Most preferably, $R_4$ is t-butyl.

In accordance with the present invention, $R_5$ may be H; $C_{1-6}$ alkyl optionally substituted with 1–3 halogens; or $C_{1-6}$ alkoxy provided $R_4$ is $C_{1-10}$ alkyl. Preferably, H or $C_{1-6}$ alkyl optionally substituted with 1–3 halogens. More preferably, $R_5$ is H.

In accordance with the present invention $R_6$ may be H, $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono-or di-halo-$C_{1-6}$ alkoxy, cyano, halo, thioalkyl, hydroxy, alkanoyl, $NO_2$, SH, amino, $C_{1-6}$ alkylamino, di $(C_{1-6})$alkylamino, di $(C_{1-6})$alkylamide, carboxyl, $(C_{1-6})$ carboxyester, $C_{1-6}$ alkylsulfone, $C_{1-6}$ alkylsulfoxide, $C_{1-6}$ alkylsulfonamide or di $(C_{1-6})$alkyl (alkoxy)amine. Preferably, $R_6$ is $C_{1-6}$ alkyl, $C_{3-7}$ cycloalkyl, or $C_{1-6}$ alkoxy. More preferably, $R_6$ is $C_{1-6}$ alkoxy.

In accordance with the present invention, $R_7$ may be H, $C_{1-6}$ alkyl, $C_{3-7}$ cycloalkyl, $C_{6-10}$ aryl, $C_{7-14}$ alkylaryl; $C_{6-10}$ aryloxy; $C_{7-14}$ alkylaryloxy; $C_{8-15}$ alkylarylester or Het.

The substituents from each grouping may be selected individually and combined in any combination which provides a stable compound in accordance with the present invention. Also, more than one substituent from each group may be substituted on the core group provided there are sufficient available binding sites. For example, more than one $R_6$ substituent can be present on the ring shown in Formula 1, e.g., 3 different $R_6$ substitutents.

In a preferred embodiment, compounds of the present invention have the structure of Formula II:

Formula II

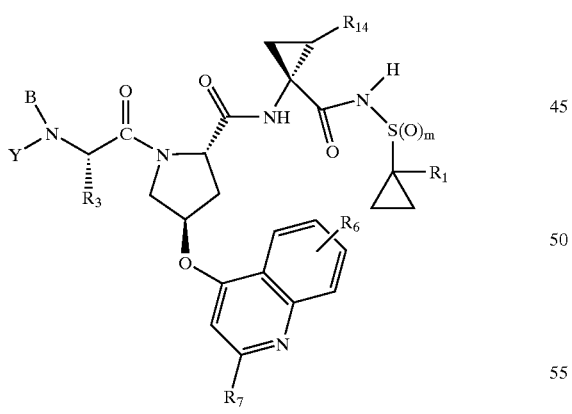

wherein $R_3$, $R_6$, $R_7$, $R_1$, m, B and Y are as defined in Formula I while $R_{14}$ is $C_{1-6}$ alkyl, $C_{2-6}$ alkenyl or H. The present invention further comprises salts or solvates compounds of Formula II, as well as pharmaceutical compositions comprising compounds of Formula II, or salts or solvates thereof.

In another preferred embodiment, compounds of the present invention have the structure of Formula III:

Formula III

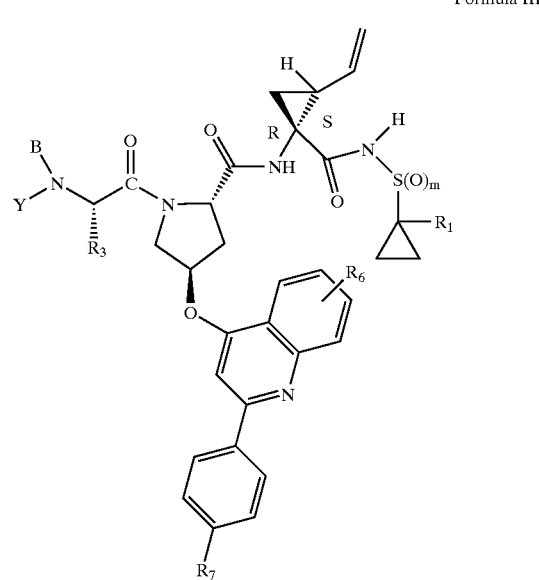

wherein $R_3$, B, $R_1$, $R_6$, $R_7$, m and Y are as defined in Formula I. The present invention further comprises salts or solvates of compounds of Formula III, as well as pharmaceutical compositions comprising compounds of Formula III, or salts or solvates thereof.

In another preferred embodiment, compounds of the present invention have the structure of Formula IV:

Formula IV

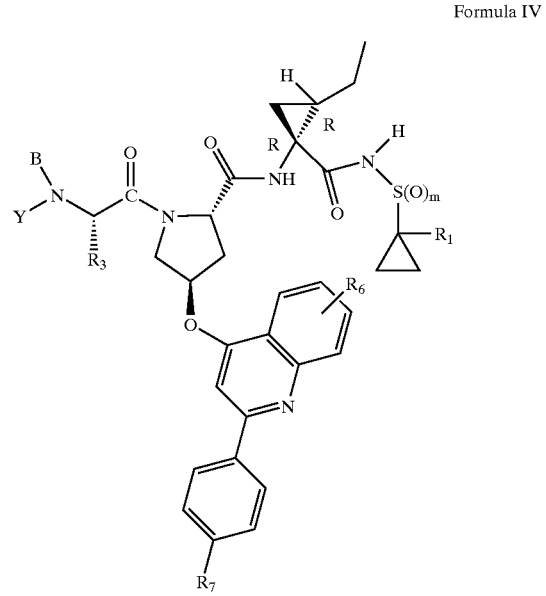

wherein $R_3$, B, $R_1$, $R_6$, $R_7$, m and Y are as defined in Formula I. The present invention further comprises salts or solvates of compounds of Formula IV, as well as pharmaceutical compositions comprising compounds of Formula IV, or salts or solvates thereof.

Preferred embodiments of the present invention include the following compounds, including their pharmaceutically acceptable solvates or salts:

| 15 | 16 |
|---|---|
| 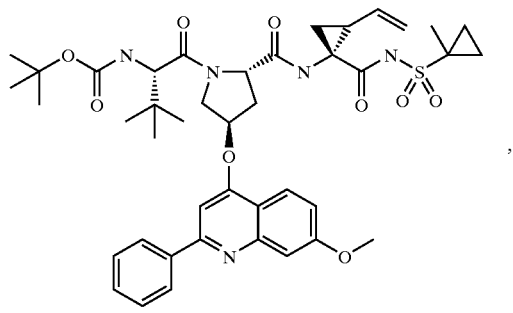 | 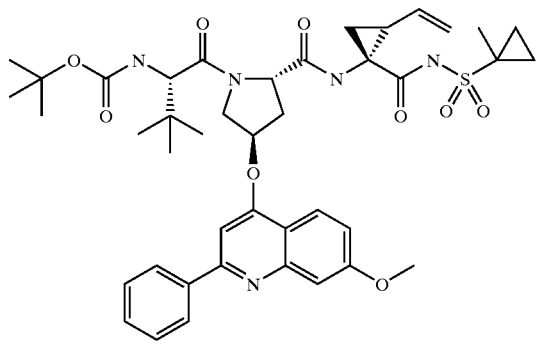 |
| 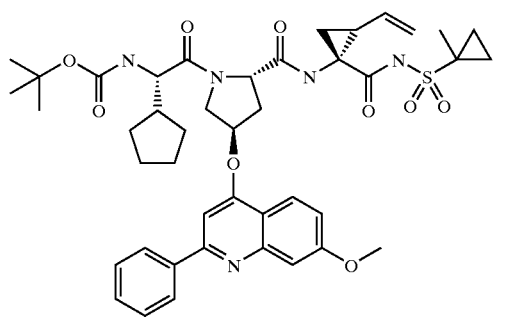 | 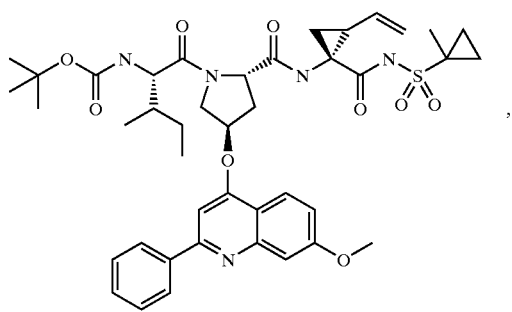 |
| 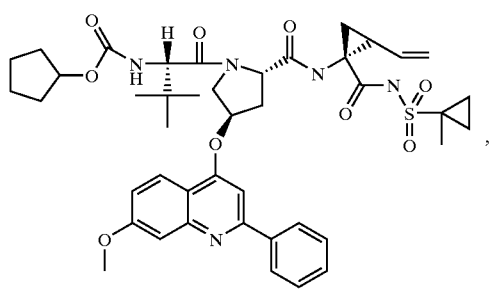 | 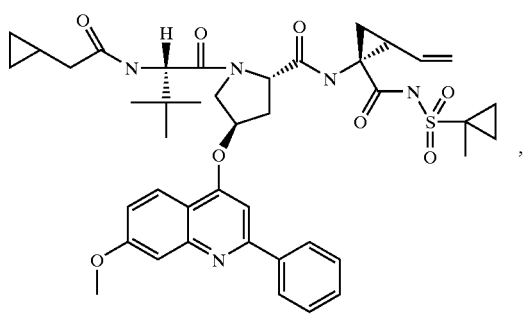 |
| 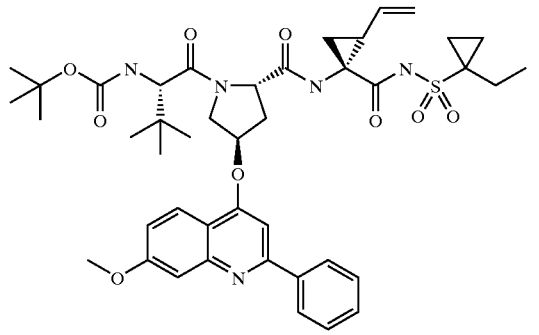 | 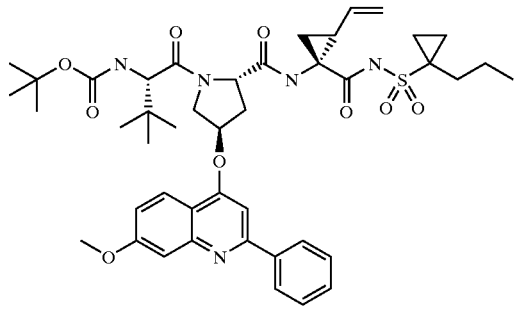 |
| 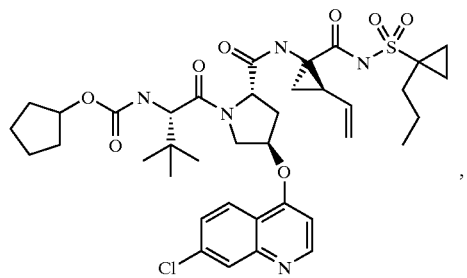 | 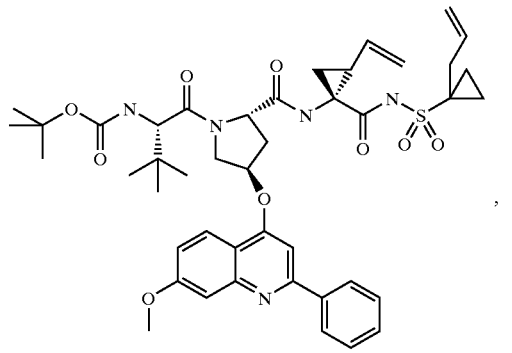 |

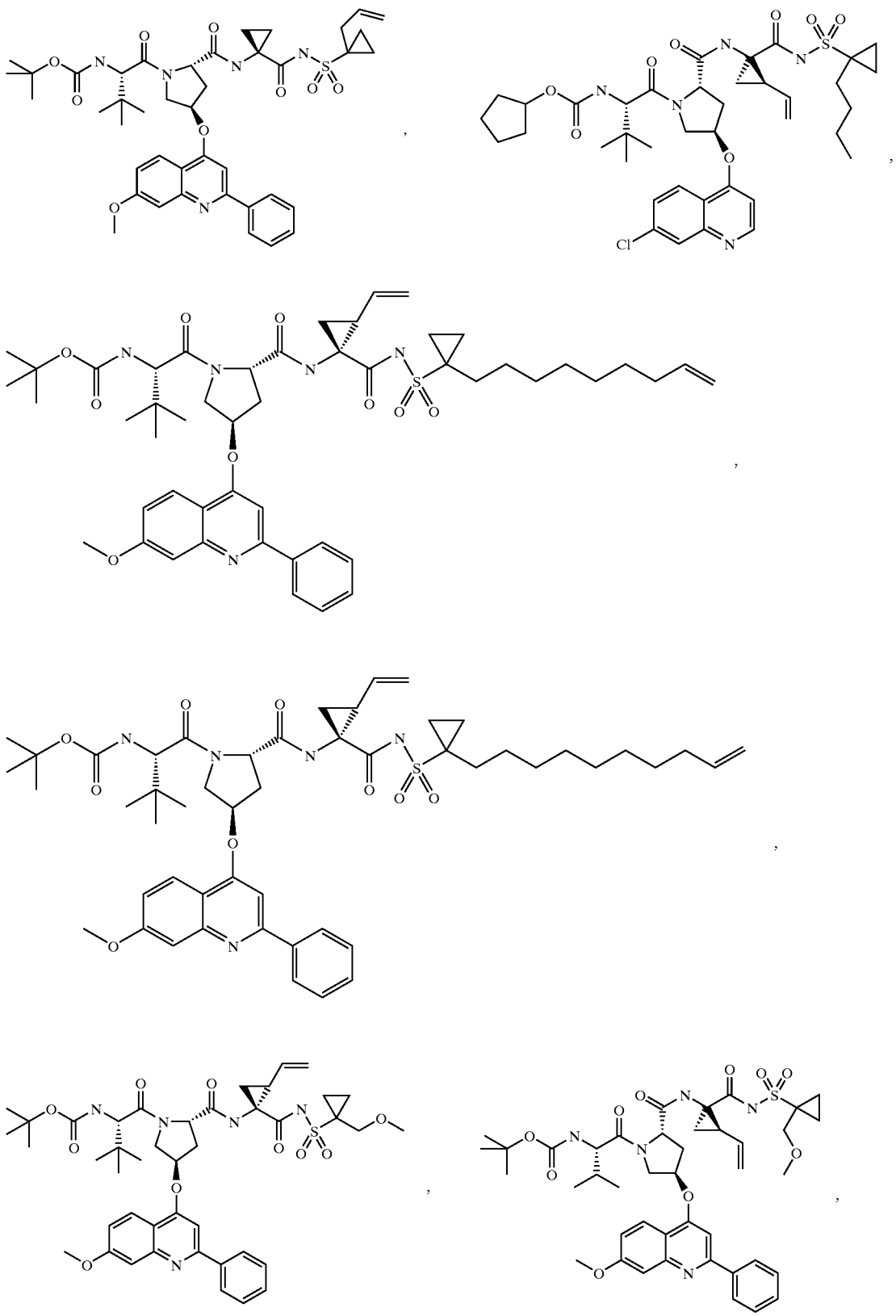

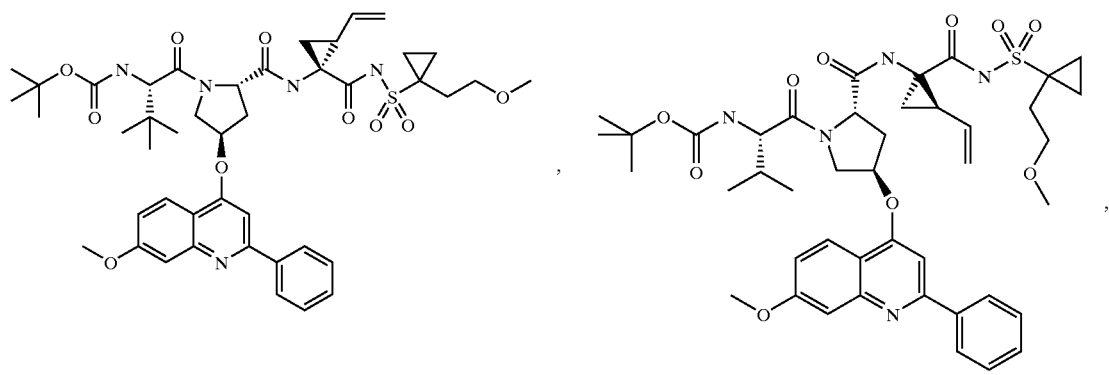
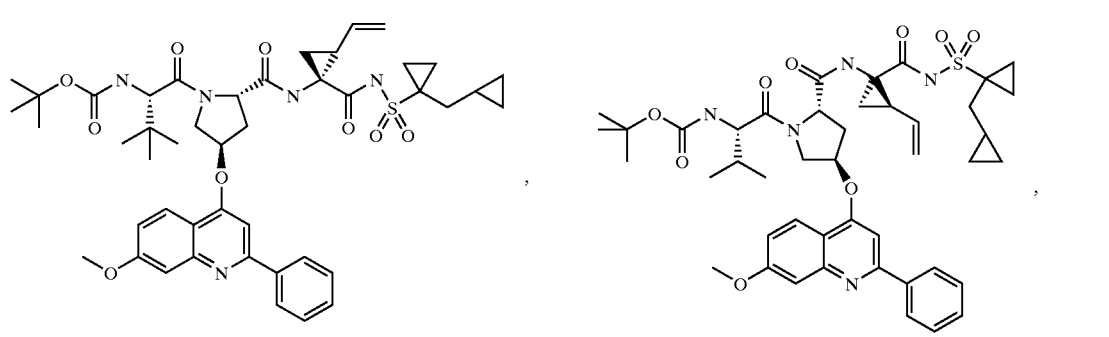
Free Base
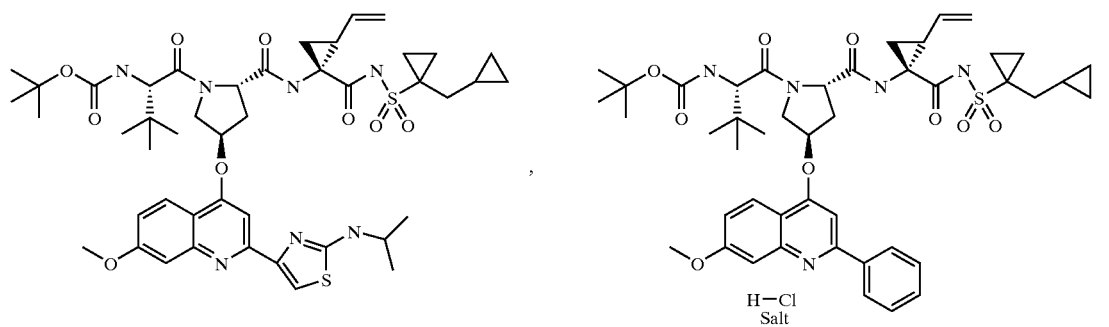
H—Cl Salt
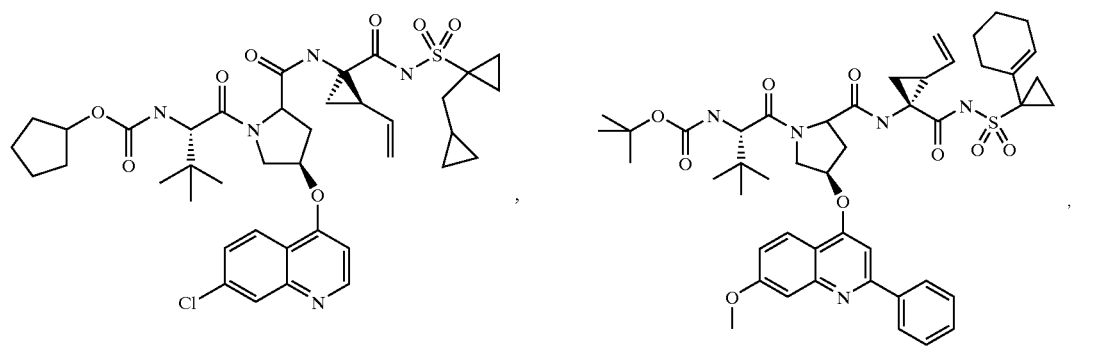

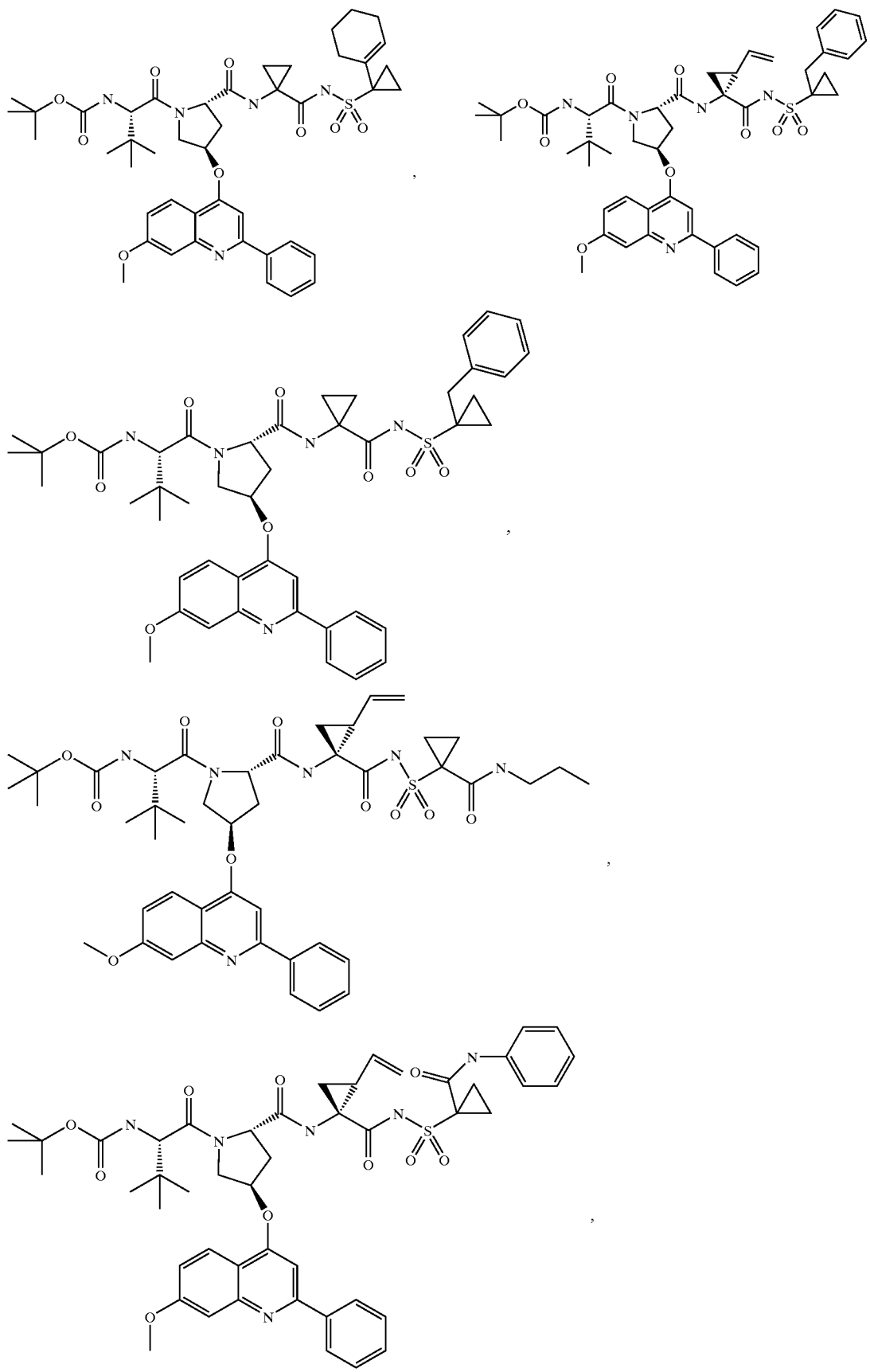

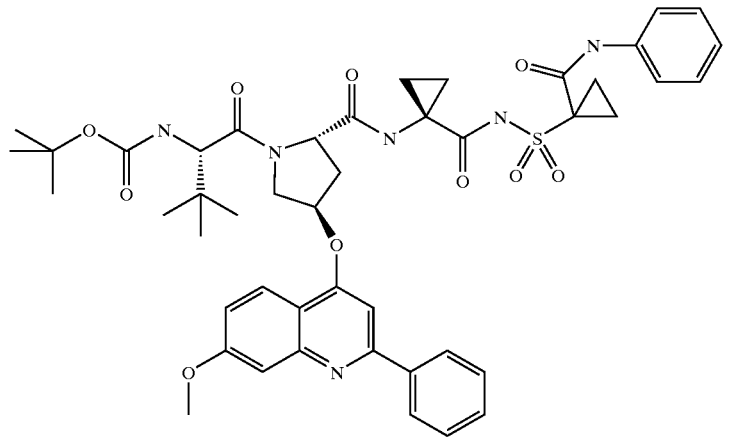
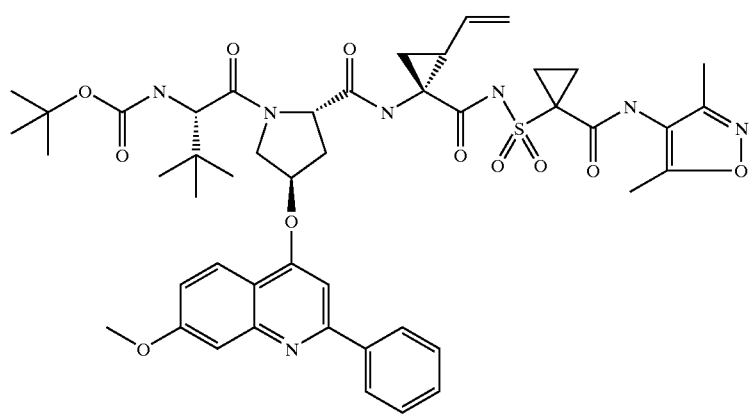
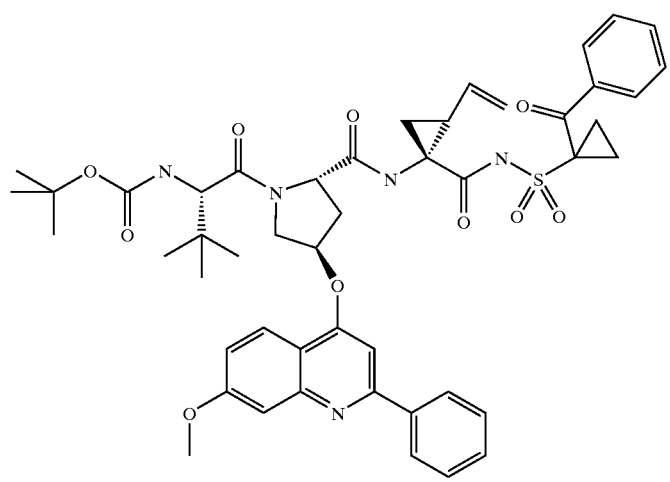

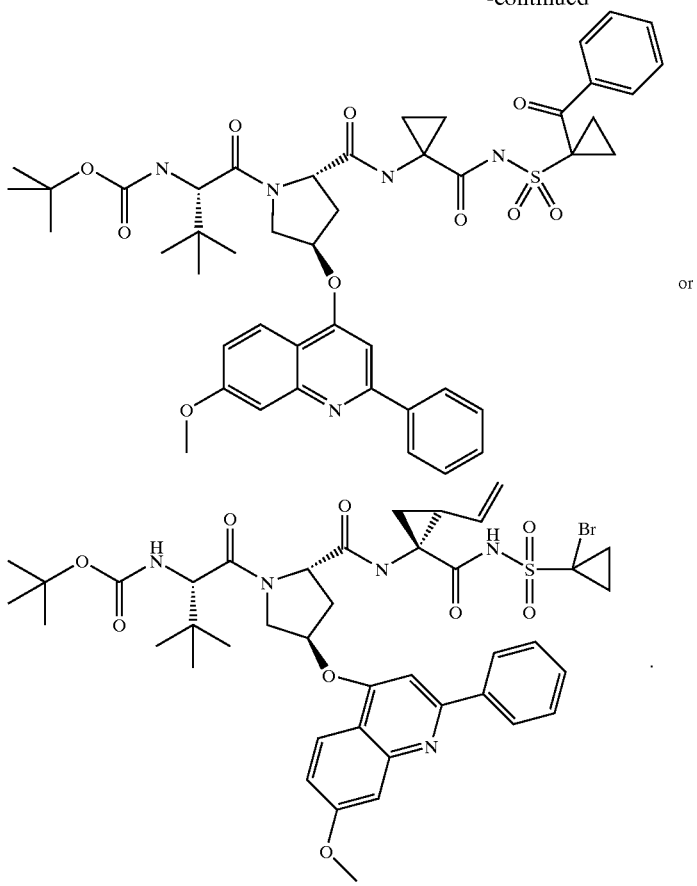

or

The compounds of the present invention, when in a basic form, can form salts by the addition of a pharmaceutically acceptable acid. The acid addition salts are formed from a compound of Formula I and a pharmaceutically acceptable inorganic acid, including but not limited to hydrochloric, hydrobromic, hydroiodic, sulfuric, phosphoric, or organic acid such as p-toluenesulfonic, methanesulfonic, acetic, benzoic, citric, malonic, fumaric, maleic, oxalic, succinic, sulfamic, or tartaric. Thus, examples of such pharmaceutically acceptable salts include chloride, bromide, iodide, sulfate, phosphate, methanesulfonate, citrate, acetate, malonate, fumarate, sulfamate, and tartrate.

Salts of an amine group may also comprise quaternary ammonium salts in which the amino nitrogen carries a suitable organic group such as an alkyl, alkenyl, alkynyl or aralkyl moiety.

Compounds of the present invention, which are substituted with an acidic group, may exist as salts formed through base addition. Such base addition salts include those derived from inorganic bases which include, for example, alkali metal salts (e.g. sodium and potassium), alkaline earth metal salts (e.g. calcium and magnesium), aluminum salts and ammonium salts. In addition, suitable base addition salts include salts of physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-β-phenethylamine, dehydroabietylamine, N,N'-bishydroabietylamine, glucamine, N-methylglucamine, collidine, quinine, quinoline, ethylenediamine, ornithine, choline, N,N'-benzylphenethylamine, chloroprocaine, diethanolamine, diethylamine, piperazine, tris(hydroxymethyl)aminomethane and tetramethylammonium hydroxide and basic amino acids such as lysine, arginine and N-methylglutamine. These salts may be prepared by methods known to those skilled in the art.

Certain compounds of the present invention, and their salts, may also exist in the form of solvates with water, for example hydrates, or with organic solvents such as methanol, ethanol or acetonitrile to form, respectively, a methanolate, ethanolate or acetonitrilate. The present invention includes each solvate and mixtures thereof.

In addition, compounds of the present invention, or a salt or solvate thereof, may exhibit polymorphism. The present invention also encompasses any such polymorphic form.

The compounds of the present invention also contain two or more chiral centers. For example, the compounds may include P1 cyclopropyl element of formula

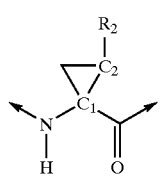

P1 wherein $C_1$ and $C_2$ each represent an asymmetric carbon atom at positions 1 and 2 of the cyclopropyl ring. Not withstanding other possible asymmetric centers at other segments of the compounds, the presence of these two asymmetric centers means that the compounds can exist as racemic mixtures of diastereomers, such as the diastereomers wherein $R_2$ is configured either syn to the amide or syn to the carbonyl as shown below:

(1R, 2S)

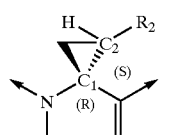

$R_2$ is syn to carbonyl (1S, 2R)

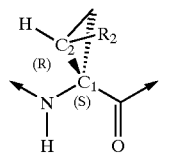

$R^2$ is syn to carbonyl (1R, 2R)

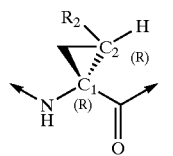

$R_2$ is syn to amide (1S, 2S)

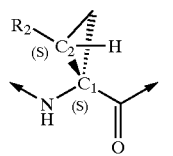

$R_2$ is syn to amide

The present invention includes both enantiomers and mixtures of enantiomers such as racemic mixtures.

The enantiomers may be resolved by methods known to those skilled in the art, for example, by formation of diastereoisomeric salts which may be separated by crystallization, gas-liquid or liquid chromatography, selective reaction of one enantiomer with an enantiomer-specific reagent. It will be appreciated that where the desired enantiomer is converted into another chemical entity by a separation technique, then an additional step is required to form the desired enantiomeric form. Alternatively, specific enantiomers may be synthesized by asymmetric synthesis using optically active reagents, substrates, catalysts or solvents, or by converting one enantiomer into the other by asymmetric transformation.

The compounds of the present invention may be in the form of a prodrug. Simple aliphatic or aromatic esters derived from, when present, acidic groups pendent on the compounds of this invention are preferred prodrugs. In some cases it is desirable to prepare double ester type prodrugs such as (acyloxy)alkyl esters or (alkoxycarbonyl)oxy)alkyl esters.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

Certain compounds of the present invention may exist in zwitterionic form and the present invention includes each zwitterionic form of these compounds and mixtures thereof.

The starting materials useful to synthesize the compounds of the present invention are known to those skilled in the art and can be readily manufactured or are commercially available.

The compounds of the present invention can be manufactured by methods known to those skilled in the art, see e.p., U.S. Pat. No. 6,323,180 and U.S. Patent Appl. 20020111313 A1. The following methods set forth below are provided for illustrative purposes and are not intended to limit the scope of the claimed invention. It will be recognized that it may be preferred or necessary to prepare such a compound in which a functional group is protected using a conventional protecting group then to remove the protecting group to provide a compound of the present invention. The details concerning the use of protecting groups in accordance with the present invention are known to those skilled in the art.

The compounds of the present invention may, for example, be synthesized according to a general process as illustrated in Scheme I (wherein CPG is a carboxyl protecting group and APG is an amino protecting group):

Scheme I

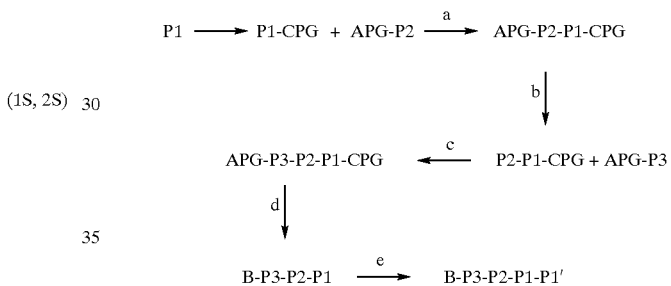

Briefly, the P1, P2, and P3 can be linked by well known peptide coupling techniques. The P1, P2, and P3 groups may be linked together in any order as long as the final compound corresponds to peptides of the invention. For example, P3 can be linked to P2-P1; or P1 linked to P3-P2.

Generally, peptides are elongated by deprotecting the α-amino group of the N-terminal residue and coupling the unprotected carboxyl group of the next suitably N-protected amino acid through a peptide linkage using the methods described. This deprotection and coupling procedure is repeated until the desired sequence is obtained. This coupling can be performed with the constituent amino acids in stepwise fashion, as depicted in Scheme I.

Coupling between two amino acids, an amino acid and a peptide, or two peptide fragments can be carried out using standard coupling procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxysuccinic imido ester) method, Woodward reagent K-method, carbonyldiimidazole method, phosphorus reagents or oxidation-reduction methods. Some of these methods (especially the carbodiimide method) can be enhanced by adding 1-hydroxybenzotriazole or 4-DMAP. These coupling reactions can be performed in either solution (liquid phase) or solid phase.

More explicitly, the coupling step involves the dehydrative coupling of a free carboxyl of one reactant with the free amino group of the other reactant in the present of a coupling agent to form a linking amide bond. Descriptions of such coupling agents are found in general textbooks on peptide chemistry, for example, M. Bodanszky, "Peptide Chemistry", $2^{nd}$ rev ed., Springer-Verlag, Berlin, Germany, (1993). Examples of suitable coupling agents are N,N'-dicyclohexylcarbodiimide, 1-hydroxybenzotriazole in the presence of N,N'-dicyclohexylcarbodiimide or N-ethyl-N'-[(3-dimethylamino)propyl]carbodiimide. A practical and useful coupling agent is the commercially available (benzotriazol-1-yloxy)tris-(dimethylamino)phosphonium hexafluorophosphate, either by itself or in the present of 1-hydroxybenzotriazole or 4-DMAP. Another practical and useful coupling agent is commercially available 2-(1H-benzotriazol-1-yl)-N,N,N',N'-tetramethyluronium tetrafluoroborate. Still another practical and useful coupling agent is commercially available O-(7-azabenzotrizol-1-yl)-N,N,N',N'-tetramethyluronium hexafluorophosphate. The coupling reaction is conducted in an inert solvent, e.g. dichloromethane, acetonitrile or dimethylformamide. An excess of a tertiary amine, e.g. diisopropylethylamine, N-methylmorpholine, N-methylpyrrolidine or 4-DMAP is added to maintain the reaction mixture at a pH of about 8. The reaction temperature usually ranges between 0° C. and 50° C. and the reaction time usually ranges between 15 min and 24 h.

The functional groups of the constituent amino acids generally must be protected during the coupling reactions to avoid formation of undesired bonds. Protecting groups that can be used are listed, for example, in Greene, "Protective Groups in Organic Chemistry", John Wiley & Sons, New York (1981) and "The Peptides: Analysis, Synthesis, Biology", Vol. 3, Academic Press, New York (1981), the disclosures of which are hereby incorporated by reference.

The α-amino group of each amino acid to be coupled to the growing peptide chain must be protected (APG). Any protecting group known in the art can be used. Examples of such groups include: 1) acyl groups such as formyl, trifluoroacetyl, phthalyl, and p-toluenesulfonyl; 2) aromatic carbamate groups such as benzyloxycarbonyl (Cbz or Z) and substituted bensyloxycarbonyls, and 9-fluorenylmethyloxycarbonyl (Fmoc); 3) aliphatic carbamate groups such as tert-butyloxycarbonyl (Boc), ethoxycarbonyl, diisopropylmethoxycarbonyl, and allyloxycarbonyl; 4) cyclic alkyl carbamate groups such as cyclopentyloxycarbonyl and adamantyloxycarbonyl; 5) alkyl groups such as triphenylmethyl and benzyl; 6)trialkylsilyl such as trimethylsilyl; and 7) thiol containing groups such as phenylthiocarbonyl and dithiasuccinoyl.

The preferred α-amino protecting group is either Boc or Fmoc. Many amino acid derivatives suitably protected for peptide synthesis are commercially available. The α-amino protecting group of the newly added amino acid residue is cleaved prior to the coupling of the next amino acid. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethylformamide. When the Fmoc group is used, the reagents of choice are piperidine or substituted piperidine in dimethylformamide, but any secondary amine can be used. The deprotection is carried out at a temperature between 0° C. and room temperature (rt or RT) usually 20–22° C.

Any of the amino acids having side chain functionalities must be protected during the preparation of the peptide using any of the above-described groups. Those skilled in the art will appreciate that the selection and use of appropriate protecting groups for these side chain functionalities depend upon the amino acid and presence of other protecting groups in the peptide. The selection of such protecting groups is important in that the group must not be removed during the deprotection and coupling of the α-amino group.

For example, when Boc is used as the α-amino protecting group, the following side chain protecting group are suitable: σ-toluenesulfonyl (tosyl) moieties can be used to protect the amino side chain of amino acids such as Lys and Arg; acetamidomethyl, benzyl (Bn), or tert-butylsulfonyl moieties can be used to protect the sulfide containing side chain of cysteine; benzyl (Bn) ethers can be used to protect the hydroxy containing side chains of serine, threonine or hydroxyproline; and benzyl esters can be used to protect the carboxy containing side chains of aspartic acid and glutamic acid.

When Fmoc is chosen for the α-amine protection, usually tert-butyl based protecting groups are acceptable. For instance, Boc can be used for lysine and arginine, tert-butyl ether for serine, threonine and hydroxyproline, and tert-butyl ester for aspartic acid and glutamic acid. Triphenylmethyl (Trityl) moiety can be used to protect the sulfide containing side chain of cysteine.

Once the elongation of the peptide is completed all of the protecting groups are removed. When a liquid phase synthesis is used, the protecting groups are removed in whatever manner is dictated by the choice of protecting groups. These procedures are well known to those skilled in the art.

Further, the following guidance may be followed in the preparation of compounds of the present invention. For example, to form a compound where $R_4$—C(O)—, $R_4$—S(O)$_2$, a protected P3 or the whole peptide or a peptide segment is coupled to an appropriate acyl chloride or sulfonyl chloride respectively, that is either commercially available or for which the synthesis is well known in the art. In preparing a compound where $R_4$O—C(O)—, a protected P3 or the whole peptide or a peptide segment is coupled to an appropriate chloroformate that is either commercially available or for which the synthesis is well known in the art. For Boc-derivatives (Boc)$_2$O is used.

For example:

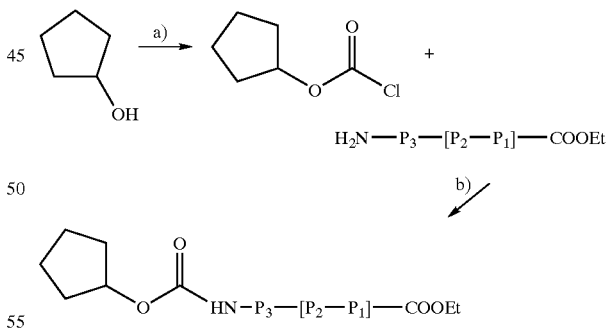

Cyclopentanol is treated with phosgene to furnish the corresponding chloroformate.

The chloroformate is treated with the desired NH$_2$-tripeptide in the presence of a base such as triethylamine to afford the cyclopentylcarbamate.

In preparing a compound where $R_4$—N(R$_5$)—C(O)—, or $R_4$—NH—C(S)—, a protected P3 or the whole peptide or a peptide segment is treated with phosgene followed by amine as described in SynLett. Feb 1995; (2); 142-144 or is reacted with the commercially available isocyanate and a suitable base such as triethylamine.

In preparing a compound where $R_4$—$N(R_5)$—$S(O_2)$, a protected P3 or the whole peptide or a peptide segment is treated with either a freshly prepared or commercially available sulfamyl chloride followed by amine as described in patent Ger. Offen.(1998), 84 pp. DE 19802350 or WO 98/32748.

The α-carboxyl group of the C-terminal residue is usually protected as an ester (CPG) that can be cleaved to give the carboxylic acid. Protecting groups that can be used include: 1) alkyl esters such as methyl, trimethylsilylethyl and t-butyl, 2) aralkyl esters such as benzyl and substituted benzyl, or 3) esters that can be cleaved by mild base treatment or mild reductive means such as trichloroethyl and phenacyl esters.

The resulting α-carboxylic acid (resulting from cleavage by mild acid, mild base treatment or mild reductive means) is coupled with a $R_1SO_2NH_2$ [prepared by treatment of $R_1SO_2Cl$ in ammonia saturated tetrahydrofuran solution] in the presence of peptide coupling agent such as CDI or EDAC in the presence of a base such as 4-dimethylaminopyridine (4-DMAP) and/or 1,8-diazabicyclo[5.4.0]undec-7-ene (DBU) to incorporate the P1' moiety, effectively assembling the tripeptide P1'-P1-P2-P3-APG. Typically, in this process, 1-5 equivalents of P1' coupling agents are used.

Furthermore, if the P3 protecting group APG is removed and replaced with a B moiety by the methods described above, and the resulting α-carboxylic acid resulting from cleavage (resulting from cleavage by mild acid, mild base treatment or mild reductive means) is coupled with a $R_1SO_2NH_2$ [prepared by treatment of $R_1SO_2Cl$ in ammonia saturated tetrahydrofuran solution or alternative methods described herein] in the presence of peptide coupling agent such as CDI or EDAC in the presence of a base such as 4-dimethylaminopyridine (4-DMAP) and/or 1,8-diazabicyclo[5.4.0]undec-7-ene (DBU) to incorporate the P1' moiety, the tripeptide P1'-P1-P2-P3-B is prepared. Typically, in this process, 1–5 equivalents of P1' coupling agents are used.

Compounds of the present invention can be prepared by many methods including those described in the examples, below, and as described in U.S. Pat. No. 6,323,180 and U.S. patent application Ser. No. 10/001,850 filed on Nov. 20, 2001. The teachings of U.S. Pat. No. 6,323,180 and U.S. patent application Ser. No. 10/001,850 are incorporated herein, in their entirety, by reference.

The present invention also provides compositions comprising a compound of the present invention, or a pharmaceutically acceptable salt, solvate or prodrug thereof, and a pharmaceutically acceptable carrier. Pharmaceutical compositions of the present invention comprise a therapeutically effective amount of a compound of the invention, or a pharmaceutically acceptable salt, solvate or prodrug thereof, and a pharmaceutically acceptable carrier, with a pharmaceutically acceptable carrier, e.g., excipient, or vehicle diluent.

The active ingredient, i.e., compound, in such compositions typically comprises from 0.1 weight percent to 99.9 percent by weight of the composition, and often comprises from about 5 to 95 weight percent.

The pharmaceutical compositions of this invention may be administered orally, parenterally or via an implanted reservoir. Oral administration or administration by injection are preferred. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, and intralesional injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents and suspending agents. The details concerning the preparation of such compounds are known to those skilled in the art.

When orally administered, the pharmaceutical compositions of this invention may be administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

Other suitable carriers for the above noted compositions can be found in standard pharmaceutical texts, e.g. in "Remington's Pharmaceutical Sciences", 19 th ed., Mack Publishing Company, Easton, Penn., 1995. Further details concerning the design and preparation of suitable delivery forms of the pharmaceutical compositions of the invention are known to those skilled in the art.

Dosage levels of between about 0.01 and about 1000 milligram per kilogram ("mg/kg") body weight per day, preferably between about 0.5 and about 250 mg/kg body weight per day of the compounds of the invention are typical in a monotherapy for the prevention and treatment of HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this invention comprise a combination of a compound of the invention and one or more additional therapeutic or prophylactic agent, both the compound and the additional agent are usually present at dosage levels of between about 10 to 100%, and more preferably between about 10 and 80% of the dosage normally administered in a monotherapy regimen.

When these compounds or their pharmaceutically acceptable salts, solvates or prodrugs are formulated together with a pharmaceutically acceptable carrier, the resulting composition may be administered in vivo to mammals, such as man, to inhibit HCV NS3 protease or to treat or prevent HCV virus infection. Such treatment may also-be achieved using the compounds of this invention in combination with agents which include, but are not limited to: immunomodulatory agents, such as interferons; other antiviral agents such as ribavirin, amantadine; other inhibitors of HCV NS3 protease; inhibitors of other targets in the HCV life cycle such as helicase, polymerase, metalloprotease, or internal ribosome entry site; or combinations thereof. The additional agents may be combined with the compounds of this invention to create a single dosage form. Alternatively these additional agents may be separately administered to a mammal as part of a multiple dosage form.

Accordingly, another aspect of this invention provides methods of inhibiting HVC NS3 protease activity in patients by administering a compound of the present invention or a pharmaceutically acceptable salt or solvate thereof, wherein the substituents are as defined above.

In a preferred embodiment, these methods are useful in decreasing HCV NS3 protease activity in the patient. If the pharmaceutical composition comprises only a compound of this invention as the active component, such methods may additionally comprise the step of administering to said patient an agent selected from an immunomodulatory agent, an antiviral agent, a HCV protease inhibitor, or an inhibitor of other targets in the HCV life cycle such as, for example, helicase, polymerase, or metalloprotease. Such additional agent may be administered to the patient prior to, concurrently with, or following the administration of the compounds of this invention.

In an alternate preferred aspect, these methods are useful for inhibiting viral replication in a patient. Such methods can be useful in treating or preventing HCV disease.

The compounds of the invention may also be used as laboratory reagents. Compounds may be instrumental in providing research tools for designing of viral replication assays, validation of animal assay systems and structural biology studies to further enhance knowledge of the HCV disease mechanisms.

The compounds of this invention may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

EXAMPLES

The specific examples that follow illustrate the syntheses of the compounds of the instant invention, and are not to be construed as limiting the invention in sphere or scope. The methods may be adapted to variations in order to produce compounds embraced by this invention but not specifically disclosed. Further, variations of the methods to produce the same compounds in somewhat different manner will also be evident to one skilled in the art.

Chemical abbreviations commonly used to identify chemical compounds in the literature include Bn: benzyl; Boc: tert-butyloxycarbonyl {Me$_3$COC(O)}; BSA: bovine serum albumin; CDI: carbonyldiimidazole; DBU: 1,8-diazabicy-clo[5.4.0]-undec-7-ene; CH$_2$Cl$_2$=DCM: methylene chloride; DEAD: diethylazodicarboxylate; DIAD: diisopropylazodi-carboxylate; DIEA: diisopropylethylamine; DIPEA: diisopropylethylamine; 4-DMAP: 4-dimethylaminopyridine; DCC: 1,3-dicyclohexylcarbodiimide; DMF: dimethylformamide; DMSO: dimethylsulfoxide; DPPA: diphenylphosphoryl azide; EDAC: ethyldimethylaminopropylcarbodiimide hydrochloride; EDTA: ethylenediaminetetraacetic acid; Et: ethyl; EtOH: ethanol; EtOAc: ethyl acetate; Et$_2$O: diethyl ether; Grubb's Catalyst: bis(tricyclohexylphosphine)benzylidene ruthenium (IV) dichloride; HATU: [O-7-azabenzotriazol-1-yl)-1, HBTU: [O-(1 H-benzotriazol-1-yl)-N,N',N'-tetramethyluronium hexafluorophosphate; PYBROP: Bromo-tris-pyrrolidino-phosphonium hexafluorophosphate; HOAT, 1-hydroxy-7-azabenzotriazole; HPLC: high performance liquid chromatography; MS: mass spectrometry; Me: methyl; MeOH: methanol; NMM: N-methylmorpholine; NMP: N-methylpyrrol-idine; Pr: propyl; Succ: 3-carboxypropanoyl; PPA: polyphosphoric acid; TBAF: tetra-n-butylammonium fluoride; 1,2-DCE or DCE: 1,2-dichloroethane; TBTU:2-(1H-benzotriazole-1-yl)-1,1,3,3-tetramethyluronium tetrafluoroborate; TFA: trifluoroacetic acid; THF: tetrahydrofuran Solution percentages express a weight to volume relationship, and solution ratios express a volume to volume relationship, unless stated otherwise. Nuclear magnetic resonance (NMR) spectra were recorded either on a Bruker 300, 400 or 500 MHz spectrometer; the chemical shifts (δ) are reported in parts per million. Flash chromatography was carried out on silica gel (SiO$_2$) evident to one skilled in the art. All Liquid Chromatography (LC) data were recorded on a Shimadzu LC-10AS liquid chromatograph using a SPD-10AV UV-Vis detector and Mass Spectrometry (MS) data were determined with a Micromass Platform for LC in electrospray mode (ES+). Flash chromatography was carried out on (SiO$_2$) silica gel evident to one skilled in the art (see W. C. Still et al., J. Org. Chem., (1978), 43, 2923).

All Liquid Chromatography (LC) data were recorded on a Shimadzu LC-10AS liquid chromatograph using a SPD-10AV UV-Vis detector and Mass Spectrometry (MS) data were determined with a Micromass Platform for LC in electrospray mode (ES+).

The following describes the construction of representative compounds of the present invention. It should be noted that this portion of the patent is broken down into sections, namely Section A, Section B etc. It should also be noted that the numbers of Compounds found in the present invention is not contiguous. Such a break in numbering is marked by a new section. (eg. in going from Section B to Section C)

Section A

Unless otherwise noted, each compound was analyzed, by LC/MS, using one of seven methodologies, having the following conditions.

Columns: (Method A)—YMC ODS S7 C18 3.0×50 mm
(Method B)—YMC ODS-A S7 C18 3.0×50 mm
(Method C)—YMC S7 C18 3.0×50 mm
(Method D)—YMC Xterra ODS S7 3.0×50 mm
(Method E)—YMC Xterra ODS S7 3.0×50 mm
(Method F)—YMC ODS-A S7 C18 3.0×50 mm
(Method G)—YMC C18 S5 4.6×50 mm]
(Method H)—Xterra S7 3.0×50 mm
(Method I)—Xterra S7 C18 3.0×50 mm
Gradient: 100% Solvent A/0% Solvent B to 0% Solvent A/100% Solvent B
Gradient time: 2 min. (A, B, D, F, G, H, I); 8 min. (C, E)
Hold time: 1 min. (A, B, D, F, G, H, I); 2 min. (C, E)
Flow rate: 5 mL/min
Detector Wavelength: 220 nm
Solvent A: 10% MeOH/90% H$_2$O/0.1% TFA
Solvent B: 10% H$_2$O/90% MeOH/0.1% TFA.

The compounds and chemical intermediates of the present invention, described in the following examples, were prepared according to the following methods.

35

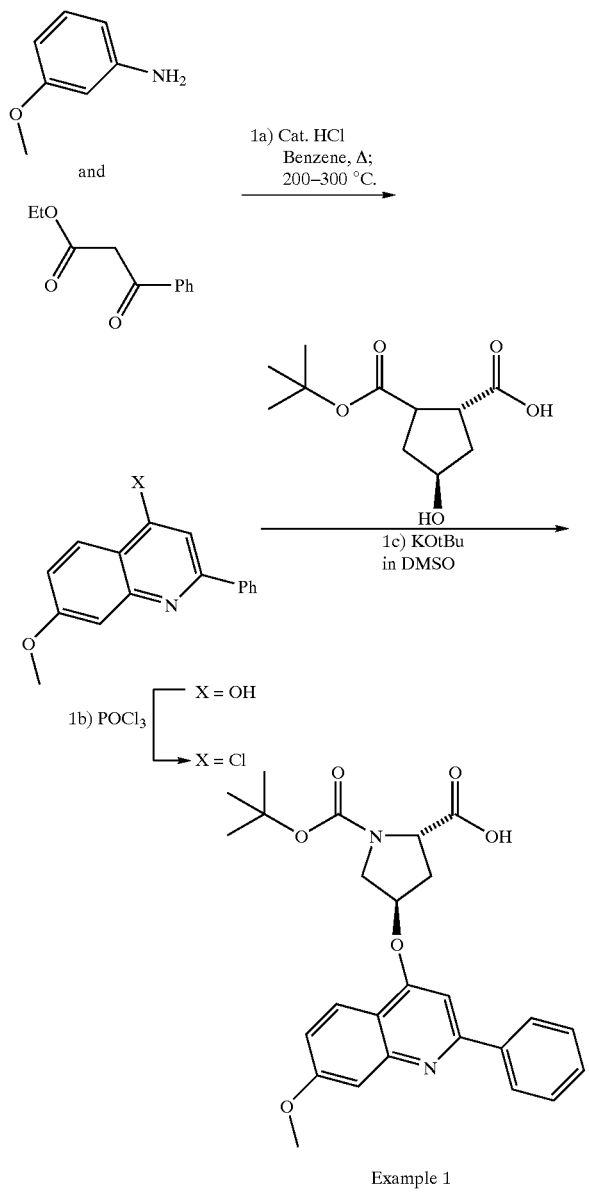

Example 1
Boc-(4R)-(2-phenyl-7-methoxyquinoline-4-oxo)-S-proline, Shown Below, was Prepared as Described in Steps 1a–c

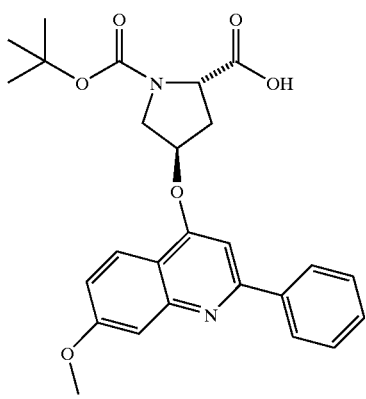

36

Step 1a: Preparation of 4-hydroxy-2-phenyl-7-methoxyquinoline, Shown Below

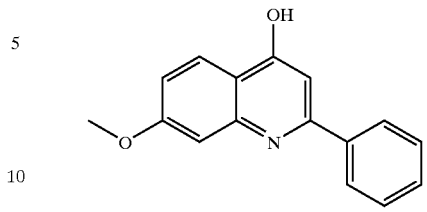

To a solution of m-anisidine (300 g, 2.44 mole) and ethyl benzoylacetate (234.2 g, 1.22 mole) in toluene (2.0 L) was added HCl (4.0 N in dioxane, 12.2 mL, 48.8 mmole). The resulting solution was refluxed for 6.5 hr using a Dean-Stark apparatus (about 56 ml of aqueous solution was collected). The mixture was cooled to rt, partitioned multiple times with aqueous HCl (10%, 3×500 mL), aqueous NaOH (1.0 N, 2×200 mL), water (3×200 mL), and the organic layer dried (MgSO$_4$) and concentrated in vacuo to supply an oily residue (329.5 g). The crude product was heated in an oil bath (280° C.) for 80 min using a Dean-Stark apparatus (about 85 mL liquid was collected). The reaction mixture was cooled down to rt, the solid residue triturated with CH$_2$Cl$_2$ (400 mL), the resulting suspension filtered, and the filter cake washed with more CH$_2$Cl$_2$ (2×150 mL). The resulting solid was dried in vacuo (50° C.; 1 torr; 1 day) affording analytically pure 4-hydroxy-7-methoxy-2-phenylquinoline as a light brown solid (60.7 g, 20% overall). $^1$H NMR δ(DMSO): 3.86 (s, 3H), 6.26 (s, 1H), 6.94 (dd, J=9.0, 2.4 Hz, 1H), 7.21 (d, J=2.4 Hz, 1H), 7.55–7.62 (m, 3H), 7.80–7.84 (m, 2H), 8.00 (d, J=9.0 Hz, 1H), 11.54 (s, 1H); $^{13}$C NMR (DMSO-d$_6$) δ: 55.38, 99.69, 107.07, 113.18, 119.22, 126.52, 127.17, 128.97, 130.34, 134.17, 142.27, 149.53, 161.92, 176.48. LC-MS (retention time: 1.26, method D), MS m/z 252 (M$^+$+1).

Step 1b: Preparation of 4-chloro-7-methoxy-2-phenylquinoline, Shown Below

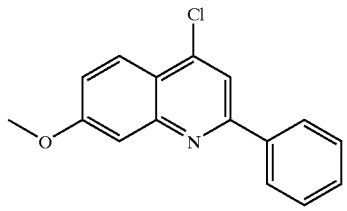

The product of Step 1a (21.7 g, 86.4 mmole) was suspended in POCl$_3$ (240 mL). The suspension was refluxed for 2 hours. After removal of the POCl$_3$ in vacuo, the residue was partitioned between EtOAc (1L), and cold aqueous NaOH (generated from 1.0N 200 mL NaOH and 20 mL 10.0 N NaOH) and stirred for 15 min. The organic layer was washed with water (2×200 mL), brine (200 mL), dried (MgSO$_4$), and concentrated in vacuo to supply 4-chloro-2-phenyl-7-methoxyquinoline (21.0 g, 90%) as a light brown solid. $^1$H NMR (DMSO-d$_6$) δ: 3.97 (s, 3H), 7.36 (dd, J=9.2, 2.6 Hz, 1H), 7.49–7.59 (m, 4H), 8.08 (d, J=9.2 Hz, 1H), 8.19 (s, 1H), 8.26–8.30 (m, 2H); $^{13}$C NMR (DMSO-d$_6$) δ: 55.72, 108.00, 116.51, 119.52, 120.48, 124.74, 127.26, 128.81, 130.00, 137.58, 141.98, 150.20, 156.65, 161.30. LC-MS (retention time: 1.547, Method D), MS m/z 270 (M$^+$+1).

Step 1c: Preparation of Boc-(4R)-(2-phenyl-7-methoxy-quinoline-4-oxo)-S-proline, Shown Below

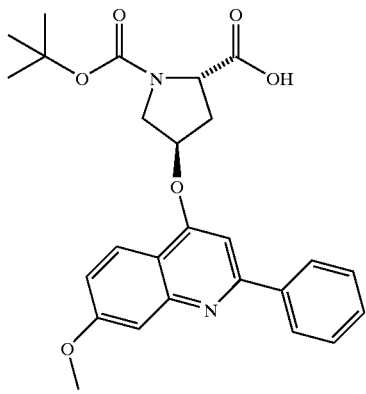

To a suspension of Boc-4R-hydroxyproline (16.44 g, 71.1 mmol) in DMSO (250 mL) was added t-BuOK (19.93 g, 177.6 mmol) at 0° C. The generated mixture was stirred for 1.5 hour and then the product of Step 1b (21.02 g, 77.9 mmol) was added in three portions over 1 h. The reaction was stirred for one day, the reaction mixture was poured into cold water (1.5L) and washed with $Et_2O$ (4×200 mL). The aqueous solution was acidified to pH 4.6, filtered to obtain a white solid, and dried in vacuo to supply the product, Boc (4R)-(2-phenyl-7-methoxyquinoline-4-oxo)proline (32.5 g, 98%). $^1$H NMR (DMSO-$d_6$) δ 1.32, 1.35 (two s (rotamers) 9H), 2.30–2.42 (m, 1H), 2.62–2.73 (m, 1H), 3.76 (m, 2H), 3.91 (s, 3H), 4.33–4.40 (m, 1H), 5.55 (m, 1H), 7.15 (dd, J=9.2, 2.6 Hz, 1H), 7.37 (d, J=2.6 Hz, 1H), 7.42–7.56 (m, 4H), 7.94–7.99 (m, 1H), 8.25, 8.28 (2s, 2H), 12.53 (brs, 1H); LC-MS (retention time: 1.40, Method D), MS m/z 465 ($M^+$+1).

Example 2

(1R,2S) P1 Isomer of 1-{[1-2-tert-Butoxycarbonylamino-3,3-dimethylbutyryl)-4-(7-methoxy-2-phenylquinolin-4-yloxy)pyrrolidine-2-carbonyl]amino}-2-vinylcyclo-propanecarboxylic Acid, Shown Below, was Prepared as Described in Steps 2a–e

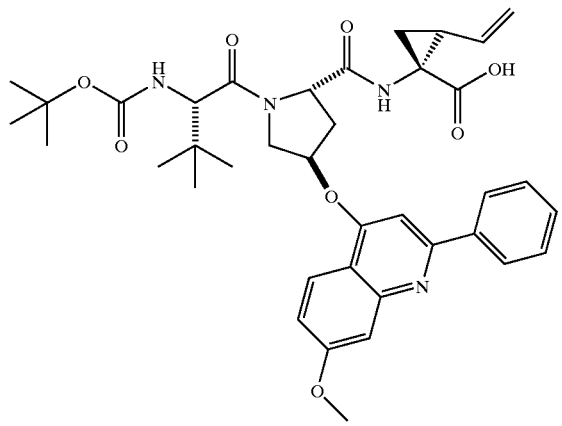

Step 2a: Preparation of (1R,2S)/(1S,2R)-1-amino-2-vinylcyclopropane carboxylic acid ethyl ester hydrochloride, Shown Below

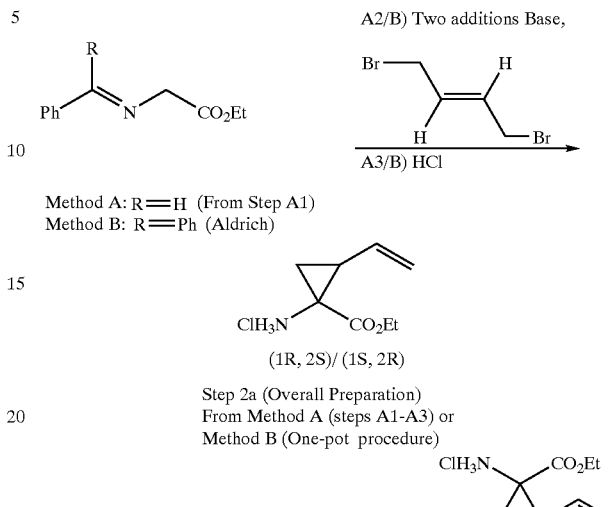

Method A: R═H (From Step A1)
Method B: R═Ph (Aldrich)

Step 2a (Overall Preparation)
From Method A (steps A1-A3) or
Method B (One-pot procedure)

The named compound was made by each of the following methods A and B.

Method A

A.1) Preparation of N-benzyl Imine of glycine ethyl ester, Shown Below

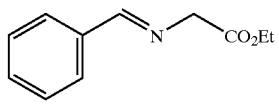

Glycine ethyl ester hydrochloride (303.8 g, 2.16 mole) was suspended in tert-butylmethyl ether (1.6 L). Benzaldehyde (231 g, 2.16 mole) and anhydrous sodium sulfate (154.6 g, 1.09 mole) were added and the mixture cooled to 0° C. using an ice-water bath. Triethylamine (455 mL, 3.26 mole) was added dropwise over 30 min and the mixture stirred for 48 h at rt. The reaction was then quenched by addition of ice-cold water (1 L) and the organic layer was separated. The aqueous phase was extracted with tert-butylmethyl ether (0.5 L) and the combined organic phases washed with a mixture of saturated aqueous $NaHCO_3$ (1 L) and brine (1 L). The solution was dried over $MgSO_4$, concentrated in vacuo to afford 392.4 g of the N-benzyl imine product as a thick yellow oil that was used directly in the next step. $^1$H NMR (CDCl$_3$, 300 MHz) δ 1.32 (t, J=7.1 Hz, 3H), 4.24 (q, J=7.1 Hz, 2H), 4.41 (d, J=1.1 Hz, 2H), 7.39–7.47 (m, 3H), 7.78–7.81 (m, 2H), 8.31 (s, 1H).

A.2) Preparation of Racemic N-Boc-(1R,2S)/(1S,2R)-1-amino-2-vinylcyclopropane carboxylic acid ethyl ester

To a suspension of lithium tert-butoxide (84.06 g, 1.05 mol) in dry toluene (1.2 L), was added dropwise a mixture of the N-benzyl imine of glycine ethyl ester (100.4 g, 0.526 mol) and trans-1,4-dibromo-2-butene (107.0 g, 0.500 mol) in dry toluene (0.6 L) over 60 min. After completion of the addition, the deep red mixture was quenched by addition of water (1 L) and tert-butylmethyl ether (TBME, 1 L). The aqueous phase was separated and extracted a second time with TBME (1 L). The organic phases were combined, 1 N HCl (1 L) was added and the mixture stirred at room temperature for 2 h. The organic phase was separated and extracted with water (0.8 L). The aqueous phases were then combined, saturated with salt (700 g), TBME (1 L) was added and the mixture cooled to 0° C. The stirred mixture was then basified to pH 14 by the dropwise addition of 10 N NaOH, the organic layer separated, and the aqueous phase extracted with TBME (2×500 mL). The combined organic extracts were dried (MgSO$_4$) and concentrated to a volume of 1L. To this solution of free amine, was added di-tert-butyldicarbonate (131.0 g, 0.6 mol) and the mixture stirred 4 days at rt. Additional di-tert-butyldicarbonate (50 g, 0.23 mol) was added to the reaction, the mixture refluxed for 3 h, and was then allowed cool to room temperature overnite. The reaction mixture was dried over MgSO$_4$ and concentrated in vacuo to afford 80 g of crude material. This residue was purified by flash chromatography (2.5 Kg of SiO$_2$, eluted with 1% to 2% MeOH/CH$_2$Cl$_2$) to afford 57 g (53%) of racemic N-Boc-(1R,2S)/(1S,2R)-1-amino-2-vinylcyclopropane carboxylic acid ethyl ester as a yellow oil which solidified while sitting in the refrigerator. $^1$H NMR (CDCl$_3$, 300 MHz) δ 1.26 (t, J=7.1 Hz, 3H), 1.46 (s, 9H), 1.43–1.49 (m, 1H), 1.76–1.82 (br m, 1H), 2.14 (q, J=8.6 Hz, 1H), 4.18 (q, J=7.2 Hz, 2H), 5.12 (dd, J=10.3, 1.7 Hz, 1H), 5.25 (br s, 1H), 5.29 (dd, J=17.6, 1.7 Hz, 1H), 5.77 (ddd, J=17.6, 10.3, 8.9 Hz, 1H); MS m/z 254.16 (M$^+$−1).

A.3 Preparation of Racemic (1R,2S)/(1S,2R) 1-amino-2-vinylcyclopropane carboxylic acid ethyl ester hydrochloride

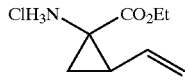

N-Boc-(1R,2S/1S,2R)-1-amino-2-vinylcyclopropane carboxylic acid ethyl ester (9.39 g, 36.8 mmol) was dissolved in 4N HCl/dioxane (90 ml, 360 mmol) and was stirred for 2 h at rt. The reaction mixture was concentrated to supply (1R,2S/1S,2R)-1-amino-2-vinylcyclopropane carboxylic acid ethyl ester hydrochloride in quanitative yield (7 g, 100%). $^1$H NMR (Methanol-d$_4$) δ: 1.32 (t, J=7.1, 3H), 1.72 (dd, J=10.2, 6.6 Hz, 1H), 1.81 (dd, J=8.3, 6.6 Hz, 1H), 2.38 (q, J=8.3 Hz, 1H), 4.26–4.34 (m, 2H), 5.24 (dd, 10.3, 1.3 Hz, 1H) 5.40 (d, J=17.2, 1H), 5.69–5.81 (m, 1H).

Method B

To a solution of potassium tert-butoxide (11.55 g, 102.9 mmol) in THF (450 mL) at −78° C. was added the commercially available N,N-dibenzyl imine of glycine ethyl ester (25.0 g, 93.53 mmol) in THF (112 mL). The reaction mixture was warmed to 0° C., stirred for 40 min, and was then cooled back to −78° C. To this solution was added trans-1,4-dibromo-2-butene (20.0 g, 93.50 mmol), the mixture stirred for 1 h at 0° C. and was cooled back to −78° C. Potassium tert-butoxide (11.55 g, 102.9 mmol) was added, the mixture immediately warmed to 0° C., and was stirred one more hour before concentrating in vacuo. The crude product was taken up in Et$_2$O (530 mL), 1N aq. HCl solution (106 mL, 106 mmol) added and the resulting biphasic mixture stirred for 3.5 h at rt. The layers were separated and the aqueous layer was washed with Et$_2$O (2×) and basified with a saturated aq. NaHCO$_3$ solution. The desired amine was extracted with Et$_2$O (3×) and the combined organic extract was washed with brine, dried (MgSO$_4$), and concentrated in vacuo to obtain the free amine. This material was treated with a 4N HCl solution in dioxane (100 mL, 400 mmol) and concentrated to afford (1R,2S)/(1S,2R)-1-amino-2-vinylcyclopropane carboxylic acid ethyl ester hydrochloride as a brown semisolid (5.3 g, 34% yield) identical to the material obtained from procedure A, except for the presence of a small unidentified aromatic impurity (8%).

Step 2b: Preparation of the (1R,2S) P1 Isomer of 2-(1-Ethoxycarbonyl-2-vinylcyclopropylcarbamyl-4-(7-methoxyl-2-phenylquinolin-4-yloxy) pyrrollindine-1-carboxylic acid tert-butyl ester or Alternative Designation 2(S)-(1 (R)-ethoxycarbonyl-2(S)-vinyl-cyclopropylcarbamoyl)-4 (R)-(7-methoxy-2-phenyl-quinolin-4-yloxy)-pyrrolidine-1-carboxylic acid tert-butyl ester, Shown Below

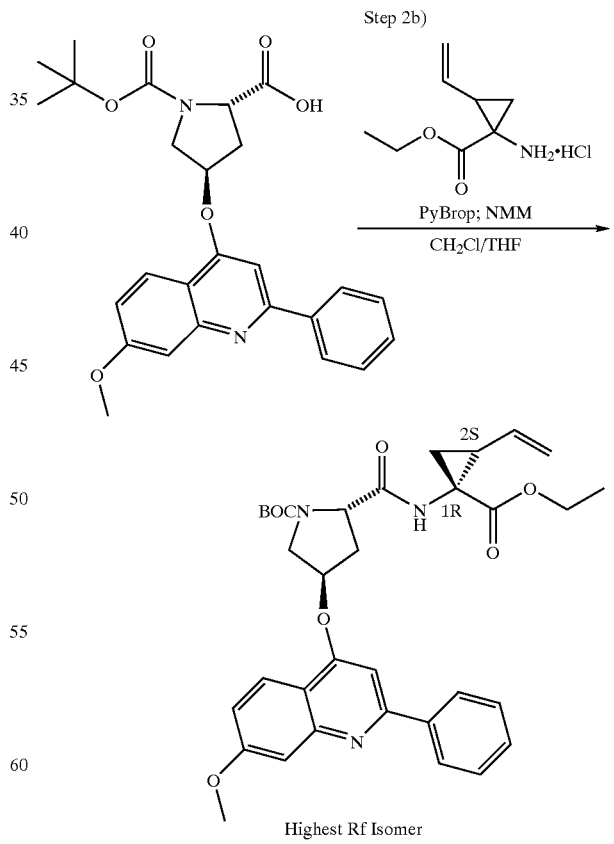

Highest Rf Isomer and

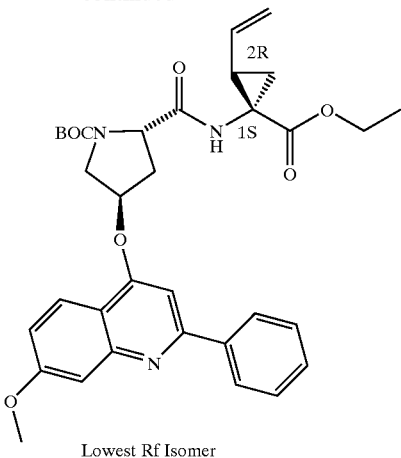

Lowest Rf Isomer

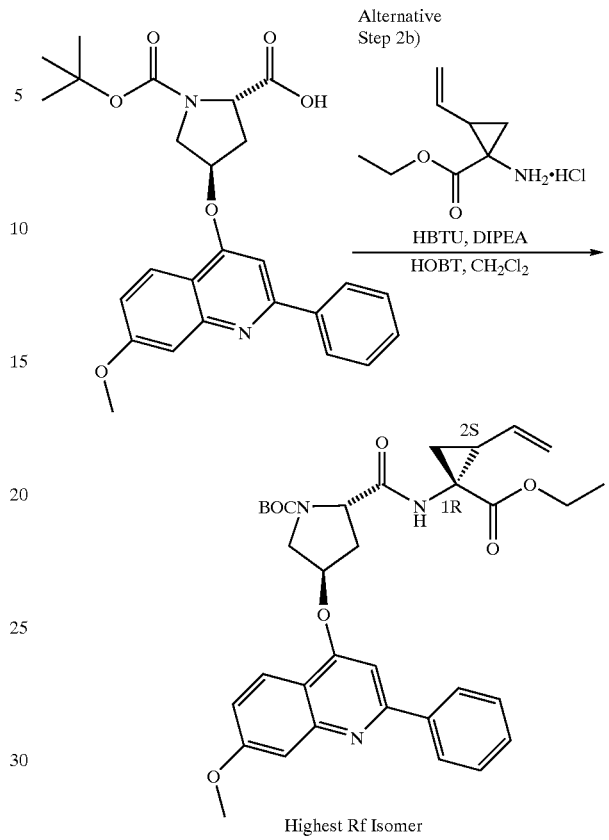

To a solution of Boc-4(R)-(2-phenyl-7-methoxyquinoline-4-oxo)proline from Step 1c (11.0 g, 23.7 mmole), HCl salt of a racemic mixture of (1R,2S) and (1S,2R) P1 derived diastereomers from Step 2a, (5.40 g, 28.2 mmole), NMM (20.8 mL; 18.9 mmole) in 500 mL of 50% CH$_2$Cl$_2$/THF was added the coupling reagent PyBrop or Bromotrispyrrolidino-phosphonium hexafluorophosphate (16.0 g, 34.3 mmole) in three portions in 10 min at 0° C. The solution was stirred at rt for one day and then was washed with pH 4.0 buffer (4×50 mL). The organic layer was washed with saturated aqueous NaHCO$_3$ (100 mL), the aqueous washing extracted with ethyl acetate (150 mL), and the organic layer backwashed with pH 4.0 buffer (50 mL), and saturated aqueous NaHCO$_3$ (50 mL). The organic solution was dried (MgSO$_4$), concentrated and purified using a Biotage 65M column (eluted with 50% EtOAc/Hexanes) to provide over 7.5 g of a 1:1 mixture of (1R,2S) and (1S,2R) P1 isomers of 2-(1-Ethoxycarbonyl-2-vinylcyclopropylcarbamyl-4-(7-methoxy-2-phenylquinolin-4-yloxy)pyrrollindine-1-carboxylic acid tert-butyl ester (50% overall) or alternatively elution over a Biotage 65M column using a slow to 15% to 60% EtOAc in hexanes gradient to supply 3.54 g (25%) of the high Rf eluted (1R,2S) P1 isomer, and 3.54 g (25%) of the low Rf eluted (1S,2R) P1 isomer.

Data for (1R,2S) P1 isomer: $^1$H NMR (CDCl$_3$) δ 1.21 (t, J=7 Hz, 3H), 1.43 (s, 9H), 1.47–1.57 (m, 1H), 1.88 (m, 1H), 2.05–2.19 (m, 1H), 2.39 (m, 1H), 2.88 (m, 1H), 3.71–3.98 (m, 2H), 3.93 (s, 3H), 4.04–4.24 (m, 2H), 4.55 (m, 1H), 5.13 (d, J=10 Hz, 1H), 5.22–5.40 (m, 1H), 5.29 (d, J=17 Hz, 1H), 5.69–5.81 (m, 1H), 7.02 (brs, 1H), 7.09 (dd, J=9, 2 Hz, 1H), 7.41–7.52 (m, 4H), 7.95 (d, J=9 Hz, 1H), 8.03, 8.05 (2s, 2H); $^{13}$C NMR (CDCl$_3$) δ: 14.22; 22.83, 28.25, 33.14, 33.58, 39.92, 51.84, 55.47, 58.32, 61.30, 75.86, 81.27, 98.14, 107.42, 115.00, 117.84, 118.27, 122.63, 123.03, 127.50, 128.72, 129.26, 133.39, 140.06, 151.23, 159.16, 160.34, 161.35, 169.78, 171.68. LC-MS (retention time: 1.62, method D), MS m/z 602 (M$^+$+1).

Data for the (1S,2R) P1 isomer: $^1$H NMR δ 1.25 (t, J=7 Hz, 3H), 1.44 (s, 9H), 1.46–1.52 (m, 1H), 1.84 (m, 1H), 2.12–2.21 (m, 1H), 2.39 (m, 1H), 2.94 (m, 1H), 3.82 (m, 2H), 3.97 (s, 3H), 4.05–4.17 (m, 2H), 4.58 (m, 1H), 5.15 (d, J=10.8 Hz, 1H), 5.33 (d, J=17 Hz, 1H), 5.30–5.43 (m, 1H), 5.72–5.85 (m, 1H), 7.05 (s, 1H), 7.13 (dd, J=9, 2 Hz, 1H), 7.46–7.60 (m, 4H), 7.98 (d, J=9 Hz, 1H), 8.06–8.10 (m, 2H). LC-MS (retention time: 1.66, method D), MS m/z 602 (M$^+$+1).

Alternative Step 2b: Preparation of 2(S)-(1(R)-ethoxycarbonyl-2(S)-vinyl-cyclopropylcarbamoyl)-4(R)-(7-methoxy-2-phenyl-quinolin-4-yloxy)-pyrrolidine-1-carboxylic acid tert-butyl ester, Shown Below The product of Step 2a, (1R,2S)/(1S,2R)-1-amino-2-vinylcyclopropane carboxylic acid ethyl ester hydrochloride (7.5 g, 39.1 mmol), was combined with diisopropylethylamine (32.5 mL, 186 mmol) in dichloromethane (150 mL). To the resulting mixture was added HOBT hydrate (6.85 g, 44.7 mmol) and the product from Step 1c, Boc-4(R)-(2- phenyl-7-methoxyquinoline-4-oxo)proline (17.3 g, 37.3 mmol), followed by addition of HBTU (16.96 g, 44.7 mmol). A slight exotherm occurred immediately, and the mixture was stirred at room temperature overnight. The mixture was then concentrated in vacuo and redissolved in ethyl acetate (600 mL). The solution was washed with water (2×200 mL), then with 10% aqueous sodium bicarbonate (2×200 mL), then with water (150 mL) and finally with brine (150 mL). The organic was dried over anhydrous magnesium sulfate and filtered, and the filtrate was concentrated in vacuo to a beige glassy solid. Purification was performed in multiple batches (7 g each) by flash chromatography on a Biotage Flash 75M cartridge (66% hexanes/ethyl acetate) to provide the (1R,2S) vinyl Acca P1 isomer of 2-(1-Ethoxycar-bonyl-2-vinylcyclopropylcarbamoyl)-4-(7-methoxy-2-phenyl-quinolin-4-yloxy)-pyrrolidine-1-carboxylic acid ethyl ester as the initial eluted isomer (9.86 g total, 44.0% yield), followed by elution of the (1S,2R) vinyl acca P1 isomer of 2-(1-Ethoxycarbonyl-2-vinylcyclopropylcarbamoyl)-4-(7-methoxy-2-phenyl-quinolin-4-yloxy)-pyrrolidine-1-carboxylic acid ethyl ester as the second eluted isomer (10.43 g total, 46.5% yield). A total of 1.97 g of mixed fractions were recovered to give an overall conversion of 99.3% to the two diastereomers.

(1R,2S) isomer—$^1$H NMR: (methanol-$d_4$) δ 1.23 (t, J=7.2 Hz, 3H), 1.4 (s, 4H), 1.45 (s, 6H), 1.73 (dd, J=7.9, 1.5 Hz, 0.4H), 1.79 (dd, J=7.8, 2.4 Hz, 0.6H), 2.21 (q, J=8.2 Hz, 1H), 2.44–2.49 (m, 1H), 2.66–2.72 (m, 0.4H), 2.73–2.78 (m, 0.6H), 3.93–3.95 (m, 2H), 3.96 (s, 3H), 4.10–4.17 (m, 2H), 4.44 (q, J=7.8 Hz, 1H), 5.13 (d, J=10.7 Hz, 1H), 5.31 (d, J=17.7 Hz, 0.4H), 5.32 (d, J=17.4 Hz, 0.6H), 5.49 (bs, 1H), 5.66–5.82 (m, 1H), 7.16 (dd, J=9.2, 2.5 Hz, 1H), 7.26 (s, 1H), 7.42 (d, J=2.4 Hz, 1H), 7.48–7.55 (m, 3H), 8.02–8.05 (m, 3H); MS m/z 602 (M$^+$+1).

Step 2c: Preparation of the (1R,2S) P1 Diastereomer of 1-{[4-(7-Methoxy-2-phenylquinolin-4yloxy)pyrrolidine-2-carbonyl]-1-amino}-2-vinylcyclo-propanecarboxylic Acid Ethyl Ester, Dihydrochloride, Shown Below

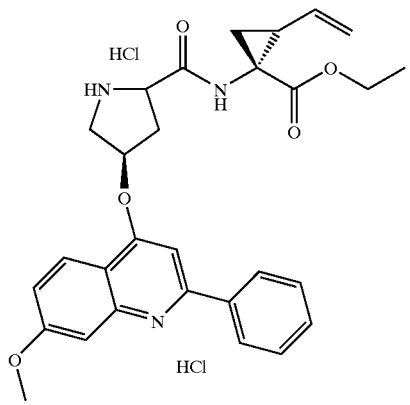

The product of Step 2b (5.88 g, 9.77 mmol), the (1R,2S) vinyl Acca P1 isomer of 2-(1-Ethoxycarbonyl-2-vinylcyclopropylcarbamoyl)-4-(7-methoxy-2-phenyl-quinolin-4-yloxy)pyrrolidine-1-carboxylic acid ethyl ester, was dissolved in HCl/dioxane (4.0M; 200 ml) and was stirred for 2.5 h at rt. The reaction mixture was concentrated to supply the titled product. $^1$H NMR (Methanol-$d_4$) δ 1.24 (t, J=7 Hz, 3H), 1.50 (dd, J=10, 5 Hz, 1H), 1.78 (dd, J=8.4, 5.5 Hz, 1H), 2.24–2.33 (m, 1H), 2.56–2.66 (m, 1H), 3.05 (dd, J=14.6, 7.3 Hz, 1H), 3.98 (s, 2H), 4.06 (s, 3H), 4.15 (q, J=7 Hz, 2H), 4.76 (dd, J=10.6, 7.3 Hz, 1H), 5.13 (dd, J=10.2, 1.8 Hz), 5.32 (dd, J=17, 2 Hz), 5.70–5.83 (m, 1H), 6.05 (m, 1H), 7.48 (dd, J=9, 2 Hz, 1H), 7.65–7.79 (m, 5H), 8.12–8.15 (m, 2H), 8.54 (d, J=9.5 Hz, 1H); $^{13}$C NMR (methanol-$d_4$) δ: 14.77, 23.23, 34.86, 37.25, 41.19, 43.90, 52.66, 60.35, 62.32, 62.83, 68.27, 72.58, 73.70, 81.21, 100.70, 102.44, 116.13, 118.67, 122.25, 126.93, 130.27, 130.94, 133.19, 134.14, 134.89, 143.79, 158.39, 166.84, 167.44, 169.57, 171.33. LC-MS (retention time: 1.55, Method D), MS m/z 502 (M$^+$+1).

Step 2d: Preparation of the (1R,2S) P1 Isomer of 1-{[1-2-tert-Butoxycarbonylamino-3,3-dimethyl-butyryl)-4-(7-methoxy-2-phenylquinolin-4-yloxy)p-pyrrolidine-2-carbonyl]amino}-2-vinyl-cyclopropanecarboxylic acid ethyl ester, Shown Below

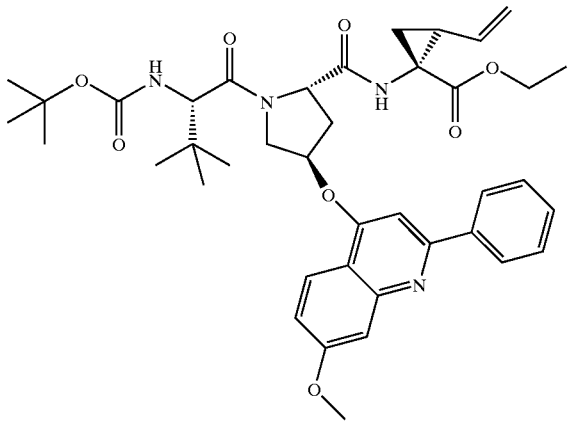

To a suspension of the product of Step 2c, the (1R,2S) vinyl Acca P1 isomer of 2-(1-Ethoxycarbonyl-2-vinylcyclopropylcarbamoyl)-4-(7-methoxy-2-phenyl-quinolin-4-yloxy)pyrrolidine-1-carboxylic acid ethyl ester (1.95 g; 3.4 mmol), N—BOC-L-tert-leucine (0.94 g, 4.08 mmol), NMM (1.87 ml, 17 mmol) in DMF (15 mL) was added HATU (1.55 g, 4.08 mmol) at 0° C. After being stirred for 2 days, the reaction mixture was diluted with EtOAc (200 mL), washed with pH 4.0 buffer (2×30 mL), saturated aqueous NaHCO$_3$ (30 mL), brine (30 mL), dried (MgSO$_4$), purified by a Biotage 40 M column (eluted with 15% to 60% EtOAc in Hexanes) to supply the titled product as a white solid (2.21 g, 90%). $^1$H NMR (CDCl$_3$) δ 1.05 (s, 9H), 1.20 (t, J=7 Hz, 3H), 1.38–1.43 (m, 1H), 1.41 (s, 9H), 1.80–1.85 (m, 1H), 2.08–2.16 (m, 1H), 2.39–2.47 (m, 1H), 2.90–2.99 (m, 1H), 3.90–4.01 (m, 1H), 3.93 (s, 3H), 4.12 (q, J=7 Hz, 2H), 4.36 (d, J=10 Hz, 1H), 4.45 (d, J=12 Hz, 1H), 4.75–4.85 (m, 1H), 5.09–5.13 (m, 1H), 5.21–5.34 (m, 2H), 5.69–5.81 (m, 1H), 7.00–7.09 (m, 2H), 7.42–7.54 (m, 5H), 8.01–8.05 (m, 3H); $^{13}$C NMR (CDCl$_3$) δ 14.30, 22.85, 26.40, 28.25, 32.20, 34.09, 35.39, 39.97, 53.86, 55.47, 58.28, 58.96, 61.29, 75.94, 79.86, 97.98, 107.43, 115.06, 117.98, 118.38, 123.03, 127.52, 128.76, 129.24, 133.40, 140.26, 151.44, 155.74, 159.16, 160.09, 161.32, 169.55, 170.64, 172.63. LC-MS (retention time: 1.85, Method D), MS m/z 715 (M$^+$+1).

Step 2e: Preparation of the Titled Product, Example 2, the (1R,2S) P1 Isomer of 1-{[1-2-tert-Butoxycarbonylamino-3,3-dimethylbutyryl)-4-(7-methoxy-2-phenylquinolin-4-yloxy)pyrrolidine-2-carbonyl]-amino}-2-vinylcyclopropanecarboxylic acid To a suspension of the product of Step 2d, the (1R,2S) isomer of 1-{[1-2-tert-Butoxycarbonylamino-3,3- dimethylbutyryl)-4-(7-methoxy-2-phenylquinolin-4-yloxy)pyrrolidine-2-carbonyl]amino}-2-vinyl-cyclopropanecarboxylic acid ethyl ester (2.63 g, 3.68 mmol) in THF(150 mL), CH₃OH (80 mL), and H₂O (20 mL) was added LiOH (1.32 g, 55.2 mmol). The reaction mixture was stirred for two days, acidified to neutral pH, and concentrated in vacuo until only the aqueous layer remained. The resulting aqueous residue was acidified to pH 3.0 by addition of 1.0 N aqueous HCl, and extracted with EtOAc (4×200 mL). Combined organic solvent was washed by brine (20 mL), dried (Na₂SO₄), filtered, and concentrated in vacuo to supply the titled product, Example 2, the (1R,2S) P1 isomer of 1-{[1-2-tert-Butoxycarbonylamino-3,3-dimethylbutyryl)-4-(7-methoxy-2-phenylquinolin-4-yloxy)pyrrolidine-2-carbonyl]-amino}-2-vinylcyclopropanecarboxylic acid as white solid (2.41 g, 96%). ¹H NMR (CDCl₃/Methanol-d₄) δ 0.98, 1.01 (two s (rotamers) 9H), 1.40, 1.42 (two s (rotamers) 9H), 1.35–1.47 (m, 1H), 1.89–1.93 (m, 1H), 2.03–2.14 (m, 1H), 2.45–2.52 (m, 1H), 2.64–2.78 (m, 1H), 3.94 (s, 3H), 3.96–4.12 (m, 1H), 4.34 (d, J=10 Hz, 1H), 4.52 (d, J=1Hz, 1H), 4.58–4.64 (m, 1H), 5.10 (d, J=12 Hz, 1H), 5.24 (d, J=16 Hz, 1H), 5.34 (m, 1H), 5.68–5.86 (m, 2H), 7.02–7.05 (m, 1H), 7.32 (m, 1H), 7.40–7.54 (m, 4H), 7.97–8.03 (m, 3H); LC-MS (retention time: 1.64, method D), MS m/z 687 (M⁺+1).

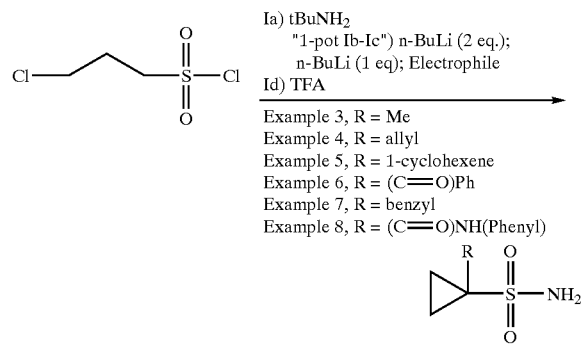

Method I (Steps a–d). Preparation of 1-Substituted Cyclopropanesulfonamides Required for N-acylsulfonamide Coupling Steps 3e–8e (Examples 3–8 used to Prepare Compounds 1–6 Respectively)

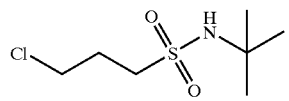

Step Ia: N-tert-Butyl-(3-chloro)propylsulfonamide

Step Ia) A neat solution of tert-Butylamine (315.3 mL, 3.0 mol) was dissolved in THF (2.5 L), cooled to −20° C., and 3-Chloropropanesulfonyl chloride (182.4 mL, 1.5 mol) was added slowly. The reaction mixture was allowed to warm to rt and stirred for 24 h. The mixture was filtered, and the filtrate was concentrated in vacuo. The residue was dissolved in CH₂Cl₂ (2.0 L). The resulting solution was washed with 1 N HCl (1.0 L), water (1.0 L), brine (1.0 L) and dried over Na₂SO₄. It was filtered and concentrated in vacuo to give a slightly yellow solid which was crystallized from hexane to afford the product as a white solid (316.0 g, 99%); ¹H NMR (CDCl₃) δ 1.38 (s, 9H), 2.30–2.27 (m, 2H), 3.22 (t, J=7.35 Hz, 2H), 3.68 (t, J=6.2 Hz, 2H), 4.35 (bs, 1H).

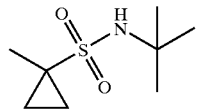

Steps 3Ib–3Ic: Preparation of N-tert-Butyl-(1-methyl)cyclopropyl-sulfonamide

Steps 3Ib–3Ic) A solution of N-tert-Butyl-(3-chloro)propylsulfonamide (4.3 g, 20 mmol) was dissolved in dry THF (100 mL) and cooled to −78° C. To this solution was added n-BuLi (17.6 mL, 44 mmol, 2.5 M in hexane) slowly. The dry ice bath was removed and the reaction mixture was allowed to warm to rt over a period of 1.5 h. This mixture was then cooled to −78° C., and a solution of n-BuLi (20 mmol, 8 mL, 2.5 M in hexane) was added. The reaction mixture was warmed to rt, recooled to −78° C. over a period of 2 h and a neat solution of methyliodide (5.68 g, 40 mmol) added. The reaction mixture was allowed to warm to rt overnight, quenched with saturated NH₄Cl (100 mL) at rt. It was extracted with EtOAc (100 mL). The organic phase was washed with brine (100 mL), dried (MgSO₄), and concentrated in vacuo to give a yellow oil which was crystallized from hexane to afford the product as a slightly yellow solid (3.1 g, 81%): ¹H NMR (CDCl₃) δ 0.79 (m, 2H), 1.36 (s, 9H), 1.52 (m, 2H), 1.62 (s, 3H), 4.10 (bs, 1H).

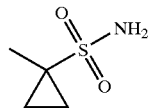

Step 3Id: Preparation of Example 3,1-methylcyclopro-pylsulfonamide

Step 3Id) A solution of N-tert-Butyl-(1-methyl)cyclopropylsulfonamide (1.91 g, 10 mmol) was dissolved in TFA (30 mL), and the reaction mixture stirred at rt for 16 h. The solvent was removed in vacuo to give a yellow oil which was crystallized from EtOAc/hexane (1:4, 40 mL) to yield Example 3, 1-methylcyclopropylsulfonamide, as a white solid (1.25 g, 96%): ¹H NMR (CDCl₃) δ 0.84 (m, 2H), 1.41 (m, 2H), 1.58 (s, 3H), 4.65 (bs, 2H). Anal. Calcd. For C₄H₉NO₂S: C, 35.54; H, 6.71; N, 10.36. Found: C, 35.67; H, 6.80; N, 10.40.

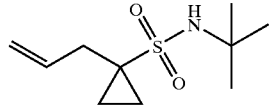

Steps 4Ib–4Ic: Preparation of N-tert-Butyl-(1-allyl)cyclopropylsulfonamide

Steps 4Ib–4Ic) This compound, N-tert-Butyl-(1-allyl)cyclopropylsulfonamide, was obtained in 97% yield according to the procedure described in the synthesis of N-tert-Butyl-(1-methyl)cyclopropylsul-fonamide except 1.25 equivalents of allyl bromide were used as electrophile. The compound was taken directly into the next reaction without purification: ¹H NMR (CDCl₃) δ 0.83 (m, 2H), 1.34 (s, 9H), 1.37 (m, 2H), 2.64 (d, J=7.3 Hz, 2H), 4.25 (bs, 1H), 5.07–5.10 (m, 2H), 6.70–6.85 (m, 1H).

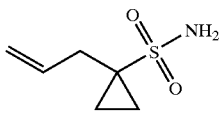

Steps 4Id: Preparation of Example 4,1-allylcyclopro-pylsulfonamide

Step 41d) This compound, Example 4,1-allylcyclopropylsulfonamide, was obtained in 40% yield from N-tert-butyl-(1-allyl)cyclopropylsulfonamide according to the procedure described in the synthesis of 1-Methylcyclopropylsulfonamide. The compound was purified by column chromotography over SiO$_2$ using 2% MeOH in CH$_2$Cl$_2$ as the eluent: $^1$H NMR (CDCl$_3$) δ 0.88 (m, 2H), 1.37 (m, 2H), 2.66 (d, J=7.0 Hz, 2H), 4.80 (s, 2H), 5.16 (m, 21 H), 5.82 (m, 1H); $^{13}$C NMR (CDCl$_3$) δ 11.2, 35.6, 40.7, 119.0, 133.6.

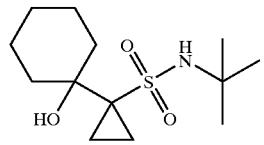

Steps 5Ib–5Ic: Preparation of N-tert-Butyl-[1-(1-hydroxy)cyclohexyl]-cyclopropylsulfonamide Steps 5Ib-5Ic) This compound was obtained in 84% yield using to the procedure described for the synthesis of N-tert-Butyl-(1-methyl)cyclopropylsulfonamide except 1.30 equivalents of cyclohexanone were used, followed by recrystallization from the minimum amount of 20% EtOAc in hexane: $^1$H NMR (CDCl$_3$) δ 1.05 (m, 4H), 1.26 (m, 2H), 1.37 (s, 9H), 1.57–1.59 (m, 6H), 1.97 (m, 2H), 2.87 (bs, 1H), 4.55 (bs, 1H).

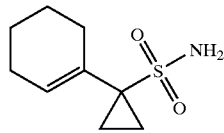

Steps 5Id: Preparation of Example 5,1-(1-cyclohexenyl)cyclopropyl-sulfonamide Step 5Id) This compound, 1-(1-cyclohexenyl)-cyclopropylsulfonamide, Example 5, was obtained in 85% yield from N-tert-butyl-[1-(1-hydroxy)cyclohexyl]-cyclopropylsulfonamide using the procedure described for the synthesis of 1-methylcyclopropylsulfonamide, followed by recrystallization from the minimum amount of EtOAc and hexane: $^1$H NMR (DMSO-d$_6$) δ 0.82 (m, 2H), 1.28 (m, 2H), 1.51 (m, 2H), 1.55 (m, 2H), 2.01 (s, 2H), 2.16 (s, 2H), 5.89 (s, 1H), 6.46 (s, 2H); $^{13}$C NMR (DMSO-d$_6$) δ 11.6, 21.5, 22.3, 25.0, 27.2, 46.9, 131.6, 132.2; LR-MS (ESI): 200 (M$^+$–1).

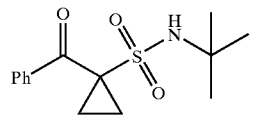

Steps 6Ib-6Ic: Preparation of N-tert-Butyl-(1-benzoyl)cyclopropyl-sulfonamide Steps 6Ib-6Ic) This compound was obtained in 66% yield using the procedure described for the synthesis of N-tert-Butyl-(1-methyl)cyclopropylsulfonamide except 1.2 equivalents of methyl benzoate was used as the electrophile. The compound was purified by column chromatography over SiO$_2$ using 30% to 100% CH$_2$Cl$_2$ in hexane: $^1$H NMR (CDCl$_3$) δ 1.31 (s, 9H), 1.52 (m, 2H), 1.81 (m, 2H), 4.16 (bs, 1H), 7.46 (m, 2H), 7.57 (m, 1H), 8.05 (d, J=8.5 Hz, 2H).

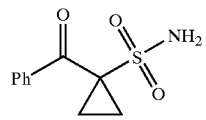

Steps 6Id: Preparation of Example 6,1-benzoylcyclo-propylsulfonamide

Steps 6Id) This compound, Example 6,1-benzoylcyclopropyl-sulfonamide, was obtained in 87% yield from N-tert-butyl(1-benzoyl)cyclopropylsul-fonamide using the procedure described for the synthesis of 1-Methylcyclopropylsulfonamide, followed by recrystallization from the minimum amount of EtOAc in hexane: $^1$H NMR (DMSO-d$_6$) δ 1.39 (m, 2H), 1.61 (m, 2H), 7.22 (s, 2H), 7.53 (t, J=7.6 Hz, 2 H), 7.65 (t, J=7.6 Hz, 1H), 8.06 (d, J=8.2 Hz, 2H); $^{13}$C NMR (DMSO-d$_6$) δ 12.3, 48.4, 128.1, 130.0, 133.4, 135.3, 192.0.

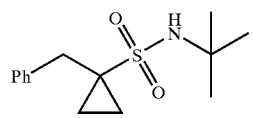

Steps 7Ib–7Ic: Preparation of N-tert-Butyl-(1-benzyl)cyclopropyl-sulfonamide Steps 7Ib–7Ic) This compound was obtained in 60% yield using the procedure described for the synthesis of N-tert-Butyl-(1-methyl)cyclopropylsulfonamide except 1.05 equivalents of benzyl bromide were used, followed by trituration with 10% EtOAc in hexane: $^1$H NMR (CDCl$_3$) δ 0.92 (m, 2H), 1.36 (m, 2H), 1.43 (s, 9H), 3.25 (s, 2H), 4.62 (bs, 1H), 7.29–7.36 (m, 5H).

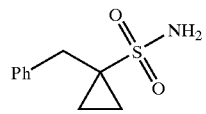

Steps 7Id: Preparation of Example 7,1-Benzylcyclo-propylsulfonamide

Step 7Id) This compound, Example 7,1-Benzylcyclopropylsulfonamide, was obtained in 66% yield from N-tert-butyl(1-benzyl)cyclopropylsul-fonamide using the procedure described for the synthesis of 1-Methylcyclopropylsulfonamide, followed by recrystallization from the minimum amount of 10% EtOAc in hexane: $^1$H NMR (CDCl$_3$) δ 0.90 (m, 2H), 1.42 (m, 2H), 3.25 (s, 2H), 4.05 (s, 2H), 7.29 (m, 3H), 7.34 (m, 2H); $^{13}$C NMR (CDCl$_3$) δ 11.1, 36.8, 41.9, 127.4, 128.8, 129.9, 136.5.

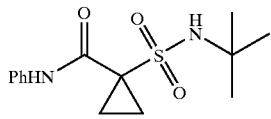

Steps 8Ib–8Ic: Preparation of N-tert-Butyl-(1-phenylaminocarboxy)cyclopropylsulfonamide Steps 8Ib-8Ic) This compound was obtained in 42% yield using the procedure described for the synthesis of N-tert-Butyl-(1-methyl)cyclopropylsulfonamide using 1 equivalent of phenylisocyanate, followed by recrystallization from the minimum amount of EtOAc in hexane: $^1$H NMR (CDCl$_3$) δ 1.38 (s, 9H), 1.67–1.71 (m, 4H), 4.30 (bs, 1H), 7.10 (t, J=7.5 Hz, 1H), 7.34 (t, J=7.5 Hz, 2H), 7.53 (t, J=7.5 Hz, 2H).

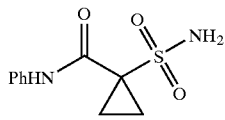

Steps 8Id: Preparation of Example 8,1-(Phenylamino-carboxy)cyclopropyl-sulfonamide Step 8Id) This compound, Example 8, 1-(Phenylaminocarboxy)cyclopropylsulfonamide, was obtained in 75% yield from N-tert-butyl(1-phenylaminocarboxy)cyclopropylsulfonamide using the procedure described for the synthesis of 1-Methylcyclopropylsulfonamide, followed by recrystallization from the minimum amount of EtOAc in hexane: $^1$H NMR (CDCl$_3$) δ 1.70 (m, 2H), 1.75 (m, 2H), 4.85 (s, 2H), 7.16 (t, J=7.6 Hz, 1H), 7.35 (t, J=7.6 Hz, 2H), 7.53 (d, J=8.2 Hz, 2H), 9.25 (s, 1H).

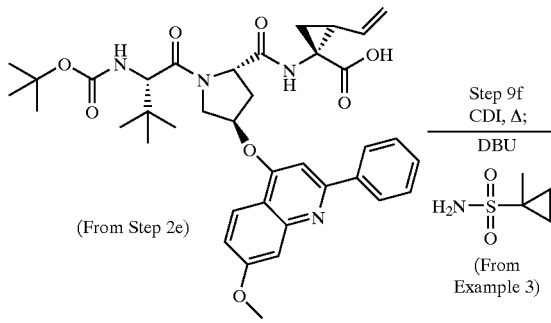

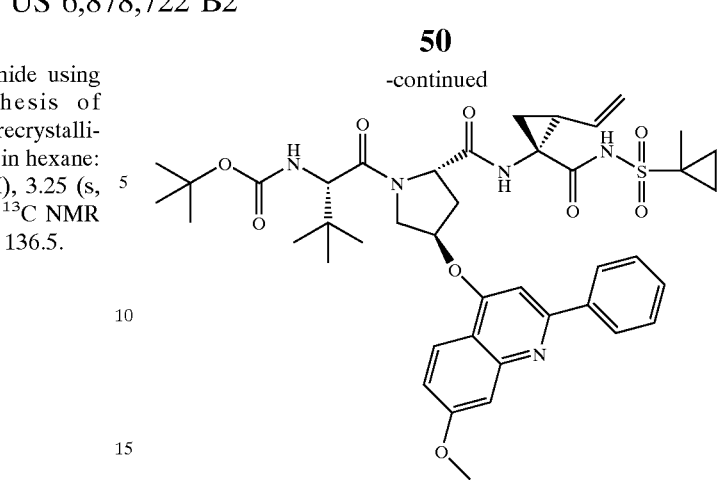

Compound 1, Example 9

Compound 1, Example 9, BOCNH—P3(L-t-BuGly)-P2[(4R)-(2-phenyl-7-methoxyquinoline-4-oxo)-S-proline]-P1(1R,2S Vinyl Acca)-CONHSO$_2$(1-methylcyclopropan-1-yl) or Alternate Designation, Compound 1, the (1R,2S) P1 Isomer of (1-{4-(7-Methoxy-2-phenylquinolin-4-yloxy)-2-[1-(1-methylcyclopropanesulfonylaminocarbonyl)-2-vinylcyclopropylcarbamoyl]pyrrolidine-1-carbonyl}-2,2-dimethylpropyl)carbamic acid tert-butyl ester, Shown Below, was Prepared as Follows Step 9f) A solution of CDI (0.068 g, 0.43 mmol) and the product of Step 2e (0.250 g, 0.364 mmol) in THF (5 mL) was refluxed for 60 min and allowed to cool down to rt. A total of 0.069 g (0.51 mmol) of 1-methylcyclopropanesulfonamide (prepared according to Example 3), followed by the addition of a solution of neat DBU (0.078 mL, 0.51 mmol). The reaction was stirred for 18 h, diluted with EtOAc (30 mL) and washed pH 4.0 buffer (3×10 mL), dried (MgSO$_4$), concentrated and purified over three 1000 □M preparative TLC plate from Analtech (20× 40 cM, eluted sequentially with 1% to 4% MeOH in CH$_2$Cl$_2$) to supply Example 9, Compound 1 (0.1374 g, 47%): $^1$H NMR (methanol-d$_4$, 300 MHz) □ 0.70–0.80 (m, 2H), 1.03 (s, 9H), 1.24–1.29 (m, 1H), 1.43–1.47 (m, 1H), 1.52 (s, 3H), 1.77–1.89 (m, 1H), 2.15 (m, 1H), 2.44 (m, 1H), 2.72 (m, 1H), 3.94 (s, 3H), 4.04–4.16 (m, 1H), 4.22–4.28 (m, 1H), 4.49–4.64 (m, 3H), 5.00–5.08 (m, 1H), 5.23 (d, J=17 Hz, 1H), 5.55 (m, 1H), 5.73–5.93 (m, 1H), 7.05–7.09 (m, 1H), 7.25 (s, 1H), 7.39 (m, 1H), 7.48–7.56 (m, 3H), 8.03–8.12 (m, 3H). LC-MS (retention time: 1.59, Method D), MS m/z 804 (M$^+$+1).

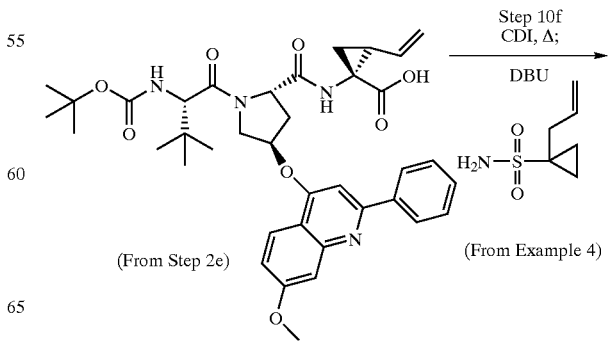

-continued

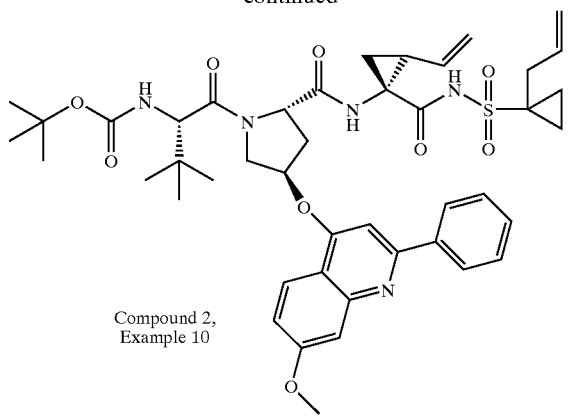

Compound 2, Example 10

Compound 2, Example 10

Compound 2, Example 10, BOCNH—P3(L-t-BuGly)-P2[(4R)-(2-phenyl-7-methoxyquinoline-4-oxo)-S-proline]-P1(1R,2S Vinyl Acca)-CONHSO$_2$ (1-allylcyclopropan-1-yl) or Alternate Designation, Compound 2, the (1R,2S) P1 Isomer of {1-[2-[1-(1-Allylcyclopropanesul-fonylaminocarbonyl)-2-vinylcyclopropylcarbamoyl]-4-(7-methoxy-2-phenylquinolin-4-yloxy)-pyrrolidine-1-carbonyl]-2,2-dimethylpropyl}carbamic acid tert-butyl ester Step 10f) This compound was prepared in 83% yield from tripeptide acid product of step 2e (Example 2) in analogous fashion to the procedure of Example 9 except that 1-allylcyclopropanesulfonamide (prepared in Example 4) was used in place of 1-methylcyclopropanesulfonamide: $^1$H NMR (CDCl$_3$/methanol-d$_4$) ☐ 0.80–0.82 (m, 2H), 1.00 (s, 9H), 1.26–1.28 (m, 2H), 1.31 (s, 9H), 1.38 (m, 1H), 1.74–1.85 (m, 1H), 1.90–2.07 (m, 1H), 2.38–2.52 (m, 1H), 2.56–2.65 (m, 3H), 3.90 (s, 3H), 3.96–4.13 (m, 1H), 4.26 (m, 1H), 4.43 (d, J=11.6 Hz, 1H), 4.56 (m, 1H), 4.90–5.00 (m, 2H), 5.07–5.15 (m, 2H), 5.34 (m, 1H), 5.54–5.91 (m, 3H), 6.98–7.04 (m, 2H), 7.33–7.36 (m, 1H), 7.41–7.49 (m, 3H), 7.93–8.00 (m, 3H). HRMS m/z (M+H)$^+$ calcd for C$_{44}$H$_{56}$N$_5$SO$_9$: 830.3799 found: 830.3812. LC-MS (retention time: 1.68, Method I), MS m/z 830 (M$^+$+1).

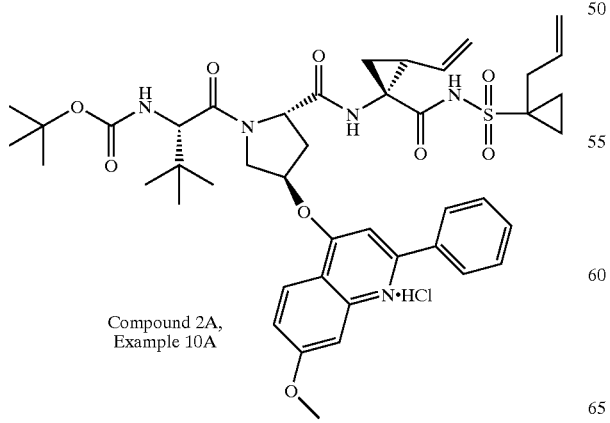

Compound 2A, Example 10A

Compound 2A, Example 10A
Compound 2, Example 11, BOCNH—P3(L-t-BuGly)-P2[(4R)-(2-phenyl-7-methoxyquinoline-4-oxo)-S-proline]-P1(1R,2S Vinyl Acca)-CONHSO$_2$ (1-cyclopropan-1-yl) hydrochloride Salt or Alternate Designation, Compound 2A, the (1R,2S) P1 Isomer of {1-[2-[1-(1-Allyl-cyclopropanesulfonylaminocarbonyl)-2-vinylcyclopropyl-carbamoyl]-4-(7-methoxy-2-phenylquinolin-4-yloxy)-pyrrolidine-1-carbonyl]-2,2-dimethylpropyl}carbamic acid tert-butyl ester hydrochloride HCl Salt of Product of Step 10f) This compound was prepared in quantitative yield from Compound 2 (Example 10) by dissolving in CH$_2$Cl$_2$ (~50 mg/mL), cooling to −78° C., adding 5 molar equivalents of 4N HCl/dioxane and then immediately concentrating in vacuo: $^1$H NMR (methanol-d$_4$) ☐ 0.83–0.98 (m, 2H), 1.04 (s, 9H), 1.19 (s, 9H), 1.36–1.60 (m, 3H), 1.81–1.88 (m, 1H), 2.22–2.35 (m, 1H), 2.38–2.50 (m, 1H), 2.59–2.70 (m, 2H), 2.75–2.84 (m, 1H), 4.05 (s, 3H), 4.08–4.16 (m, 2H), 4.61–4.69 (m, 2H), 5.16–5.18 (m, 3H), 5.28–5.37 (m, 1H), 5.63–5.80 (m, 2H), 5.82–5.89 (m, 1H), 7.38 (d, J=9.5, 2.2 Hz, 1H), 7.57 (d, J=2.2 Hz, 1H), 7.64 (s, 1H), 7.69–7.76 (m, 3H), 8.08–8.11 (m, 2H); 8.34 (d, J=9.5 Hz, 1H). HRMS nm/z (M+H)$^+$ calcd for C$_{44}$H$_{56}$N$_5$SO$_9$: 830.3799 found: 830.3812. LC-MS (retention time: 1.68, Method D with hold time changed from 2 to 3 min), MS m/z 830 (M$^+$+1).

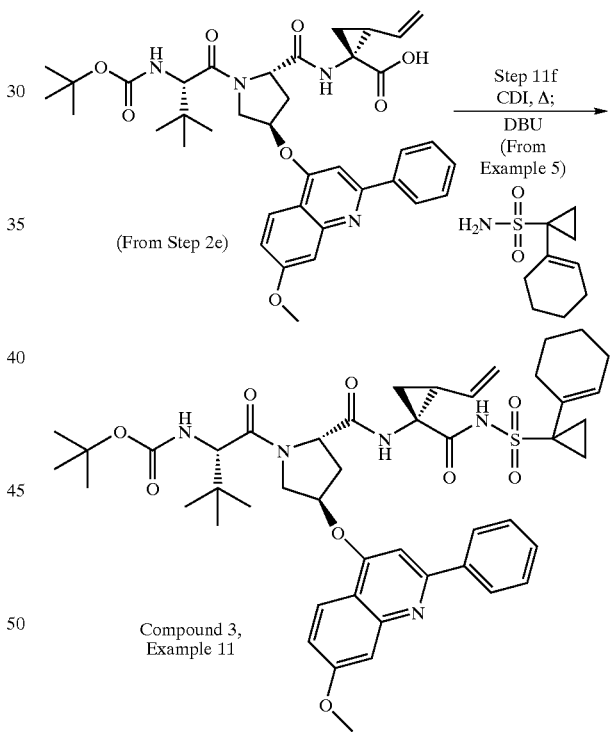

Compound 3, Example 11

Compound 3, Example 11
Compound 3, Example 11, BOCNH—P3(L-t-BuGly)-P2[(4R)-(2-phenyl-7-methoxyquinoline-4-oxo)-S-proline]-P1(1R,2S Vinyl Acca)-CONHSO$_2$ (1-Cyclohex-1-enyl-cyclopropan-1-yl) or Alternate Designation, Compound 1, the (1R,2S) P1 Isomer of {1-[2-[1-(1-Cyclohex-1-enyl-cyclopropanesulfonylaminocarbonyl)-2-vinylcyclopropylcarbamoyl]-4-(7-methoxy-2-phenyl-quinolin-4-yloxy)pyrrolidine-1-carbonyl]-2,2-dimethylpropyl}carbamic acid tert-butyl ester Step 11f) This compound was prepared in 74% yield from tripeptide acid product of step 2e (Example 2) in analogous fashion to the procedure of Example 9 except that 1-(1-cyclohexenyl)cyclopropylsulfonamide (prepared in Example 5) was used in place of 1-methylcyclopropanesulfonamide: $^1$H NMR (CDCl$_3$/methanol-d$_4$) ☐ 0.70–1.10 (m, 3H), 1.00 (s, 9H), 1.17–1.61 (m, 6H), 1.32 (s, 9H), 1.87–2.227 (m, 5H), 2.34–2.52 (m, 1H), 2.54–2.69 (m, 1H), 3.90 (s, 3H), 4.00–4.04 (m, 1H), 4.26 (m, 1H), 4.35–4.48 (m, 1H), 4.48–4.66 (m, 1H), 4.88–5.03 (m, 1H), 5.07–5.20 (m, 1 H), 5.34 (m, 1H), 5.73–5.94 (m, 1H), 6.99 (m, 2H), 7.36 (s, 1H), 7.41–7.51 (m, 3H), 7.93–7.99 (m, 3H). LRMS m/z (M+H)+calcd for C$_{47}$H$_{60}$N$_5$O$_9$S: 870.4112 found: 870.4119. LC-MS (retention time: 1.82, Method I), MS m/z 870 (M$^+$+1).

5.52–5.72 (m, 1H), 6.94–7.00 (m, 2H), 7.20–7.47 (m, 7H), 7.91–7.98 (m, 3H), 7.98–8.04 (m, 2H). HRMS m/z (M+H)$^+$ calcd for C$_{48}$H$_{56}$N$_5$O$_9$S: 894.3748 found: 894.3756. LC-MS (retention time: 1.72, Method I), MS m/z 894 (M$^+$+1).

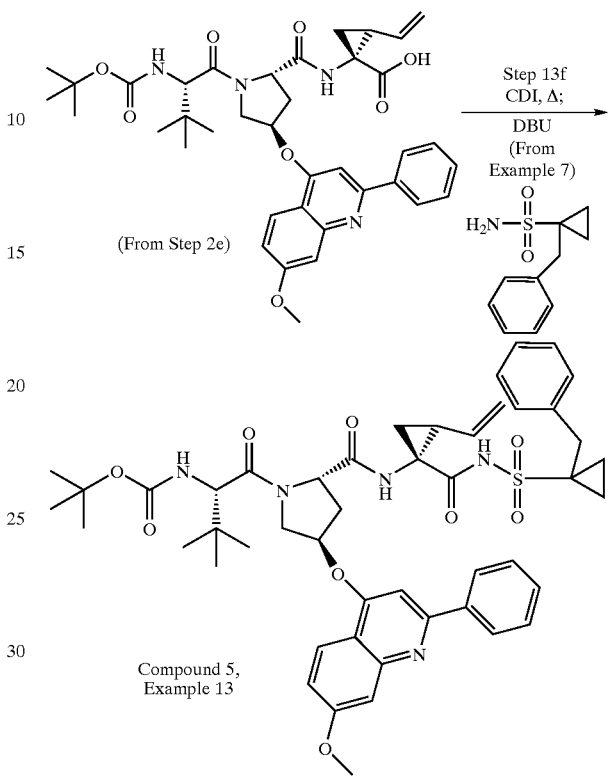

Compound 5, Example 13

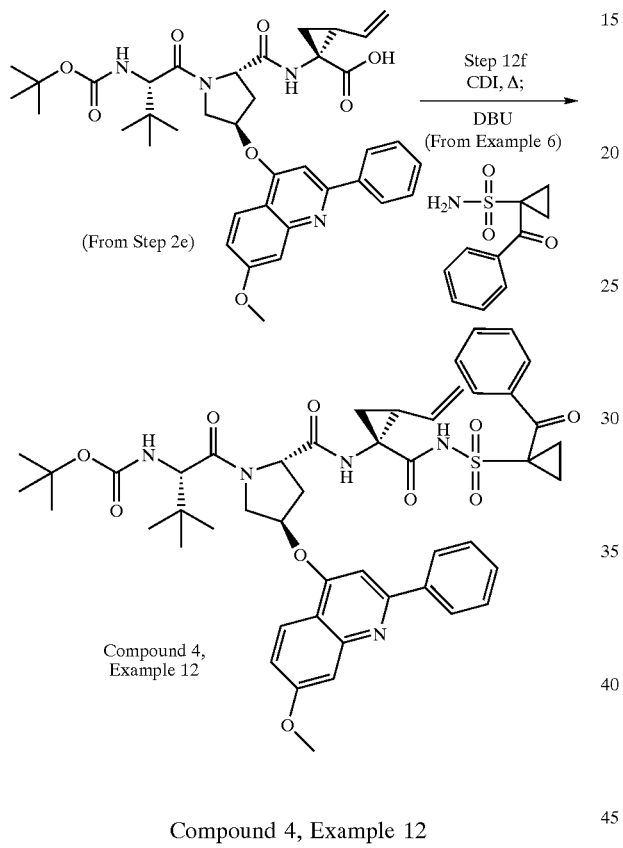

Compound 4, Example 12

Compound 5, Example 13

Compound 4, Example 12, BOCNH—P3(L-t-BuGly)-P2[(4R)-(2-phenyl-7-methoxyquinoline-4-oxo)-S-proline]-P1(1R,2S Vinyl Acca)-CONHSO$_2$ (1-Benzoylcyclopropan-1-yl) or Alternate Designation, Compound 4, the (1R,2S) P1 Isomer of {1-[2-[1-(1-Benzoylcyclopropanesulfonyl-aminocarbonyl)-2-vinyl-cyclopropylcarbamoyl]-4-(7-methoxy-2-phenylquinolin-4-yloxy)-pyrrolidine-1-carbonyl]-2,2-dimethylpropyl}-carbamic acid tert-butyl ester Step 12f) This compound was prepared in 77% yield from tripeptide acid product of step 2e (Example 2) in analogous fashion to the procedure of Example 9 except that 1-benzoylcyclo-propylsulfonamide (prepared in Example 6) was used in place of 1-methylcyclopropanesulfonamide: $^1$H NMR (CDCl$_3$/methanol-d$_4$) ☐ 0.95 (s, 9H), 1.13–1.35 (m, 3H), 1.29 (s, 9H), 1.54–1.75 (m, 3H), 1.81–1.98 (m, 1H), 2.38–2.59 (m, 2H), 3.87 (s, 3H), 3.99–4.02 (m, 1H), 4.20–4.26 (m, 1H), 4.33–4.41 (m, 1H), 4.45–4.55 (m, 1H), 4.77–4.90 (m, 1H), 4.99–5.11 (m, 1H), 5.22–5.30 (m, 1H), Compound 5, Example 13, BOCNH—P3(L-t-BuGly)-P2[(4R)-(2-phenyl-7-methoxyquinoline-4-oxo)-S-proline]-P1(1R,2S Vinyl Acca)-CONHSO$_2$ (1-Benzylcyclopropan-1-yl) or Alternate Designation, Compound 5, the (1R,2S) P1 Isomer of {1-[2-[1-(1-Benzylcyclopropanesulfonyl-aminocarbonyl)-2-vinyl-cyclopropylcarbamoyl]-4-(7-methoxy-2-phenylquinolin-4-yloxy)-pyrrolidine-1-carbonyl]-2,2-dimethylpropyl}-carbamic acid tert-butyl ester Step 13f) This compound was prepared in 26% yield from tripeptide acid product of step 2e (Example 2) in analogous fashion to the procedure of Example 9 except that 1-benzylcyclo-propylsulfonamide (prepared in Example 7) was used in place of 1-methylcyclopropanesulfonamide: $^1$H NMR (CDCl$_3$/methanol-d$_4$) ☐ 0.80–1.42 (m, 5H), 1.02 (s, 9H), 1.35 (s, 9H), 1.75–2.08 (m, 2H), 2.41–2.54 (m, 1H), 2.57–2.71 (m, 1H), 3.26–3.30 (m, 2H), 3.93 (s, 3H), 4.03–4.18 (m, 1H), 4.45 (d, J=12 Hz, H), 4.47–4.67 (m, 1H),4.96–5.04 (m, 1H), 5.11–5.20 (m, 1H), 5.34 (m, 1H), 5.78–6.04 (m, 1H), 6.99–7.20 (m, 6H), 7.38–7.50 (m, 5H), 7.95–8.05 (m, 3H). HRMS m/z (M+H)+ calcd for C$_{48}$H$_{58}$N$_5$O$_9$S: 880.3955, found: 880.3939. LC-MS (retention time: 1.78, Method I), MS m/z 880 (M$^+$+1).

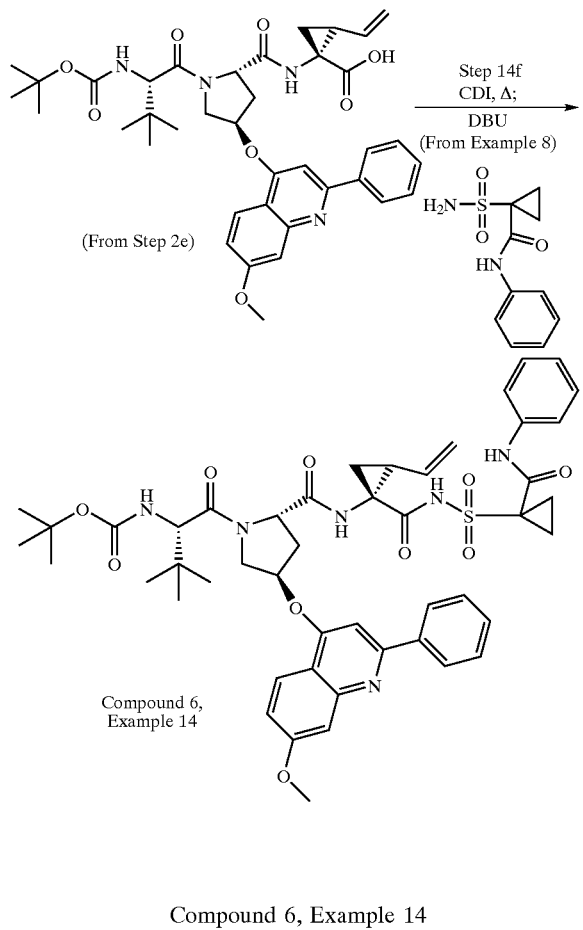

Compound 6, Example 14

Compound 6, Example 14, BOCNH—P3(L-t-BuGly)-P2[(4R)-(2-phenyl-7-methoxyquinoline-4-oxo)-S-proline]-P1(1R,2S Vinyl Acca)-CONHSO₂ (1-phenylcarbamoyl-cyclopropan-1-yl) or Alternate Designation, Compound 6, the (1R,2S) P1 Isomer of (1-{4-(7-Methoxy-2-phenyl-quinolin-4-yloxy)-2-[1-(1-phenylcarbamoyl-cyclopropane-sulfonylaminocarbonyl)-2-vinylcyclopropylcarbamoyl]-pyrrolidine-1-carbonyl}-2,2-dimethyl-propyl)carbamic acid tert-butyl ester Step 14f) This compound was prepared in 78% yield from the tripeptide acid product of step 2e (Example 2) in analogous fashion to the procedure of Example 9 except that 1-phenylcarbamoylcyclopropanesulfonamide (prepared in Example 8) was used in place of 1-methylcyclopropanesulfonamide: $^1$H NMR (CDCl$_3$/methanol-d$_4$) ☐ 0.97 (s, 9H), 1.19–1.40 (m, 1H) 1.30 (s, 9H), 1.40–1.60 (m, 4H), 1.61–1.74 (m, 1H), 1.89–1.94 (m, 1H), 2.30–2.38 (m, 1H), 2.43–2.53 (m, 1H), 3.90 (s, 3H), 4.17–4.24 (m, 1H), 4.37–4.49 (m, 1H), 4.81–4.89 (m, 1H), 5.05–5.11 (m, 1H), 5.16 (m, 1H), 5.81–5.88 (m, 1H), 6.93–7.06 (m, 3H), 7.13–7.17 (m, 2H), 7.35 (m, 1H), 7.43–7.56 (m, 5H), 7.92–8.06 (m, 3H). HRMS m/z (M+H)$^+$ calcd for C$_{48}$H$_{57}$N$_6$O$_{10}$S: 909.3857, found: 909.3857. LC (retention time: 1.73, Method I). LRMS m/z 909 (M$^+$+1).

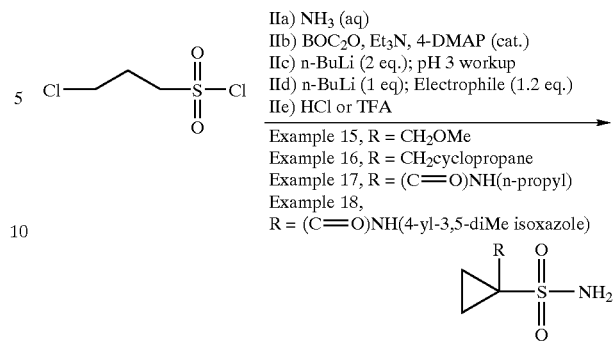

IIa) NH$_3$ (aq)
IIb) BOC$_2$O, Et$_3$N, 4-DMAP (cat.)
IIc) n-BuLi (2 eq.); pH 3 workup
IId) n-BuLi (1 eq); Electrophile (1.2 eq.)
IIe) HCl or TFA Example 15, R = CH$_2$OMe
Example 16, R = CH$_2$cyclopropane
Example 17, R = (C═O)NH(n-propyl)
Example 18, R = (C═O)NH(4-yl-3,5-diMe isoxazole)

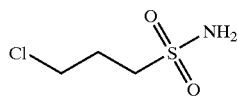

Method II (Steps a-e). Preparation of 1-Substituted Cyclopropanesulfonamides Required for N-acylsulfonamide Coupling Steps 15e–18e (Examples 15–18 used to Prepare Compounds 7–10, Respectively)

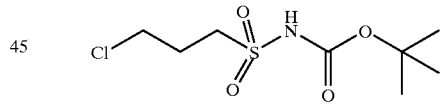

Step IIa: 3-chloropropylsulfonamide

Step IIa) A solution of 3-Chloropropanesulfonyl chloride (55 g, 310.7 mmol) was dissolved in THF (200 mL) and added dropwise over 30 min to a solution of NH$_4$OH (200 mL) cooled to 0° C. The reaction mixture was warmed to rt, stirred 1 h, and the aqueous layer partioned multiple time with CH$_2$Cl$_2$ (4×500-mL). The combined CH$_2$Cl$_2$ layer was washed with 1 N HCl (150 mL), water (150 mL), dried over MgSO$_4$ and concentrated in vacuo. The crude solid was recrystallized from the minimum amount of CH$_2$Cl$_2$ in hexanes to afford 3-chloropropylsulfonamide as a white solid (45.3 g, 93%). $^1$H NMR (CDCl$_3$) δ 2.34 (m, 2H), 3.32 (t, J=7.3 Hz, 2H), 3.70 (t, J=6.2 Hz, 2H), 4.83 (s, 2H); $^{13}$C NMR (CDCl$_3$) δ 27.10, 42.63, 52.57.

Step IIb: 3-chloropropylsulfonylamine tert-butylcarbamate

Step IIb) To a solution of 3-chloropropylsulfonamide (30.2 g, 191.5 mmol), Et$_3$N (30.2 mL, 217.0 mmol), and 4-DMAP (2.40 g, 19.6 mmol) in CH$_2$Cl$_2$ (350 mL) cooled to 0° C. was added slowly dropwise a solution of BOC$_{2O}$ (47.2 g, 216.9 mmol) in CH$_2$Cl$_2$ (250 mL) over 30 min. The reaction mixture was allowed to warm to rt, stirred an additional 3 h and was partioned with 1 N HCl (300 mL), water (300 mL), brine (300 mL), dried over MgSO$_4$ and concentrated in vacuo to afford the crude product. This material was triturated with 70 mL of 5% CH$_2$Cl$_2$ in hexanes to afford 3-chloropropylsulfonylamine tert-butylcarbamate as an offwhite solid (47.2 g, 96%):

$^1$H NMR (CDCl$_3$) δ 1.51 (s, 9H), 2.33 (m, 2H), 3.60 (t, J=7.3 Hz, 2H), 3.68 (t, J=6.21 Hz, 2H); $^{13}$C NMR (CDCl$_3$) δ 26.50, 27.95, 42.37, 50.40, 84.76, 149.53.

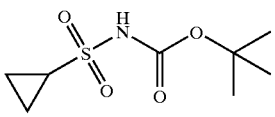

Step IIc: Preparation of cyclopropylsulfonylamine tert-butyl carbamate

Step IIc) A solution of n-BuLi (74.7 mL, 119.5 mmol, 1.6 M in hexane) was dissolved in dry THF (105 mL) and cooled to −78° C. under a Argon atmosphere. To this solution was added a solution of 3-chloropropylsulfonylamine tert-butylcarbamate (14 g, 54.3 mmol) in dry THF (105 mL) slowly dropwise over 20–30 min. The dry ice bath was removed and the reaction mixture was allowed to warm to rt over a period of 2 h. The reaction mixture was quenched with glacial AcOH (3.4 mL), concentrated in vacuo, and partitioned between $CH_2Cl_2$ (100 mL) and water (100 mL). The organic phase was washed with brine (100 mL), dried ($MgSO_4$), and concentrated in vacuo to afford the cyclopropylsulfonylamine tert-butyl carbamate as a waxy offwhite solid (12.08 g, 100%): $^1$H NMR ($CDCl_3$) δ 1.10 (m, 2H), 1.34 (m, 2H), 1.50 (s, 9H), 2.88 (m, 1H), 7.43 (s, 1H). $^{13}$C NMR ($CDCl_3$) δ 6.21, 28.00, 31.13, 84.07, 149.82.

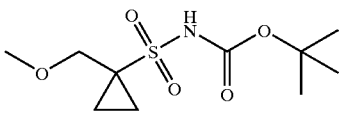

Step 15IId: Preparation of 1-methoxymethylcyclopropyl-sulfonylamine tert-butylcarbamate Step 15IId) To a solution of cyclopropylsulfonylamine tert-butyl carbamate (1.0 g, 4.5 mmol) dissolved in THF (30 mL) cooled to −78° C., was added n-BuLi (6.4 mL, 10.2 mmol, 1.6 M in hexane) and the reaction mixture was stirred for 1 h. To this solution was added a neat solution of chloromethyl methyl ether (0.40 mL, 5.24 mmol), and the mixture was slowly allowed to warm to room temperature overnite. The solution pH was adjusted to 3 using 1N aqueous HCl and was then extracted with EtOAc (4×50 mL portions). The combined extracts were dried ($MgSO_4$) and concentrated to afford Example 18, 1-methoxymethylcyclopropylsulfonylamine tert-butylcarbamate, as a waxy solid (1.20 g, 100%) which was taken directly into the next reaction without further purification: $^1$H NMR ($CDCl_3$) δ 1.03 (m, 2H), 1.52 (s, 9H), 1.66 (m, 2H), 3.38 (s, 3H), 3.68 (s, 2H), 7.54 (s, 1H); $^{13}$C NMR ($CDCl_3$) δ 11.37, 28.29, 40.38, 58.94, 73.43, 83.61, 149.57.

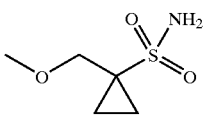

Step 15IIe: Preparation of Example 15, 1-methoxymethylcyclopropysulfonamide

Step 15IIe) A solution of 1-methoxymethylcyclopropylsulfonylamine tert-butylcarbamate (1.14 g, 4.30 mmol) was dissolved in a solution of 50% TFA/$CH_2Cl_2$ (30 mL) and was stirred stirred at rt for 16 h. The solvent was removed in vacuo and the residue chromatographed over 80 g of $SiO_2$ (eluting with 0% to 60% EtOAC/Hexanes to afford Example 15, 1-methoxymethylcyclopropylsulfonamide, as a white solid (0.55 g, 77% overall over two steps): $^1$H NMR ($CDCl_3$) δ 0.95 (m, 2H), 1.44 (m, 2H), 3.36 (s, 3H), 3.65 (s, 2H), 4.85 (s, 2H); $^{13}$C NMR ($CDCl_3$) δ 11.17, 40.87, 59.23, 74.80; LRMS m/z 183 ($M^+$+$NH_4$).

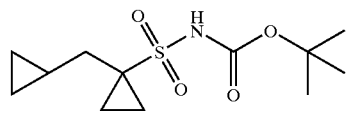

Step 16IId: Preparation of 1-cyclopropylmethylcyclo-propylsulfonylamine tert-butylcarbamate Step 16IId) This compound, 1-cyclopropylmethylcyclopropylsulfonylamine tert-butylcarbamate, was obtained in 92% yield according to the procedure described in the synthesis of 1-methoxymethylcyclopropylsulfonylamine tert-butylcarbamate (Step 15IId) except 1.10 equivalents of cyclopropylmethyl bromide were used as electrophile. The compound was taken directly into the next reaction without purification: $^1$H NMR ($CDCl_3$) δ 0.10 (m, 2H), 0.51 (m, 2H), 0.67 (m, 1H), 1.10 (m, 2H), 1.49 (s, 9H), 1.62 (m, 2H), 1.87 (d, J=7.0 Hz, 2H).

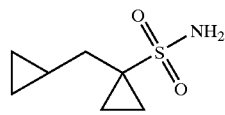

Steps 16IIe: Preparation of Example 16, 1-cyclopropylmethyl-cyclopropylsulfonamide Step 16IId) This compound, Example 16, 1-cyclopropylmethylcyclopropylsulfonamide, was obtained in 65% yield from 1-cyclopropylmethylcyclopropylsulfonylamine tert-butylcarbamate (from step 16IId) according to the procedure described for the synthesis of 1-Methoxymethylcyclopropylsulfonamide (step 15IIe). The compound was purified by column chromatography over $SiO_2$ using 0% to 60% EtOAc in Hexanes as the eluent: $^1$H NMR ($CDCl_3$) δ 0.15 (m, 2H), 0.51 (m, 2H), 1.01 (m, 2H), 1.34 (m, 3H), 1.86 (d, J=7.0 Hz, 2H), 4.83 (s, 2H); $^{13}$C NMR ($CDCl_3$) δ 4.65, 7.74, 11.26, 35.62, 41.21; LRMS m/z 193 ($M^+$+$NH_4$).

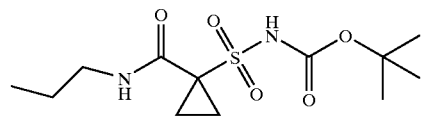

Step 17IId: Preparation of 1-propylcarbamoylcyclopro-panesulfonamide tert-butylcarbamate Step 17IId) This compound, 1-propylcarbamoylcyclopropanesulfonamide tert-butylcarbamate, was obtained in a crude 100% yield according to the procedure described for the synthesis of 1-methoxymethylcyclopropylsulfonylamine tert-butylcarbamate (Step 15IId) except that 1.10 equivalents of n-propyl isocyanate was used as the electrophile. The compound was taken directly into the next reaction without purification: ¹H NMR (CDCl₃) δ 0.10 (m, 2H), 0.51 (m, 2H), 0.67 (m, 1H), 1.10 (m, 2H), 1.49 (s, 9H), 1.62 (m, 2H), 1.87 (d, J=7.0 Hz, 2H).

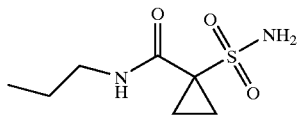

Steps 17IIe: Preparation of Example 17, 1-propylcarbamoylcyclopropanesulfonamide Step 17IIe) This compound, Example 17, 1-propylcarbamoylcyclopropanesulfonamide, was obtained in an optimized 50% yield from 1-propylcarbamoylcyclopropanesulfonamide tert-butylcarbamate (from step 17IId) according to the procedure described for the synthesis of 1-Methoxymethylcyclopropylsulfonamide (step 15IIe), except that no chromatography was used as the material was recrystallized from the minimum amount of CH₂Cl₂/Hexanes: ¹H NMR (CDCl₃) δ 0.15 (m, 2H), 0.51 (m, 2H), 1.01 (m, 2H), 1.34 (m, 3H), 1.86 (d, J=7.0 Hz, 2H), 4.83 (s, 2H); ¹³C NMR (CDCl₃) δ 4.65, 7.74, 11.26, 35.62, 41.21; LRMS m/z 193 (M⁺+NH₄).

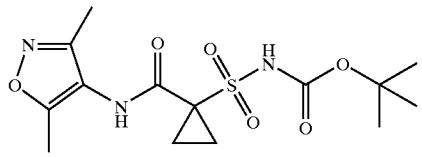

Step 18IId: Preparation of 1-(3,5-dimethylisoxazol-4-yl)carbamoyl-cyclopropanesulfonamide tert-butylcar-bamate Step 18IId) This compound, 1-(3,5-dimethylisoxazol-4-yl)carbamoylcyclopropanesulfonamide tert-butylcarbamate, was obtained in a crude 100% yield according to the procedure described for the synthesis of 1-methoxymethylcyclopropylsulfonylamine tert-butylcarbamate (Step 15IId) except that 1.20 equivalents of 3,5-dimethylisoxazole-4-isocyanate was used as the electrophile. The compound was taken directly into the next reaction without purification.

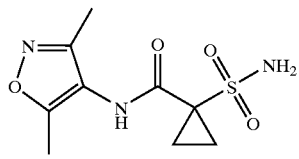

Steps 18IIe: Preparation of Example 18, 1-(3,5-dimethylisoxazol-4yl)carbamoylcyclopropanesulfonamide Step 18IIe) This compound, Example 18, 1-(3,5-dimethylisoxazol-4yl)carbamoylcyclopropanesulfonamide, was obtained in 50% yield (580 mg) from 1.62 g (4.52 mmol) of 1-(3,5-dimethylisoxazol-4-yl)carbamoylcyclopropanesulfonamide tert-butylcarbamate using 30 mL (120 mmol) of 4N HCl/dioxanes, stirring overnite, concentration and chromatography over a Biotage 40M column (eluting with 0% to 5% MeOH/CH₂Cl₂: ¹H NMR (methanol-d₄) δ 1.57 (m, 2H), 1.61 (m 2H), 2.15 (s, 3H), 2.30 (s, 3H), 4.84(s, 3H); ¹³C NMR (methanol-d₄) δ 9.65, 10.94, 15.01, 46.11, 114.82, 159.45, 165.55, 168.15; LRMS m/z 260 (M⁺+H).

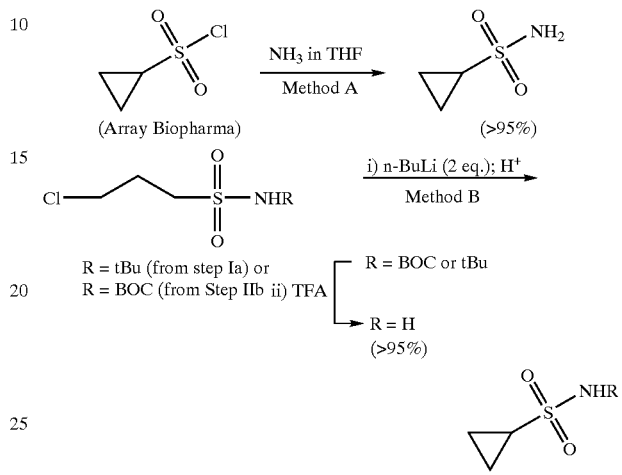

General Processes for the Preparation of Unsubstituted Cyclopropylsulfonamide (Method A or Method B)

Method A: To a solution of 100 mL of THF cooled to 0° C. was bubbled in gaseous ammonia until saturation was reached. To this solution was added a solution of 5 g (28.45 mmol) of cyclopropylsulfonyl chloride (purchased from Array Biopharma) in 50 mL of THF, the solution warmed to rt overnite and stirred one additional day. The mixture was concentrated until 1–2 mL of solvent remained, applied onto 30 g plug of SiO₂ (eluted with 30% to 60% EtOAc/Hexanes) to afford 3.45 g (100%) of cyclopropylsulfonamide as a white solid.

Method B, Step i (R=tBu) A solution of n-BuLi (86.7 mL, 138.8 mmol, 1.6 M in hexane) was dissolved in dry THF (120 mL) and cooled to −78° C. under a Argon atmosphere. To this solution was added a solution of N-tert-Butyl-(3-chloro)propylsulfonamide from Step 1a,(14.5 g, 67.8 mmol) in dry THF (160 mL slowly dropwise over 60 min. The dry ice bath was removed and the reaction mixture was allowed to warm to rt over a period of 2 h. The reaction mixture was quenched with glacial AcOH (3.4 mL), concentrated in vacuo, and partitioned between CH₂Cl₂ (100 mL) and water (100 mL). The organic phase was washed with aqueous 1N NaOH (150 mL), brine (100 mL), dried (MgSO₄), and concentrated in vacuo to afford the N-tert-Butyl cyclopropylsulfonamide as a waxy offwhite solid (12 g, 100%): ¹H NMR (CDCl₃) δ 0.98 (m, 2H), 1.17 (m, 2H), 1.38 (s, 9H), 2.45 (m, 1H), 4.45 (bs, 1H). ¹³C NMR (CDCl₃) δ 6.5, 30.6, 33.5, 54.2. MS (ESI) 176 (M⁺–H).

Method B, Step ii (R=tBu to H) A yield >95% was routinely obtained of cyclopropylsulfonamide following the same TFA deprotection procedure used in step 31d, except that of N-tert-Butyl cyclopropylsulfonamide was used in place of N-tert-Butyl-(1-methyl)cyclopropyl-sulfonamide.

Method B, Step i same as Step IIc (R=BOC) The preparation of cyclopropylsulfonylamine tert-butyl carbamate from 3-chloropropylsulfonylamine tert-butylcarbamate is described already in Step IIc (100%).

Method B, Step ii (R=BOC to R=H) The preparation of cyclopropylsulfonylamine tert-butyl carbamate. A yield >95% was routinely obtained of cyclopropylsulfonamide following the same TFA deprotection procedure used in step 31d, except that of cyclopropylsulfonylamine tert-butyl carbamate was used in place of N-tert-Butyl-(1-methyl) cyclopropyl-sulfonamide. Data for cyclopropylsulfonamide: ¹H NMR (methanol-d₄) δ 0.94–1.07 (m, 4H), 2.52–2.60 (m, 1H); ¹H NMR (DMSO-d₆) δ 0.88 (ml 2H), 0.92 (m, 2H), 2.47 (m, 1H), 6.70 (bs, 2H); ¹³C NMR (methanol-d₄) δ 5.92, 33.01; ¹³C NMR (DMSO-d₆) δ 4.85, 31.80. Anal. Calcd. For C₃H₇NO₂S: C, 29.74; H, 5.82; N, 11.56. Found: C, 29.99; H, 5.89, N, 11.50.

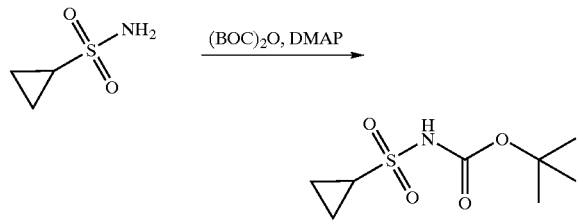

Alternative Preparation of Product of Step IIc

Alternative Preparation of the Product of Step IIc: Cyclopropylsulfonylamine tert-butyl carbamate Step ii) To a solution of cyclopropylsulfonamide (6.0 g, 50.0 mmol) in CH₂Cl₂ (50 mL) was added BOC₂O(13.0 g, 59.0 mmol), Et₃N (7.5 mL, 74 mmol), and 4-DMAP (0.30 g, 2.5 mmol). The reaction mixture was stirred overnite at rt, diluted with EtOAc (300 mL), partitioned with 1 N HCl (3×100 mL), dried over MgSO₄ and concentrated in vacuo to afford 9.3 g (85%) of cyclopropylsulfonylamine tert-butylcarbamate as a white solid having identical data to its preparation in Step IIc.

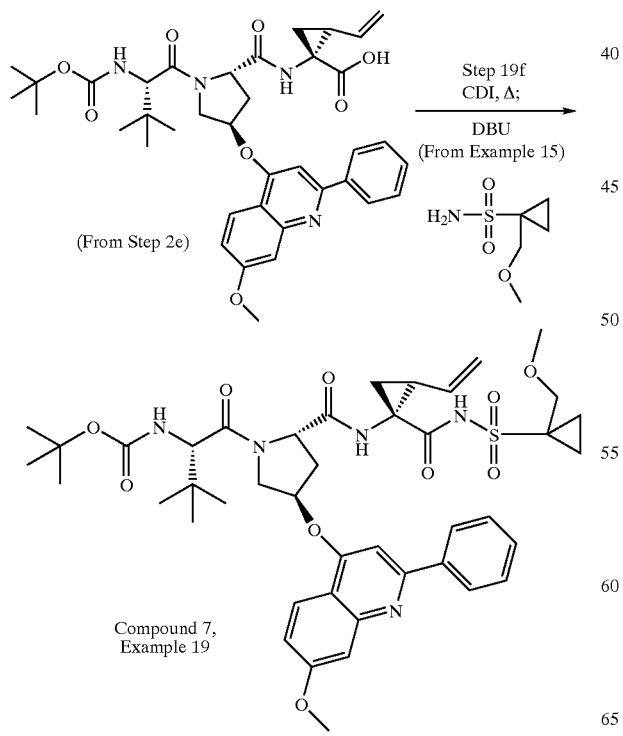

Compound 7, Example 19

Compound 7, Example 19

Compound 7, Example 19, BOCNH—P3(L-t-BuGly)-P2[(4R)-(2-phenyl-7-methoxyquinoline-4-oxo)-S-proline]-P1(1R,2S Vinyl Acca)-CONHSO₂ (1-methoxymethyl-cyclopropan-1-yl) or Alternate Designation, Compound 7, the (1R,2S) P1 Isomer of {1-[2-[1-(1-Methoxymethylcyclopropanesulfonylaminocarbonyl)-2-vinylcyclopropylcarbamoyl]-4-(7-methoxy-2-phenyl-quinolin-4--yloxy)pyrrolidine-1-carbonyl]-2,2-dimeth-ylpropyl}-carbamic acid tert-butyl ester Step 19f) This compound was prepared in 63.4% yield from the tripeptide acid product of step 2e (Example 2) in analogous fashion to the procedure of Example 9 except that 1-methoxymethylcyclopropanesulfonamide (prepared in Example 15) was used in place of 1-methylcyclopropanesulfonamide: ¹H NMR (methanol-d₄) □ 0.94–1.11 (m, 1H), 1.05 (s, 9H), 1.28 (s, 9H), 1.38–1.66 (m, 3H), 1.78–1.87 (m, 2H), 1.97–2.00 (m, 1H), 2.17–2.36 (m, 2H), 2.63–2.71 (m, 1H), 3.94 (s, 3H), 4.08 (d, J=10 Hz, 1H), 4.24–4.27 (m, 1H), 4.52–4.57 (m, 2H), 5.09 (d, J=11 Hz, 1H), 5.22–5.31 (m, 1H), 5.56 (m, 1H), 5.71–5.86 (m, 1H), 7.07 (d, J=9, 2 Hz, 1H), 7.25 (s, 1H), 7.38 (d, J=2 Hz, 1H), 7.47–7.57 (m, 3H), 8.04–8.12 (m, 3H). HRMS m/z (M−H) calcd for C₄₃H₅₄N₅O₁₀S: 832.3591, found: 832.3592. LC-MS (retention time: 1.61, Method A), MS m/z 833 (M⁺+1).

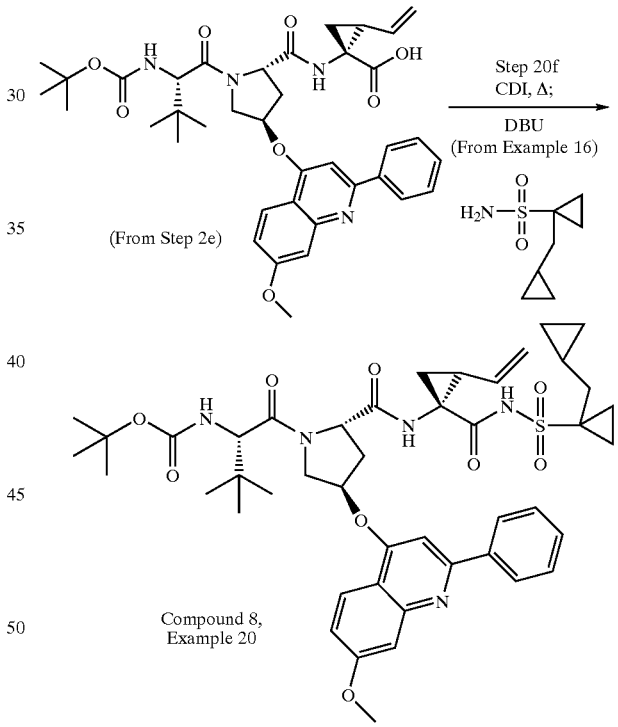

Compound 8, Example 20

Compound 8, Example 20

Compound 8, Example 20, BOCNH—P3(L-t-BuGly)-P2[(4R)-(2-phenyl-7-methoxyquinoline-4-oxo)-S-proline]-P1(1R,2S Vinyl Acca)-CONHSO₂ (1-cyclopropylmethyl-cyclopropan-1-yl) or Alternate Designation, Compound 8, the (1R,2S) P1 Isomer of {1-[2-[1-(1-Cyclopropylmethyl-cyclopropanesulfonylaminocarbonyl)-2-vinyl-cyclopropylcarbamoyl]-4-(7-methoxy-2-phenyl-quinolin-4-yloxy)-pyrrolidine-1-carbonyl]-2,2-dime-thylpropyl}-carbamic acid tert-butyl ester Step 20f ) This compound was prepared in 71% yield from the tripeptide acid product of step 2e (Example 2) in analogous fashion to the procedure of Example 9 except that 1-cyclopropylmethlcyclopropanesulfonamide (prepared in Example 16) was used in place pf 1-methylcyclopropanesulfonamide: $^1$H NMR (methanol-$d_4$) ☐ 0.00–0.14 (m, 2H), 0.38–0.53 (m, 2H), 0.61.–0.74 (m, 1H), 0.83–1.65 (m, 5H), 1.04(s, 9H), 1.28 (s, 9H), 1.72–1.96 (m, 3H), 2.18–2.40 (m, 2H), 2.63–2.73 (m, 1H), 3.95 (s, 3H), 4.10 (d, j=10 Hz, 1H), 4.26 (d, J=9 Hz, 1H), 4.46–4.59 (m, 2H), 5.09 (d, J=11 Hz, 1H), 5.23–5.33 (m, 1H), 5.57 (m, 1H), 5.65–5.77 (m, 1H), 7.08 (dd, j=9, 2 Hz, 1H), 7.25 (s, 1H), 7.39 (d, J=2 Hz, 1H), 7.47–7.57 (m. 3H), 8.04–8.09 (m, 3H), HRMS m/z (M–H) clcd for $C_{45}H_{56}N_5O_9S$: 844.3955, found: 844.3804. LC-MS (retention time: 1.76, Method I), MS m/z 844 (M$^+$+1).

☐ 0.89–0.96 (m, 3H), 1.05 (s, 9H), 1.21 (s, 9H), 1.29–1.85 (m, 8H), 2.20–2.30 (m, 1H), 2.42–2.54 (m, 1H), 2.76–2.83 (m, 1H), 3.14–3.25 (m, 2H), 4.05 (s, 3H), 4.10–4.18 (m, 2H), 4.60–4.71 (m, 2H), 5.10–5.15 (m, 1H), 5.23–5.33 (m, 1H), 5.58–5.71 (m, 1H), 5.83 (m, 1H), 7.36 (dd, J=9, 2.2 Hz, 1H), 7.54 (d, J=2.2 Hz, 1H), 7.63 (s, 1H), 7.68–7.77 (m, 3H), 8.07–8.10 (m, 2H), 8.34 (d, J=9 Hz, 1H). HRMS m/z (M–H) calcd for $C_{45}H_{57}N_5O_{10}S$: 873.3857, found: 873.3895. LC-MS (retention time: 1.69, Method I), MS m/z 875 (M$^+$+1).

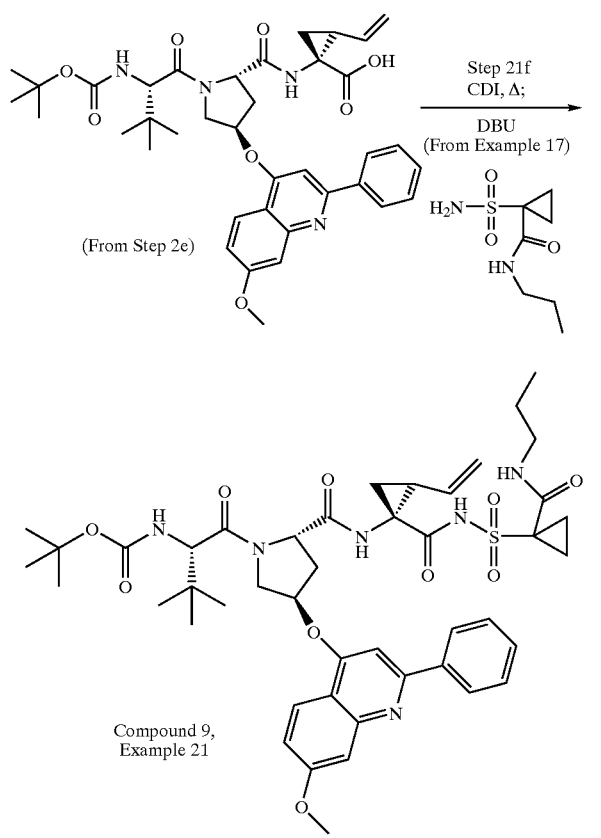

Compound 9, Example 21

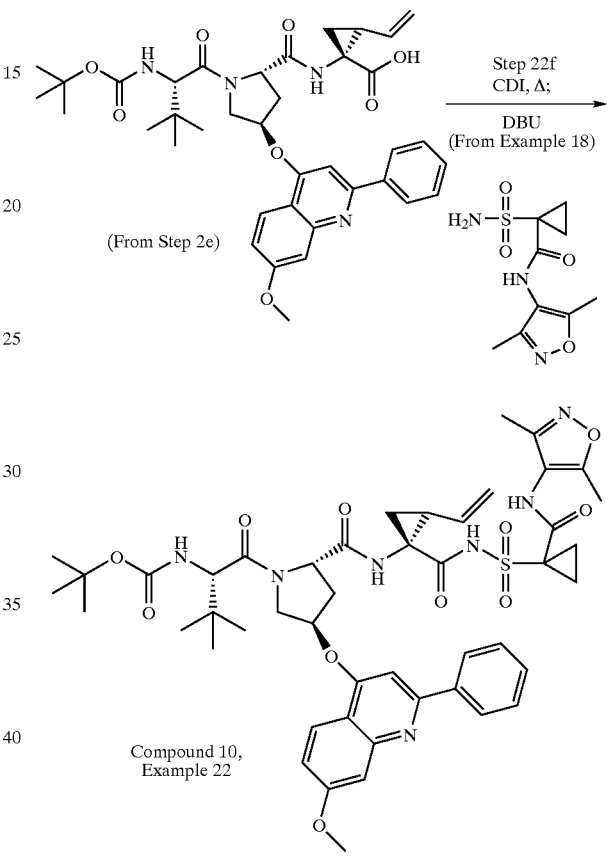

Compound 10, Example 22

Compound 9, Example 21

Compound 9, Example 21, BOCNH—P3(L-t-BuGly)-P2[(4R)-(2-phenyl-7-methoxyquinoline-4-oxo)-S-proline]-P1(1R,2S Vinyl Acca)-CONHSO$_2$ (1-propylcarbamoyl-cyclopropan-1-yl) or Alternate Designation, Compound 9, the (1R,2S) P1 Isomer of (1-{4-(7-Methoxy-2-phenylquinolin-4-yloxy)-2-[1-(1-propylcarbamoyl-cyclopropanesulfonylaminocarbonyl)-2-vinylcyclopropylcarbamoyl]pyrrolidine-1-carbonyl}-2,2-dimethyl-propyl)carbamic acid tert-butyl ester Step 21f) This compound was prepared in 59% yield from the tripeptide acid product of step 2e (Example 2) in analogous fashion to the procedure of Example 9 except that 1-propylcarbamoylcyclopropanesulfonamide (prepared in Example 17) was used in place of 1-methylcyclopropanesulfonamide: $^1$H NMR (methanol-$d_4$)

Compound 10, Example 22

Compound 10, Example 22, BOCNH—P3(L-t-BuGly)-P2[(4R)-(2-phenyl-7-methoxyquinoline-4-oxo)-S-proline]-P1(1R,2S Vinyl Acca)-CONHSO$_2$ (1-propylcarbamoyl-cyclopropan-1-yl) or Alternate Designation, Compound 10, the (1R,2S) P1 Isomer of {1-[2-{1-[1-(3,5-Dimethylisoxazol-4-ylcarbamoyl)cyclopropanesul-fonylaminocarbonyl]-2-vinylcyclopropylcarbamoyl}-4-(7-methoxy-2-phenylquinolin-4-yloxy)pyrrolidine-1-carbon-yl]-2,2-dimethylpropyl}carbamicacid tert-butyl ester Step 22f) This compound was prepared in 53% yield from the tripeptide acid product of step 2e (Example 2) in analogous fashion to the procedure of Example 9 except that 1-(3,5-Dimethylisoxazol-4-ylcarbamoyl)cyclopropanesulfonamide (prepared in Example 18) was used in place of 1-methylcyclopropanesulfonamide: $^1$H NMR (methanol-$d_4$) δ 0.98 (s, 9H), 1.01 (m, 1H), 1.27–1.41 (m, 2H), 1.30 (s, 9H), 1.43–1.49 (m, 1H), 1.54–1.59 (m, 1H), 1.61–1.67 (m, 2H), 2.04–2.09 (m 1H), 2.14, 2.16 (2s, 3H), 2.29 (s, 3H), 2.46–2.51 (m, 1H), 2.68 (dd, J=14, 8 Hz, 1H), 3.83–3.86 (m, 1H), 3.93 (s, 3H), 4.20–4.24 (m, 1H), 4.46 (d, J=12 Hz, 1H), 4.51–4.54 (m, 1H), 4.92–4.95 (m, 1H), 5.11–5.18 (m, 1H), 5.44 (m, 1H), 5.84–5.99 (m, 1H), 7.02–7.04 (m, 1H), 7.20–7.25 (m, 1H), 7.36–7.38 (m, 1H), 7.47–7.55 (m, 3H), 8.05–8.09 (m, 3H). HRMS m/z (M–H) calcd for $C_{47}H_{56}N_7O_{11}S$: 926.3786, found: 926.3777. LC (retention time: 1.35, Method I).

Method III (Steps IIIa-IIIb). Formation of Example 23, 1-Bromocyclopropanesulfonamide

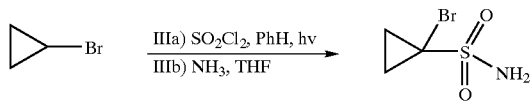

Step IIIa: Formation of 1-Bromocyclopropanesulfonyl Choride

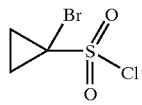

Step IIIa) Cyclopropyl bromide (10L, 125 mmol) was dissolved in benzene (11.2 mL). To this solution was added 2 drops of pyridine. The resulting mixture was stirred and irradiated with a 250 W lamp, two inches from the flask while sulfuryl chloride (5.0 mL, 62.4 mmol) was added dropwise over 14 minutes. After 15 addition minutes of stirring with irradiation, the reaction was concentrated in vacuo. Upon standing for one hour, crystals formed which were filtered off and discarded. The residual oil was then distilled under high vacuum (60° C., 0.05 mm) to yield the titled product 1.18 g (4.3%) as a yellow oil: $^1$H NMR (CDCl$_3$,) δ 1.73 (2H, t), 2.15 (2H, t): $^{13}$C NMR (CDCl$_3$) 49.1, 20.3.

Step IIIb: Formation of Example 23, 1-Bromocyclopropanesulfonamide

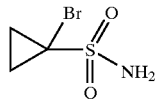

Step IIIb) 1-Bromocyclopropanesulfonyl chloride (0.9 g, 4.10 mmol) was dissolved in 15 mL of THF saturated with NH$_3$. The solution was stirred overnight and then the NH$_4$Cl was filtered away. The filtrate was concentrated to yield Example 23, 1-Bromocyclopropanesulfonamide, 980 mgs (91%) as a tan solid: $^1$H NMR (acetone-d6) δ 1.70 (2H, t), 1.41 (2H, t). MS m/z 201 (M+H).

Compound 11, Example 24

Preparation of Compound 11, Example 24, BocNH—P3(t-BuGly)-P2[(4R)-(2-phenyl-7-methoxyquinoline-4-oxo)-S-proline]-P1(1R,2S Vinyl Acca)-CONHSO$_2$(1-bromo-cyclopropan-1-yl) or Alternate Designation, Compound 11, the (1R, 2S) P1 Isomer of {1-[2-[1-(1-Bromocyclopropanesulfonylaminocarbonyl)-2-vinylcy-clopropylcarbamoyl]-4-(7-methoxy-2-phenylquinolin-4-yloxy)pyrrolidine-1-carbonyl]-2,2-dimethylpropyl}-carbamic acid tert-butyl ester

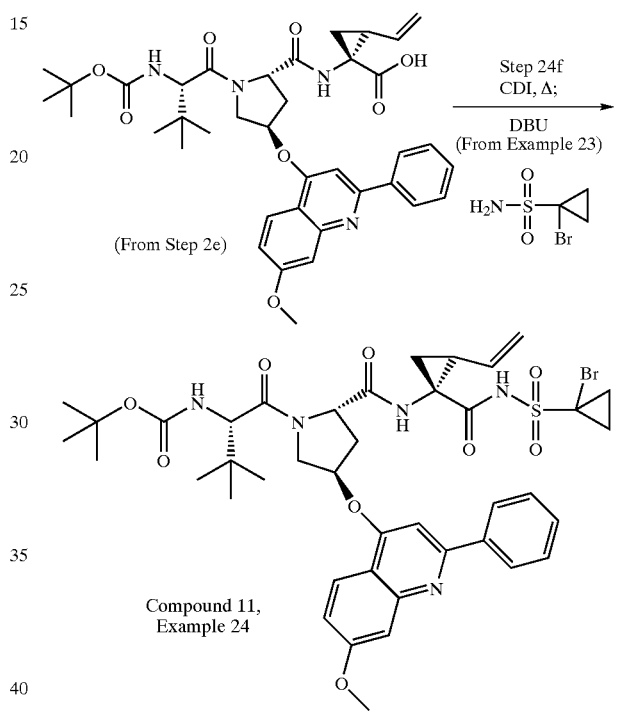

Step 24f) The Product of Example 2 (Step 2e), BocNH—P3(t-BuGly)-P2[(4R)-(2-phenyl-7-methoxyquin-oline-4-oxo)-S-proline)]-P1(1R,2S Vinyl Acca)-OH (18 mgs, 0.026 mmol) was dissolved in 500 μL THF. To this solution was added DBU (8 μL, 0.052 mmol) and CDI (6 mgs, 0.034 mmol. The resulting mixture was refluxed for 40 minutes and cooled to room temperature. 1-bromocyclopropanesulfonamide (13 mgs, 0.066 mmol) prepared in Example 23 using Method III (Steps a-b), was then added and the solution brought to reflux for 24 hours. After cooling, the solution was diluted with ethyl acetate, washed with 1N HCl and brine and dried over Na$_2$SO$_4$. The volatiles were removed in vacuo. The product was purified by a Biotage 40M silica column eluting with 95:5 ethyl acetate: methanol to yield Compound II, Example 24, 19 mgs (83%) as a white solid: $^1$H NMR (methanol-d$_4$) δ 8.03–8.09 (m, 3H), 7.48–7.54 (m, 3H), 7.37 (m, 1H), 7.25 (s, 1H), 7.07 (m, 1H), 6.57 (d, 1H, J=8.9 Hz), 5.99 (m, 1H), 5.54 (bs, 1H), 5.21 (m, 1H), 5.02 (d, 1H, J=10.4 Hz), 4.50–4.58 (m, 1H), 4.24 (m, 1H), 4.11 (m, 1H), 3.93 (s, 1H), 2.72 (m, 1H), 2.55 (m, 1H), 2.12 (m, 1H), 1.73–1.81 (m, 3H), 1.45 (m, 1H), 1.31–1.36 (m, 2H), 1.27 (s, 9H), 1.04 (s, 9H), 0.91 (m, 2H). MS m/z 868.47 (M+H).

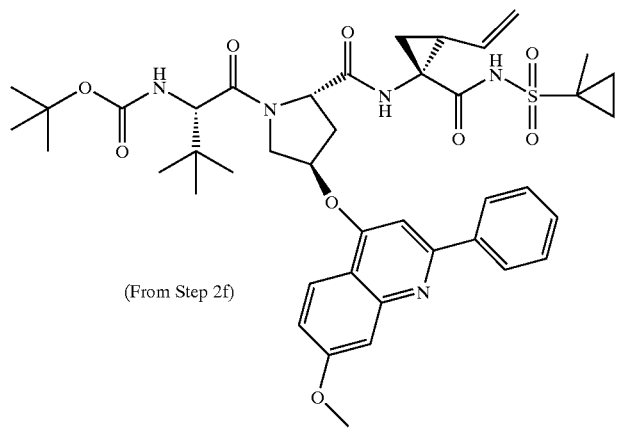

(From Step 2f)

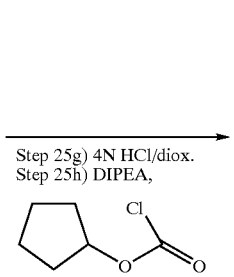

Step 25g) 4N HCl/diox.
Step 25h) DIPEA,

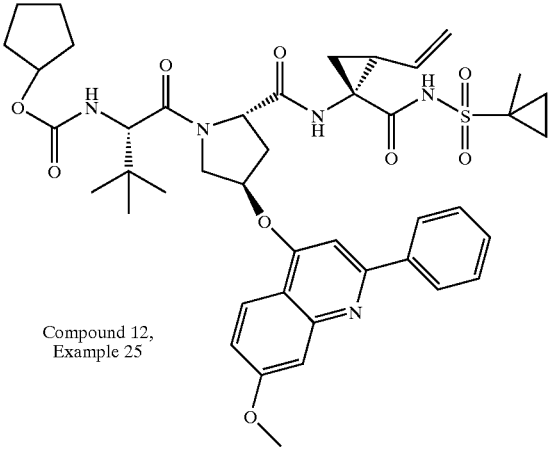

Compound 12,
Example 25

Compound 12, Example 25

Compound 12, Example 25, (cyclopentyl-O(C=O) NH—P3(L-t-BuGly)-P2[(4R)-(2-phenyl-7-methoxyquinoline-4-oxo)-S-proline]-P1(1R,2S Vinyl Acca)-CONHSO₂(1-methyl-1-cyclopropane) or Alternate Designation, Compound 12, the (1R, 2S) P1 Isomer of (1-{4-(7-Methoxy-2-phenyl-quinolin-4-yloxy)-2-[1-(1-methylcyclopropanesulfonyl-aminocarbonyl)-2-vinyl-cyclopropylcarbamoyl]-pyrrolidine-1-carbonyl}-2,2-dimethylpropyl)carbamic acid cyclopentyl ester Preparation of Cyclopentyl Chloroformate

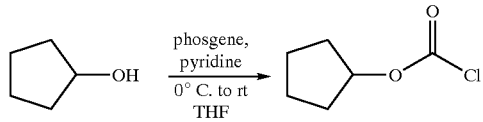

This procedure was used for the preparation of non-commercially available chloroformates. To a solution of (5.8 g, 67.6 mmol) of commercially available (Aldrich) reagents of cyclopentanol and pyridine (5.8 mL; 72 mmol) in THF (150 mL) cooled to 0° C. was added a 1.93 M solution of phosgene in toluene (48 mL, 92.6 mmol over 10 min under argon. The resulting solution was allowed to warm to rt over 2 h, the resulting solid filtered, and the mother liquor carefully concentrated in vacuo at room temperature until theoretical mass was obtained. The resulting residue was dissolved in 100 mL of THF to prepare a 0.68M stock solution of cyclopentyl chloroformate that could be stored in the freezer until use. In analogous fashion, other commercially available alcohols could be converted to 0.68M stock solutions of the corresponding chloroformates.

Step 25 g) A solution of 172 mg (0.214 mmol)of the product of Step 2f, (1R,2S) P1 diastereomer of (1-{4-(7-Methoxy-2-phenylquinolin-4-yloxy)-2-[1-(1-methyl-cyclopropanesulfonylaminocarbonyl)-2-vinylcycloropylcarbamoyl]pyrrolidine-1-carbonyl}-2,2-dimethyl-propyl)carbamic acid tert-butyl ester was treated with 8 mL (32 mmol) of 4N HCl in dioxane for 2 h and then concentrated in vacuo to afford 168 mg of the Bis HCl product. LC-MS (retention time: 1.23, Method A (hold time changed from 2 min to 3 min), MS m/z 704 (M⁺+1).

Step 25h) To a slurry of 80 mg (0.103 mmol) of the Bis HCl salt product of Step 25 g and 67 mg (0.52 mmol) of DIPEA in 2 mL of CH₂Cl₂, was added 0.34 mL (0.24 mmol) of a 0.68M solution of cyclopentyl chloroformate, and the mixture stirred overnite. MeOH was added and the mixture concentrated. The crude was then resubjected to reaction conditions and MeOH added to quench. The mixture was concentrated in vacuo and the residue chromatographed over two 1000 µ PTLC plates from Analtech (each 20×40 cm, eluted sequentially with 0% to 3% MeOH in CH₂Cl₂) to afford 40 mg (48%) of the desired P4 carbamate, Compound 12, Example 25, the (1R,2S) P1 isomer of (1-{4-(7-Methoxy-2-phenyl-quinolin-4-yloxy)-2-[1-(1-methylcyclopropanesulfonyl-aminocarbonyl)-2-vinylcyclopropylcarbamoyl]-pyrrolidine-1-carbonyl}-2,2-dimethylpropyl)carbamic acid cyclopentyl ester: ¹H NMR (methanol-d₄) δ 0.63–0.80 (m, 2H), 0.87–0.95 (m, 2H), 1.02 (s, 9H), 1.10–1.85 (m, 13H), 2.06–2.17 (m, 1H), 2.41–2.57 (m, 1H), 2.68–2.77 (m, 1H), 3.92, 3.93 (two s, 3H), 3.99–4.12 (m, 1H), 4.28 (s, 1H), 4.45–4.50 (m, 1H), 4.56–4.61 (m, 1H), 4.67–4.74 (m, 1H), 4.94–5.06 (m, 1H), 5.20 (d, J=17 Hz, 1H), 5.53 (m, 1H), 5.82–6.05 (m, 1H), 7.06 (dd, J=9, 2 Hz, 1H), 7.23 (m, 1H), 7.37–7.38 (m, 1H), 7.46–7.54 (m, 3H), 8.04–8.08 (m, 3H).

methylcyclopropanesulfonylaminocarbonyl)-2-vinylcyclopropyl]amide: ¹H NMR (methanol-d₄) δ 0.09–0.13 (m, 2H), 0.39–0.46 (m, 2H), 0.74–0.98 (m, 5H), 1.06 (s, 9H), 1.34–1.39 (m, 1H), 1.84 (dd, J=7.9, 5.2 Hz, 1H), 1.98–2.03 (m, 1H), 2.13–2.20 (m, 1H), 2.36–2.48 (m, 1H), 2.66–2.75 (m, 1H), 3.94 (s, 3H), 4.08–4.16 (m, 1H), 4.42–4.46 (m, 1H), 4.54–4.59 (m, 2H), 4.63–4.66 (m, 1H), 5.03–5.08 (m, 1H), 5.23–5.27 (m, 1H), 5.56 (m, 1H),

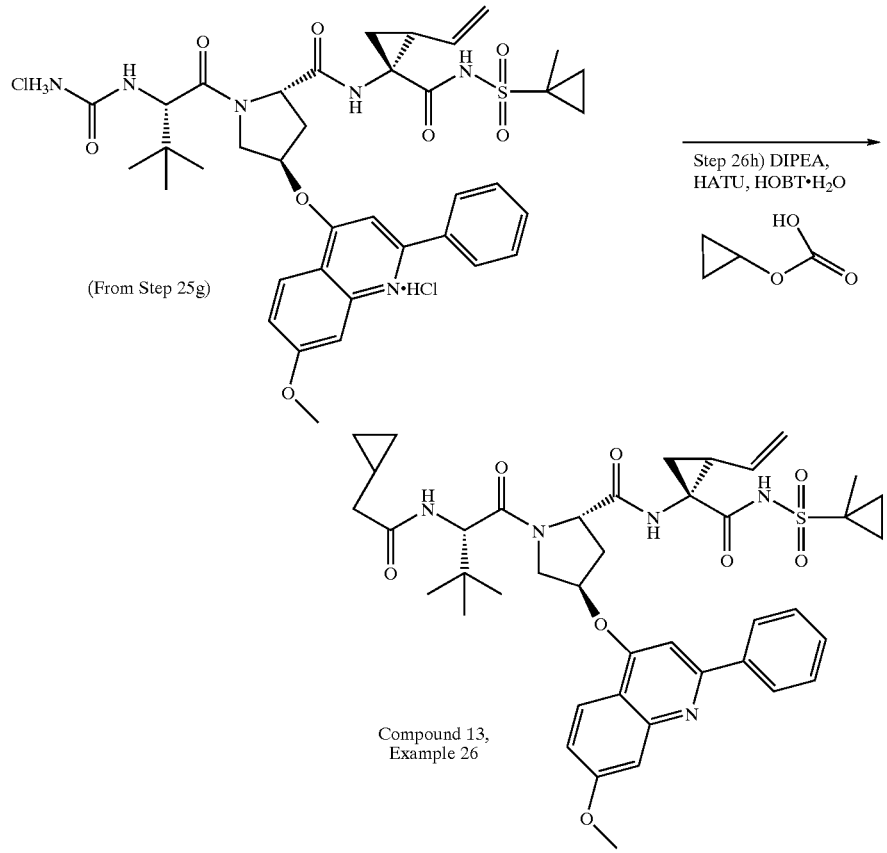

5.76–5.84 (m, 1H), 7.08–7.10 (m, 1H), 7.23–7.25 (m, 1H), 7.30 (d, J=2 Hz, 1H), 7.47–7.55 (m, 3H), 8.01–8.06 (m, 3H).

Section B

The following columns and conditions were used in the Examples cited in Section B.

Columns: (Method A)—YMC ODS S7 C18 3.0×50 mm
(Method B)—YMC ODS-A S7 C18 3.0×50 mm
(Method C)—YMC S7 C18 3.0×50 mm
(Method D)—YMC Xterra ODS S7 3.0×50 mm
(Method E)—YMC Xterra ODS S7 3.0×50 mm
(Method F)—YMC ODS-A S7 C18 3.0×50 mm
(Method H),—Xterra S7 3.0×50 mm
(Method I)—Xterra S7 C18 3.0×50 mm
(Method G)—YMC C18 S5 4.6×50 mm
(Method J)—Xterra ODS S7 3.0×50 mm
(Method K)—YMC ODS-A S7 C18 3.0×50 mm
(Method L)—Xterra ODS S7 3.0×50 mm
(Method M)—Xterra ODS S5 3.0×50 mm
(Method N)—Xterra C-18 S5 4.6×50 mm Gradient: 100% Solvent A/0% Solvent B to 0% Solvent A/100% Solvent B Compound 13 Example 26

Preparation of P4(cyclopropylCH₂(C=O)NH)—P3(L-t-BuGly)-P2[(4R)-(2-phenyl-7-methoxyquinoline-4-oxo)-S-proline]-P1(1R,2S Vinyl Acca)-CONHSO₂(1-methyl-1-cyclopropane) or Alternate Designation, Compound 13 the (1R,2S) P1 Isomer of 1-[2-(2-Cyclopropyl-acetylamino)-3,3-dimethyl-butyryl]-4-(7-methoxy-2-phenylquinolin-4-yloxy)-pyrrolidine-2-carboxylic acid [1-(1-methylcyclopropanesulfonylaminocarbonyl)-2-vinylcyclopropyl]amide Step 26h) To a slurry of 80 mg (0.103 mmol) of the Bis HCl salt product of Step 25 g, 19 mg (0.12 mmol) of HOBT.H₂O, 12.4 mg (0.124 mmol) of cyclopropyl acetic acid (Aldrich) and 67 mg (0.52 mmol) of DIPEA in 2 mL of CH₂Cl₂, was added 47 mg (0.124 mmol) of HATU, and the mixture stirred overnite. The mixture was concentrated in vacuo and the residue chromatographed over two 1000 μ PTLC plates from Analtech (each 20×40 cm, eluted sequentially with 0% to 3% MeOH in CH₂Cl₂) to afford 51 mg (63%) of the desired P4 carbamate, Compound 13, Example 26, the (1R,2S) P1 isomer of 1-[2-(2-Cyclopropylacetylamino)-3,3-dimethyl-butyryl]-4-(7-methoxy-2-phenyl-quinolin-4-yloxy)-pyrrolidine-2-carboxylic acid [1-(1-

Gradient time: 2 min. (A, B, D, F, G, H, I, L); 8 min. (C, E); 4 min (J); 3 min (K)
Hold time: 1 min. (A, B, D, F, G, H, I, J, K, L, N); 2 min. (C, E)
Flow rate: 5 mL/min (A, B, C, D, E, F, G)
Flow rate: 4 ml/min (J, K, N)
Detector Wavelength: 220 nm
Solvent A: 10% MeOH/90% H$_2$O/0.1% TFA
Solvent B: 10% H$_2$O/90% MeOH/0.1% TFA.

Compound 27 Example 27 compound 27

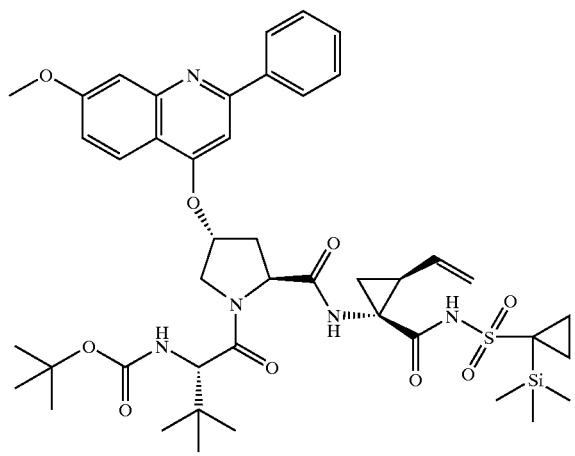

Compound 27, Example 27, BOCNH—P3(L-t-BuGly)-P2[(4R)-(2-phenyl-7-methoxyquinoline-4-oxo)-S-proline]-P1(1R,2S Vinyl Acca)-CONHSO$_2$(1-trimethylsilanylcyclopropan-1-yl) or Alternate Designation, Compound 27, Example 27, {1-[2-[2-Ethyl-1-(1-trimethylsilanyl-cyclopropanesulfonylaminocarbonyl)-cyclopropylcarbamoyl]-4-(7-methoxy-2-phenyl-quinolin-4-yloxy)-pyrrolidine-1-carbonyl]-2,2-dimethyl-propyl}-carbamic acid tert-butyl ester Step 27a: N-tert-Butyl-(1-trimethylsilanyl)cyclopropylsulfonamide compound 27a

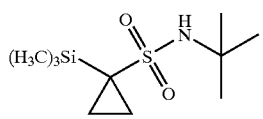

Step 27a) This compound was obtained in 84% yield from N-tert-Butyl-(3-chloro) propylsulfonamide according to the procedure of Steps 3Ib–3Ic (Example 2) described in the synthesis of N-tert-Butyl-(1-methyl) cyclopropylsulfonamide and 2.0 equivalents of trimethylsilyl chloride was used 4sed as electrophile. The compound was used as crude.

Step 27b: Preparation of (1-trimethylsilanyl)cyclopropylsulfonamide compound 27b

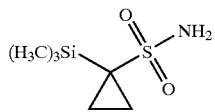

Step 27b) This compound was obtained in 73% yield from N-tert-butyl-(1-trimethylsilanyl)cyclopropylsulfonamide according to the procedure of Steps 3Id (Example 2) described in the synthesis of 1-methylcyclopropylsulfonamide. The compound was recrystallized from EtOAc/hexanes: $^1$H NMR (CHLOROFORM-D) δ ppm 0.17 (s, 9H), 0.91 (m, 2H), 1.33 (m, 2H), 4.47 (s, 2H).

Step 27c: Preparation of Comppound 27, Example 27, BOCNH—P3(L-t-BuGly)-P2[(4R)-(2-phenyl-7-methoxyquinoline-4-oxo)-S-proline]-P1(1R,2S Vinyl Acca)-CONHSO$_2$(1-trimethylsilanyl-cyclopropan-1-yl) or Alternate Designation, Compound 27, Example 27, {1-[2-[2-Ethyl-1-(1-trimethylsilanyl-cyclopropanesulfonylaminocarbonyl)-cyclopropylcarbomoyl]-4-(7-methoxy-2-phenyl-quinolin-4-yloxy)-pyrrolidine-1-carbonyl]-2,2-dimethyl-propyl}-carbamic acid tert-butyl ester

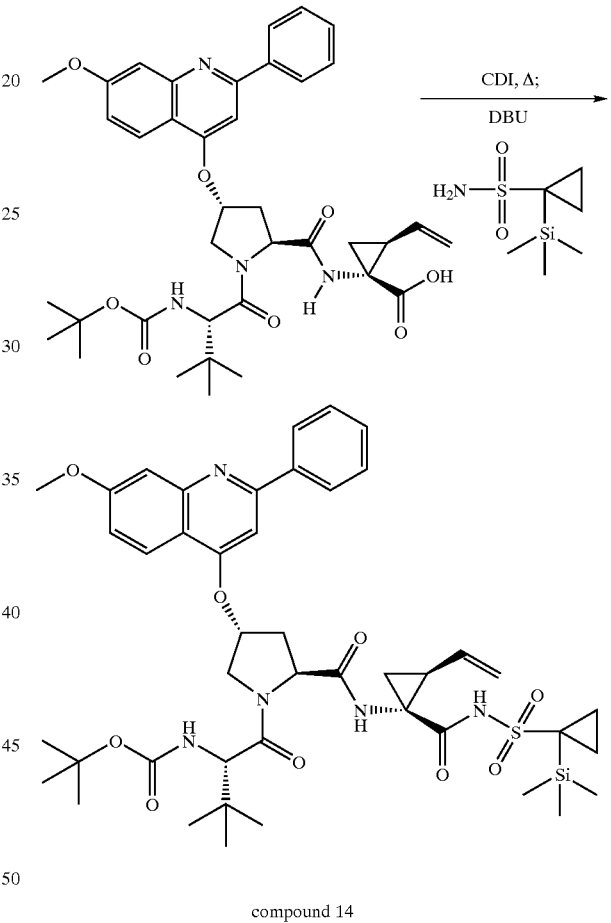

compound 14

Step 27c) To a solution of the tripeptide acid (0.080 g, 0.116 mmol) of the product of step 2e (Example 2) in THF (2 mL) was added CDI (0.0264 g, 0.16 mmol), and the resulting solution was heated at 72° C. for 1 h and allowed to cool down to rt. 1-Trimethylsilanylcyclopropylsulfonamide (0.027 g, 0.14 mmol) and neat DBU (0.024 mL, 0.16 mmol) were added. The reaction mixture was stirred for 16 h, diluted with EtOAc (150 mL) and washed pH 4.0 buffer (2×30 mL), dried (Na$_2$SO$_4$/MgSO$_4$), concentrated. The residue was purified over 20×40 cM 1000 □ Analtech PTLC plates (MeOH/CH$_2$Cl$_2$: 2 to 4%) to afford the desired product (Compound 27) 0.0811 g (88%) as a white foam: $^1$H NMR (CDCl$_3$/methanol-d$_4$) □ ppm 0.12 (s, 9H), 1.04 (m, 24H), 1.76 (m, 1H), 1.98 (m, 1H), 2.59 (m, 1H), 3.90 (s, 3H), 4.03 (m, 1H), 4.25 (d, J=4.88 Hz, 1H), 4.43 (d, J=11.29 Hz, 1H), 4.58 (s, 1H), 4.96 (s, 1H), 5.12 (m, 1H), 5.34 (s, 1H), 5.84 (m, 1H), 7.02 (m, 2H), 7.36 (m, 1H), 7.46 (m, 3H), 7.95 (m, 3H). HRMS d/z (M+H)⁺calcd for $C_{44}H_{60}N_5SSiO_9$: 862.3881 found: 862.3888. LC-MS (retention time: 1.78, Method I), MS m/z 862(M⁺+1).

Compound 28 Example 28 compound 28

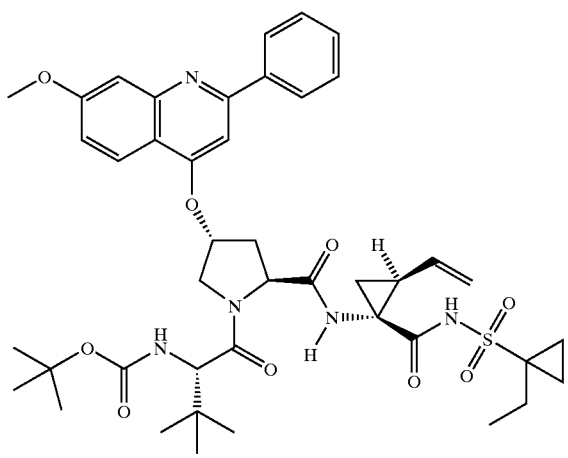

Step 28a: Preparation of N-tert-Butyl-1-ethyl-cyclopropylsulfonamide compound 28a

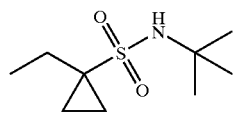

Step 28a) This compound was prepared form N-tert-Butyl-(3-chloro) propylsulfonamide (59 g, 276 mmol) and ethyl iodide (86.11 g, 552 mmol) according to the procedure of Steps 3Ib-3Ic (Example 2) described in the synthesis of N-tert-Butyl-(1-methyl) cyclopropylsulfonamide. The compound was used as crude: ¹H NMR (CHLOROFORM-D) □ ppm 0.82 (m, 2H), 0.99 (t, J=7.48 Hz, 3H), 1.33 (m, 11H), 1.92 (q, J=7.53 Hz, 2H), 3.91 (s, 1H).

Step 28b: Preparation 1-ethyl-cycloproplsulfonamide compound 28b

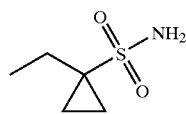

Step 28b) This compound was obtained in 49% yield (19 g) in two steps according to the procedure of Steps 3Id (Example 2) described in the synthesis of 1-methylcyclopropylsulfonamide. The compound was recrystallized from EtOAc/hexanes as a white solid: ¹H NMR (CHLOROFORM-D) δ ppm 0.85 (m, 2H), 1.03 (t, J=7.48 Hz, 3H), 1.34 (m, 2H), 1.96 (q, J=7.32 Hz, 2H), 4.61 (s, 2H).

Step 28c: Preparation of Compound 28, Example 28, BOCNH—P3(L-t-BuGly)-P2[(4R)-(2-phenyl-7-methoxyquinoline-4-oxo)-S-proline]-P1(1R,2S Vinyl Acca)-CONHSO₂(1-ethyl-cyclopropan-1-yl) or Alternate Designation Compound 28, Example 28, {1-[2-[2-Ethyl-1-(1-ethyl-cyclopropanesulfonylaminocarbonyl)-cyclopropylcarbamoyl]-4-(7-methoxy-2-phenyl-quinolin-4-yloxy)-pyrrolidine-1-carbonyl]-2,2-dimethyl-propyl}-carbamic acid tert-butyl ester

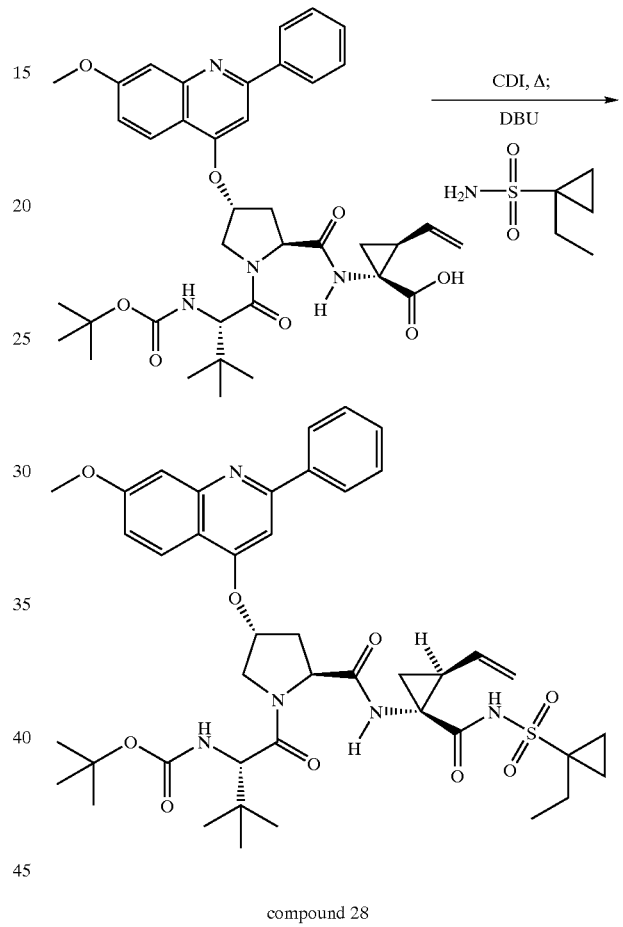

compound 28

Step 28c) Compound 28 was prepared in 63% yield (0.1878 g) from tripeptide acid (0.25 g, 0.36 mmol) of the product of step 2e (Example 2) in analogous fashion to the procedure of Step 27c of Example 27 except that 1-ethyl-cyclopropanesulfonic acid amide was used in place of 1-trimethylsilanyl-cyclopropanesulfonamide: ¹H NMR (methanol-d₄) □ ppm 0.91 (m, 2H), 0.96 (t, J=7.48 Hz, 3H), 1.04 (s, 9H), 1.27 (s, 9H), 1.47 (m, 3H), 1.83 (m, 2H), 1.95 (m, 1H), 2.26 (m, 2H), 2.67 (m, 1H), 3.94 (s, 3H), 4.08 (d, J=10.38 Hz, 1H), 4.24 (dd, J=16.79, 9.16 Hz, 1H), 4.52 (m, 2H), 5.10 (m, 1H), 5.28 (m, 1H), 5.53 (s, 1H), 5.68 (m, 1H), 7.06 (d, J=8.85 Hz, 1H), 7.22 (s, 1H), 7.38 (s, 1H), 7.51 (m, 3H), 8.05 (m, 3H). HRMS m/z (M−H)⁻ calcd for $C_{43}H_{54}N_5SO_9$: 816.3642 found: 816.3651. LC-MS (retention time: 1.65, Method I), MS m/z 818 (M⁺+1).

Compound 29 Example 29

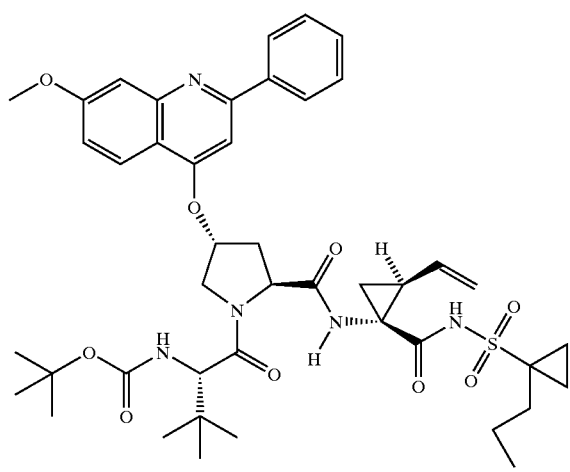

compound 29

Step 29a: Preparation of N-tert-Butyl-1-propyl-cyclopropylsulfonamide

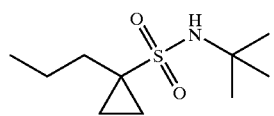

compound 29a

Step 29a) This compound was prepared in 70% (42.2 g) form N-butyl-3-chloropropane sulfonamide (59 g, 276 mmol) and propyl bromide (552 mmol) according to the procedure of Steps 3Ib–3Ic (Example 2) described in the synthesis of N-tert-butyl-(1-methyl) cyclopropylsulfonamide. The compound was used as crude: $^1$H NMR (300 MHz, CHLOROFORM-D) □ ppm 0.82 (m, 2H), 0.92 (t, J=7.32 Hz, 3H), 1.35 (s, 9H), 1.82 (m, 2H), 3.90 (s, 1H).

Step 29b: Preparation 1-propyl-cyclopropylsulfonamide

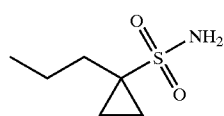

compound 29b

Step 29b) This compound was made from Compound 29a in 80% yield (25.15 g) from N-tert-butyl-(1-propyl) cyclopropylsulfonamide (42.2 g, 193 mmol) according to the procedure of Steps 3Id (Example 2) described in the synthesis of 1-methylcyclopropylsulfonamide. The compound was recrystallized from EtOAc/hexanes as a white solid: $^1$H NMR CHLOROFORM-D) δ ppm 0.85 (m, 2H), 0.94 (t, J=7.32 Hz, 3H), 1.36 (m, 2H), 1.47 (m, 2H), 1.87 (m, 2H), 4.42 (s, 2H).

Step 29c: Preparation of Compound 29, Example 29, BOCNH—P3(L-t-BuGly)-P2[(4R)-(2-phenyl-7-methoxyquinoline-4-oxo)-S-proline]-P1 (1R,2S Vinyl Acca)-CONHSO$_2$(1-propyl-cyclopropan-1-yl) or Alternate Designation, Compound 29, Example 29, (1-{4-(7-Methoxy-2-phenyl-quinolin-4-yloxy)-2-[1-(1-propyl-cyclopropanesulfonylaminocarbonyl)-2-vinyl-cyclopropylcarbamoyl]-pyrrolidine-1-carbonyl}-2,2-dimethyl-propyl)-carbamic acid tert-butyl ester

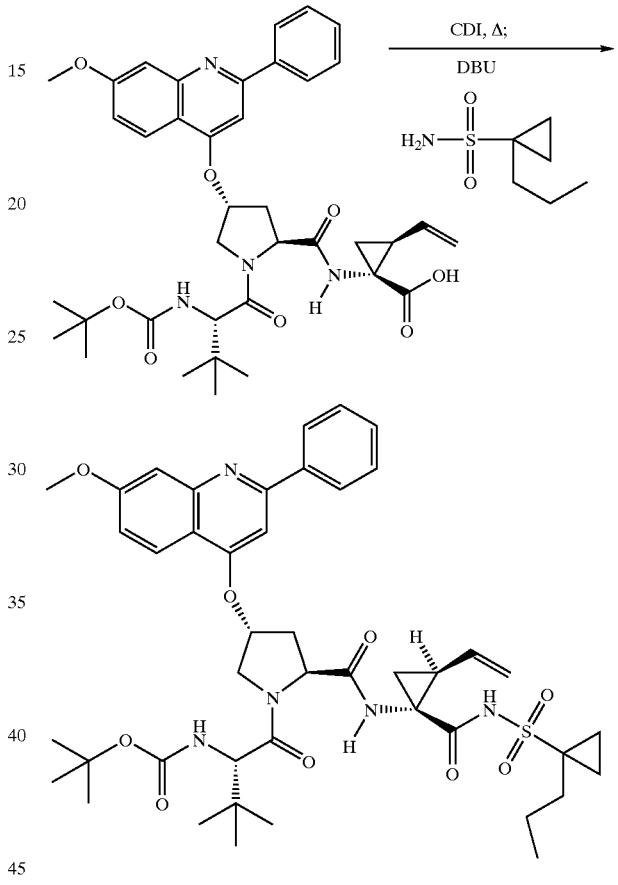

compound 29

Step 29c) This compound was prepared in 62% yield (0.190 g) from tripeptide acid (0.250 g, 0.36 mmol) of the product of step 2e (Example 2) in analogous fashion to the procedure of Step 27c of Example 27 except that 1-propyl-cyclopropanesulfonic acid amide was used in place of 1-trimethylsilanylcyclopropanesulfonamide: $^1$H NMR (methanol-d$_4$) □ ppm 0.87 (m, 5H), 1.05 (s, 9H), 1.28 (s, 9H), 1.45 (m, 5H), 1.80 (m, 3H), 2.16 (m, 1H), 2.43 (m, 1H), 2.69 (dd, J=15.00, 8.05 Hz, 1H), 3.95 (s, 3H), 4.13 (m, 1H), 4.26 (d, J=8.78 Hz, 1H), 4.53 (m, 2H), 5.07 (d, J=10.98 Hz, 1H), 5.24 (d, J=16.83 Hz, 1H), 5.57 (s, 1H), 5.75 (m, 1H), 7.07 (dd, J=8.97, 2.01 Hz, 1H), 7.26 (s, 1H), 7.39 (d, J=2.20 Hz, 1H), 7.52 (m, 3H), 8.05 (m, 3H). HRMS m/z (M–H)$^-$ calcd for C$_{44}$H$_{56}$N$_5$SO$_9$: 830.3799 found: 830.3816. LC (retention time: 1.83, Method H), MS m/z 833 (M$^+$+1).

Compound 30 Example 30 compound 30

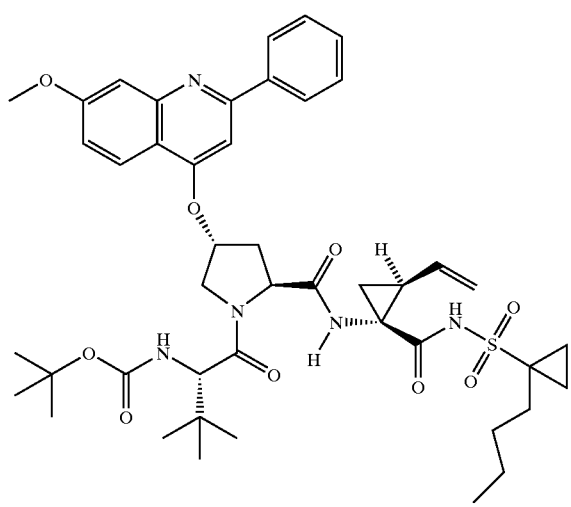

Step 30a: Preparation 1-butyl-cyclopropanesulfonamide-tert-butylcarbamate

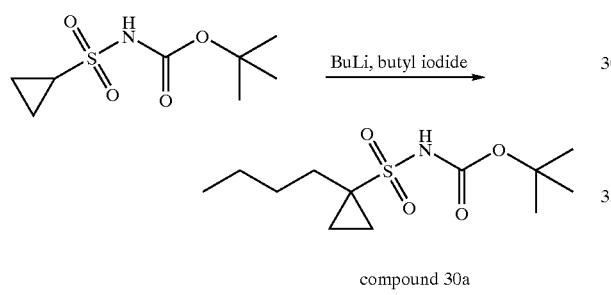

compound 30a

Step 30a) This compound, 1-butyl-cyclopropanesulfonamide-tert-butylcarbamate, was obtained in 89% yield (1.12 g) from 1.0 g (4.5 mmol) of cyclopropanesulfonamide-tert-butylcarbamate according to the procedure described in the synthesis of 1-methoxymethylcyclopropylsulfonylamine tert-butylcarbamate (Step 15IId) except 1.1 equivalents of butyl iodide was used as electrophile. The compound was purified by flash chromatography over $SiO_2$ using EtOAc/Hexanes (0% to 50%) as the eluent: $^1$H NMR ($CDCl_3$) □ ppm 0.91 (m, 5H), 1.31 (m, 2H), 1.40 (m, 2H), 1.50 (s, 9H), 1.62 (m, 2H), 1.86 (m, 2H), 6.77 (s, 1H); $^{13}$C NMR ($CDCl_3$) □ ppm 12.36, 13.93, 22.80, 28.06, 28.48, 31.33, 40.65, 83.92, 149.25.

Step 30b: Preparation of 1-butyl-cyclopropanesulfonamide compound 30b

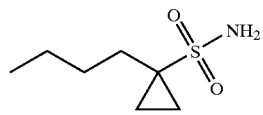

Step 30b) A mixture of 1-butyl-cyclopropylsulfonylamine tert-butylcarbamate (1.2 g, 4.3 mmol) and TFA (2 mL, 26 mmol) was stirred at rt overnite. The solvent was removed in vacuo and the residue was chromatographed over $SiO_2$ eluting with EtOAC/Hexanes (0% to 50%) to afford 1-butyl-cyclopropanesulfonic acid amide, as a white solid (0.69 g, 90%): $^1$H NMR (methanol-$d_4$) □ ppm 0.83 (m, 2H), 0.92 (t, J=7.32 Hz, 2H), 1.24 (m, 2H), 1.34 (m, 2H), 1.47 (m, 2H), 1.87 (m, 2H); $^1$CNMR (methanol-$d_4$) □ ppm 12.09, 14.25, 23.93, 29.82, 32.38, 41.92.

Step 30c: Preparation of Compound 30, Example 30, BOCNH—P3(L-t-BuGly)-P2[(4R)-(2-phenyl-7-methoxyquinoline-4-oxo)-S-proline]-P1 (1R,2S Vinyl Acca)-$CONHSO_2$(1-butyl-cyclopropan-1-yl) or Alternate Designation, Compound 30, Example 30, {1-[2-[1-(1-Butyl-cyclopropanesulfonylaminocarbonyl)-2-vinyl-cyclopropylcarbamoyl]-4-(7-methoxy-2-phenyl-quinolin-4-yloxy)-pyrrolidine-1-carbonyl]-2,2-dimethyl-propyl}-carbamic acid tert-butyl ester

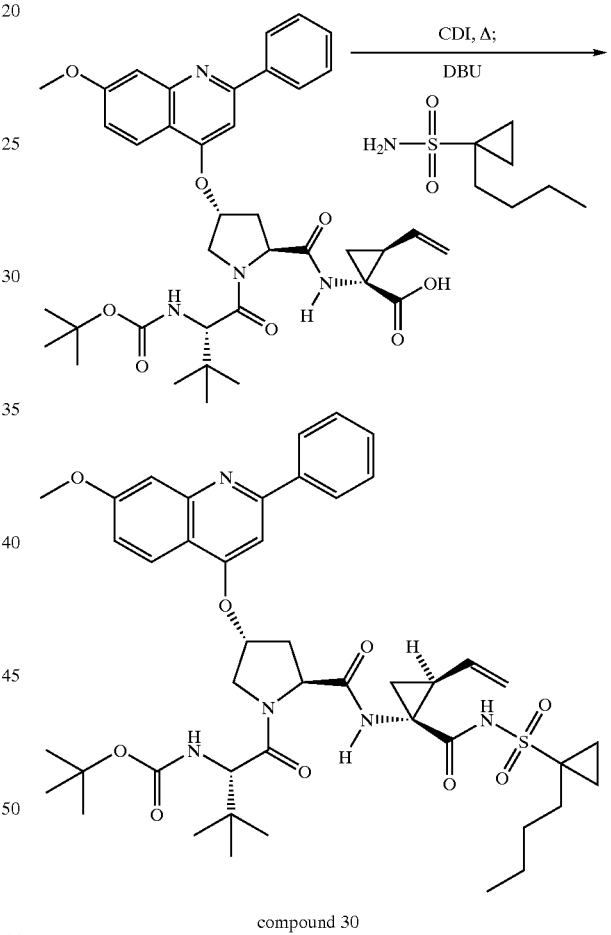

compound 30

Step 30c) This compound was prepared in 30% yield (22.1 g) from tripeptide acid (0.060 g, 0.09 mmol)) of the product of step 2e (Example 2) in analogous fashion to the procedure Step 27c of Example 27 except that 1-butyl-cyclopropanesulfonamide (Step 30b) was used in place of 1-trimethylsilanyl-cyclopropanesulfonamide and purified by PTLC (MeOH/$CH_2Cl_2$) and preparative HPLC (solvent B: 35% to 85%): $^1$H NMR (methanol-$d_4$) □ ppm 0.83 (m, 5H), 1.03 (s, 9H), 1.27 (s, 9H), 1.34 (m, 7H), 1.82 (m, 3H), 2.14 (m, 1H), 2.44 (m, 1H), 2.68 (dd, J=12.99, 7.14 Hz, 1H), 3.92 (s, 3H), 4.06 (m, 1H), 4.24 (s, 1H), 4.53 (m, 2H), 5.02 (d, J=10.61 Hz, 1H), 5.20 (d, J=16.83 Hz, 1H), 5.51 (s, 1H), 5.92 (m, 1H), 7.04 (d, J=8.78 Hz, 1H), 7.21 (s, 1H), 7.36 (s, 1H), 7.50 (m, 3H), 8.04 (m, 3H). LC-MS (retention time: 1.80, Method I), MS m/z 846 (M$^+$+1).

Compound 31 Example 31

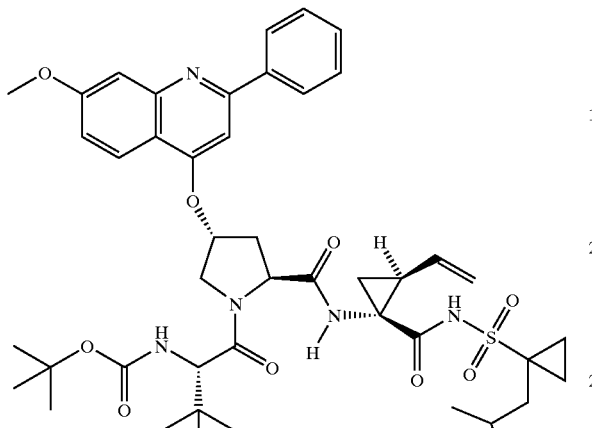

compound 31

Step 31a: Preparation of 1-iso-butyl-cyclopropanesulfonamide-tert-butylcarbamate Step 31a) To a solution of N,N-diisopropylamine (1.1 ml, 9.54 mmol) dissolved in THF (10 mL) cooled to −78° C., was added n-BuLi (1.6 M in hexane, 5.9 mL, 9.54 mmol). The mixture was stirred for 1 h, and a THF (10 mL) solution of cyclopropylsulfonylamine tert-butyl carbamate (1.0 g, 4.52 mmol) was added dropwise, the generated solution was stirred for 1 h. To this solution was added neat iso-butyl iodide (0.57 mL, 5.0 mmol). The reaction mixture was allowed slowly to warm up overnite. The reaction mixture was poured into cold pH 4.0 buffer and the pH was adjusted to <4 and extracted with EtOAc (3×). The combined extracts were dried (MgSO$_4$), concentrated. The residue was chromatographed over SiO$_2$ eluting with EtOAC/Hexanes (0% to 50%) to afford the product in 69% yield (0.87 g) as a white solid: $^1$H NMR (CDCl$_3$) □ ppm 0.92 (m, 2H), 0.95 (d, J=6.71 Hz, 6H), 1.49 (s, 9H), 1.69 (m, 2H), 1.71 (s, 2H), 1.95 (m, 1H), 6.80 (s, 1H).

Step 31b: Preparation of 1-iso-butyl-cyclopropanesulfonamide

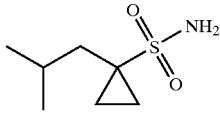

compound 31b

Step 31b) This compound, 1-isobutyl-cyclopropanesulfonic acid amide, was obtained in 69% yield (0.40 g) from 0.61 g (2.2 mmole) of 1-iso-butyl-cyclopropanesulfonamide-tert-butylcarbamate, according to the procedure described in the synthesis of 1-butyl-cyclopropanesulfonamide (Step 30b, Example 30) to provide the product as a white solid: $^1$H NMR (CDCl$_3$) □ ppm 0.83 (m, 2H), 0.96 (d, J=6.71 Hz, 6H), 1.39 (m, 2H), 1.72 (d, J=7.32 Hz, 2H), 2.01 (m, 1H), 4.51 (s, 2H); $^{13}$C NMR (CDCl$_3$) □ ppm 12.94, 23.40, 27.34, 40.32, 42.60.

Step 31c: Preparation of Compound 31, Example 31, BOCNH—P3(L-t-BuGly)-P2[(4R)-(2-phenyl-7-methoxyquinoline-4-oxo)-S-proline]-P1(1R,2S Vinyl Acca)-CONHSO$_2$(1-iso-butyl-cyclopropan-1-yl) or Alternate Designation, Compound 31, Example 31, {1-[2-[1-(1-Isobutyl-cyclopropanesulfonylaminocarbonyl)-2-vinyl-cyclopropylcarbamoyl]-4-(7-methoxy-2-phenyl-quinolin-4-yloxy)-pyrrolidine-1-carbonyl]-2,2-dimethyl-propyl}-carbamic acid tert-butyl ester

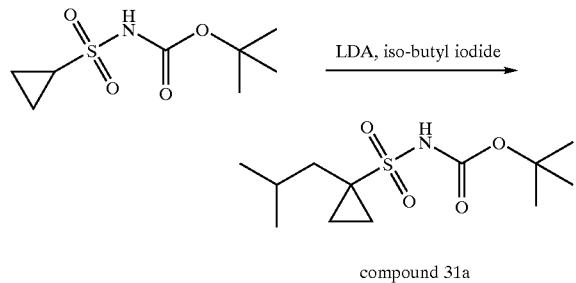

compound 31

Step 31c) Compound 31 was prepared in 48% yield (0.0352 g) from tripeptide acid (0.060 g, 0.09 mmol)) of the product of step 2e (Example 2) in analogous fashion to the procedure of Step 27c (Example 27) except that 1-isobutyl-cyclopropanesulfonamide (step 31b) was used in place of 1-trimethylsilanyl-cyclopropanesulfonamide and purified by PTLC plates from Analtech (catalog #2053) using MeOH/CH$_2$Cl$_2$ as eluent (50% to 0% to 5%) and EM Plates (catalog #5744-7) using MeOH/CH$_2$Cl$_2$ as eluent (MeOH/CH$_2$Cl$_2$: 1% to 2.5%) to provide the product as a white foam: $^1$H NMR (methanol-d$_4$) ☐ ppm 0.87 (m, 2H), 0.95 (d, J=6.71 Hz, 6H), 1.05 (s, 9H), 1.29 (m, 9H), 1.50 (m, 4H), 1.80 (m, 1H), 2.06 (m, 3H), 2.44 (m, 1H), 2.68 (dd, J=13.58, 7.17 Hz, 1H), 3.94 (s, 3H), 4.14 (m, 1H), 4.26 (m, 1H), 4.53 (m, 2H), 5.04 (m, 1H), 5.23 (m, 1H), 5.55 (s, 1H), 5.77 (m, 1H), 7.06 (dd, J=9.16, 2.14 Hz, 1H), 7.24 (s, 1H), 7.38 (d, J=2.14 Hz, 1H), 7.51 (m, 3H), 8.07 (m, 3H). LC-MS (retention time:1.79, Method I), MS m/z 846 (M$^+$+1).

Compound 32 Example 32

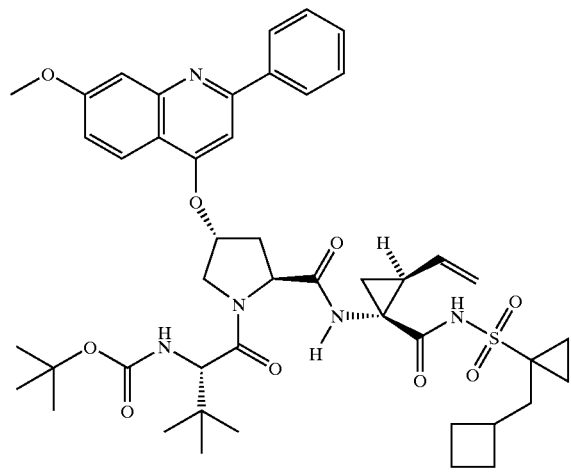

compound 32

Step 32a: Preparation of 1-cyclobutylmethyl-cyclopropanesulfonamide-tert-butylcarbamate

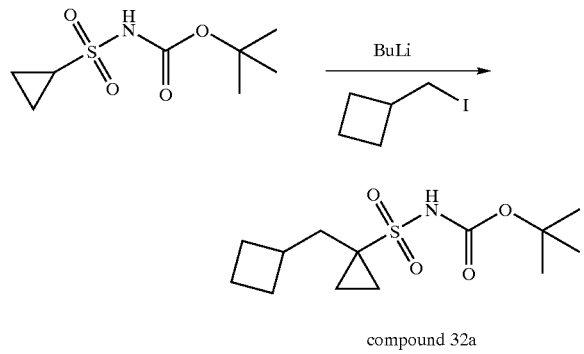

compound 32a

Step 32a) This compound, 1-cyclobutylmethyl-cyclopropanesulfonamide-tert-butylcarbamate, was obtained in 55% yield (0.72 g) from 1.0 g (4.52 mmol) of cyclopropanesulfonamide-tert-butylcarbamate according to the procedure described in the synthesis of 1-butylcyclopropanesulfonamide (Step 30a) except that 1.10 equivalents of cyclobutylmethyl iodide was used as electrophile: $^1$H NMR (CDCl$_3$) ☐ ppm 0.89 (m, 2H), 1.49 (s, 9H), 1.55 (m, 2H), 1.64 (m, 2H), 1.82 (m, 2H), 2.02 (d, J=7.32 Hz, 2H), 2.07 (m, 2H), 2.37 (m, 1H); $^{13}$C NMR (CDCl$_3$) ☐ ppm 11.29, 18.75, 27.96, 29.14, 32.84, 37.29, 39.44, 83.78, 149.31.

Step 32b: Preparation of (1-cyclobutylmethyl-cyclopropane) sulfonamide

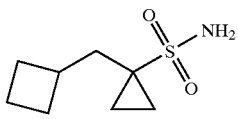

compound 32b

Step 32b) This compound, 1-cyclobutylmethyl-cyclopropanesulfonic acid amide, was obtained in 99% yield (0.136 g) from 0.21 g (0.76 mmole) of 1-cyclobutylmethyl-cyclopropanesulfonamide-tert-butylcarbamate, according to the procedure described in the synthesis of 1-butyl-cyclopropanesulfonamide (Step 30b, Example 30) to provide the product as a white solid: $^1$H NMR (Methanol-d$_4$) ☐ ppm 0.82 (m, 2H), 1.18 (m, 2H), 1.68 (m, 2H), 1.80 (m, 1H), 1.89 (m, 1H), 2.04 (d, J=7.32 Hz, 2H), 2.08 (m, 2H), 2.51 (dd, J=15.87, 7.93 Hz, 1H); $^{13}$C NMR (Methanol-d$_4$) ☐ ppm 11.12, 19.67, 30.20, 34.52, 38.48, 40.82.

Step 32c: Preparation of Compound 32, Example 32, BOCNH—P3(L-t-BuGly)-P2[(4R)-(2-phenyl-7-methoxyquinoline-4-oxo)-S-proline]-P1 (1R, 2S Vinyl Acca)-CONHSO$_2$(1-cyclobutylmethylcyclopropan-1-yl) or Alternate Designation, Compound 32, Example 32, {1-[2-[1-(1-Cyclobutylmethyl-cyclopropanesulfonylaminocarbonyl)-2-vinyl-cyclopropylcarbamoyl]-4-(7-methoxy-2-phenyl-quinolin-4-yloxy)-pyrrolidine-1-carbonyl]-2,2-dimethyl-propyl}-carbamic acid tert-butyl ester

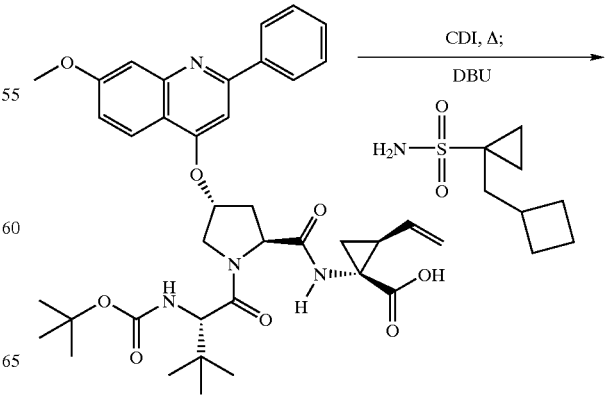

compound 32

Step 32c) Compound 32 was prepared in 34% yield (0.0255 g) from tripeptide acid product (0.060 g, 0.09 mmol) of step 2e (Example 2) in analogous fashion to the procedure of Step 27c of Example 27 except that 1-Cyclobutylmethyl-cyclopropanesulfonic acid amide was used in place of 1-trimethylsilanylcyclopropanesulfonamide and purified by preparative HPLC (solvent B: 35% to 85%) to afford the product as a foam: $^1$H NMR (methanol-$d_4$) □ ppm 0.70 (m, 2H), 1.04 (s, 9H), 1.28 (s, 9H), 1.33 (m, 3H), 1.70 (m, 5H), 2.04 (m, 5H), 2.38 (m, 2H), 2.69 (dd, J=13.54, 6.95 Hz, 1H), 3.93 (s, 3H), 4.08 (m, 1H), 4.24 (s, 1H), 4.53 (m, 2H), 5.02 (d, J=10.98 Hz, 1H), 5.20 (d, J=17.20 Hz, 1H), 5.54 (s, 1H), 5.99 (m, 1H), 7.07 (m, 1H), 7.23 (s, 1H), 7.37 (d, J=1.83 Hz, 1H), 7.49 (m, 3H), 8.05 (m, 3H). LC-MS (retention time: 1.91, Method D), MS m/z 858(M++1).

Compound 33 Example 33 compound 33

Preparation of {1-[2-[1-(1-non-9-enyl-cyclopropanesulfonylaminocarbonyl)-2-vinyl-cyclopropylcarbamoyl]-4-(7-methoxy-2-phenyl-quinolin-4-yloxy)-pyrrolidine-1-carbonyl]-2,2-dimethyl-propyl}-carbamic acid tert-butyl ester Step 33a: Preparation of 1-dec-9-enyl-cyclopropanesulfonamide-tert-butylcarbamate

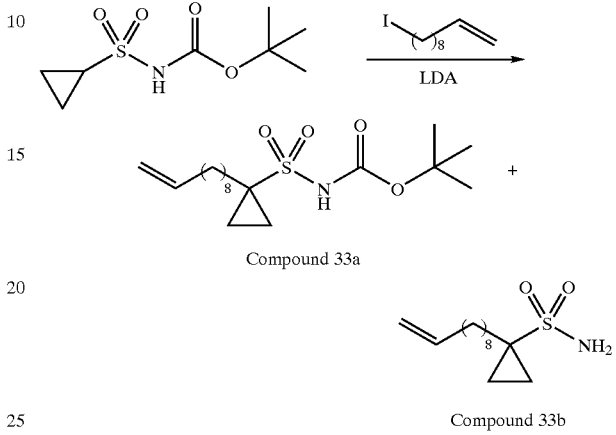

Compound 33a

Compound 33b

Step 33a) To a solution of diisopropyl-amine (2.5 ml) dissolved in THF (30 mL) cooled to −78° C., was added n-BuLi (10.6 mL, 17 mmol, 1.6 M in hexane). The mixture was stirred for 1 h, and a THF (10 mL) solution of cyclopropylsulfonylamine tert-butyl carbamate (1.5 g, 6.78 mmol) was added dropwise. After the reaction mixture was stirred for 1 h, neat 1-dec-9-enyl iodide (1.42 mL, 7.46 mmol) was added. The reaction mixture was allowed slowly to warm to rt overnite. The reaction mixture was poured into cold pH 4.0 buffer and the pH was adjusted to <4 and was then extracted with EtOAc (2×100 mL). The combined extracts were dried (MgSO$_4$), concentrated and purified by flash chromatograph over SiO$_2$ using EtOAc/Hexanes (0% to 80%) as the eluent to afford 1.41 g (58%) yield of compound 33a as a white solid and 0.22 g (13%) of compound 33b as an amber solid. Compound 33a: $^1$H NMR.(CDCl$_3$) □ ppm 0.87 (m, 2H), 1.44 (s, 9H), 1.43 (m, 17H), 2.01 (m, 2H), 4.92 (d, J=10.38 Hz, 1H), 4.98 (dd, J=17.24, 1.68 Hz, 1H); compound 33b: $^1$H NMR (CDCl$_3$) □ ppm 0.85 (m, 3H), 1.27 (s, 8H), 1.35 (m, 6H), 1.87 (m, 2H), 2.02 (m, 2H), 4.46 (s, 2H), 4.92 (dd, J=9.61, 1.68 Hz, 1H), 5.80 (m, 1H).

Step 33b: Preparation of 1-dec-9-enyl-cyclopropanesulfonamide

Compound 33b

Step 33b) Compound 33b was also obtained in the following method. 1-Dec-9-enyl-cyclopropanesulfonamide-tert-butylcarbamate, 0.94 g (2.6 mmole) was added into a HCl/dioxane solution (30 mL, 120 mmol). The reaction mixture was stirred for 6 h at rt. The solvent was removed in vacuo and the residue was chromatographed over SiO$_2$ using EtOAc/hexanes (0% to 50%) as the eluent to afford 0.51 g (75%) of compound 33b as a white solid.

85

Step 33c: Preparation of Compound 33, Example 33, BOCNH—P3(L-t-BuGly)-P2[(4R)-(2-phenyl-7-methoxyquinoline-4-oxo)-S-proline]-P1 (1R,2S Vinyl Acca)-CONHSO₂[1-(1-dec-9-enyl) cyclopropan-1-yl] or Alternate Designation, Compound 33, Example 33, {{1-[2-[1-(1-dec-9-enyl-cyclopropanesulfonylaminocarbonyl)-2-vinyl-cyclopropylcarbamoyl]-4-(7-methoxy-2-phenyl-quinolin-4-yloxy)-pyrrolidine-1-arbonyl]-2,2-dimethyl-propyl}-carbamic acid tert-butyl ester

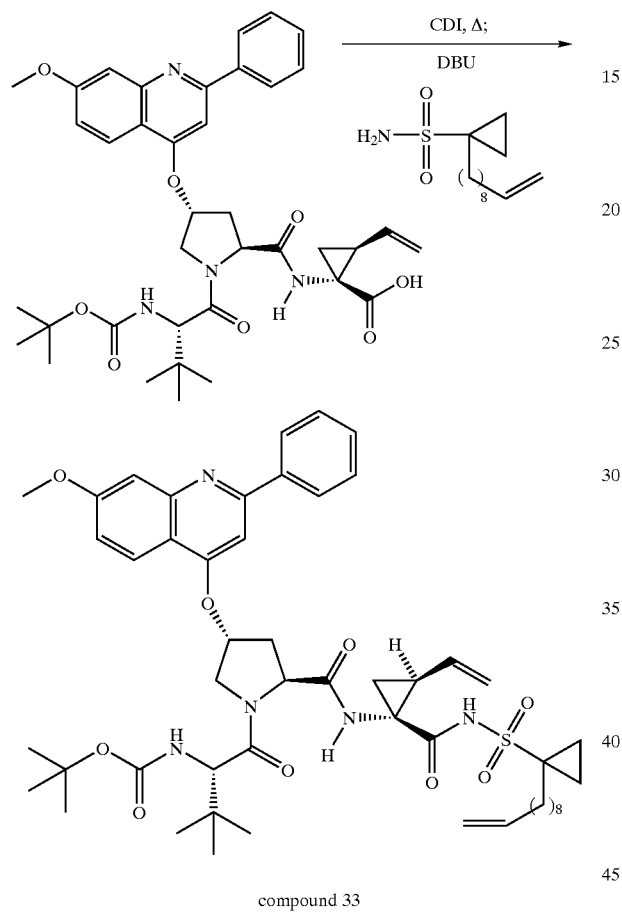

compound 33

Step 33c) Compound 33 was prepared in 63% yield (0.170 g) from tripeptide acid (0.200 g, 0.29 mmol) of the product of step 2e (Example 2) in analogous fashion to the procedure of Step 27c (Example 27) except that 1-dec-9-enyl-cyclopropanesulfonic acid amide was used in place of 1-trimethylsilanylcyclopropanesulfonamide and purified over PTLC plates from Analtech (catalog # 2050) using MeOH/CH₂Cl₂ as eluent (1% to 5%) as a white foam: $^1$H NMR (methanol-d₄) □ ppm 1.07 (s, 9H), 1.72 (m, 27H), 1.84 (m, 3H), 2.04 (m, 4H), 2.59 (m, 1H), 2.72 (m, 1H), 3.95 (s, 3H), 4.14 (m, 1H), 4.28 (s, 1H), 4.58 (m, 1H), 4.89 (s, 3H), 4.95 (m, 3H), 5.20 (d, J=17.09 Hz, 1H), 5.51 (m, 2H), 5.78 (m, 1H), 5.98 (m, 1H), 7.10 (m, 1H), 7.25 (s, 1H), 7.39 (d, J=2.44 Hz, 1H), 7.53 (m, 3H). HRMS m/z (M–H)⁻ calcd for $C_{51}H_{68}N_5SO_9$: 926.4738 found: 926.4750. LC-MS (retention time: 2.10, Method F).

86

Compound 34 Example 34

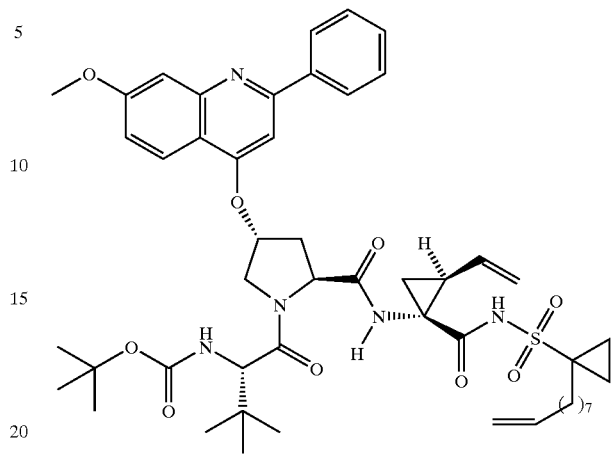

compound 34

Step 34a: Preparation of 1-non-8-enyl-cyclopropanesulfonamide-tert-butylcarbamate

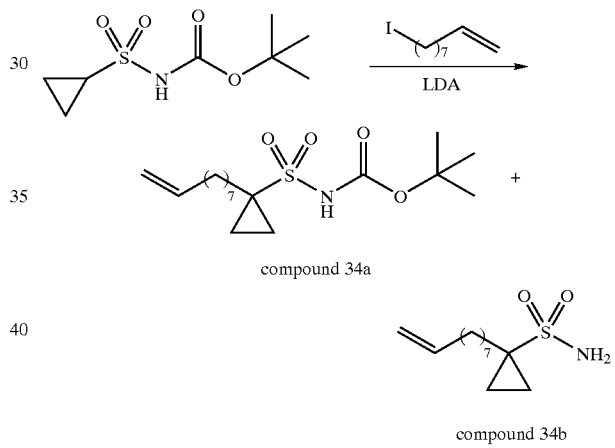

compound 34a compound 34b

Step 34a) These compounds, 1-non-8-enyl-cyclopropanesulfonamide-tert-butylcarbamate (compound 33a) in 50% yield (1.17 g), and -non-8-enyl-cyclopropanesulfonic acid amide (33b) in 25% (0.41 g) were obtained from 1.5 g (6.78 mmol) of cyclopropanesulfonamide-tert-butylcarbamate according to the procedure of Step 33a (Example 33) described in the synthesis of preparation of 1-dec-9-enyl-cyclopropanesulfonamide-tert-butylcarbamate except 1.10 equivalents of 1-non-8-enyl iodide was used as electrophile. Compound 34a: $^1$H NMR □ ppm 0.91 (m, 2H), 1.34 (m, 12H), 1.49 (s, 7H), 1.60 (m, 2H), 1.84 (m, 2H), 2.02 (q, J=7.02 Hz, 2H), 4.91 (m, 1H), 4.97 (m, 1H), 5.78 (m, 1H), 7.07 (s, 1H); $^{13}$C NMR (CDCl₃) □ ppm 12.30, 26.27, 28.01, 28.84, 28.98, 29.24, 29.58, 31.53, 33.73, 40.62, 83.83, 114.25, 139.07, 149.34; compound 33b: $^1$H NMR (CDCl₃) □ ppm 0.85 (m, 2H), 1.36 (m, 13H), 1.87 (m, 2H), 2.02 (m, 2H), 4.45 (s, 2H), 4.92 (m, 1H), 4.98 (m, 1H).

Step 34b: Preparation of 1-non-8-enyl-cyclopropanesulfonamide

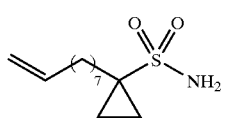

compound 34b

Step 33b) This compound, 1-non-8-enyl-cyclopropanesulfonic acid amide, was also obtained in 60% yield (0.193 g) from 0.451 g (1.31 mmole) of 1-non-8-enyl-cyclopropanesulfonamide-tert-butylcarbamate, according to the procedure of Step 33b (Example 33) described in the synthesis of 1-dec-9-enyl-cyclopropanesulfonamide as a white solid.

Step 34c: Preparation of Compound 34, Example 34, BOCNH—P3(L-t-BuGly)-P2[(4R)-(2-phenyl-7-methoxyquinoline-4-oxo)-S-proline]-P1 (1R,2S Vinyl Acca)-CONHSO$_2$[1-(1-non-8-enyl) cyclopropan-1-yl] or Alternate Designation, Compound 34, Example 34, (1-{4-(7-Methoxy-2-phenyl-quinolin-4-yloxy)-2-[1-(1-non-8-enyl-cyclopropanesulfonylaminocarbonyl)-2-vinyl-cyclopropylcarbamoyl]-1-pyrrolidine-1-carbonyl}-2,2-dimethyl-propyl)-carbamic acid tert-butyl ester

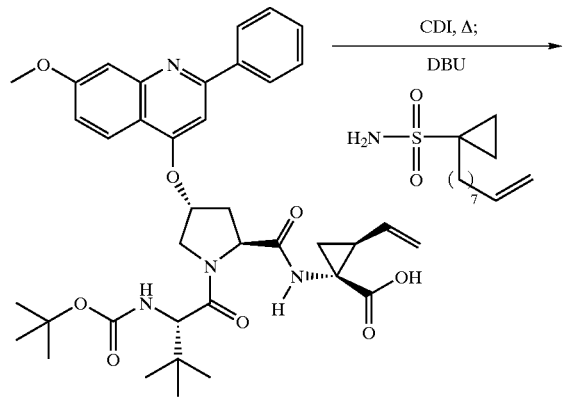

compound 34

Step 34c) Compound 34 was prepared in 61% (0.1619 g) yield from tripeptide acid product (200 g) of step 2e (Example 2) in analogous fashion to the procedure of Step 27c (Example 27) except that 1-non-8-enyl-cyclopropanesulfonamide was used in place of 1-tirmethylsilanyl-cyclopropanesulfonamide: $^1$H NMR (methanol-d$_4$) ☐ ppm 0.71 (m, 2H), 1.04 (s, 9H), 1.28 (m, 22H), 1.85 (m, 5H), 2.09 (m, 1H), 2.53 (s, 1H), 2.72 (m, 1H), 3.94 (m, 3H), 4.10 (m, 1H), 4.24 (s, 1H), 4.53 (m, 2H), 4.95 (m, 3H), 5.18 (m, 1H), 5.54 (s, 1H), 5.72 (m, 1H), 5.96 (s, 1H), 7.05 (m, 1H), 7.24 (s, 1H), 7.38 (m, 1H), 7.51 (m, 3H), 8.08 (m, 3H). HRMS m/z (M–H)$^-$ calcd for C$_{50}$H$_{66}$N$_5$SO$_9$: 912.4581 found: 912.4564. LC-MS (retention time: 2.03 Method F).

Compound 35 Example 35

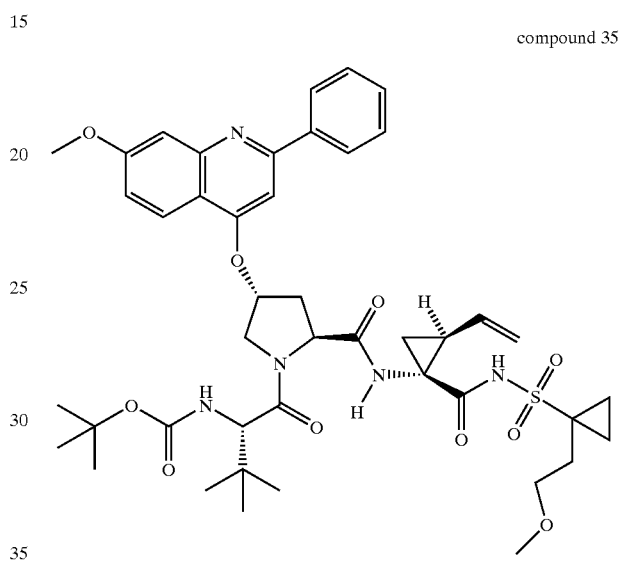

compound 35

Step 35a: Preparation of 1-(2-methoxy-ethyl)-cyclopropanesulfonamide-tert-butylcarbamate

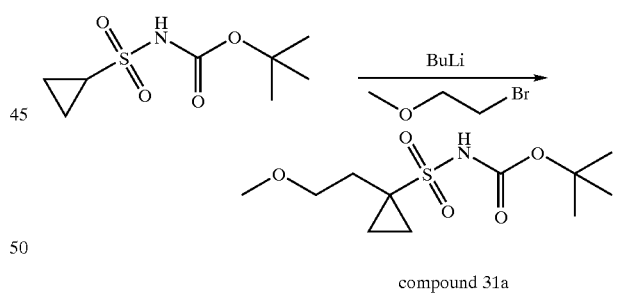

compound 31a

Step 35a) This compound, 1-(2-methoxy-ethyl)-cyclopropanesulfonamide-tert-butylcarbamate, was obtained in 96% yield (1.55 g) from 1.28 g (6.78 mmol) of cyclopropanesulfonamide-tert-butylcarbamate according to the procedure described in the synthesis of 1-methoxymethyl-cyclopropylsulfonylamine tert-butylcarbamate (Step 15IId) except 1.10 equivalents of 2-methoxy-ethyl bromide was used as electrophile. The compound was taken directly into the next reaction without purification: $^1$H NMR (CDCl$_3$) ☐ ppm 1.00 (m, 2H), 1.50 (s, 9H), 1.66 (m, 2H), 2.14 (t, J=6.22 Hz, 2H), 3.34 (s, 3H), 3.57 (t, J=6.40 Hz, 2H), 7.55 (s, 1H).

Step 35b: Preparation of 1 of 1-(2-methoxy-ethyl)-cyclopropanesulfonic acid amide

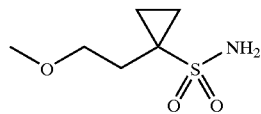

compound 35b

Step 35b) This compound, 1 of 1-(2-methoxy-ethyl)-cyclopropanesulfonic acid amide, was obtained in 45% yield (0.364 g) from 1.25 g (5.55 mmole) of 1-cyclobutylmethyl-cyclopropanesulfonamide-tert-butylcarbamate, according to the procedure described in the synthesis of 1-butyl-cyclopropanesulfonic acid amide (Step 30d, Example 30) but chromatographed over SiO$_2$ eluting with EtOAC/Hexanes (15% to 60%) and followed by recrystalizing from minimum amount of MeOH/CH$_2$Cl$_2$/hexanes: $^1$H NMR (CDCl$_3$) ☐ ppm 0.88 (m, 2H), 1.41 (m, 2H), 2.11 (t, J=5.67 Hz, 2H), 3.34 (s, 3H), 3.59 (t, J=5.67 Hz, 2H), 5.21 (s, 2H); $^{13}$C NMR (CDCl$_3$) ☐ ppm 12.82, 32.64, 40.37, 58.46, 70.56.

Step 35c: Preparation of Compound 35, Example 35, BOCNH—P3(L-t-BuGly)-P2[(4R)-(2-phenyl-7-methoxyquinoline-4-oxo)-S-proline]-P1(1R,2S Vinyl Acca)-CONHSO$_2$(1-(2-methoxyethyl)-cyclopropan-1-yl) or Alternate Designation, Compound 35, Example 35, {1-[2-{1-[1-(2-Methoxy-ethyl)-cyclopropanesulfonylaminocarbonyl]-2-vinyl-cyclopropylcarbamoyl}-4-(7-methoxy-2-phenyl-quinolin-4-yloxy)-pyrrolidine-1-carbonyl]-2,2-dimethyl-propyl}-carbamic acid tert-butyl ester

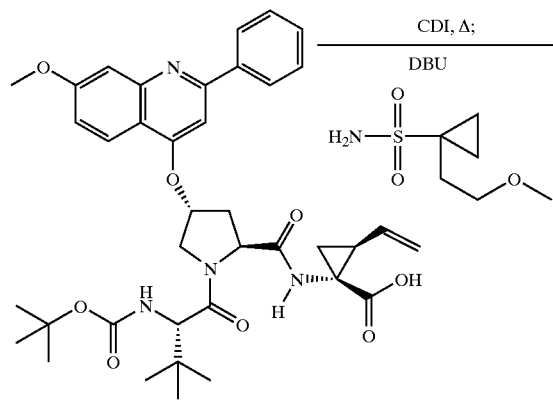

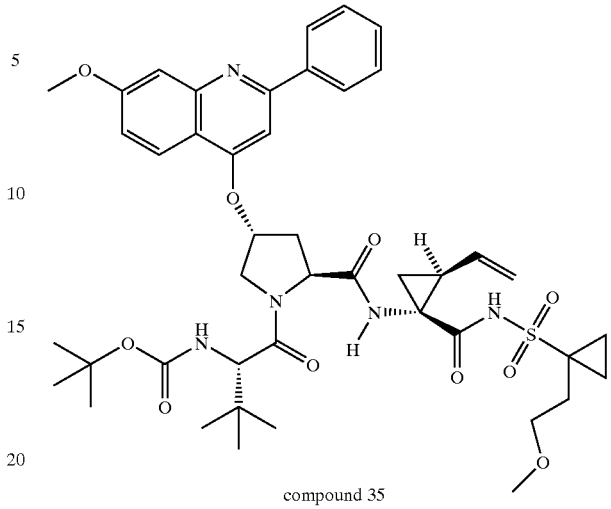

compound 35

Step 35c) Compound 35 was prepared in 71% (0.1103 g) yield from tripeptide acid (0.125 g, 0.18 mmol) of the product of step 2e (Example 2) in analogous fashion to the procedure of Step 27c (Example 27) except that 1-(2-methoxy-ethyl)-cyclopropanesulfonamide (compound 35b, Example 35) was used in place of 1-trimetmethylsilanylcyclopropanesulfonamide: $^1$H NMR (methanol-d$_4$) ☐ ppm 0.96 (m, 2H), 1.04 (s, 9H), 1.28 (s, 9H), 1.42 (m, 3H), 1.81 (dd, J=7.68, 5.12 Hz, 1H), 2.09 (m, 3H), 2.38 (m, 1H), 2.68 (dd, J=13.91, 6.95 Hz, 1H), 3.25 (s, 3H), 3.53 (m, 2H), 3.93 (s, 3H), 4.12 (m, 1H), 4.25 (m, 1H), 4.53 (m, 2H), 5.07 (d, J=10.61 Hz, 1H), 5.24 (d, J=16.83 Hz, 1H), 5.53 (s, 1H), 5.76 (m, 1H), 7.06 (d, J=9.15 Hz, 1H), 7.23 (s, 1H), 7.38 (s, 1H), 7.53 (m, 3H), 8.07 (m, 3H). LC-MS (retention time: 1.64, Method B), MS m/z 848 (M$^+$+1).

Compound 36 Example 36

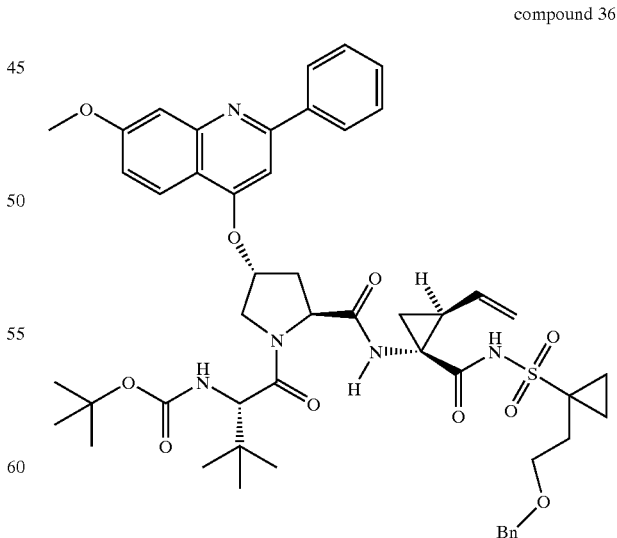

compound 36

Step 36a: Preparation of 1-(2-benzyloxy-ethyl)-cyclopropanesulfonamide-tert-butylcarbamate

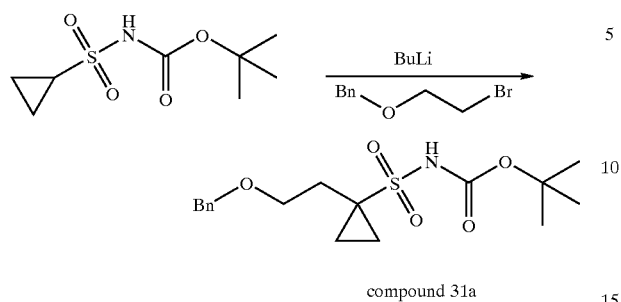

compound 31a

Step 36a) This compound, 1-(2-Benzyloxy-ethyl)-cyclopropanesulfonamide-tert-butylcarbamate, was obtained in 47% yield (1.15 g) from 1.5 g (6.78 mmol) of cyclopropanesulfonamide-tert-butylcarbamate according to the procedure described in the synthesis of 1-methoxymethylcyclopropylsulfonylamine tert-butylcarbamate (Step 15IId) except 1.10 equivalents of (2-Bromo-ethoxy)-benzene was used as electrophile: $^1$H NMR (CHLOROFORM-D) □ ppm 1.05 (s, 2H), 1.48 (m, 11H), 2.16 (t, J=6.59 Hz, 2H), 3.69 (t, J=6.77 Hz, 2H), 4.48 (s, 2H), 7.32 (m, 5H).

Step 36b: Preparation of 1-(2-Benzyloxy-ethyl)-cyclopropanesulfonic acid amide

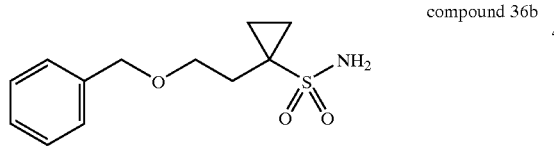

compound 36b

Step 36b) This compound, 1-(2-Benzyloxy-ethyl)-cyclopropanesulfonic acid amide, was obtained in 85% yield (0.702 g) from 1.15 g (3.24 mmole) of 1-cyclobutylmethyl-cyclopropanesulfonamide-tert-butylcarbamate, according to the procedure described in the synthesis of 1-butyl-cyclopropanesulfonic acid amide (Step 30b, Example 30) and the compound was purified over Biotage 40M using EtOAc/Hexanes (0% to 60%) as eluent: $^1$H NMR (Methanol-d$_4$) □ ppm 0.94 (m, 2H), 1.26 (m, 2H), 2.18 (t, J=6.56 Hz, 2H), 3.72 (t, J=6.56 Hz, 2H), 4.49 (s, 2H), 7.27 (m, 1H), 7.32 (m, 4H)); $^{13}$C NMR (Methanol-d$_4$) □ ppm 12.42, 32.79, 69.31, 74.02, 128.72, 128.92, 129.39, 139.56. $^1$H NMR (methanol-d$_4$) □ ppm 0.94 (m, 2H), 1.26 (m, 2H), 2.18 (t, J=6.56 Hz, 2H), 3.72 (t, J=6.56 Hz, 2H), 4.49 (s, 2H), 7.27 (m, 1H), 7.32 (m, 4H).

Step 36c: Preparation of Compound 36, Example 36, BOCNH—P3(L-t-BuGly)-P2[(4R)-(2-phenyl-7-methoxyquinoline-4-oxo)-S-proline]-P1(1R,2S Vinyl Acca)-CONHSO$_2$(1-(2-benzoxyethyl)-cyclopropan-1-yl) or Alternate Designation, Compound 36, Example 36, {1-[2-{1-[1-(2-Benzyloxy-ethyl)-cyclopropanesulfonylaminocarbonyl]-2-vinyl-cyclopropylcarbamoyl}-4-(7-methoxy-2-phenyl-quinolin-4-yloxy)-pyrrolidine-1-carbonyl]-2,2-dimethyl-propyl}-carbamic acid tert-butyl ester

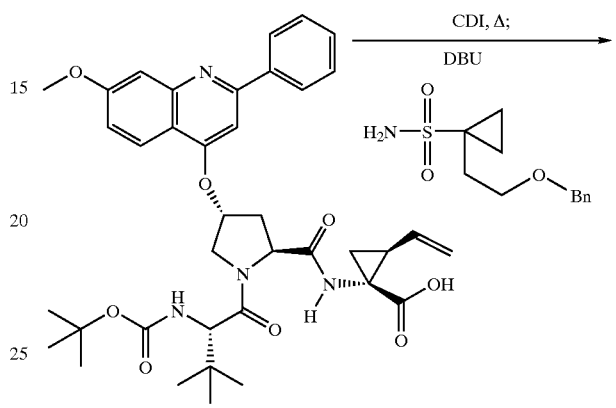

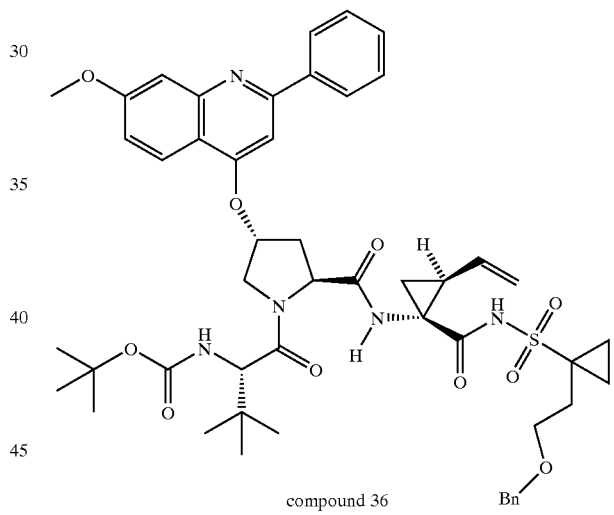

compound 36

Step 36c) Compound 36 was prepared in 66% (0.1031 g) yield from tripeptide acid (0.120 g, 0.17 mmol) of the product of step 2e (Example 2) in analogous fashion to the procedure of Step 27c of Example 27 except that 1-(2-benzyloxy-ethyl)-cyclopropanesulfonamide (compound 36b, Example 36) was used in place of 1-trimethylsilanyl-cyclopropanesulfonamide and purified by preparative HPLC (solvent B: 30% to 100%) to provide the product as a thick oil which solidified upon storage: $^1$H NMR (methanol-d$_4$) □ ppm 0.91 (m, 2H), 1.06 (s, 9H), 1.30 (s, 9H), 1.38 (m, 3H), 1.82 (m, 1H), 2.20 (m, 3H), 2.52 (m, 1H), 2.72 (dd, J=14.19, 7.17 Hz, 1H), 3.68 (t, J=6.56 Hz, 2H), 3.97 (m, 3H), 4.12 (m, 1H), 4.27 (s, 1H), 4.42 (d, J=7.63 Hz, 2H), 4.56 (m, 2H), 5.01 (m, 1H), 5.22 (d, J=16.79 Hz, 1H), 5.53 (m, 1H), 5.93 (m, 1H), 7.10 (m, 1H), 7.26 (m, 6H), 7.41 (m, 1H), 7.53 (m, 3H), 8.09 (m, 3H). MS m/z 924(M$^+$+1), MS m/z 922(M$^-$−1): HPLC (retention time: 1.88, Method D).

Compound 37 Example 37 compound 37

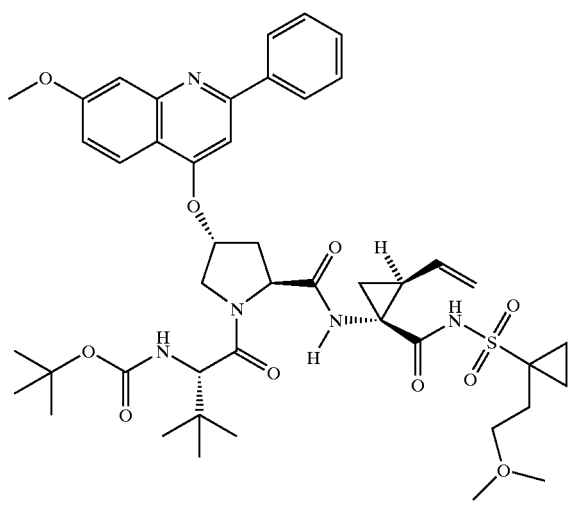

Step 37a: Preparation of 1-iso-propoxymethylcyclopropanesulfonamide-tert-butylcarbamate

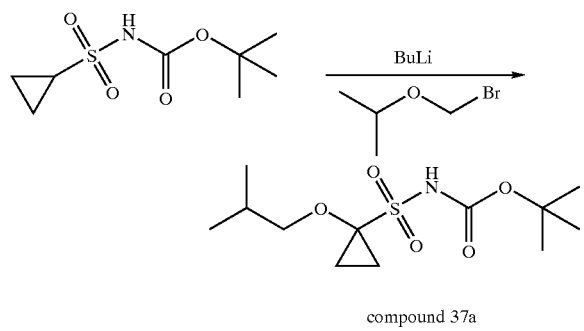

compound 37a

Step 37a) This compound, 1-iso-propoxymethyl-cyclopropanesulfonamide-tert-butylcarbamate, was obtained 79% (0.98 g) from 1.0 g (4.52 mmol) of cyclopropanesulfonamide-tert-butylcarbamate according to the procedure described in the synthesis of 1-methoxymethylcyclo-propylsulfonylamine tert-butylcarbamate (Step 15IId) except 1.10 equivalents of 2-bromomethoxylpropane was used as electrophile as a white solid and furthered to net step.

Step 37b: Preparation of 1-iso-propoxymethylcyclopropanesulfonamide compound 37b

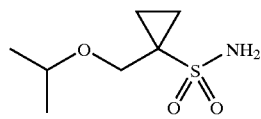

Step 37b) This compound, 1-iso-propoxymethyl-cyclopropanesulfonic acid amide, was obtained in 98% yield (0.62 g) from 0.96 g (0.58 mmole) of 1-iso-propoxymethylcyclopropanesulfonamide-tert-butylcarbamate, according to the procedure described in the synthesis of 1-butyl-cyclopropanesulfonic acid amide (Step 30b, Example 30) as a white solid: $^1$H NMR (Methanol-$d_4$) □ ppm 0.98 (dd, J=7.02, 4.88 Hz, 2H), 1.16 (d, J=6.10 Hz, 6H), 1.30 (m, 2H), 3.66 (m, 1H), 3.76 (s, 2H).

Step 37c: Preparation of Compound 37, BOCNH—P3(L-t-BuGly)-P2[(4R)-(2-phenyl-7-methoxyquinoline-4-oxo)-S-proline]-P1 (1R,2S Vinyl Acca)-CONHSO$_2$(1-iso-propoxyethyl)-cyclopropan-1-yl) or Alternate Designation, Compound 37, Example 37 {1-[2-[1-(1-Isopropoxymethyl-cyclopropanesulfonylaminocarbonyl)-2-vinyl-cyclopropylcarbamoyl]-4-(7-methoxy-2-phenyl-quinolin-4-yloxy)-pyrrolidine-1-carbonyl]-2,2-dimethyl-propyl}-1-carbamic acid tert-butyl ester

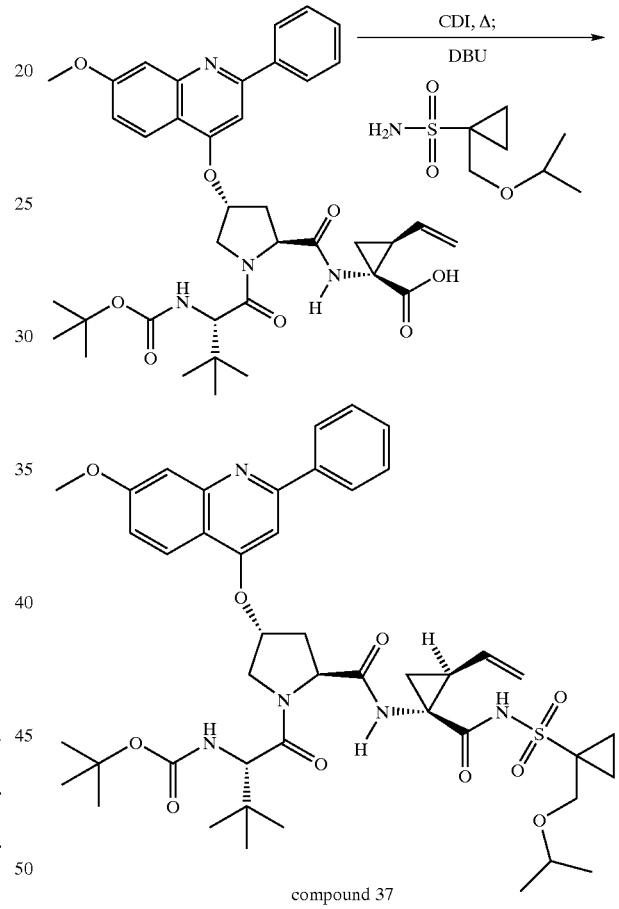

compound 37

Step 37c) Compound 37 was prepared in 52% yield (0.065 g) from tripeptide acid product (0.100 g, 0.15 mmol)) of step 2e (Example 2) in analogous fashion to the procedure of Step 27c of Example 27 except that 1-iso-propoxymethyl-cyclopropanesulfonamide was used in place of 1-trimethylsilanyl-cyclopropanesulfonamide and purified over 20×40 cM 1000□ Analtech PTLC plates (MeOH/CH$_2$Cl$_2$:5%) to afford the desired product as a white foam: $^1$H NMR (methanol-$d_4$) □ ppm 1.03 (m, 8H), 1.04 (s, 9H), 1.28 (s, 9H), 1.33 (m, 3H), 1.78 (m, 1H), 2.16 (m, 1H), 2.50 (m, 1H), 2.72 (m, 1H), 3.54 (m, 1H), 3.82 (m, 2H), 3.93 (d, J=4.58 Hz, 3H), 4.10 (m, 1H), 4.25 (m, 1H), 4.54 (m, 2H), 5.01 (dd, J=20.45, 9.77 Hz, 1H), 5.21 (m, 1H), 5.51 (m, 1H), 5.92 (m, 1H), 7.05 (dd, J=9.16, 2.14 Hz, 1H), 7.22 (m, 1H), 7.38 (m, 1H), 7.49 (m, 3H), 8.05 (m, 3H). LC-MS (retention time: 1.81, Method L), MS m/z 862 (M$^+$+1).

Compound 38 Example 38

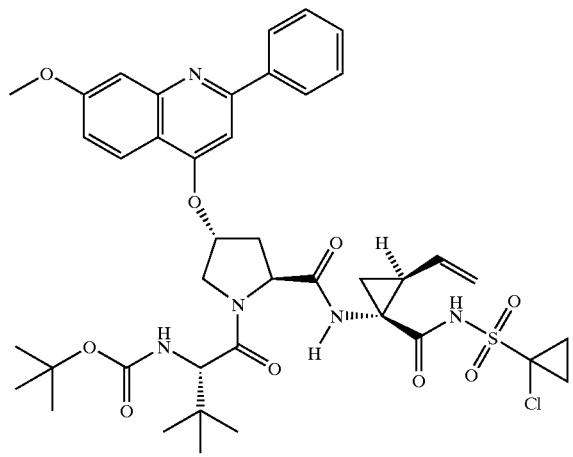

compound 38

Step 38a: Preparation of 1-chloro-cyclopropanesulfonamide-tert-butylcarbamate

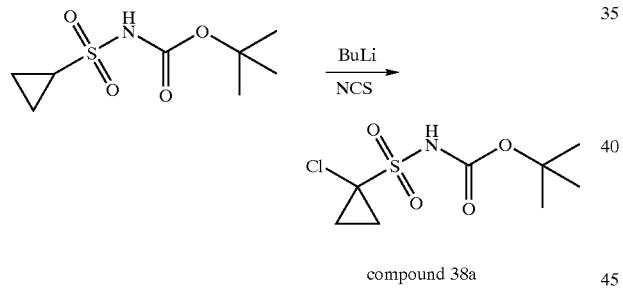

compound 38a step 3.8a) To a solution of cyclopropylsulfonylamine tert-butyl carbamate (1.0 g, 4.52 mmol) dissolved in THF (10 mL) cooled to −78° C., was added n-BuLi (6.4 mL, 10.2 mmol, 1.6 M in hexane) and the reaction mixture was stirred for 1 h. To this solution was added a THF (10 mL) solution of NCS (0.86 g, 6.34 mmol). After stirred for 5 min, the bath was changed to ice bath and the mixture was stirred for 3 h at the temperature. The reaction mixture was diluted with ice water, the pH was adjusted to <4. The aqueous mixtire was extracted with EtOAc. The combined extracts were dried (MgSO$_4$), concentrated and purified by flash chromatography over SiO$_2$ using EtOAc/hexanes (0% to 60%) as the eluent to afford 0.98 g (67%) of 1-chloro-cyclopropanesulfonamide-tert-butylcarbamate as a white solid: $^1$H NMR (CDCl$_3$) δ ppm 1.51 (m, II H), 2.01 (m, 2H), 7.60 (s, 1H).

Step 38b: Preparation of 1-chloro-cyclopropanesulfonamide

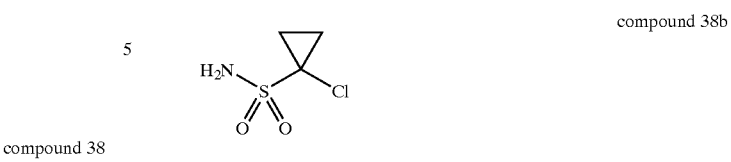

compound 38b

Step 38b) This compound, 1-chloro-cyclopropanesulfonic acid amide, was obtained in 100% yield (0.09 g) from 0.148 g (0.58 mmole) of 1-chloro-cyclopropanesulfonamide-tert-butylcarbamate, according to the procedure described in the synthesis of 1-butyl-cyclopropanesulfonic acid amide (step 30b, Example 30) but without purification as a light brown solid: $^1$H NMR (Methanol-d$_4$) □ ppm 1.38 (m, 2H), 1.70 (m, 2H).

Step 38c: Preparation of Compound 38, Example 38, BOCNH—P3(L-t-BuGly)-P2[(4R)-(2-phenyl-7-methoxyquinoline-4-oxo)-S-proline]-P1 (1R,2S Vinyl Acca)-CONHSO$_2$(1-chlorocyclopropan-1-yl) or alternate designation, Compound 38, Example 38, {1-[2-[1-(1-Chloro-cyclopropanesulfonylaminocarbonyl)-2-vinyl-cyclopropylcarbamoyl]-4-(7-methoxy-2-phenyl-quinolin-4-yloxy)-pyrrolidine-1-carbonyl]-2,2-dimethyl-propyl}-carbamic acid tert-butyl ester

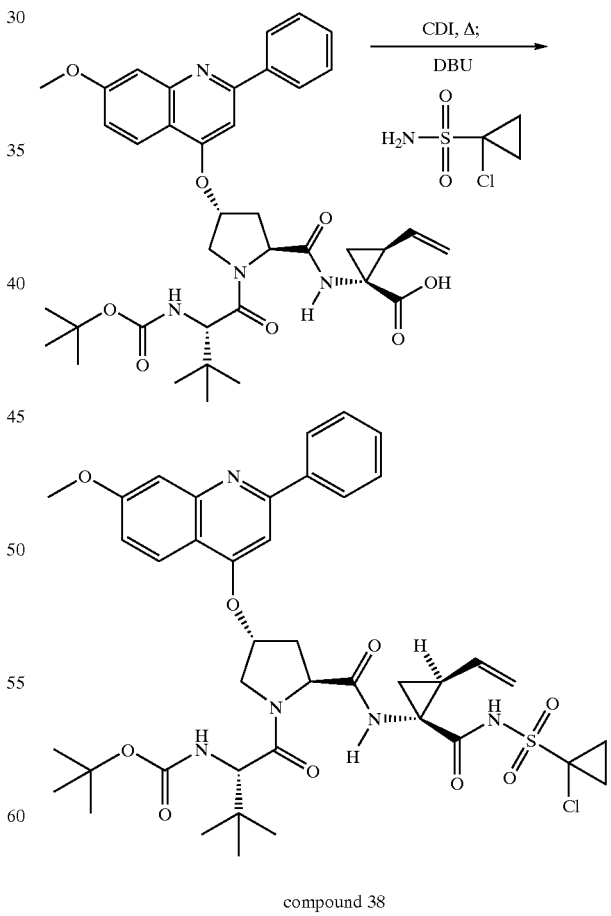

compound 38

Step 38c) Compound 38 was prepared in 39% (0.0464 g) yield from tripeptide acid product (0.100 g, 0.15 mmol) of step 2e (Example 2) in analogous fashion to the procedure of Step 27c (Example 27) except that 1-chlorocyclopropanesulfonic acid amide was used in place of 1-trimethylsilanyl-cyclopropanesulfonamide and purified by preparative HPLC, (solvent B: 30% to 100%) as a white foam: $^1$H NMR (methanol-d$_4$) □ ppm 1.07 (s, 9H), 1.22 (s, 9H), 1.43 (m, 2H), 1.46 (dd, J=9.61, 5.65 Hz, 1H), 1.91 (dd, J=8.09, 5.65 Hz, 1H), 1.96 (m, 1H), 2.05 (m, 1H), 2.30 (q, J=8.85 Hz, 1H), 2.47 (m, 1H), 2.81 (dd, J=14.04, 7.02 Hz, 1H), 4.08 (s, 3H), 4.17 (m, 2H), 4.67 (dd, J=10.22, 7.17 Hz, 1H), 4.72 (d, J=12.21 Hz, 1H), 5.17 (d, J=10.38 Hz, 1H), 5.33 (d, J=17.09 Hz, 1H), 5.73 (m, 1H), 5.87 (s, 1H), 7.42 (dd, J=9.31, 2.29 Hz, 1H), 7.57 (d, J=2.14 Hz, 1H), 7.69 (s, 1H), 7.79 (m, 3H), 8.11 (d, J=7.02 Hz, 2H), 8.38 (m, 1H). LC-MS (retention time: 1.60, Method H), MS m/z 824 (M$^+$+1).

Compound 39 Example 39 compound 39

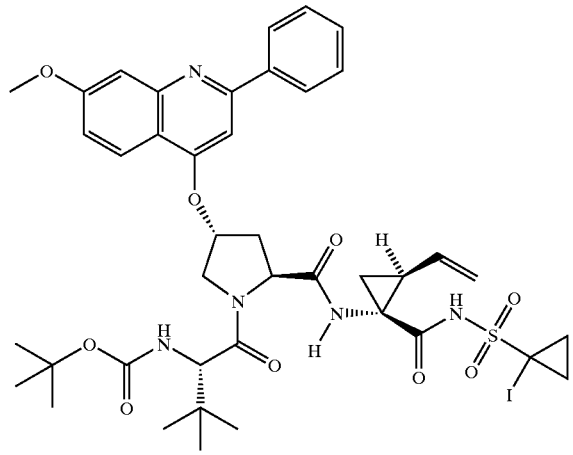

Step 39a: Preparation of 1-iodo-cyclopropanesulfonamide

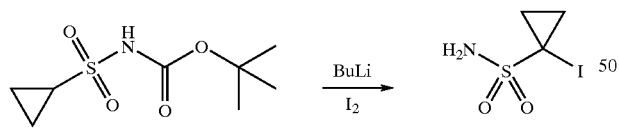

compound 39a

Step 39a) This compound, 1-iodo-cyclopropanesulfonic acid amide, was obtained in 78% (0.87 g) yield from 1.0 g (4.52 mmol) of cyclopropanesulfonamide-tert-butylcarbamate according to the procedure described in the synthesis of 1-chloro-cyclopropanesulfonamide-tert-butylcarbamate (Step 38a, Example 38) except 1.4 equivalent iodine was used as electrophile and purified by flash chromatograph (EtOAc/hexanes: 0% to 60%) to provide the product as a pale brown solid: $^1$H NMR (CDCl$_3$) □ ppm 1.37 (m, 2H), 1.78 (m, 2H), 4.75 (s, 2H).

Step 39b: Preparation Compound 39, BOCNH—P3 (L-t-BuGly)-P2[(4R)-(2-phenyl-7-methoxyquinoline-4-oxo)-S-proline]-P1(1R,2S Vinyl Acca)-CONHSO$_2$(1-iodocyclopropan-1-yl) or Alternate Designation, Compound 39, Example 39, {1-[2-[1-(1-Iodo-cyclopropanesulfonylaminocarbonyl)-2-vinyl-cyclopropylcarbamoyl]-4-(7-methoxy-2-phenyl-quinolin-4-yloxy)-pyrrolidine-1-carbonyl]-2,2-dimethyl-propyl}-carbamic acid tert-butyl ester

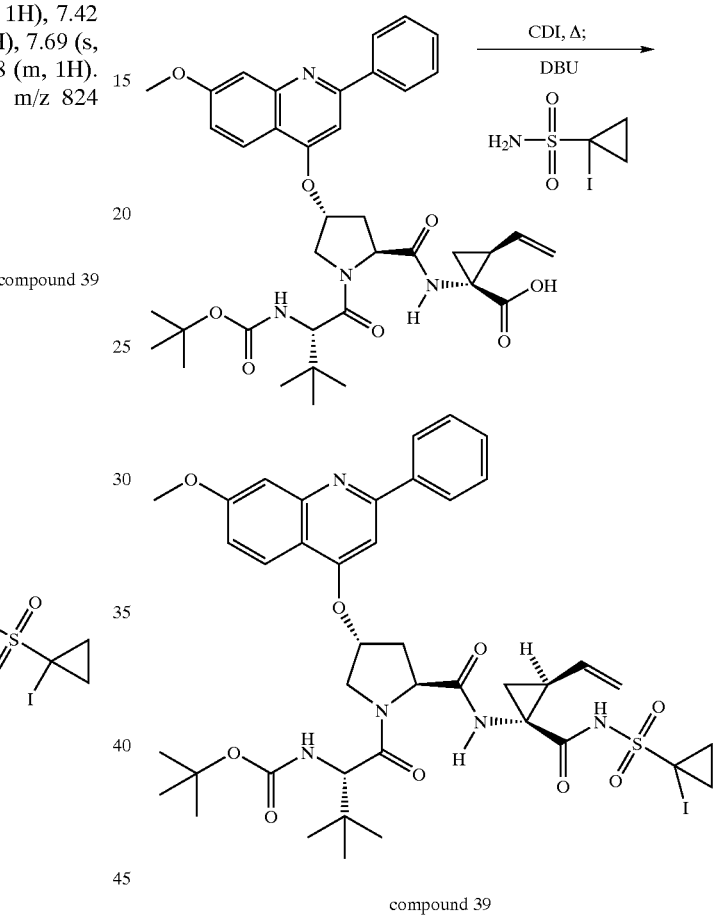

compound 39

Step 39b) Compound 39 was prepared in 65% (0.1077 g) yield from tripeptide acid product (0.125 g, 0.18 mmol) of step 2e (Example 2) in analogous fashion to the procedure of Step 27c of Example 27 except that 1-iodo-cyclopropanesulfonamide was used in place of 1-trimethylsilanyl-cyclopropanesulfonamide and purified by repeatedly PTLC to provide the product as a foam: ($^1$H NMR (methanol-d$_4$) □ ppm 1.05 (s, 9H), 1.12 (m, 2H), 1.27 (s, 9H), 1.33 (m, 2H), 1.76 (m, 2H), 1.99 (m, 1H), 2.66 (m, 1H), 2.77 (m, 1H), 3.94 (s,3H), 4.14 (m, 2H), 4.53 (m, 2H), 4.97 (m, 1H), 5.15 (d, J=17.09 Hz, 1H), 5.55 (s, 1H), 5.96 (m, 1H), 7.06 (dd, J=9.00, 2.29 Hz, 1H), 7.26 (s, 1H), 7.38 (m, 1H), 7.51 (m, 3H), 8.06 (m, 3H). HRMS m/z (M+H)$^+$ calcd for C$_{41}$H$_{49}$IN$_5$SO$_9$: 914.2296 found: 914.2301. HPLC (retention time: 1.65, Method I).

Compound 40 Example 40

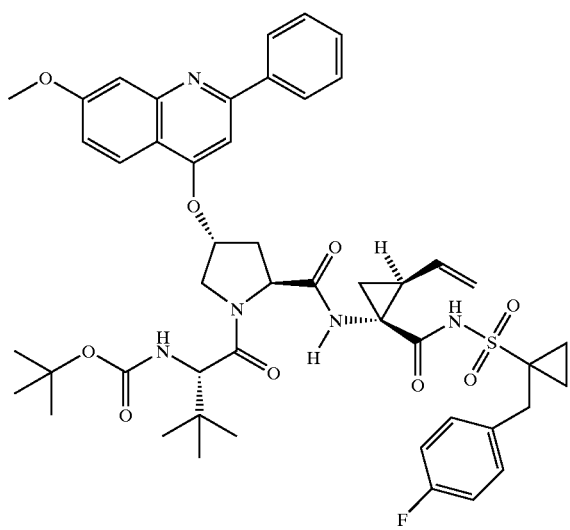

compound 40

Step 40a: Preparation of 1-(4-floro-benzyl)-cyclopropanesulfonamide-tert-butylcarbamate

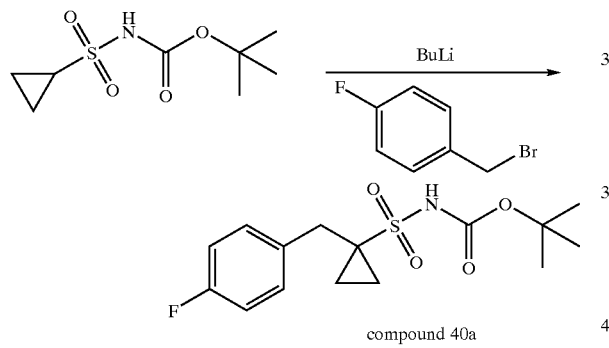

compound 40a

Step 40a) This compound, 1-(4-floro-benzyl)-cyclopropanesulfonamide-tert-butylcarbamate, was obtained from 1.0 g (4.52 mmol) of cyclopropanesulfonamide-tert-butylcarbamate according to the procedure described in the synthesis of 1-methoxymethylcyclo-propylsulfonylamine tert-butylcarbamate (Step 15IId) except 1.2 equivalents of 4-floro-benzyl bromide was used as electrophile. The crude product was directly used in next step.

Step 40b: Preparation of 1-(4-floro-benzyl)-cyclopropanesulfonamide

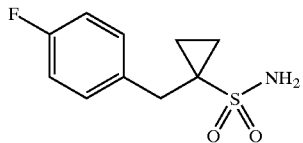

compound 40b

Step 40b) This compound, 1-(4-floro-benzyl)-cyclopropanesulfonamide, was obtained in 25% yield (0.26 g) in two steps from crude product of step 40a according to the procedure described in the synthesis of 1-butyl-cyclopropanesulfonic acid amide (Step 30a) and purified by Biotage 40 L column using EtOAc/hexanes (5% to 100%) as the eluent to provide the product as a white solid: $^1$H NMR (CDCl$_3$) □ ppm 0.83 (m, 2H), 1.39 (m, 2H), 3.23 (s, 2H), 4.16 (s, 2H), 7.02 (m, 2H); $^{13}$C NMR (CDCl$_3$) □ ppm 11.00, 35.99, 41.76, 76.75, 115.60, 115.77, 131.30, 131.37, 132.06, 132.09, 161.10, 163.06.

Step 40c: Preparation of Compound 40, Example 40, BOCNH—P3(L-t-BuGly)-P2[(4R)-(2-phenyl-7-methoxyquinoline-4-oxo)-S-proline]-P1(1R,2S Vinyl Acca)-CONHSO$_2$[1-(4-fluorobenzyl)-clopropan-1-yl) or Alternate Designation, Compound 40, Example 40, {1-[2-{1-[1-(4-Fluoro-benzyl)-cyclopropanesulfonylaminocarbonyl]-2-vinyl-cyclopropylcarbamoyl}-4-(7-methoxy-2-phenyl-quinolin-4-yloxy)-pyrrolidine-1-carbonyl]-2,2-dimethyl-propyl}-carbamic acid tert-butyl ester

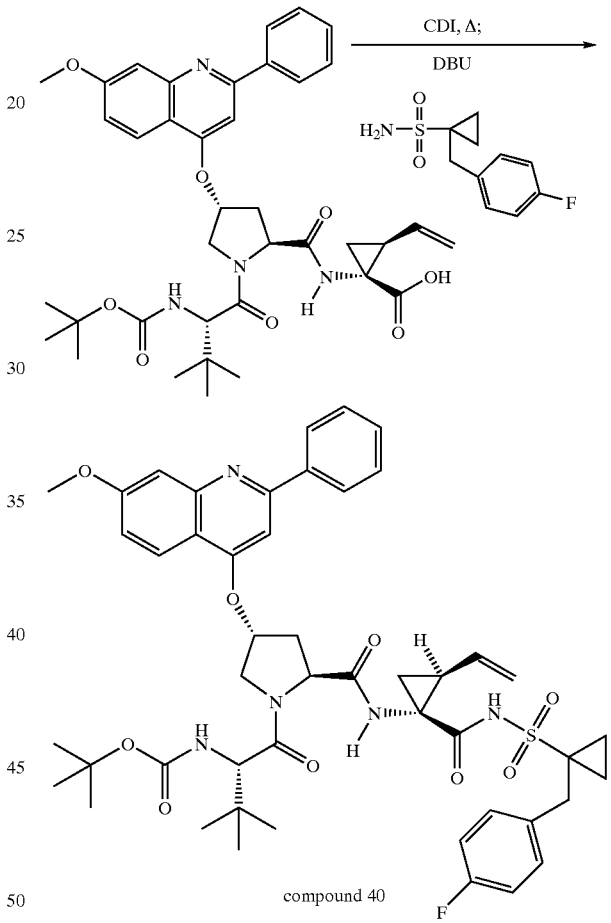

compound 40

Step 40c) Compound 40 was prepared in 41% (32.0) yield from tripeptide acid product (0.060 g, 0.09 mmol)) of step 2e (Example 2) in analogous fashion to the procedure of Step 27c of Example 27 except that 1-(4-fluoro-benzyl)-cyclopropanesulfonamide was used in place of 1-trimethylsilanyl-cyclopropanesulfonamide and purified by preparative HPLC (solvent B: 30% to 100%): $^1$H NMR (methanol-d$_4$) □ ppm 0.91 (m, 2H), 0.97 (s, 9H), 1.24 (s, 9H), 1.47 (m, 3H), 1.86 (m, 1H), 2.26 (m, 1H), 2.35 (m, 1H), 2.71 (dd, J=13.73, 6.71 Hz, 1H), 3.24 (d, J=14.04 Hz, 1H), 3.33 (d, J=12.21 Hz, 1H), 3.97 (s, 3H), 4.08 (m, 1H), 4.21 (m, 1H), 4.59 (m, 2H), 5.15 (d, J=8.24 Hz, 1H), 5.32 (d, J=17.09 Hz, 1H), 5.63 (s, 1H), 5.77 (m, 1H), 6.99 (d, J=4.88 Hz, 2H), 7.16 (m, 3H), 7.35 (s, 1H), 7.43 (d, J=2.14 Hz, 1H), 7.57 (m, 3H), 8.03 (d, J=3.05 Hz, 2H), 8.17 (d, J=9.15 Hz, 1H). LC-MS (retention time: 1.83, Method L), MS m/z 898 (M⁺+1).

Compound 41 Example 41

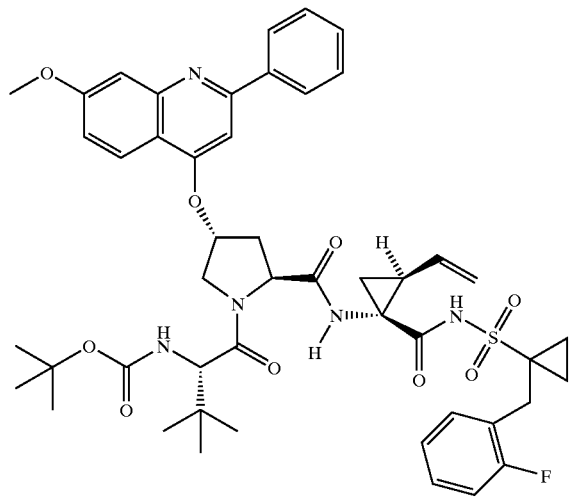

compound 41

Step 41a: Preparation of 1-(2-floro-benzyl)-cyclopropanesulfonamide-tert-butylcarbamate

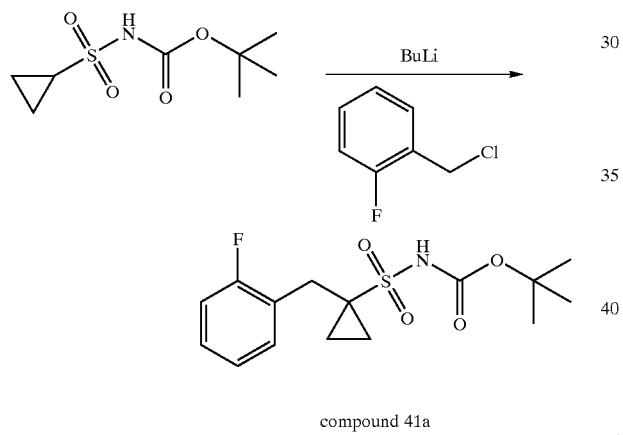

compound 41a

Step 41a) This compound, 1-(2-floro-benzyl)-cyclopropanesulfonamide-tert-butylcarbamate, was obtained from 1.0 g (4.52 mmol) of cyclopropanesulfonamide-tert-butylcarbamate according to the procedure described in the synthesis of 1-methoxymethylcyclo-propylsulfonylamine tert-butylcarbamate (Step 15IId) except 1.1 equivalents of 2-floro-benzyl chloride was used as electrophile. The crude product was directly used in next step.

Step 41b: Preparation of 1-(2-floro-benzyl)-cyclopropanesulfonamide

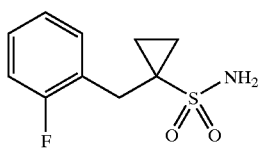

compound 41b

Step 41b) This compound, 1-(2-floro-benzyl)-cyclopropanesulfonamide, was obtained in 36% yield (0.41 g) in two steps from crude product of step step 41a according to the procedure described in the synthesis of 1-butyl-cyclopropanesulfonic acid amide (Step 30b) and purified by Biotage 40L column using EtOAc (5% to 100%) as eluent: $^1$H NMR (CDCl$_3$) □ ppm 0.83 (m, 2H), 1.39 (m, 2H), 3.23 (s, 2H), 4.16 (s, 2H), 7.02 (m, 2H).

Step 41c: Preparation of Compound 41, Example 41, BOCNH—P3(L-t-BuGly)-P2[(4R)-(2-phenyl-7-methoxyquinoline-4-oxo)-S-proline]-P1(1R,2S Vinyl Acca)-CONHSO$_2$[1-(2-fluorobenzyl)-clopropan-1-yl) or Alternate Designation, Compound 41, Example 41, {1-[2-{1-[1-(2-Fluoro-benzyl)-cyclopropanesulfonylaminocarbonyl]-2-vinyl-cyclopropylcarbamoyl}-4-(7-methoxy-2-phenyl-quinolin-4-yloxy)-pyrrolidine-1-carbonyl]-2,2-dimethyl-propyl}-carbamic acid tert-butyl ester

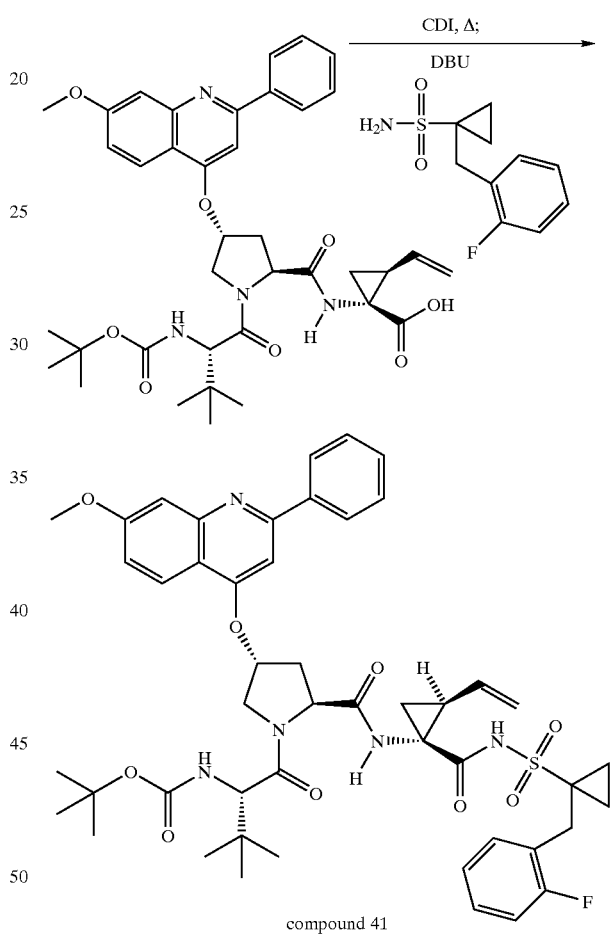

compound 41

Step 41c) Compound 41 was prepared in 47% (0.037 g) yield from tripeptide acid product (0.060 g, 0.09 mmol) of step 2e (Example 2) in analogous fashion to the procedure of Step 27c of Example 27 except that 1-(2-Fluoro-benzyl)-cyclopropanesulfonamide (41b) was used in place of 1-trimethylsilanyl-cyclopropanesulfonamide and purified by preparative HPLC (solvent B: 30% to 100%): $^1$H NMR (methanol-d$_4$) □ ppm 0.94 (m, 2H), 0.98 (s, 9H), 1.23 (s, 9H), 1.40 (m, 3H), 1.87 (m, 1H), 2.27 (m, 1H), 2.40 (s, 1H), 2.75 (dd, J=13.17, 6.59 Hz, 1H), 3.39 (s, 2H), 3.99 (s, 3H), 4.09 (m, 1H), 4.19 (s, 1H), 4.61 (m, 2H), 5.15 (m, 1H), 5.31 (d, J=17.57 Hz, 1H), 5.70 (s, 1H), 5.77 (s, 1H), 7.06 (m, 2H), 7.24 (m, 3H), 7.43 (s, 1H), 7.48 (d, J=2.20 Hz, 1H), 7.62 (m, 3H), 8.04 (m, 2H), 8.22 (d, J=9.15 Hz, 1H). LC-MS (retention time: 1.76, Method H), MS m/z 898 (M⁺+1).

Compound 42 Example 42 compound 42

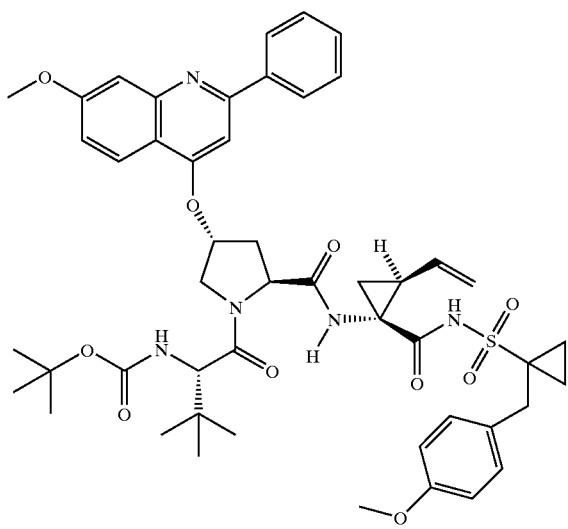

Step 42a: Preparation of 1-(4-methoxy-benzyl)-cyclopropanesulfonamide-tert-butylcarbamate

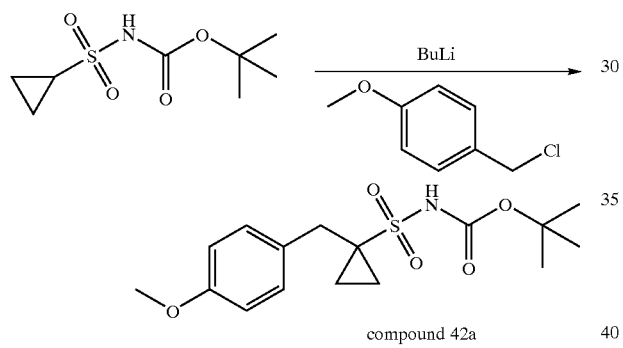

compound 42a

Step 42a) This compound, 1-(4-methoxy-benzyl)-cyclopropanesulfonamide-tert-butylcarbamate, was obtained 1.2 g (78%) from 1.0 g (4.52 mmol) of cyclopropanesulfonamide-tert-butylcarbamate according to the procedure described in the synthesis of 1-methoxymethylcyclo-propylsulfonylamine tert-butylcarbamate (Step 15IId) except 1.1 equivalents of 4-methoxy-benzyl chloride was used as electrophile: $^1$H NMR (Methanol-d$_4$) □ ppm 0.78 (m, 2H), 1.46 (s, 9H), 1.47 (m, 2H), 3.20 (s, 2H), 3.76 (s, 3H), 6.87 (m, 2H), 7.09 (m, 2H).

Step 42b: Preparation of 1-(4-methoxybenzyl)-cyclopropanesulfonamide compound 42b

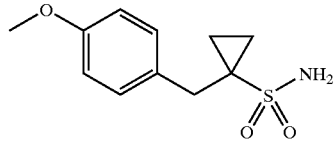

Step 42b) This compound, 1-(4-methoxy-benzyl)-cyclopropanesulfonamide, was obtained in 89% yield (0.63 g) in two steps from 1.0 g (2.93 mmol) of 1-(4-methoxy-benzyl)-cyclopropanesulfonamide-tert-butylcarbamate according to the procedure, described in the synthesis of 1-butyl-cyclopropanesulfonamide (Step 30b, Example 30) as a white solid: $^1$H NMR (CDCl$_3$) □ ppm 0.86 (m, 2H), 1.38 (m, 2H), 3.18 (s, 2H), 3.78 (s, 31H), 4.11 (s, 2H), 6.85 (m, 21H), 7.18 (d, J=8.55 Hz, 2H); $^{13}$C NMR (CDCl$_3$) □ ppm 11.07, 36.18, 42.00, 55.24, 114.20, 128.31, 130.76, 158.88.

Step 42c: Preparation of Compound 42, BOCNH—P3(L-t-BuGly)-P2[(4R)-(2-phenyl-7-methoxyquinoline-4-oxo)-S-proline]-P1(R,2S Vinyl Acca)-CONHSO$_2$[1-(4-methoxybenzyl)-clopropan-1-yl) or Alternate Designation, Compound 42, Example 42, {1-[2-{1-[1-(4-Methoxy-benzyl)-cyclopropanesulfonylaminocarbonyl]-2-vinyl-cyclopropylcarbamoyl}-4-(7-methoxy-2-phenyl-quinolin-4-yloxy)-pyrrolidine-1-carbonyl]-2,2-dimethyl-propyl}-carbamic acid tert-butyl ester

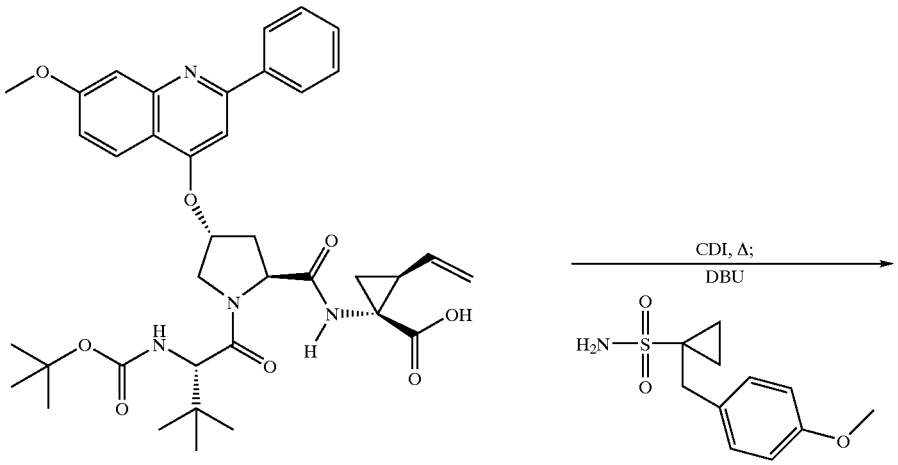

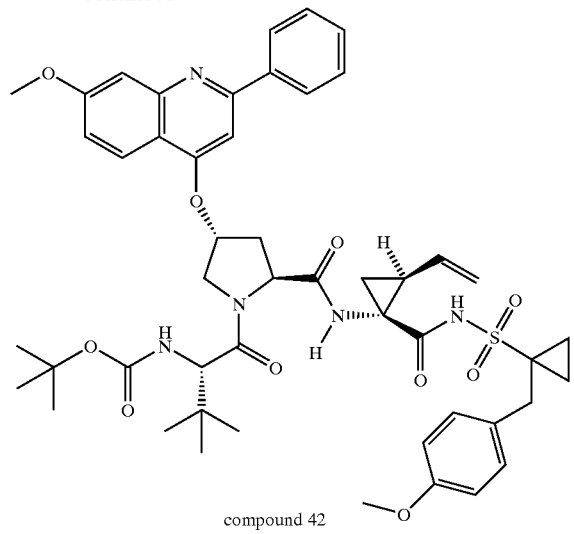

compound 42

Step 42c) Compound 42 was prepared in 25% (0.033 g) yield from tripeptide acid product (0.100 g, 0.15 mmol) of step 2e (Example 2) in analogous fashion to the procedure of Step 27c of Example 27 except that 1-(4-methoxy-benzyl)-cyclopropanesulfonamide (compond 42b was used in place of 1-trimethylsilanyl-cyclopropanesulfonamide and purified by PTLC (MeOH/CH$_2$Cl$_2$: 2% to 5%) and preparative HPLC (solvent B: 35 to 100%): $^1$H NMR (methanol-d$_4$) □ ppm 0.94 (m, 2H), 0.98 (s, 9H), 1.24 (s, 9H), 1.39 (m, 3H), 1.88 (m, 1H), 2.36 (m, 2H), 2.73 (dd, J=13.36, 7.14 Hz, 1H), 3.23 (m, 2H), 3.74 (s, 3H), 3.98 (s, 3H), 4.10 (m, 1H), 4.20 (s, 1H), 4.60 (m, 2H), 5.16 (d, J=9.15 Hz, 1H), 5.33 (d, J=17.20 Hz, 1H), 5.67 (s, 1H), 5.79 (s, 1H), 6.82 (d, J=6.59 Hz, 2H), 7.04 (d, J=8.78 Hz, 2H), 7.20 (dd, J=9.15, 2.20 Hz, 1H), 7.40 (s, 1H), 7.45 (d, J=2.56 Hz, 1H), 7.61 (m, 3H), 8.04 (d, J=3.66 Hz, 2H), 8.20 (d, J=9.15 Hz, 1H). MS m/z 908 (M$^-$−1), LC-MS (retention time: 1.53, Method H).

Compound 43 Example 43

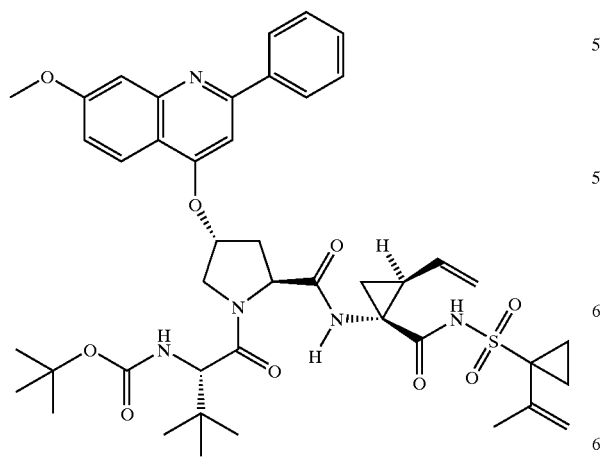

compound 43

Step 43a: Preparation of 1-1-(1-hydroxy-1-methylethyl)-cyclopropanesulfonamide-tert-butylcarbamate

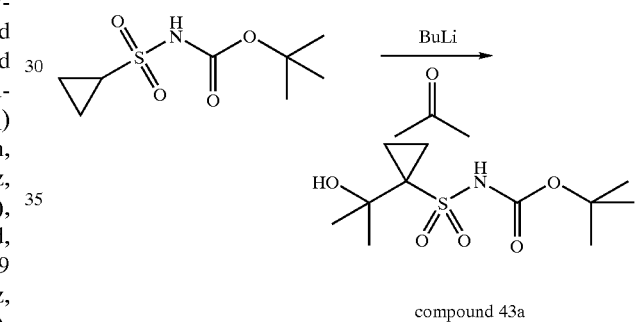

compound 43a

Step 43a) Compound 43a, 1-(1-hydroxy-1-methylethyl)-cyclopropanesulfonamide-tert-butylcarbamate, was obtained in 49% (1.23 g) from 2.0 g (9.04 mmol) of cyclopropanesulfonamide-tert-butylcarbamate according to the procedure described in the synthesis of 1-methoxymethylcyclo-propylsulfonylamine tert-butylcarbamate (Step 15IId) except 1.1 equivalents of 2-acetone was used as electrophile and purified by Biotage 40M column using EtOAc/hexanes (0% to 60%) as the eluent: $^1$H NM (CDCl$_3$) □ ppm 1.13 (m, 2H), 1.40 (s, 6H), 1.48 (s, 9H), 1.68 (m, 2H), 2.59 (m, 1H), 7.42 (s, 1H); $^{13}$C NMR (CDCl$_3$) □ ppm 10.94, 27.96, 28.49, 48.46, 83.91, 149.35.

Step 43b: Preparation of 1-(2-floro-benzyl)-cyclopropanesulfonic acid amide compound 43b Step 43b) This compound, 1-isopropenyl-cyclopropanesulfonamide, was obtained in 94% yield (0.36 g) from 0.6 g (2.15 mmol) of 1-(1-hydroxy-1-methyl-ethyl)-cyclopropanesulfonamide-tert-butylcarbamate according to the procedure described in the synthesis of 1-butyl-cyclopropanesulfonic acid amide (Step 30b) and purified by Redisep 35 g column using EtOAc/hexanes (5% to 100%) as the eluent: $^1$H NMR (Methanol-d$_4$) ☐ ppm 1.00 (m, 2H), 1.42 (m, 2H), 1.97 (s, 3H), 5.27 (d, J=6.59 Hz, 2H).

Step 43c: Preparation of Compound 43, Example 43, BOCNH—P3(L-t-BuGly)-P2[(4R)-(2-phenyl-7-methoxyquinoline-4-oxo)-S-proline]-P1(1R,2S Vinyl Acca)-CONHSO$_2$(1-iso-propenylclopropan-1-yl) or Alternate Designation, Compound 43, Example 43, {1-[2-[1-(1-Isopropenyl-cyclopropanesulfonylaminocarbonyl)-2-vinyl-cyclopropylcarbamoyl]-4-(7-methoxy-2-phenyl-quinolin-4-yloxy)-pyrrolidine-1-carbonyl]-2,2-dimethyl-propyl}-carbamic acid tert-butyl ester

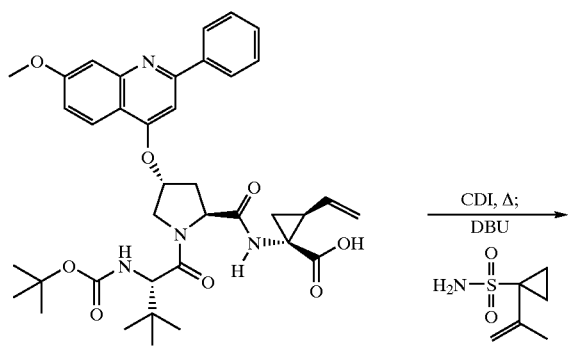

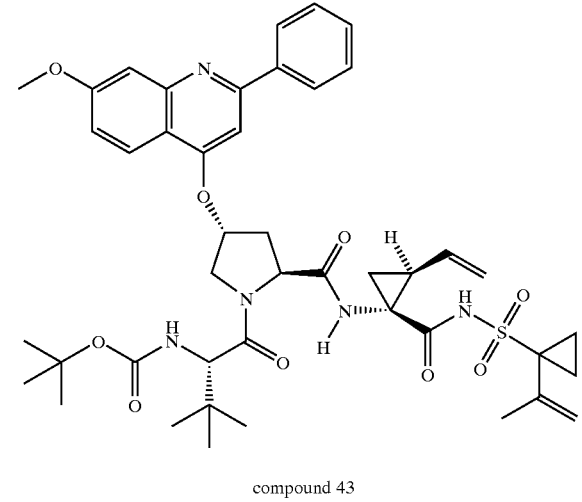

compound 43

Step 43c) Compound 43 was obtained in 30% (0.0215 g) yield from tripeptide acid product (0.060 g, 0.09 mmol) of step 2e (Example 2) in analogous fashion to the procedure of Step 27c of Example 27 except that 1-isopropenyl-cyclopropanesulfonamide was used in place of 1-trimethylsilanyl-cyclopropanesulfonamide: $^1$H NMR (methanol-d$_4$) ☐ ppm 0.96 (m, 2H), 1.03 (s, 9H), 1.27 (s, 9H), 1.37 (dd, J=9.33, 4.94 Hz, 1H), 1.58 (m, 2H), 1.77 (m, 1H), 1.94 (s, 3H), 2.14 (m, 1H), 2.42 (m, 1H), 2.68 (dd, J=13.54, 7.32 Hz, 1H), 3.93 (s, 3H), 4.06 (m, 1H), 4.24 (s, 1H), 4.53 (m, 2H), 5.14 (m, 4H), 5.52 (s, 1H), 5.90 (m, 1H), 7.06 (d, J=8.78 Hz, 1H), 7.22 (s, 1H), 7.37 (d, J=2.20 Hz, 1H), 7.50 (m, 3H), 8.06 (m, 3H). LC-MS (retention time: 1.74, Method I), MS m/z 830(M$^+$+1).

Compound 44 Example 44

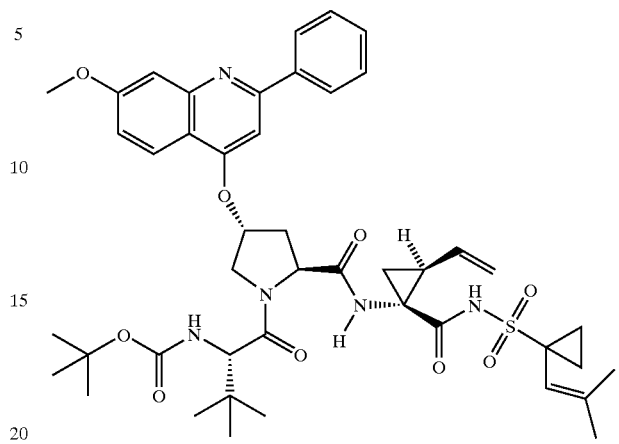

compound 44

Step 44a: Preparation of 1-iso-butenylcyclopropanesulfonamide-tert-butylcarbamate

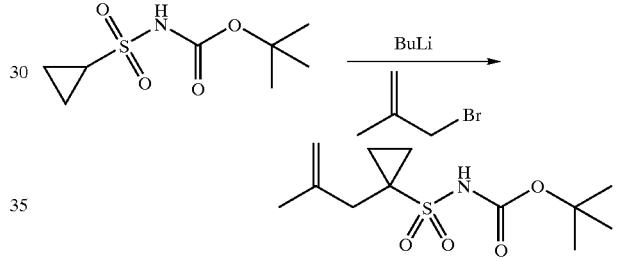

compound 44a

Step 44a) This compound, 1-(2-Methyl-allyl)-cyclopropanesulfonamide-tert-butylcarbamate, was obtained in 95% (1.18 g) from 1.0 g (4.52 mmol) of cyclopropanesulfonamide-tert-butylcarbamate according to the procedure described in the synthesis of 1-methoxymethylcyclo-propylsulfonylamine tert-butylcarbamate (Step 15IId) except 1.1 equivalents of iso-butyl bromide was used as electrophile: $^1$H NMR (CDCl$_3$) ☐ ppm 0.93 (m, 2H), 1.49 (s, 9H), 1.73 (m, 2H), 1.78 (d, J=7.93 Hz, 3H), 2.58 (s, 2H), 4.87 (m, 1H), 4.88 (m, 1H), 6.77 (s, 1H).

Step 44b: Preparation of 1-iso-butenylclopropanesulfonamide

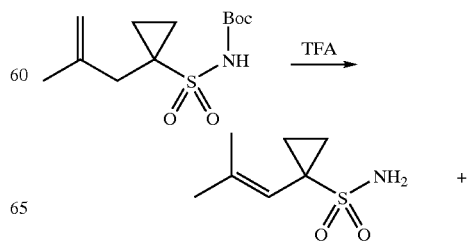

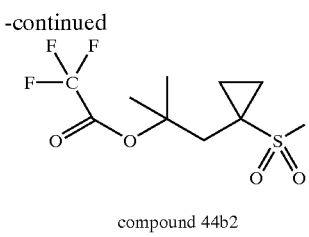

compound 44b2

Step 44b) A 1/1 mixtur of compound 44b1 and compound 44b2 (0.31 g) was obtained from 1.0 g (3.6 mmol) of 1-iso-butenylcyclopropanesulfonamide-tert-butylcarbamate (compound 44a) by fellowing the procedure described in the synthesis of 1-butyl-cyclopropanesulfonic acid amide (Step 30b) as a white solid: $^1$H NMR (Methanol-d$_4$) □ ppm 0.97 (m, 2H), 1.09 (m, 1H), 1.35 (m, 2H), 1.40 (s, 6H), 1.49 (m, 2H), 1.80 (s, 3H), 1.88 (s, 3H), 2.25 (s, 2H), 5.49 (s, 1H).

Step 44c: Preparation of Compound 44, Example 44, BOCNH—P3(L-t-BuGly)-P2[(4R)-(2-phenyl-7-methoxyquinoline-4-oxo)-S-proline]-P1(1R,2S Vinyl Acca)-CONHSO$_2$[1-(2-methyl-propen-3-yl)-clopropan-1-yl) or Alternate Designation, Compound 44, Example 44, [1-(4-(7-Methoxy-2-phenyl-quinolin-4-yloxy)-2-{1-[1-(2-methyl-propenyl)-cyclopropanesulfonylaminocarbonyl]-2-vinyl-cyclopropylcarbamoyl}-pyrrolidine-1-carbonyl)-2,2-dimethyl-propyl]-carbamic acid tert-butyl ester

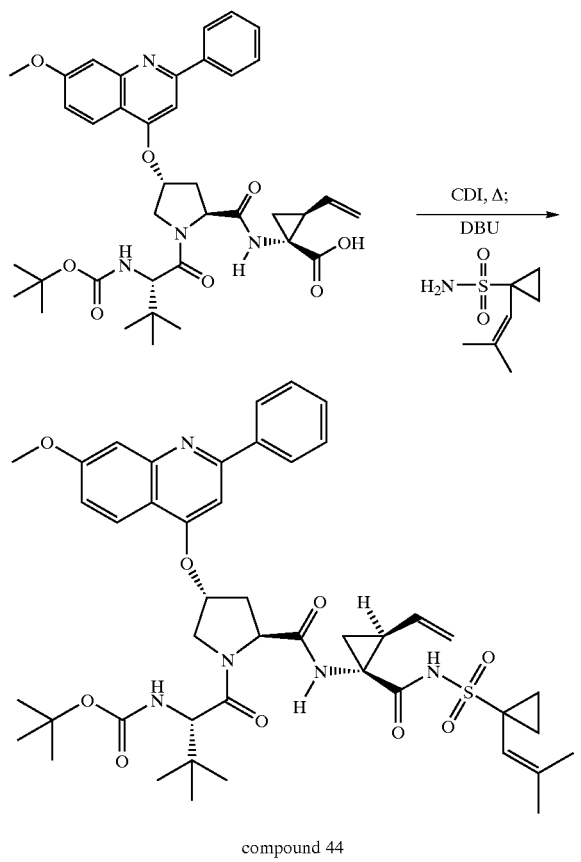

compound 44

Step 44c) Compound 44 was prepared in 28% (0.0346 g) yield from tripeptide acid product (0.100 g, 0.09 mmol) of step 2e (Example 2) in analogous fashion to the procedure of Step 27c of Example 27 except that 1-(2-methyl-propenyl)-cyclopropanesulfonamide (compound 44b) was used in place of 1-trimethylsilanyl-cyclopropanesulfonamide and purified by preparative HPLC (solvent B: 40–85%): $^1$H NMR (methanol-d$_4$) □ ppm 0.85 (m, 2H), 1.04 (s, 9H), 1.28 (s, 9H), 1.58 (m, 10H), 2.10 (m, 1H), 2.47 (m, 1H), 3.03 (m, 1H), 3.93 (s, 3H), 4.08 (m, 1H), 4.24 (s, 1H), 4.55 (m, 2H), 5.00 (m, 1H), 5.21 (d, J=17.57 Hz, 1H), 5.37 (s, 1H), 5.53 (s, 1H), 5.89 (m, 1H), 7.05 (dd, J=9.15, 2.20 Hz, 1H), 7.23 (s, 1H), 7.37 (d, J=2.20 Hz, 1H), 7.49 (m, 3H), 8.07 (m, 3H). LC-MS (retention time: 1.82, Method L), MS m/z 844 (M$^+$+1).

Compound 45 Example 45

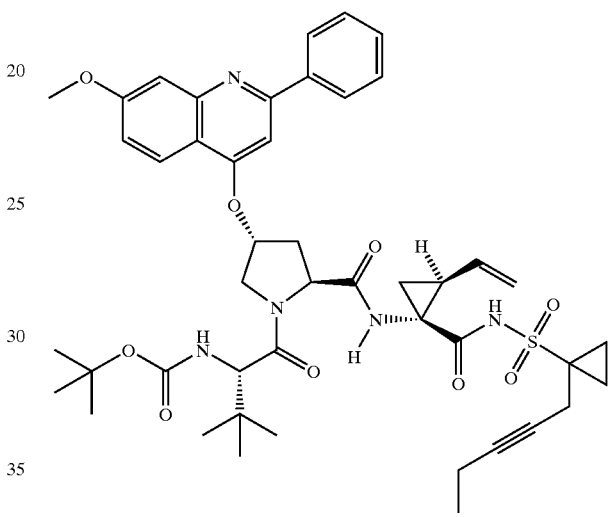

compound 45

Step 45a: Preparation of 1-Pent-2-ynyl-cyclopropanesulfonamide-tert-butylcarbamate

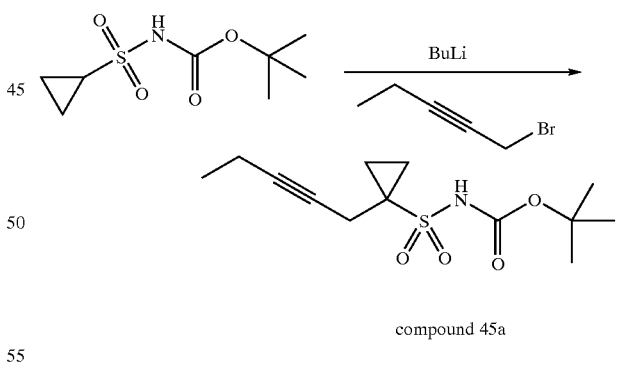

compound 45a

Step 45a) This compound, 1-Pent-2-ynyl-cyclopropanesulfonamide-tert-butylcarbamate, was obtained 79% (1.03 g) from 1.0 g (4.52 mmol) of cyclopropanesulfonamide-tert-butylcarbamate according to the procedure described in the synthesis of 1-methoxymethylcyclo-propylsulfonylamine tert-butylcarbamate (Step 15IId) except 1.1 equivalents of 1-bromo-pent-2-yne was used as electrophile: $^1$H NMR (CDCl$_3$) □ ppm 1.10 (t, J=7.48 Hz, 3-H), 1.15 (m, 2H), 1.50 (s, 9H), 1.62 (m, 2H), 2.14 (m, 2H), 2.90 (t, J=2.44 Hz, 2H), 6.91 (s, 1H).

Step 45b: Preparation of 1-Pent-2-ynyl-cyclopropanesulfonamide

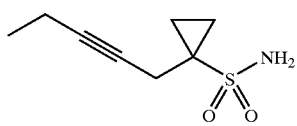

compound 45b

Step 45b) This compound, 1-Pent-2-ynyl-cyclopropanesulfonic acid amide, was obtained in 100% yield (0.72 g) from 1.1 g (3.83 mmole) of 1-Pent-2-ynyl-cyclopropanesulfonamide-tert-butylcarbamate, according to the procedure described in the synthesis of 1-butyl-cyclopropanesulfonic acid amide (Step 29IIe) as a white solid: $^1$H NMR (Methanol-d$_4$) □ ppm 1.06 (m, 2H), 1.09 (t, J=7.48 Hz, 3H), 1.23 (m, 2H), 2.14 (m, 2H), 2.94 (t, J=2.44 Hz, 2H).

Step 45c: Preparation of Compound 45, Example 45, BOCNH—P3(L-t-BuGly)-P2[(4R)-(2-phenyl-7-methoxyquinoline-4-oxo)-S-proline]-P1(1R,2S Vinyl Acca)-CONHSO$_2$[1(1-pent-2-ynyl)-clopropan-1-yl) or Alternate Designation, Compound 45, Example 45, (1-{4-(7-Methoxy-2-phenyl-quinolin-4-yloxy)-2-[1-(1-pent-2-ynyl-cyclopropanesulfonylaminocarbonyl)-2-vinyl-cyclopropylcarbamoyl]-pyrrolidine-1-carbonyl}-2,2- dimethyl-propyl)-carbamic acid tert-butyl ester

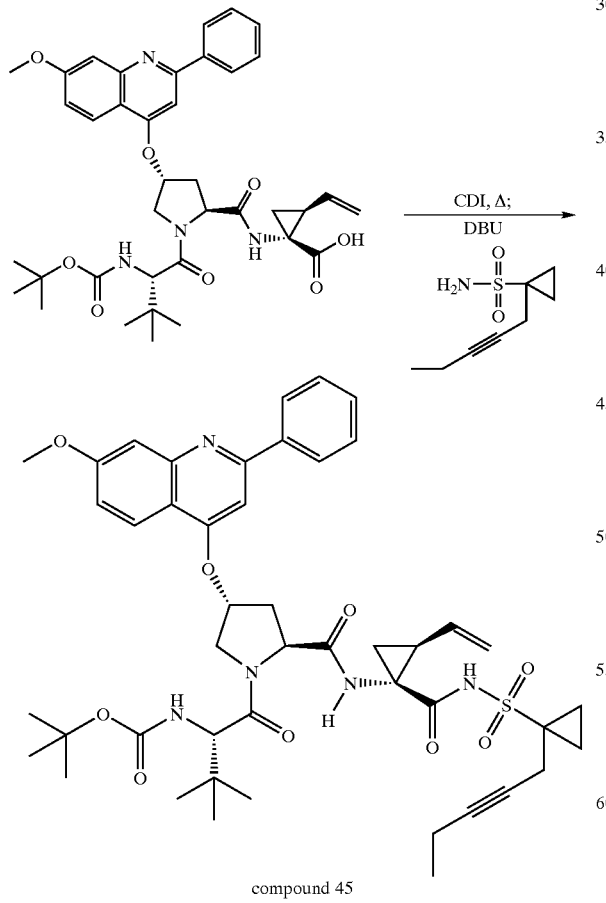

compound 45

Step 45c) Compound 45 was prepared in 31% (0.0382 g) yield from tripeptide acid product (0.100 g, 0.15 mmol) of step 2e (Example 2) in analogous fashion to the procedure of Step 27c of Example 27 except that 1-Pent-2-ynyl-cyclopropanesulfonic acid amide was used in place of 1-trimethylsilanyl-cyclopropanesulfonamide and purified by preparative HPLC (solvent B: 40-100%): $^1$H NMR (methanol-d$_4$) 0 ppm 0.97 (m, 5H), 1.04 (s, 9H), 1.26 (s, 9H), 1.30 (m, 3H), 1.83 (m, 1H), 2.03 (m, 3H), 2.50 (m, 1H), 2.73 (m, 1H), 2.99 (s, 2H), 3.92 (s, 3H), 4.08 (m, 1H), 4.25 (m, 1H), 4.56 (m, 2H), 5.01 (m, 1H), 5.20 (d, J=17.09 Hz, 1H), 5.52 (s, 1H), 5.91 (m, 1H), 7.05 (m, 1H), 7.20 (m, 1H), 7.37 (m, 1H), 7.50 (m, 3H), 8.07 (m, 3H). LC-MS (retention time: 1.86, Method L), MS m/z 856 (M$^+$+1).

Compound 46 Example 46

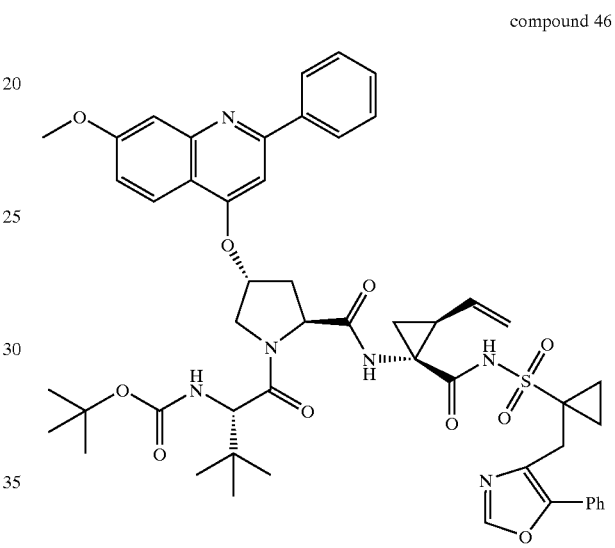

compound 46

Step 46a: Preparation of 1-(5-phenyl-oxazol-4-ylmethyl)-cyclopropanesulfonamide-tert-butylcarbamate

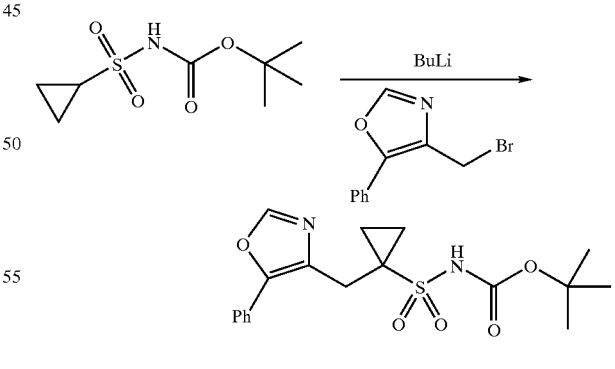

compound 46a

Step 46a) This compound, 1-(5-phenyl-oxazol-4-ylmethyl)-cyclopropanesulfonamide-tert-butylcarbamate, was obtained 27% (0.461 g) from 1.0 g (4.52 mmol) of cyclopropanesulfonamide-tert-butylcarbamate according to the procedure described in the synthesis of 1-methoxymethylcyclo-propylsulfonylamine tert-butylcarbamate (Step 15IId) except 1.1 equivalents of 5-bromomethyl-3-phenyl-isoxazole was used as electrophile: ¹H NMR (CDCl₃) δ ppm 1.06 (m, 2H), 1.48 (s, 9H), 1.66 (m, 2H), 3.51 (s, 2H), 7.41 (m, 4H), 7.55 (m, 1H), 7.63 (d, J=6.95 Hz, 1H), 7.85 (s, 1H).

Step 46b: Preparation of 1-(5-Phenyl-oxazol-4-ylmethyl)-cyclopropanesulfonamide compound 46b

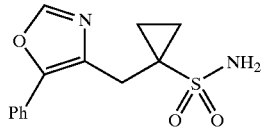

Step 46b) This compound, 1-(5-phenyl-oxazol-4-ylmethyl)-cyclopropanesulfonic acid amide, was obtained in 54% yield (0.126 g) from 0.32 g (3.83 mmole) of 1-Pent-2-ynyl-cyclopropanesulfonamide-tert-butylcarbamate, according to the procedure described in the synthesis of 1-butyl-cyclopropanesulfonic acid amide (Step 30a, Example 30) but without purification: ¹H NMR (Methanol-d₄) □ ppm 0.79 (m, 2H), 1.26 (m, 2H), 3.59 (s, 2H), 7.37 (m, 2H), 7.50 (m, 2H), 7.72 (d, J=6.95 Hz, 1H), 8.17 (s, 1H).

Step 46c: Preparation of Compound 46. Example 46, BOCNH—P3(L-t-BuGly)-P2[(4R)-(2-phenyl-7-methoxyquinoline-4-oxo)-S-proline]-P1(R,2S Vinyl Acca)-CONHSO₂-[1-(5-phenyl-oxazol-4-ylmethyl)-clopropan-1yl] or Alternate Designation, Compound 46, Example 46, [[1-(4-(7-Methoxy-2-phenyl-quinolin-4-yloxy)-2-{1-[1-(5-phenyl-oxazol-4-ylmethyl)-cyclopropanesulfonylaminocarbonyl]-2-vinyl-yclopropylcarbamoyl}-pyrrolidine-1-carbonyl)-2,2-dimethyl-propyl]-carbamic acid tert-butyl ester

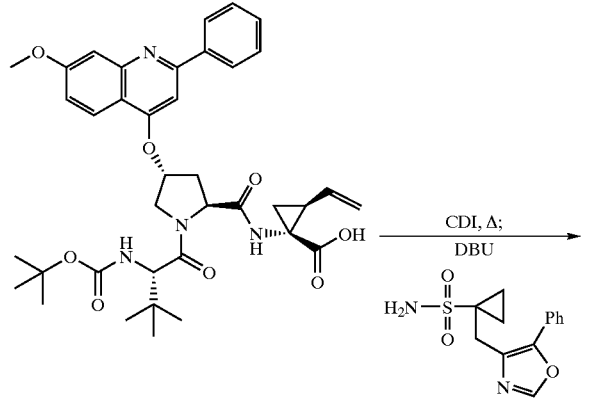

-continued

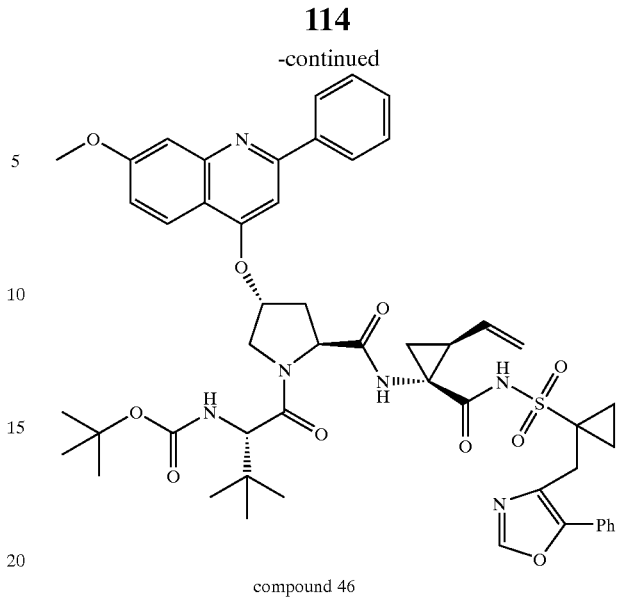

compound 46

Step 46c) Compound 46 was prepared in 18% (0.0255 g) yield from tripeptide acid product (0.080 g, 0.12 mmol) of step 2e (Example 2) in analogous fashion to the procedure of Step 27c of Example 27 except that 1-(4-phenyl-isoxazol-5-ylmethyl)-cyclopropanesulfonamide of the product of Step 46b (Example 46) was used in place of 1-trimethylsilanyl-cyclopropanesulfonamide and purified by preparative HPLC (solvent B: 40-90%): ¹H NMR (methanol-d₄) □ ppm 1.04 (s, 9H), 1.32 (s, 9H), 1.41 (m, 4H), 1.68 (m, 1H), 1.84 (dd, J=7.32, 4.88 Hz, 1H), 2.06 (m, 1H), 2.60 (m, 1H), 2.72 (m, 1H), 3.57 (d, J=14.65 Hz, 1H), 3.62 (m, 1H), 4.17 (m, 3H), 4.23 (dd, J=5.49, 3.05 Hz, 1H), 4.28 (s, 1H), 4.51 (d, J=11.60 Hz, 1H), 4.56 (t, J=8.55 Hz, 1H), 4.97 (d, J=11.29 Hz, 1H), 5.18 (d, J=17.09 Hz, 1H), 5.54 (s, 1H), 6.05 (m, 1H), 7.06 (dd, J=9.00, 1.98 Hz, 1H), 7.27 (m, 2H), 7.41 (m, 3H), 7.49 (m, 3H), 7.68 (m, 3H), 8.01 (m, 3H). MS m/z 946 (M⁻-1) HPLC (retention time: 1.96, Method M).

Compound 47 Example 47 compound 47

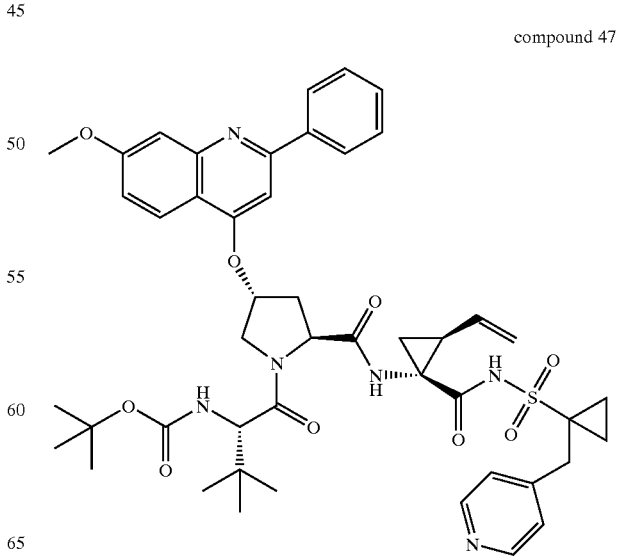

Step 47a: Preparation of 1-(4-pyridyl)-cyclopropanesulfonamide

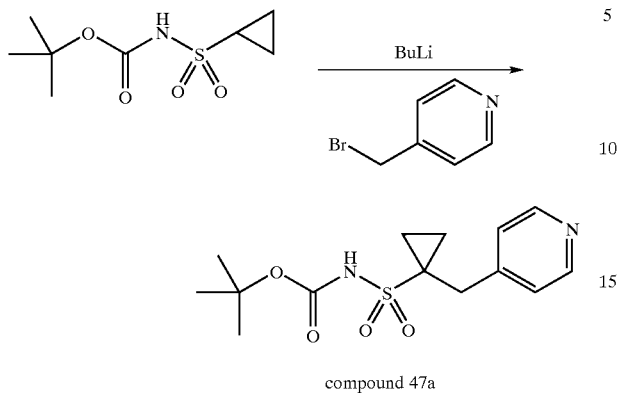

compound 47a step 47a) To a solution of cyclopropylsulfonylamine tert-butyl carbamate (105 g, 4.52 mmol) in THF (9 mL) cooled to −78° C., was added n-BuLi (6.2 mL, 9.2 mmol, 1.6 M in hexane). The mixture was stirred for 1 h at −78° C., and 0.55 mL (0.5 mmol) of fresh 4-(bromomethyl)pyridine was injected in one portion. The fresh 4-(bromomethyl)-pyridine was made from 4-(bromomethyl)pyridine hydrobromide by tributing between aqueous sodium bicarbonate and ether, ether layer was quickly separated, dried (MgSO$_4$), removed solvent in vacuo, and immediately used to the reaction. The reaction mixture was stirred for 5 min at −78° C., changed the bath into ice water, and stirred for another 1 h. The reaction mixture was diluted with pH 4.0 buffer, adjusted pH to 4, and extracted with EtOAc. The combined extractions were dried (MgSO$_4$), concentrated, and purified by pre-HPLC to afford a mixture (only 0.42 g) with 1-(4-pyridyl)-cyclopropanesulfonamide-tert-butylcarbamate and the mixture was used in next step.

Step 47b: Preparation of 1-(4-pyridyl)-cyclopropanesulfonamide

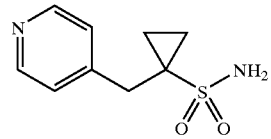

compound 47b

Step 47b) This compound, 1-Pyridin-2-ylmethyl)-cyclopropanesulfonic acid amide, was obtained in 13% yield (0.12 g) two steps from the mixture of 47 according to the procedure described in the synthesis of 1-butyl-cyclopropanesulfonamide (Step 30b) and purified by prep-HPLC (solvent B: 0–80%) as a white solid: $^1$H NMR (Methanol-d$_4$) ☐ ppm 0.90 (m, 2H), 1.38 (m, 2H), 3.38 (s, 2H), 7.55 (d, J=6.22 Hz, 2H), 8.50 (d, J=4.39 Hz, 2H).

Step 47c: Preparation of Compound 47, Example 47, BOCNH—P3(L-t-BuGly)-P2[(4R)-(2-phenyl-7-methoxyquinoline-4-oxo)-S-proline]-P1(R,2S Vinyl Acca)-CONHSO$_2$-[1-(1-pyridin-4-ylmethyl)-clopropan-1-yl] or Alternate Designation, Compound 47, Example 47, (1-14-(7-Methoxy-2-phenyl-quinolin-4-yloxy)-2-[1-(1-pyridin-4-ylmethyl-cyclopropanesulfonylaminocarbonyl)-2-vinyl-cyclopropylcarbamoyl]-pyrrolidine-1-carbonyl}-2,2-dimethyl-propyl)-carbamic acid tert-butyl ester

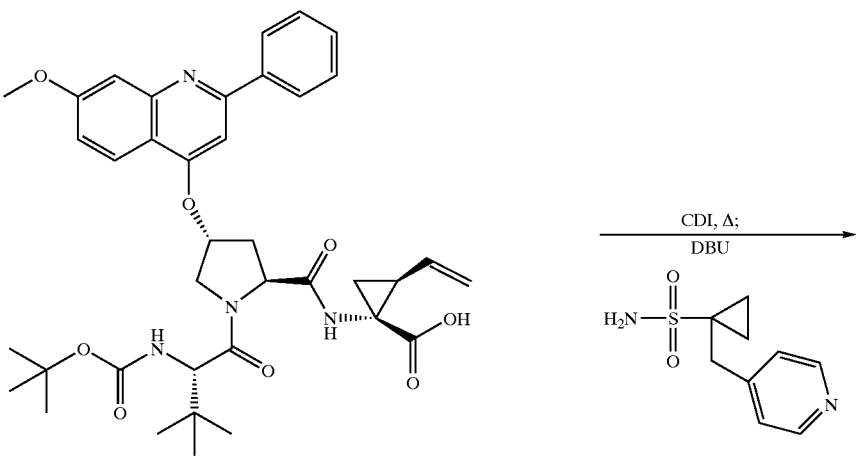

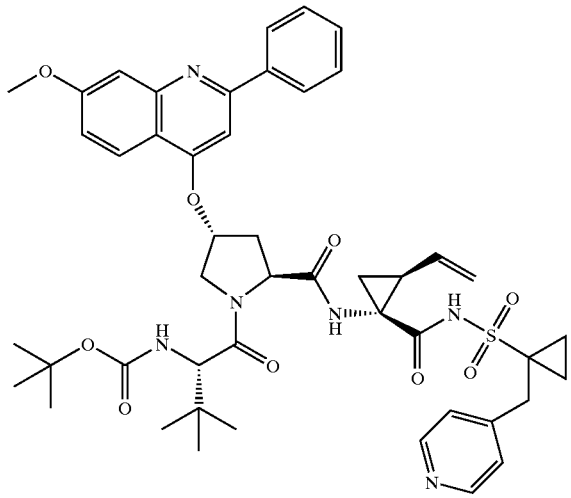

compound 47

Step 47c) Compound 47 was prepared in 58% (0.0739 g) yield from tripeptide acid product (0.120 g, 0.17 mmol) of step 2e (Example 2) in analogous fashion to the procedure of Step 27c of Example 27 except that 1-pyridin-4-ylmethyl cyclopropanesulfonamide (compound 47b, Example 47) was used in place of 1-trimethylsilanyl-cyclopropanesulfonamide and purified by preparative HPLC (solvent B: 0–85%): $^1$H NMR (methanol-d$_4$) ☐ ppm 2.30 (m, 1H), 2.39 (m, 1H), 2.76 (dd, J=13.43, 6.71 Hz, 1H), 3.37 (m, 2H), 4.01 (s, 3H), 4.12 (d, J=9.46 Hz, 1H), 4.23 (s, 1H), 4.65 (m, 2H), 5.19 (d, J=8.85 Hz, 1H), 5.35 (d, J=16.79 Hz, 1H), 5.67 (s, 1H), 5.77 (s, 1H), 6.94 (s, 1H), 7.21 (d, J=9.16 Hz, 1H), 7.41 (s, 3H), 7.47 (s, 1H), 7.62 (s, 3H), 8.07 (s, 2H), 8.22 (d, J=9.16 Hz, 1H), 8.48 (s, 2H). MS m/z 881 (M$^+$+1), MS m/z 799 (M$^-$−1). LC-MS (retention time: 1.39, Method H), MS m/z 881 (M$^+$+1).

Compound 48 Example 48 compound 48

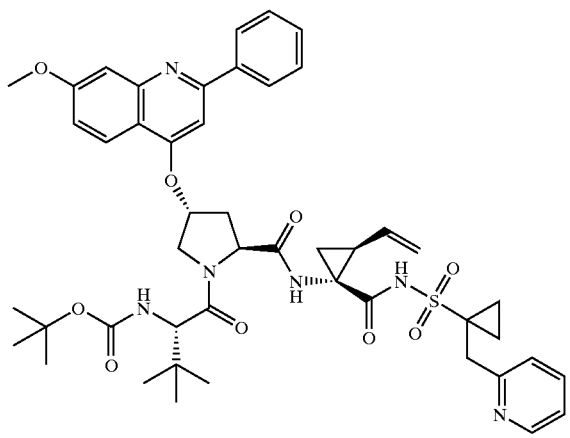

Step 48a: Preparation of 1-Pyridin-2-ylmethyl-cyclopropanesulfonamide-tert-butylcarbamate

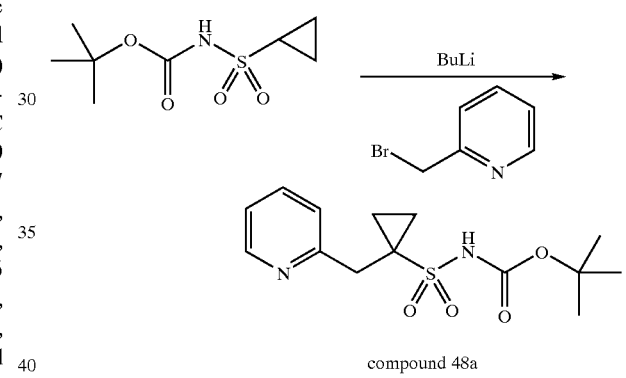

compound 48a step 48a) This umpure compound, 1-Pyridin-2-ylmethyl-cyclopropanesulfonamide-tert-butylcarbamate, was obtained 0.61 g from 1.0 g (4.52 mmol) cyclopropanesulfonamide-tert-butylcarbamate, according to the procedure described in the synthesis of 1-pyridin-4-ylmethyl-cyclopropanesulfonamide-tert-butylcarbamate (step 47a). The umpure product was used in next step.

Step 48b: Preparation of 1-pyridin-2-ylmethyl-cyclopropanesulfonamide compound 48b

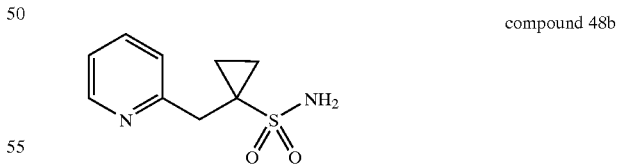

Step 48b) This compound, 1-(pyridin-2-ylmethyl)-cyclopropanesulfonamide-tert-butylcarbamate, was obtained in 18% yield (0.171 g) in two steps from umpure product of Step 48a according to the procedure described in the synthesis of 1-pyridin-4-ylmethyl-cyclopropanesulfonamide-tert-butylcarbamate (Step 47b) and purified by preparative HPLC (solvent B: 0 to 80%) as a white solid as a white solid: $^1$H NMR (Methanol-d$_4$) ☐ ppm 1.19 (m, 2H), 1.48 (m, 2H), 3.60 (s, 2H), 7.89 (t, J=6.77 Hz, 1H), 8.09 (d, J=8.42 Hz, 1H), 8.46 (t, J=7.87 Hz, 1H), 8.71 (d, J=5.86 Hz, 1H).

Step 48c: Preparation of Compound 48, Example 48, BOCNH—P3(L-t-BuGly)-P2[(4R)-(2-phenyl-7-methoxyquinoline-4-oxo)-S-proline]-P1(1R,2S Vinyl Acca)-CONHSO₂-[1-(1-pyridin-2-ylmethyl)-clopropan-1-yl] or Alternate Designation, Compound 48, Example 48, (1-{4-(7-Methoxy-2-phenyl-quinolin-4-yloxy)-2-[1-(1-pyridin-2-ylmethyl-cyclopropanesulfonylaminocarbonyl)-2-vinyl-cyclopropylcarbamoyl]-pyrrolidine-1-carbonyl}-2,2-dimethyl-propyl)-carbamic acid tert-butyl ester

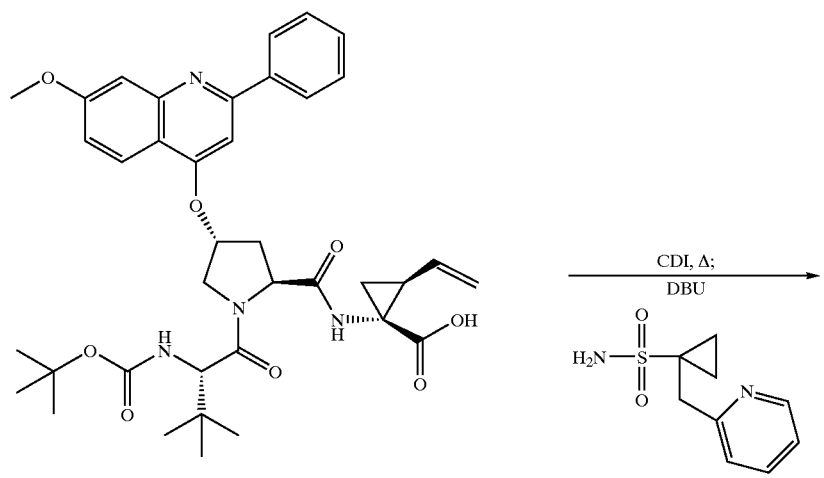

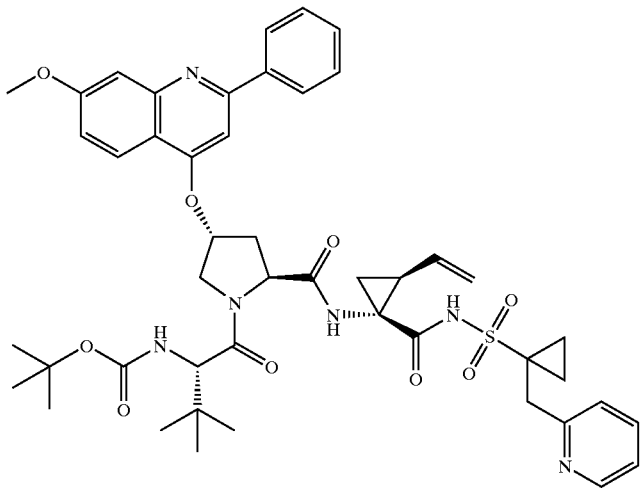

compound 48

Step 48c) Compound 48 was prepared in 67% (0.086 g) yield from tripeptide acid product (0.120 g, 0.17 mmol) of step 2e (Example 2) in analogous fashion to the procedure of Step 27c of Example 27 except that 1-pyridin-2-ylmethyl cyclopropanesulfonamide (Compound 48b) was used in place of 1-trimethylsilanyl-cyclopropanesulfonamide preparative HPLC (solvent 0 to 85%): $^1$H NMR (methanol-d₄) ☐ ppm 0.97 (s, 9H), 0.99 (m, 2H), 1.22 (s, 9H), 1.48 (m, 3H), 1.85 (m, 1H), 2.27 (q, J=8.90 Hz, 1H), 2.41 (m, 1H), 2.76 (dd, J=13.54, 6.95 Hz, 1H), 3.39 (d, J=13.91 Hz, 1H), 3.50 (m, 1H), 3.99 (s, 3H), 4.09 (d, J=12.08 Hz, 1H), 4.18 (s, 1H), 4.62 (m, 2H), 5.14 (d, J=10.25 Hz, 1H), 5.31 (d, J=16.83 Hz, 1H), 5.76 (m, 2H), 7.25 (dd, J=9.15, 2.20 Hz, 1H), 7.31 (dd, J=7.68, 5.12 Hz, 1H), 7.46 (m, 3H), 7.64 (m, 3H), 7.78 (m, 1H), 8.05 (m, 2H), 8.24 (d, J=9.15 Hz, 1H), 8.44 (d, J=4.03 Hz, 1H). MS m/z 881 (M⁺+1), MS m/z 799 (M⁻−1). LC-MS (retention time: 1.43, Method H), MS m/z 881 (M⁺+1).

Compound 49 Example 49

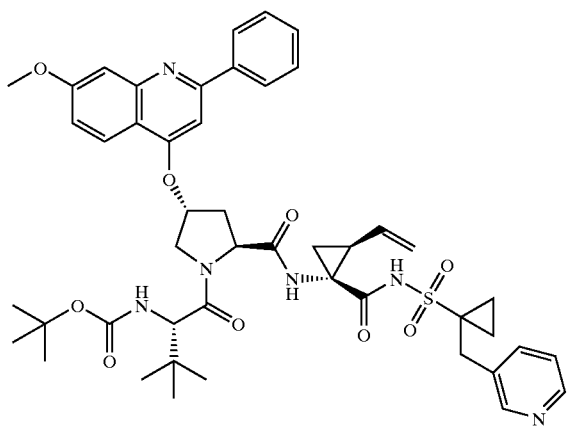

compound 49

Step 49a: Preparation of 1-Pyridin-3-ylmethyl cyclopropanesulfonamide-tert-butylcarbamate

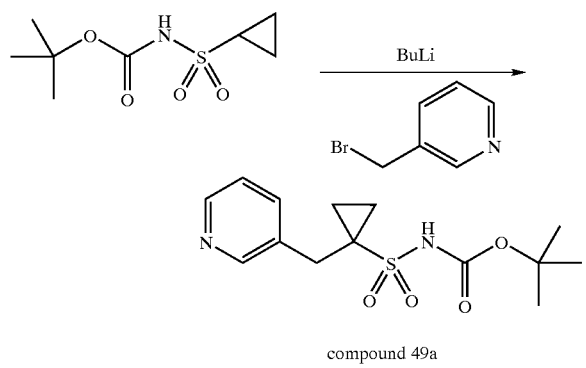

compound 49a

Step 49a) To a solution of cyclopropylsulfonylamine tert-butyl carbamate (105 g, 4.52 mmol) in THF (9 mL) cooled to −78° C., was added n-BuLi (6.2 mL, 9.2 mmol, 1.6 M in hexane). The mixture was stirred for 1 h at −78° C., and fresh ether solution (2 mL) of 3-(bromomethyl)pyridine was injected in one portion. The fresh 3-(bromomethyl)pyridine was made from 1.5 g (5.9 mmol) of 3-(bromomethyl) pyridine hydrobromide tributed between aqueous sodium bicarbonate and ether. The ether layer was quickly separated, dried (MgSO$_4$), and concentrated in vacuo till about 2 mL liquid left. The reaction mixture was stirred for 4 min, changed the bath into ice water, and stirred for 1 h. The reaction mixture was diluted with pH 4.0 buffer, adjusted pH to 4, and extracted with EtOAc. The extraction was dried (MgSO$_4$), concentrated, and purified by prep-HPLC (sovent B: 0 to 80%) to afford 0.61 g mixture with 1-(3-pyridyl)-cyclopropanesulfonamide-tert-butylcarbamate, and the mixture was used in next step.

Step 49b: Preparation of 1-(Pyridin-2-ylmethyl)-cyclopropanesulfonamide

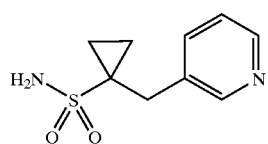

compound 49b

Step 49b) This compound, 1-(Pyridin-2-ylmethyl)-cyclopropanesulfonic acid amide, was obtained in 11% yield (0.107 g, two steps) from 0.5 g of impure 1-(pyridin-3-ylmethyl)-)-cyclopropanesulfonamide-tert-butylcarbamate according to the procedure described in the synthesis of 1-(Pyridin-4-ylmethyl)-cyclopropanesulfonic acid amide (Step 48b, Example 48): $^1$H NMR (Methanol-d$_4$) □ ppm 1.11 (m, 2H), 1.46 (m, 2H), 3.44 (s, 2H), 7.94 (dd, J=8.09, 5.65 Hz, 1H), 8.53 (d, J=8.24 Hz, 1H), 8.71 (d, J=5.19 Hz, 1H), 8.82 (s, 1H).

Step 49c: Preparation of Compound 49, Example 49, BOCNH—P3(L-t-BuGly)-P2[(4R)-(2-phenyl-7-methoxyquinoline-4-oxo)-S-proline]-P1(1R,2S Vinyl Acca)-CONHSO$_2$-[1-(1-pyridin-3-ylmethyl)-clopropan-1-yl] or Alternate Designation, Compound 49, Example 49, (1-{4-(7-Methoxy-2-phenyl-quinolin-4-yloxy)-2-[1-(1-pyridin-3-ylmethyl-cyclopropanesulfonylaminocarbonyl)-2-vinyl-cyclopropylcarbamoyl]-pyrrolidine-1-carbonyl}-2,2-dimethyl-propyl)-carbamic acid tert-butyl

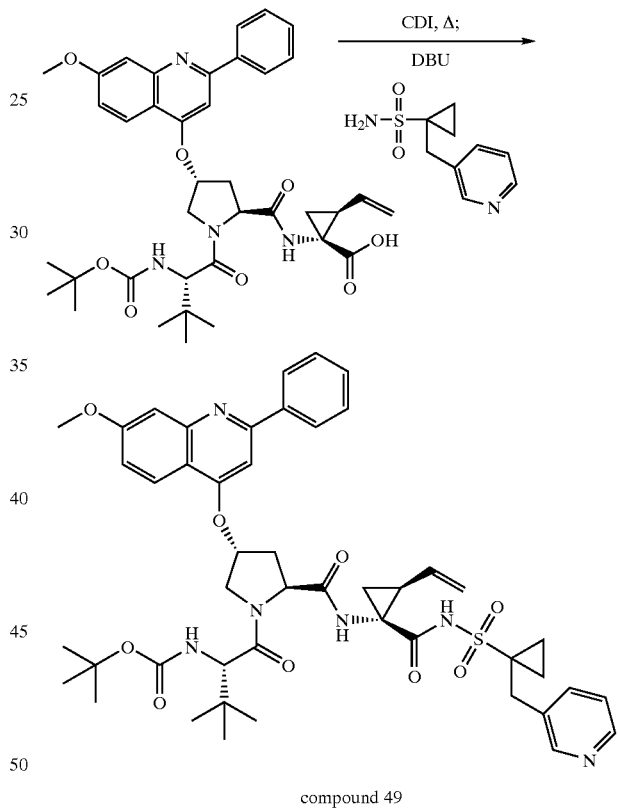

compound 49

Step 49c) Compound 49 was prepared in 14% (0.0127 g)yield from tripeptide acid product (0.080 g, 0.12 mmol)of step 2e (Example 2) in analogous fashion to the procedure of Step 27c of Example 27 except that 1-pyridin-3-ylmethyl-cyclopropanesulfonamide was used in place of 1-trimethylsilanyl-cyclopropanesulfonamide and purified by preparative HPLC (solvent B: 0 to 85%): $^1$H NMR (methanol-d$_4$) □ ppm 0.97 (s, 9 □ 1.20 (s, 9 □ 1.31 (m, 4 □ 1.58 (m, 1 □ 1.91 (dd, J=8.24, 5.49 Hz, 1 □ 2.29 (m, 1 □ 2.41 (m, 1 □ 2.77 (dd, J=14.19, 6.87 Hz, 1 □ 3.30 (m, 1 □ 3.39 (m, 1 □ 4.03 (s, 3 □ 4.11 (dd, J=12.05, 2.90 Hz, 1 □ 4.17 (s, 1 □ 4.65 (m, 2 □ 5.18 (m, 1 □ 5.34 (d, J=17.09 Hz, 1 □ 5.75 (m, 2 □ 6.92 (s, 1 □ 7.32 (m, 1 □ 7.46 (s, 1 □ 7.49 (s, 1 □ 7.56 (s, 1 □ 7.71 (m, 3

☐ 7.86 (d, J=6.41 Hz, 1 ☐ 8.06 (dd, J=7.78, 1.68 Hz, 2 ☐ 8.30 (d, J=8.85 Hz, 1 ☐ 8.49 (s, 1H). LC-MS (retention time: 1.49, Method I), MS m/z 881 (M$^+$+1).

Compound 50 Example 50

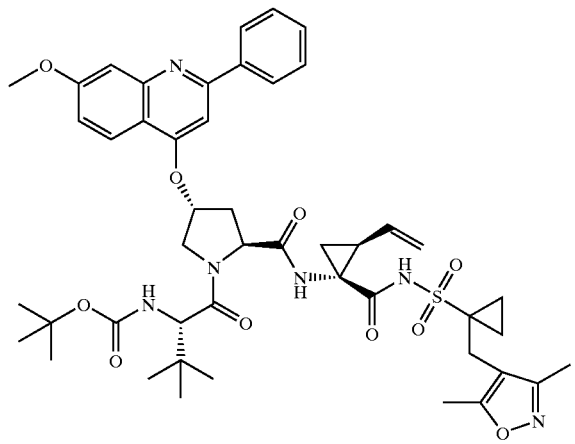

compound 50

Step 50a: Preparation of 1-(3,5-Dimethyl-isoxazol-4-ylmethyl)-cyclopropanesulfonamide-tert-butylcarbamate

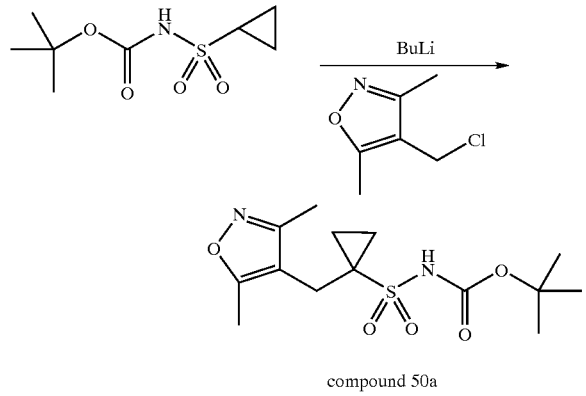

compound 50a

Step 50a) This compound, 1-(3,5-Dimethyl-isoxazol-4-ylmethyl)-cyclopropanesulfonamide-tert-butylcarbamate, was obtained 45% (0.672 g) from 1.0 g (4.52 mmol) of cyclopropanesulfonamide-tert-butylcarbamate according to the procedure described in the synthesis of 1-methoxymethylcyclo-propylsulfonylamine tert-butylcarbamate (Step 15IId) except 1.1 equivalents of 4-chloromethyl-3,5-dimethyl-isoxazole was used as electrophile and purified over Biotage 40L using EtOAc/Hexanes (5% to 100%) as the eluent: $^1$H NMR (CDCl$_3$) ☐ ppm 0.66 (m, 2H), 1.50 (s, 9H), 1.64 (m, 2H), 2.20 (s, 3H), 2.32 (s, 3H), 3.07 (s, 2H), 6.80 (s, 1H).

Step 50b: Preparation of 1-(3,5-Dimethyl-isoxazol-4-ylmethyl)-cyclopronanesulfonic acid amide

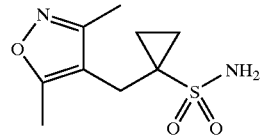

compound 50b

Step 50b) Compound 50b, 1-(3,5-Dimethyl-isoxazol-4-ylmethyl)-cyclopropanesulfonic acid amide, was obtained in 24% yield (0.083 g) from 0.48 g (of 1-(3,5-Dimethyl-isoxazol-4-ylmethyl)-cyclopropanesulfonamide-tert-butylcarbamate according to the procedure described in the synthesis of 1-(Pyridin-4-ylmethyl)-cyclopropanesulfonic acid amide (Step 47b, example 47): $^1$H NMR (Methanol-d$_4$) ☐ ppm 0.47 (m, 2H), 1.18 (m, 2H), 2.14 (s, 3H), 2.26 (s, 3H), 3.06 (s, 2H), 4.73 (s, 2H).

Step 50c: Preparation of Compound 50, Example 50. BOCNH—P3(L-t-BuGly)-P2[(4R)-(2-phenyl-7-methoxyquinoline-4-oxo)-S-proline]-P1(1R,2S Vinyl Acca)-CONHSO$_2$-[1-(3,5-Dimethyl-isoxazol-4-ylmethyl)-clopropan-1-yl] or Alternate Designation. Compound 50, Example 50, {1-[2-{1-[1-(3,5-Dimethyl-isoxazol-4-ylmethyl)-cyclopropanesulfonylaminocarbonyl]-2-vinyl-cyclopropylcarbamoyl}-4-(7-methoxy-2-phenyl-quinolin-4-yloxy)-pyrrolidine-1-carbonyl]-2,2-dimethyl-propyl}-carbamic acid tert-butyl ester

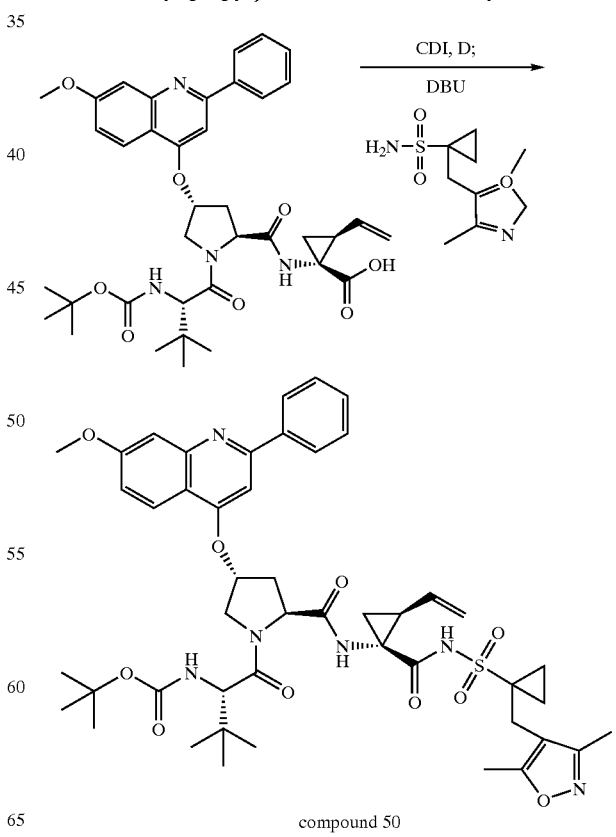

compound 50

Step 50c) Compound 50 was prepared in 32% (0.0254 g) yield from tripeptide acid product (0.060 g) of step 2e (Example 2) in analogous fashion to the procedure of Step 27c of Example 27 except that 1-(3,5-dimethyl-isoxazol-4-ylmethyl)-cyclopropanesulfonamide (Compound 50b, Example 50) was used in place of 1-trimethylsilanyl-cyclopropanesulfonamide and purified by preparative HPLC (solvent B: 40 to 85%): $^1$H NMR (methanol-$d_4$) ☐ ppm 0.60 (m, 2H), 0.95 (s, 9H), 1.19 (s, 9H), 1.43 (m, 2H), 1.61 (m, 1H), 1.90 (dd, J=S8.1, 5.3 Hz, 1H), 2.19 (s,3H), 2.28 (m, 1H), 2.32 (s, 3H), 2.38 (m, 1H), 2.77 (dd, J=13.9, 7.2 Hz, 1H), 3.07 (d, J=14.7 Hz, 1H), 3.15 (m, 1H), 4.03 (s, 3H), 4.10 (m, 1H), 4.16 (s, 1H), 4.65 (m, 2H), 5.15 (m, 1H), 5.33 (m, 1H), 5.74 (m, 2H), 7.34 (dd, J=9.2, 2.14 Hz, 1H), 7.50 (d, J=2 Hz, 1H), 7.57 (s, 1H), 7.70 (m, 3 ☐ 8.06 (m, 2H), 8.31 (m, 1H). LC-MS (retention time: 1.69, Method I) MS m/z 899 (M$^+$+1).

Compound 51 Example 51

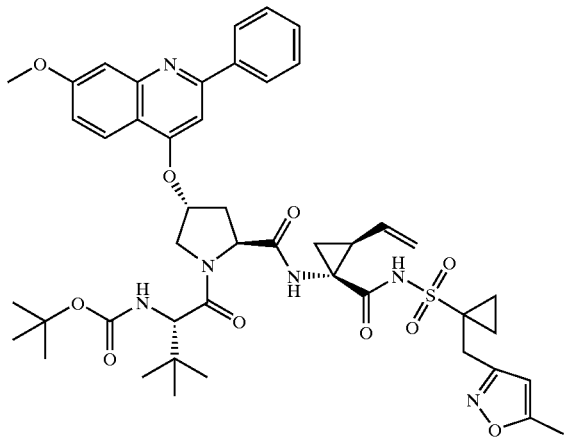

compound 51

Step 51a: Preparation of 1-(5-Methyl-isoxazol-3-ylmethyl)-cyclopropanesulfonamide-tert-butylcarbamate

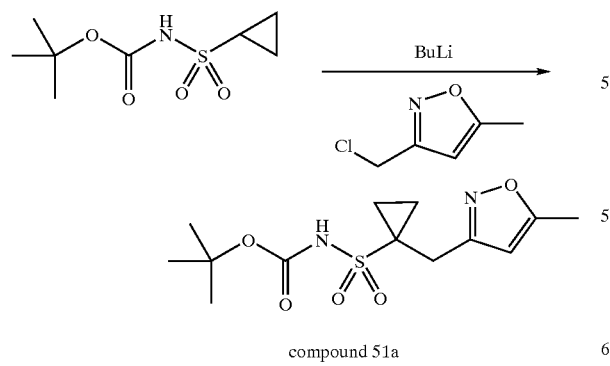

compound 51a

Step 51a) This compound, 1-(5-methyl-isoxazol-3-ylmethyl)-cyclopropanesulfonamide-tert-butylcarbamate, was obtained 34% (0.486 g) from 1.0 g (4.52 mmol) of cyclopropanesulfonamide-tert-butylcarbamate according to the procedure described in the synthesis of -(3,5-Dimethyl-isoxazol-4-ylmethyl)-cyclopropanesulfonamide-tert-butylcarbamate (Step 50a) except 1.1 equivalents of 3-Chloromethyl-5-methyl-isoxazole was used as electrophile: $^1$H NMR (CDCl$_3$) ☐ ppm 1.04 (m, 2H), 1.45 (s, 9H), 1.71 (m, 2H), 2.37 (s, 3H), 3.23 (s, 2H), 5.98 (s, 1H), 7.65 (s, 1H).

Step 51b Preparation of Compound 1-(5-Methyl-isoxazol-3-ylmethyl)-cyclopropanesulfonic acid amide

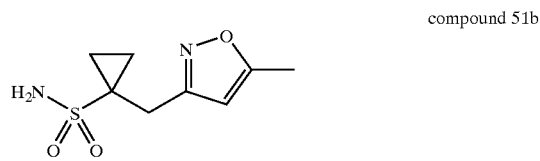

compound 51b

Step 51b) This compound 1-(5-methyl-isoxazol-3-ylmethyl)-cyclopropanesulfonic acid amide, was obtained in 24% yield (0.0813 g) from 0.48 g (of 1-(3,5-Dimethyl-isoxazol-4-ylmethyl)-cyclopropanesulfonamide-tert-butylcarbamate according to the procedure described in the synthesis of 1-butylcyclopropanesulfonic acid amide (Step 20b): $^1$H NMR (Methanol-$d_4$) ☐ ppm 0.89 (m, 2H), 1.33 (m, 2H), 2.38 (s, 3H), 3.26 (s, 2H), 6.16 (s, 1H).

Step 51c: Preparation of Compound 51, Example 51, BOCNH—P3(L-t-BuGly)-P2[(4R)-(2-phenyl-7-methoxyquinoline-4-oxo)-S-proline]-P1(1R,2S Vinyl Acca)-CONHSO$_2$-[1-(5-methyl-isoxazol-3-ylmethyl)-clopropan-1-yl] or Alternate Designation, Compound 51, Example 51, [1-(4-(7-Methoxy-2-phenyl-quinolin-4-yloxy)-2-{1-[1-(5-methyl-isoxazol-3-ylmethyl)-cyclopropanesulfonylaminocarbonyl]-2-vinyl-cyclopropylcarbamoyl}-pyrrolidine-1-carbonyl)-2,2-dimethyl-propyl]-carbamic acid tert-butyl ester

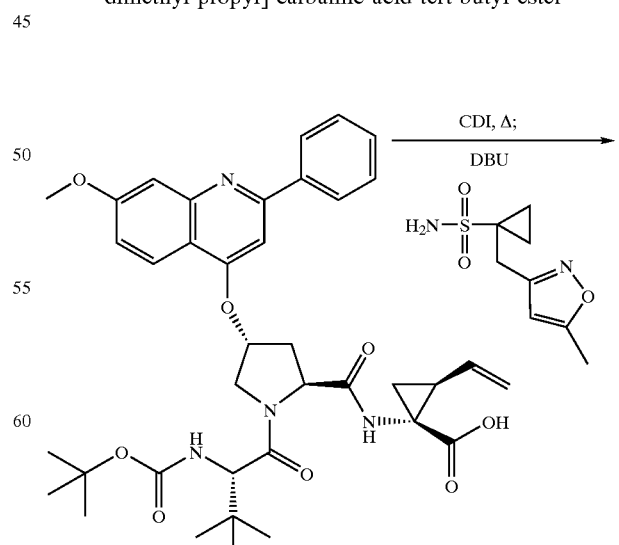

1H), 7.50 (m, 3H), 8.05 (m, 3H). LC-MS (retention time: 1.69, Method I), MS m/z 885 (M$^+$+1).

Compound 52 Example 52 compound 52

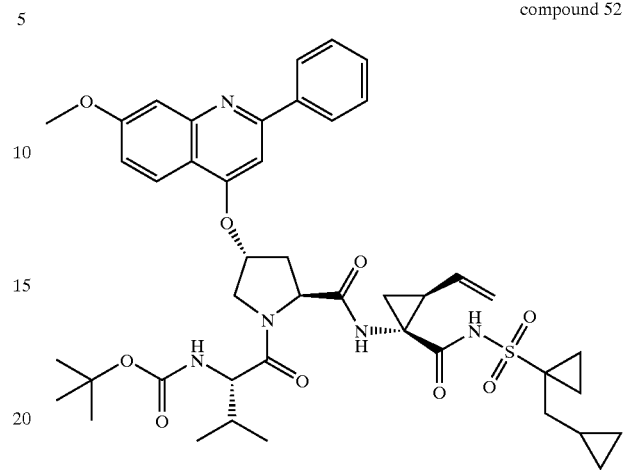

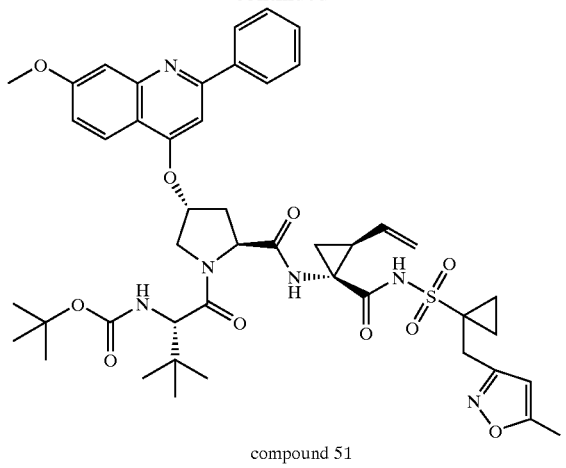

compound 51

Step 51c) Compound 51 was prepared in 7% (0.0058 g) yield from tripeptide acid product (0.060 g) of step 2e (Example 2) in analogous fashion to the procedure of Step 27c of Example 27 except that 1-(5-Methyl-isoxazol-3-ylmethyl)-cyclopropanesulfonamide was used in place of 1-trimethylsilanyl-cyclopropanesulfonamide and purified by preparative HPLC (solvent B: 30 to 100%): $^1$H NMR (methanol-d$_4$) ☐ ppm 0.89 (m, 2H), 1.02 (s, 9H), 1.28 (s, 9H), 1.26 (m, 2H), 1.60 (m, 1H), 1.78 (m, 1H), 2.12 (m, 1H), 2.31 (s, 3H), 2.50 (m, 1H), 2.76 (m, 1H), 3.28 (m, 2H), 3.94 (m, 3H), 4.10 (m, 1H), 4.24 (s, 1H), 4.54 (m, 2H), 5.02 (s, 1H), 5.20 (d, J=16.79 Hz, 1H), 5.55 (s, 1H), 5.91 (m, 1H), 6.10 (s, 1H), 7.06 (d, J=8.85 Hz, 1H), 7.24 (s, 1H), 7.39 (m, Step 52a: Preparation of Compound 52a, Example 52a, BOCNH—P3(L-val)-P2[(4R)-(2-phenyl-7-methoxyquinoline-4-oxo)-S-proline]-P1(1R,2S Vinyl Acca)-Carboxylic acid ethyl ester or Alternate Designation Compound 52a, Example 52a, 1-[{1-(2-tert-Butoxycarbonylamino-3-methyl-butyryl)-4-(7-methoxy-2-phenyl-quinolin-4-yloxy) pyrrolidine-2-carbonyl]-amino}-2-vinyl-cyclopropanecarboxylic acid ethyl ester

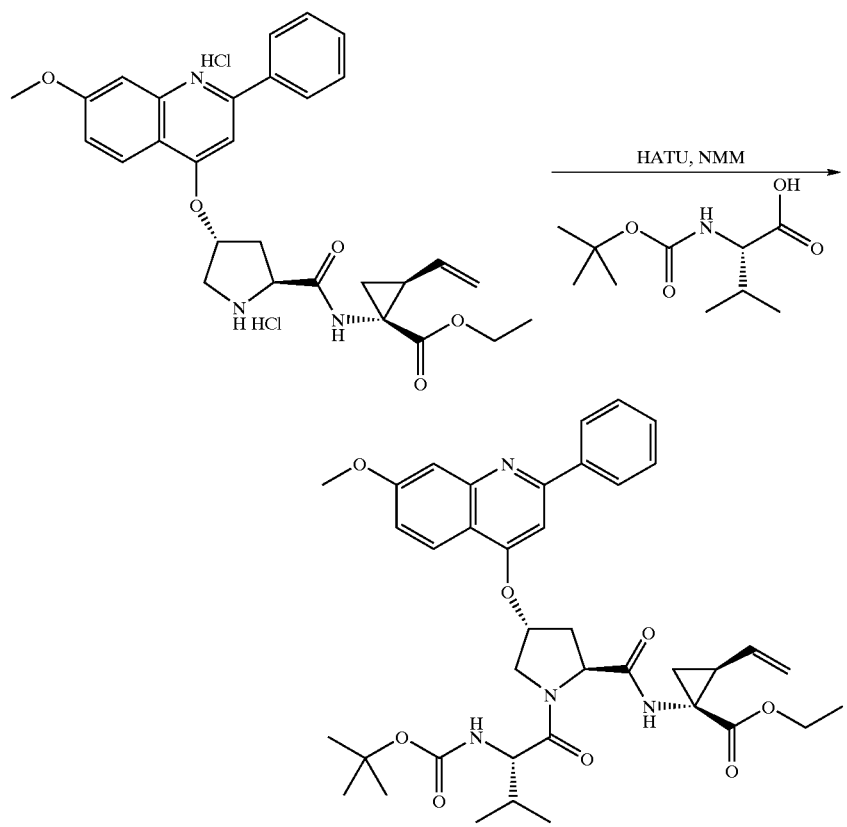

compound 52a

Step 52a) To a suspension of the product of Step 2c (Example 2), the HCl salt of (1R,2S) vinyl Acca P1isomer of 2-(1-Ethoxycarbonyl-2-vinylcyclopropylcarbamoyl)-4-(7-methoxy-2-phenyl-quinolin-4-yloxy)pyrrolidine-1-carboxylic acid ethyl ester (1.2 g; 1.99 mmol), N—BOC-L-valine (0.65 g, 2.39 mmol), NMM (1.0 g, 9.97 mmol) in DMF (12 mL) was added HATU (1.0 g, 2.59 mmol). After being stirred for overnite, the reaction mixture was diluted with EtOAc (200 mL), washed with pH 4.0 buffer (2×), saturated aqueous $NaHCO_3$ (30 mL), brine (30 mL), dried ($MgSO_4$), purified by a Biotage 40 M column (eluted with 15% to 60% EtOAc in Hexanes) to supply the titled product as a white solid (0.98 g, 70%). $^1$H NMR (methanol-$d_4$) □ ppm 0.95 (m, 6H), 1.23 (m, 12H), 1.42 (m, 1H), 1.71 (dd, J=8.05, 5.49 Hz, 1H), 1.97 (m, 1H), 2.22 (m, 1H), 2.42 (m, 1H), 2.73 (m, 1H), 3.95 (s, 3H), 4.10 (m, 4H), 4.60 (m, 2H), 5.09 (dd, J=10.43, 1.65 Hz, 1H), 5.2 (dd, J=17.02, 1.65 Hz, 1H), 5.57 (s, 1H), 5.76 (m, 1H), 7.10 (dd, J=8.97, 2.38 Hz, 1H), 7.25 (s, 1H), 7.39 (d, J=2.56 Hz, 1H), 7.54 (m, 3H), 8.07 (m, 3H).

Step 52b: Preparation of Compound 52b, Example 52b, BOCNH—P3(L-val)-P2[(4R)-(2-phenyl-7-methoxyquinoline-4-oxo)-S-proline]-P1(1R,2S Vinyl Acca)-Carboxylic acid or Alternate Designation, Compound 52b, Example 52b, 1-{[1-(2-tert-Butoxycarbonylamino-3-methyl-butyryl)-4-(7-methoxy-2-phenyl-quinolin-4-yloxy)-pyrrolidine-2-carbonyl]-amino}-2-vinyl-cyclopropanecarboxylic acid

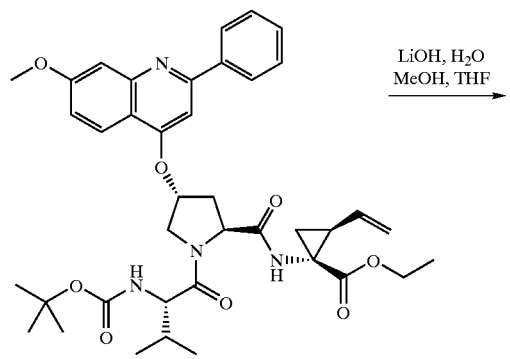

LiOH, $H_2O$
MeOH, THF

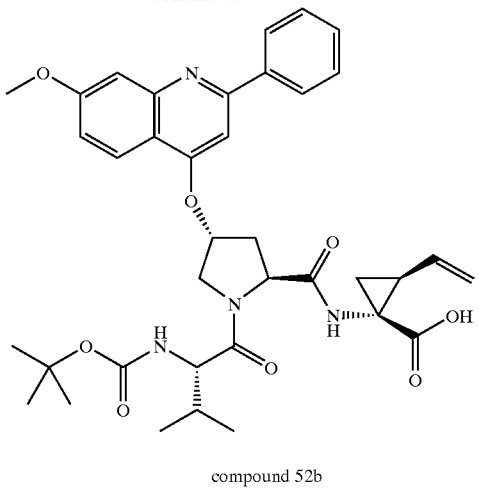

compound 52b

Step 52b) Compound 52b was prepared in 96% (0.90 g) yield from compound 52a product of step 52a (Example 52) in analogous fashion to the procedure of Example 2, Step 2e as a pale yellow foam: $^1$H NMR (methanol-$d_4$) □ ppm 0.93 (m, 6H), 1.23 (s, 9H), 1.42 (m, 1H), 1.69 (dd, J=8.05, 5.49 Hz, 1H), 1.97 (m, 1H), 2.21 (m, 1H), 2.47 (m, 1H), 2.75 (m, 1H), 3.95 (s, 3H), 4.03 (m, 2H), 4.60 (m, 2H), 5.08 (d, J=10.25 Hz, 1H), 5.26 (d, J=17.20 Hz, 1H), 5.57 (s, 1H), 5.83 (m, 1H), 7.11 (dd, J=8.97, 2.38 Hz, 1H), 7.27 (s, 1H), 7.40 (d, J=2.20 Hz, 1H), 7.54 (m, 3H), 8.06 (m, 3H).

Step 52c: Preparation of Compound 52, Example 52, BOCNH—P3(L-t-Val)-P2[(4R)-(2-phenyl-7-methoxyquinoline-4-oxo)-S-proline]-P1(1R,2S Vinyl Acca)-$CONHSO_2$-(1-cyclopropylmethylclopropan-1-yl) or Alternate Designation, Compound 52, Example 52, {1-[2-[1-(1-Cyclopropylmethyl-cyclopropanesulfonylaminocarbonyl)-2-vinyl-cyclopropylcarbamoyl]-4-(7-methoxy-2-phenyl-quinolin-4-yloxy)-pyrrolidine-1-carbonyl]-2-methyl-propyl}-carbamic acid tert-butyl ester

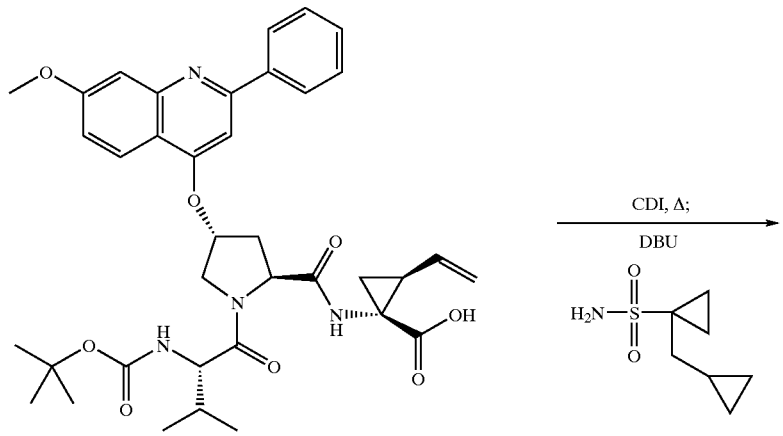

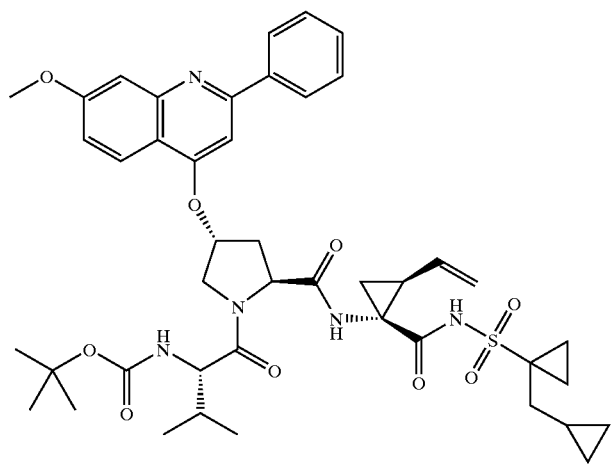

compound 52

Step 52c) Compound 52 was prepared in 26% (0.0447 g,) yield from the tripeptide acid product (0.140 g, 0.21 mmol) of step 52b (Example 52) in analogous fashion to the procedure of Step 27c of Example 27 but that valine tripeptide acid product (Step 52b) was used in place of tripeptide acid product of step 2e (Example 2) and 1-cyclopropylmethyl-cyclopropane sulfonamide in place of 1-trimethylsilanyl-cyclopropanesulfonamide. The reaction mixture was purified by PTLC (MeOH/CH$_2$Cl$_2$): $^1$H NMR (methanol-d$_4$) $^1$H NMR (methanol-d$_4$) □ ppm 0.05 (m, 2H), 0.44 (m, 2H), 0.68 (m, 1H), 0.95 (dd, J=17.70, 6.41 Hz, 6H), 1.09 (m, 2H), 1.24 (s, 9H), 1.39 (dd, J=9.31, 5.34 Hz, 1H), 1.50 (m, 2H), 1.83 (m, 3H), 2.14 (m, 2H), 2.37 (t, J=10.53 Hz, 1H), 2.62 (dd, J=13.58, 6.56 Hz, 1H), 3.93 (s, 3H), 4.07 (m, 2H), 4.54 (m, 2H), 5.07 (d, J=10.38 Hz, 1H), 5.26 (d, J=17.09 Hz, 1H), 5.53 (s, 1H), 5.76 (m, 1H), 7.07 (dd, J=9.16, 2.14 Hz, 1H), 7.21 (s, 1H), 7.37 (d, J=2.14 Hz, 1H), 7.50 (m, 3H), 8.05 (m, 3H). calcd for C$_{44}$H$_{56}$N$_5$SO$_9$: found: LC-MS (retention time: 1.68, Method I), MS m/z 830 (M$^+$+1).

Compound 53 Example 53 compound 53

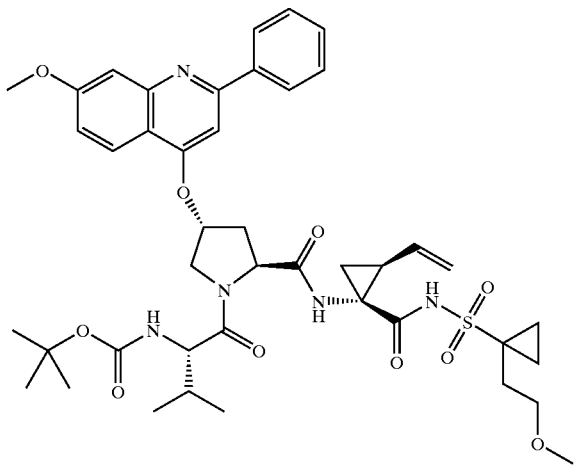

Step 53: Preparation of Compound 53, Example 53, BOCNH—P3(L-t-Val)-P2[(4R)-(2-phenyl-7-methoxyquinoline-4-oxo)-S-proline]-P1(1R,2S Vinyl Acca)-CONHSO$_2$-[1-(2-methoxyethyl)-clopropan-1-yl] or Alternate Designation, Compound 53, Example 54, {1-[2-{1-[1-(2-Methoxy-ethyl)-cyclopropanesulfonylaminocarbonyl]-2-vinyl-cyclopropylcarbamoyl}-4-(7-methoxy-2-phenyl-quinolin-4-yloxy)-pyrrolidine-1-carbonyl]-2-methyl-propyl}-carbamic acid tert-butyl ester

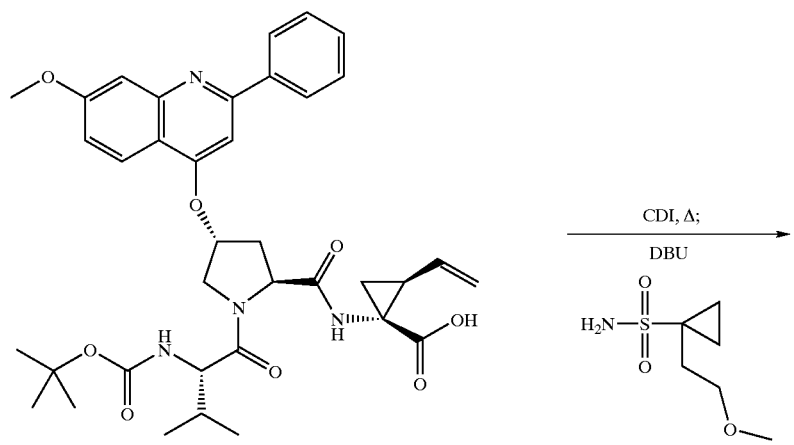

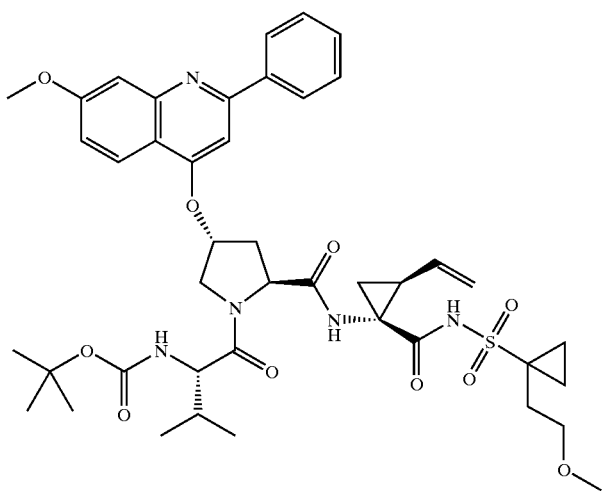

compound 53

Step 53) Compound 53 was prepared in 61% (0.1063 g) yield from the tripeptide acid product (0.140 g, 0.21 mmol) of step 52b (Example 52) in analogous fashion to the procedure of Step 52c except that 1-(2-methoxy-ethyl)-cyclopropanesulfonamide was used in place of 1-cyclopropylmethylcyclopropanesulfonamide: $^1$H NMR (methanol-14) □ ppm 0.84 (d, J=6.10 Hz, 6H), 1.02 (m, 11H), 1.32 (m, 3H), 1.97 (m, 2H), 2.11 (m, 2H), 2.21 (m, 2H), 2.58 (dd, J=12.97, 5.04 Hz, 1H), 3.31 (s, 3H), 3.69 (t, J=7.17 Hz, 2H), 3.94 (m, 1H), 3.95 (s, 3H), 4.08 (m, 1H), 4.22 (d, J=8.85 Hz, 1H), 4.57 (m, 1H), 4.96 (d, J=10.68 Hz, 1H), 5.12 (d, J=17.09 Hz, 1H), 5.44 (s, 1H), 6.01 (m, 1H), 6.70 (d, J=7.63 Hz, 1H), 7.14 (s, 1H), 7.36 (dd, J=9.77, 2.75 Hz, 1H), 7.50 (m, 3H), 7.77 (d, J=7.32 Hz, 1H), 8.03 (d, J=7.02 Hz, 2H),. LC-MS (retention time: 1.56, Method I), MS m/z 834 (M$^+$+1).

Compound 54 Example 54 compound 54

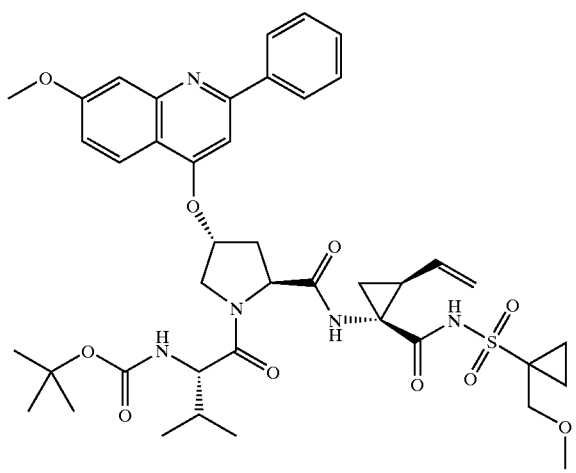

Step 54: Preparation of Compound 54, Example 54, BOCNH—P3(L-t-Val)-P2[(4R)-(2-phenyl-7-methoxyquinoline-4-oxo)-S-proline]-P1(1R,2S Vinyl Acca)-CONHSO$_2$-(1-methoxymethylclopropan-1-yl) or Alternate Designation, Compound 54, Example 55, {1-[2-[1-(1-Methoxymethyl-cyclopropanesulfonylaminocarbonyl)-2-vinyl-cyclopropylcarbamoyl]-4-(7-methoxy-2-phenyl-quinolin-4-yloxy)-pyrrolidine-1-carbonyl]-2-methyl-propyl]-carbamic acid tert-butyl ester

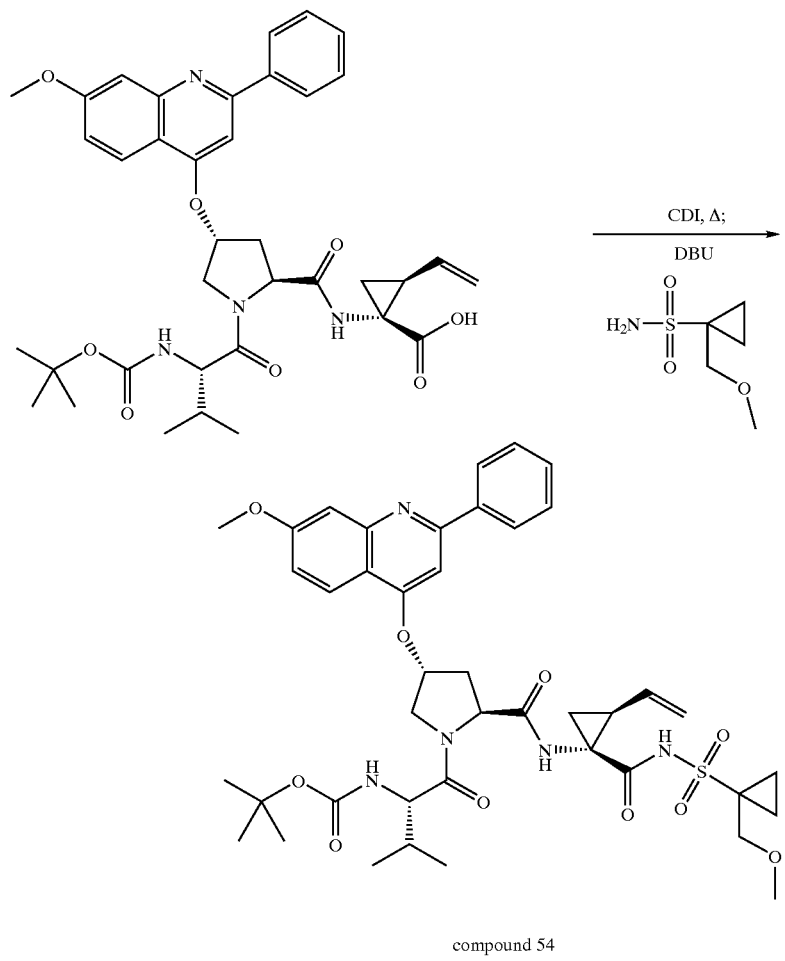

compound 54

Step 54) Compound 54 was prepared in 25% (0.0404 g) yield from the tripeptide acid product (0.140 g, 0.21 mmol) of step 52b (Example 52) in analogous fashion to the procedure of Step 52c (Example 52) except that 1-(2-methoxy-ethyl)-cyclopropanesulfonamide was used in place of 1-cyclopropylmethyl-cyclopropanesulfonamide and: $^1$H NMR (Solvent methanol-d$_4$) □ ppm 0.94 (m, 8H), 1.25 (s, 9H), 1.40 (m, 3H), 1.81 (dd, J=7.68, 5.49 Hz, 1H), 2.08 (m, 2H), 2.45 (t, J=10.25 Hz, 1H), 2.67 (m, 1H), 3.30 (s, 3H), 3.66 (d, J=10.98 Hz, 1H), 3.75 (d, J=10.98 Hz, 1H), 3.93 (s, 3H), 4.09 (m, 2H), 4.56 (m, 2H), 5.04 (d, J=10.61 Hz, 1H), 5.23 (d, J=17.20 Hz, 1H), 5.53 (s, 1H), 5.83 (m, 1H), 7.07 (m, 1H), 7.22 (s, 1H), 7.37 (s, 1H), 7.51 (m, 3H), 8.07 (m, 3H). LC-MS (retention time: 1.53, Method I), MS m/z 820 (M$^+$+1).

Compound 55 Example 55 compound 55

Step 55a: Preparation bis HCl Salt of 1-(2-Amino-3,3-dimethyl-butyryl)4-(7-methoxy-2-phenyl-quinolin-4-yloxy)-pyrrolidine-2-carboxylic Acid [1-(1-benzyl-cyclopropanesulfonylaminocarbonyl)-2-vinyl-cyclopropyl]-amide Step 55a) This his HCl salt was prepared in 100% (0.678 g) yield from compound 5 (0.700 g, 0.795 mmol) in analogous fashion to the procedure of example 25 step 15 g: $^1$H NMR (methanol-$d_4$) □ ppm 0.64 (m, 2H), 1.12 (s, 9H), 1.17 (m, 4H), 1.45 (m, 3H), 1.94 (dd, J=8.05, 5.49 Hz, 1H), 2.34 (m, 1H), 2.44 (m, 1H), 2.82 (dd, J=14.64, 6.95 Hz, 1H), 3.24 (d, J=13.54 Hz, 1H), 3.35 (m, 1H), 4.19 (m, 1H), 4.52 (d, J=12.44 Hz, 1H), 4.75 (dd, J=10.25, 6.95 Hz, 1H), 5.21 (d, J=10.25 Hz, 1H), 5.37 (d, J=17.20 Hz, 1H), 5.77 (m, 1H), 5.84 (s, 1H), 7.15 (m, 2H), 7.26 (m, 4H), 7.43 (dd, J=9.33, 2.38 Hz, 1H), 7.56 (m, 2H), 7.69 (m, 3H), 8.11 (dd, J=7.68, 1.83 Hz, 2H), 8.40 (d, J=9.51 Hz, 1H). LC-MS (retention time: 2.06, Method K), MS m/z 780 (M$^+$+1).

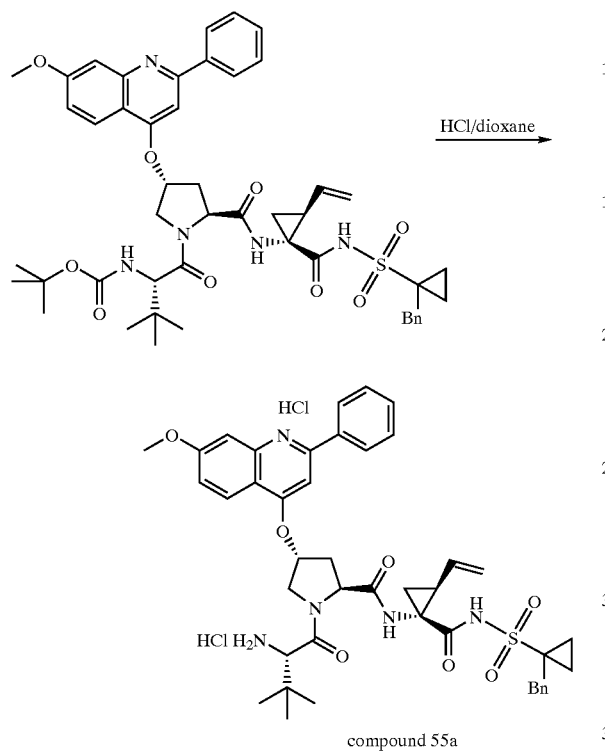

Step 55b: Preparation of Compound 55 Example 55, N-cyclopentoxycarbonyl-NH—P3(L-t-BuGly)-P2[(4R)-(2-phenyl-7-methoxyquinoline-4-oxo)-S-proline]-P1(1R,2S Vinyl Acca)-CONHSO$_2$(1-benzylcyclopropan-1-yl) or Alternate Designation, Compound 55, Example 55, {1-[2-[1-(1-Benzyl-cycloprolanesulfonylaminocarbonyl)-2-vinyl-cycloproylcarbamoyl]-4-(7-methoxy-2-phenyl-quinolin-4-yloxy)-pyrrolidine-1-carbonyl]-2,2-dimethyl-propyl}-carbamic acid cyclopentyl ester

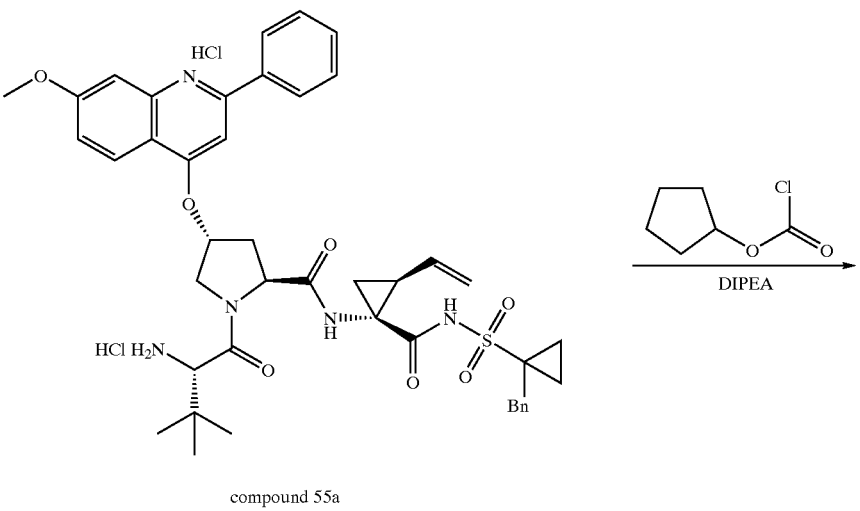

compound 55a

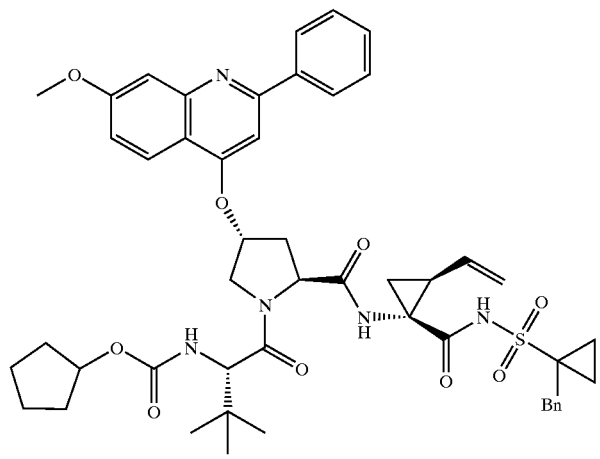

compound 55

Step 55b) Compound 55 was prepared in 95% (0.124 g) yield from the bis HCl salt (0.125 g, 0.15 mmol) of the product of Step 55a (Example 55) in analogous fashion to the procedure of Example 25 step 25h in preparation of Compound 12 and purified by preparative HPLC (solvent B: 45% to 85%): $^1$H NMR (methanol-$d_4$) L ppm 0.63 (s, 2H), 0.96 (s, 9H), 1.50 (m, 12H), 2.32 (m, 2H), 2.73 (dd, J=13.54, 7.32 Hz, 1H), 3.30 (m, 2H), 3.99 (s, 3H), 4.09 (m, 1,H), 4.24 (m, 1H), 4.60 (m, 3H), 5.18 (d, J=10.98 Hz, 1H), 5.34 (d, J=17.20 Hz, 1H), 5.68 (s, 1H), 5.79 (m, 1H), 7.14 (m, 2H), 7.23 (m, 4H), 7.44 (m, 2H), 7.61 (m, 3H), 8.06 (m, 2H), 8.18 (d, J=9.15 Hz, 1H). calcd for $C_{44}H_{56}N_5SO_9$: LC-MS (retention time: 3.40, Method J), MS m/z 892 (M$^+$+1)

Compound 56 Example 56

Step 56: Preparation of compound 56, Example 56, N-tetrahydro-pyran-4-yloxy carbonyl-NH—P3(L-t-BuGly)-P2[(4R)-(2-phenyl-7-methoxyquinoline-4-oxo)-S-proline]-P1(1R,2S Vinyl Acca)-CONHSO$_2$(1-benzylcyclopropan-1-yl) or Alternate Designation, Compound 56, Example 56, {1-[2-[1-(1-Benzyl-cyclopropanesulfonylaminocarbonyl)-2-vinyl-cyclopropylcarbamoyl]-4-(7-methoxy-2-phenyl-quinolin-4-yloxy)-pyrrolidine-1-carbonyl]-2,2-dimethyl-propyl}-carbamic acid tetrahydro-pyran-4-yl Ester compound 56

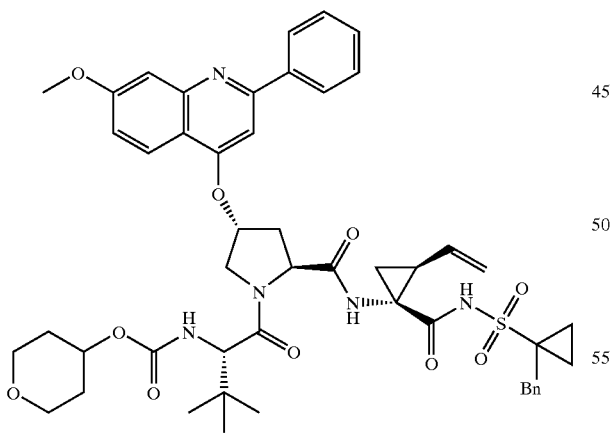

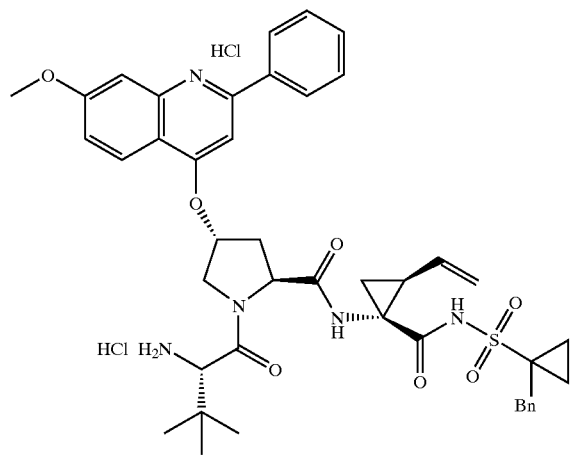

compound 55a

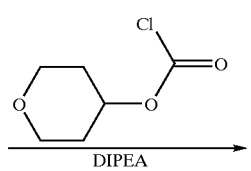

DIPEA

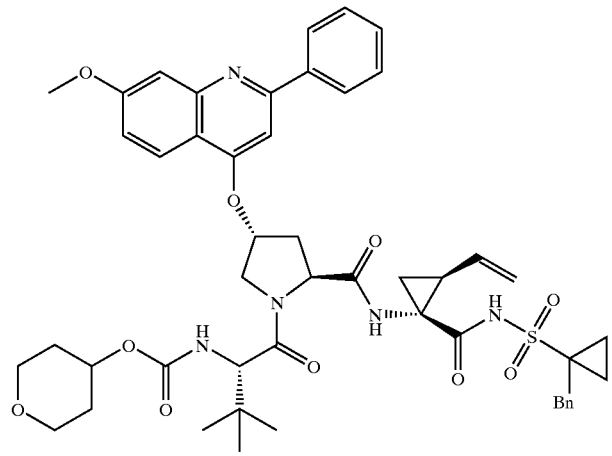

compound 56

Step 56) Compound 56 was prepared in 46% (0.072 g) yield from the bis HCl salt (0.150 g, 0.18 mmol) of the product of Step 55a (Example 55) in analogous fashion to the procedure of step 55b (Example 55) in preparation of Compound 55 except that tetrahydro-pyran-4-yl chloroformate was used in place of cyclopentyl chloroformate: $^1$H NMR (methanol-$d_4$) □ ppm 0.65 (m, 2H), 0.96 (s, 9H), 1.02 (m, 1H), 1.44 (m, 6H), 1.74 (m, 1H), 1.93 (dd, J=8.05, 5.49 Hz, 1H), 2.34 (m, 2H), 2.74 (dd, J=13.36, 6.77 Hz, 1H), 3.34 (m, 2H), 3.77 (m, 2H), 4.00 (s, 3H), 4.08 (m, 1H), 4.27 (m, 3H), 4.63 (m, 2H), 5.19 (d, J=10.25 Hz, 1H), 5.35 (d, J=16.83 Hz, 1H), 5.74 (m, 2H), 7.14 (m, 2H), 7.27 (m, 4H), 7.46 (m, 2H), 7.63 (m, 3H), 8.07 (m, 2H), 8.19 (d, J=9.15 Hz, 1H). MS m/z 908 (M$^+$+1), MS m/z 906 (M−1). HPLC (retention time: 3.08, Method J).

Compound 57 Example 57 compound 57

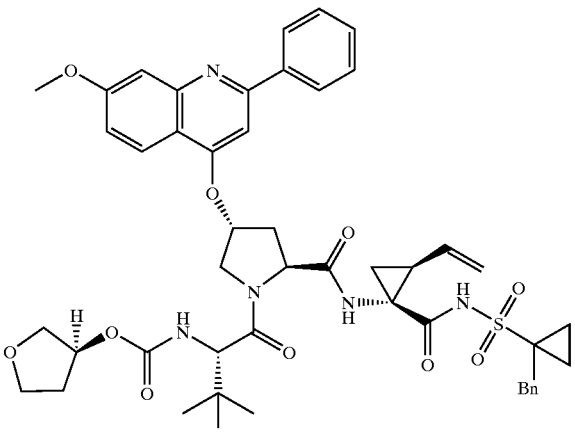

Step 57: Preparation of {1-[2-[1-(1-Benzyl-cyclopropanesulfonylaminocarbonyl)-2-vinyl-cyclopropylcarbamoyl]-4-(7-methoxy-2-phenyl-quinolin-4-yloxy)-pyrrolidine-1-carbonyl]-2,2-dimethyl-propyl}-carbamic acid tetrahydro-furan-3-yl ester

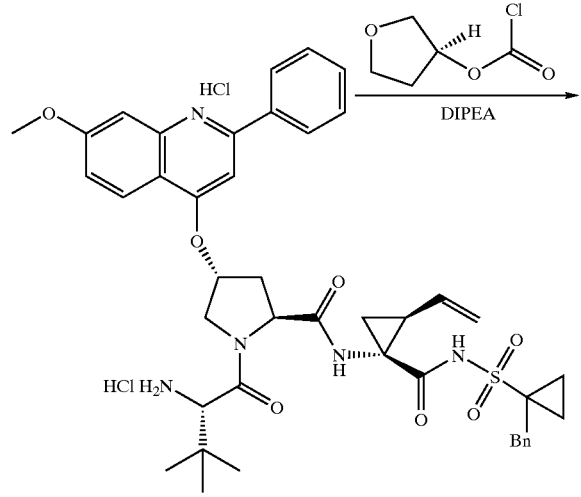

compound 55a

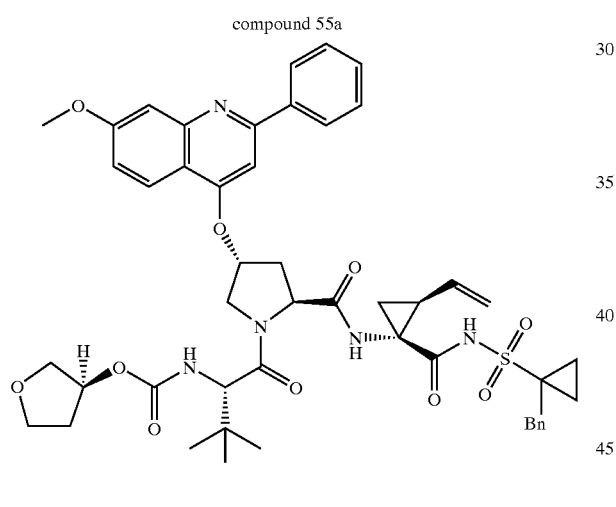

compound 57

Step 57) Compound 57 was prepared in 95% (0.085 g) yield from the bis HCl salt (0.125 g, 0.12 mmol) of Compound 55a (Step 55a) in analogous fashion to the procedure of Example 55 (Step 55b) in preparation of compound 55 except that (S)-tetrahydro-furan-3-yl chloroformate was used in place of cyclopentyl chloroformate purified by preparative HPLC (solvent B: 45% to 85%): $^1$H NMR (CDCl$_3$) □ ppm 1.02 (s, 9H), 1.40 (dd, J=8.97, 5.67 Hz, 1H), 1.60 (m, 4H), 1.91 (m, 2H), 2.03 (m, 2H), 2.60 (m, 2H), 3.19 (d, J=13.91 Hz, 1H), 3.31 (d, J=13.91 Hz, 1H), 3.82 (m, 3H), 3.95 (s, 3H), 4.02 (dd, J=11.34, 3.66 Hz, 1H), 4.29 (d, J=9.15 Hz, 1H), 4.49 (m, 2H), 5.05 (m, 1H), 5.21 (d, J=11.34 Hz, 1H), 5.29 (d, J=16.47 Hz, 1H), 5.38 (m, 1H), 5.45 (d, J=9.51 Hz, 1H), 5.78 (m, 1H), 7.01 (s, 1H), 7.07 (dd, J=9.15, 2.56 Hz, 1H), 7.12 (m, 2H), 7.24 (m, 3H), 7.50 (m, 4H), 8.03 (m, 3H). LC-MS (retention time: 3.08, Method J), MS m/z 894 (M$^+$+1).

Compound 58 Example 58

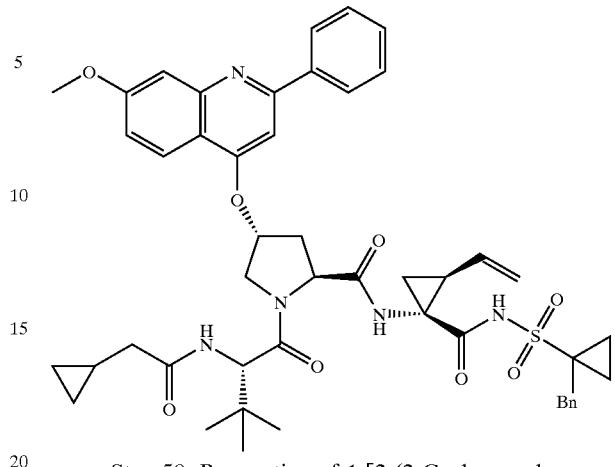

compound 58

Step 58: Preparation of 1-[2-(2-Cyclopropyl-acetylamino)-3,3-dimethyl-butyryl]-4-(7-methoxy-2-phenyl-quinolin-4-yloxy)-pyrrolidine-2-carboxylic acid [1-(1-benzyl-cyclopropanesulfonylaminocarbonyl)-2-vinyl-cyclopropyl]-amide

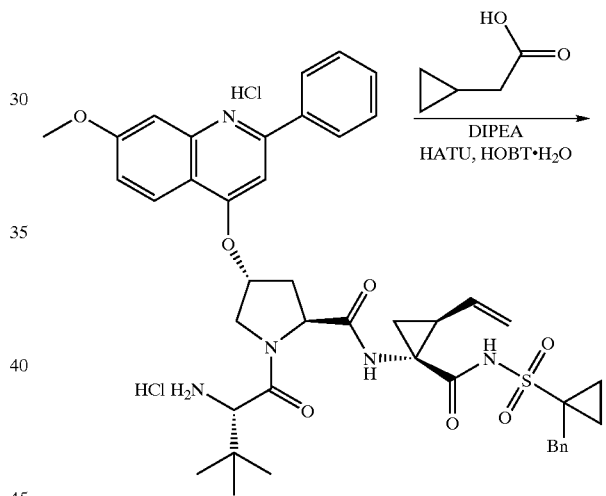

compound 55a

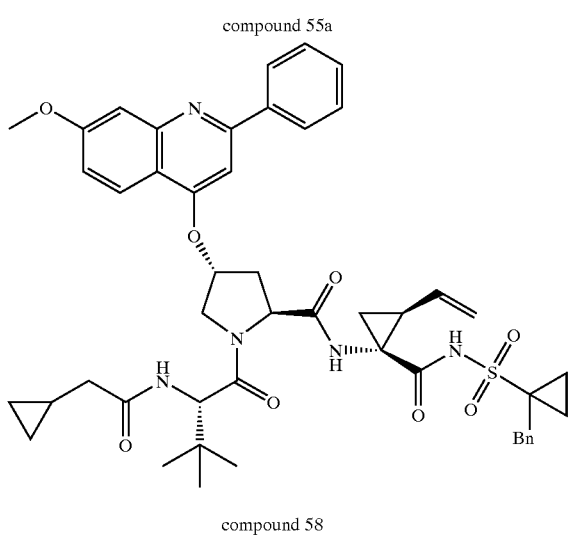

compound 58

Step 58) Compound 58 was prepared in 71% (0.0903 g) yield from the bis HCl salt (0.125 g, 0.15 mmol) of the product of Step 55a (Example 55) in analogous fashion to the procedure of Example 26 step 26h in preparation of compound 13 and purified by preparative HPLC (solvent B: 45% 85%): $^1$H NMR (methanol-d$_4$) □ ppm 0.44 (m, 2H), 0.63 (m, 2H), 0.86 (m, 1H), 0.99 (s, 9H), 1.04 (m, 2H), 1.45 (m, 3H), 1.92 (dd, J=8.05, 5.49 Hz, 1H), 2.01 (d, J=6.95 Hz, 2H), 2.32 (m, 2H), 2.69 (dd, J=13.72, 7.14 Hz, 1H), 3.31 (m, 2H), 3.97 (s, 3H), 4.13 (dd, J=12.08, 3.29 Hz, 1H), 4.57 (m, 3H), 5.17 (m, 1H), 5.34 (d, J=16.83 Hz, 1H), 5.63 (s, 1H), 5.78 (m, 1H), 7.15 (m, 3H), 7.28 (m, 4H), 7.42 (d, J=2.56 Hz, 1H), 7.56 (m, 3H), 8.07 (t, J=8.23 Hz, 3H). LC-MS (retention time: 3.25, Method J), MS m/z 862 (M$^+$+1).

Compound 59 Example 59

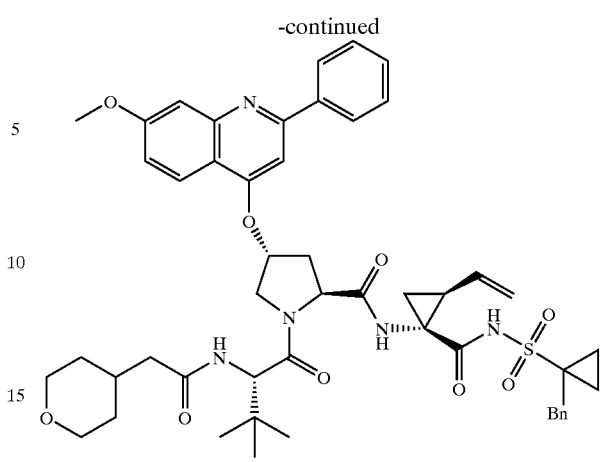

compound 59

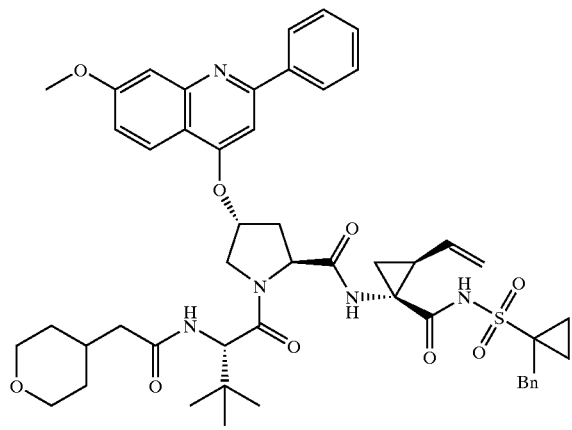

Step 59: Preparation of 1-[3,3-Dimethyl-2-(2-tetrahydro-pyran-4-yl-acetylamino)-butyryl]-4-(7-methoxy-2-phenyl-quinolin-4-yloxy)-pyrrolidine-2-carboxylic acid [1-(1-benzyl-cyclopropanesulfonylaminocarbonyl)-2-vinyl-cyclopropyl]-amide Step 59) Compound 59 was prepared in 81% (0.1084 g) yield from the bis HCl salt (0.125 g, 0.15 mmol) of product of Step 55a (Example 55) in analogous fashion to the procedure of Example 26 step 26 h in preparation of compound 13 except that copmound 55a was used in place of the Bis HCl salt product of Step 26 g, and purified by preparative HPLC (solvent B: 45 to 85%): $^1$H NMR (methanol-d$_4$) □ ppm 0.63 (m, 2H), 0.98 (s, 9H), 1.22 (m, 2H), 1.47 (m, 6H), 1.92 (m, 4H), 2.31 (m, 2H), 2.68 (dd, J=13.17, 6.59 Hz, 1H), 2.67 (m, 1H), 3.27 (m, 2H), 3.80 (m, 2H), 3.97 (s, 3H), 4.11 (dd, J=11.53, 3.11 Hz, 1H), 4.56 (m, 3H), 5.18 (d, J=10.25 Hz, 1H), 5.34 (d, J=16.83 Hz, 1H), 5.59 (s, 1H), 5.77 (m, 1H), 7.15 (m, 3H), 7.27 (m, 4H), 7.42 (d, J=2.20 Hz, 1H), 7.56 (m, 3H), 8.07 (m, 3H). HPLC (retention time: 3.11, Method J).MS m/z 906 (M$^+$+1), 904 (M$^-$-1), Compound 60 Example 60

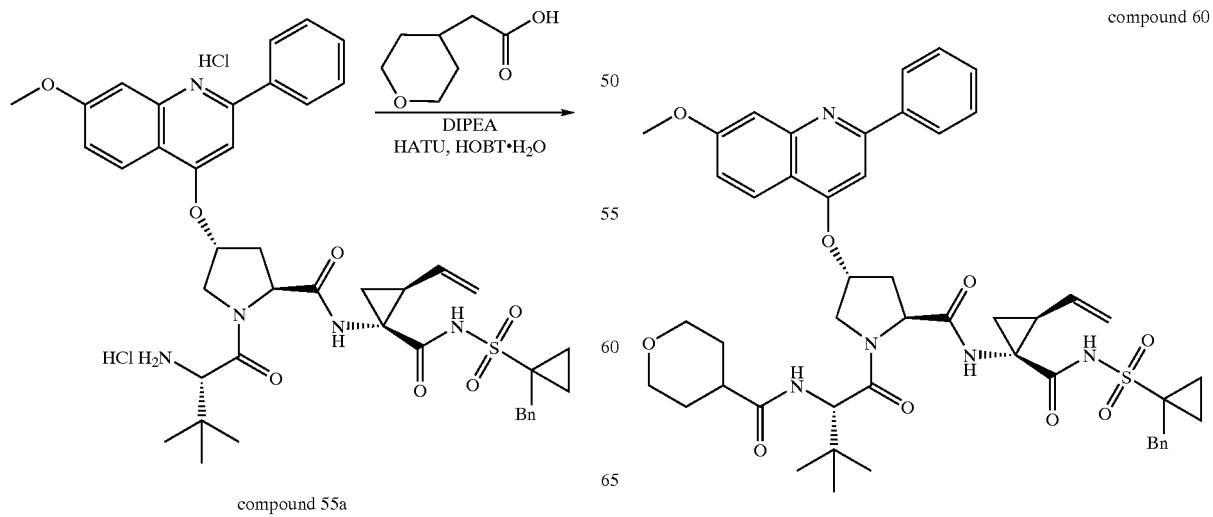

Step 60: Preparation of 1-{3,3-Dimethyl-2-[(tetrahydro-pyran-4-carbonyl)-amino]-butyryl}-4-(7-methoxy-2-phenyl-quinolin-4-yloxy)-pyrrolidine-2-carboxylic acid [1-(1-benzyl-cyclopropanesulfonylaminocarbonyl)-2-vinyl-cyclopropyl]-amide

Compound 61 Example 61

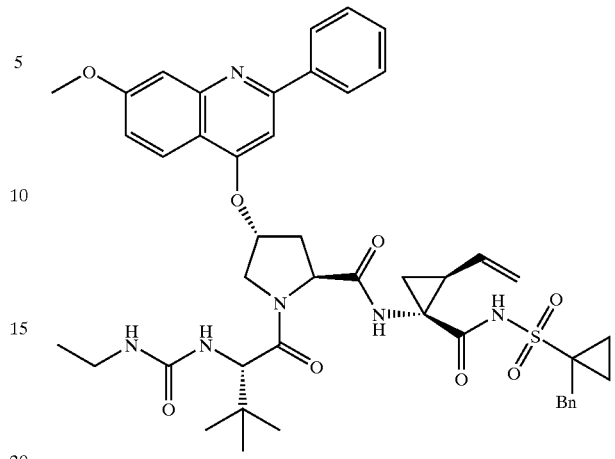

compound 61

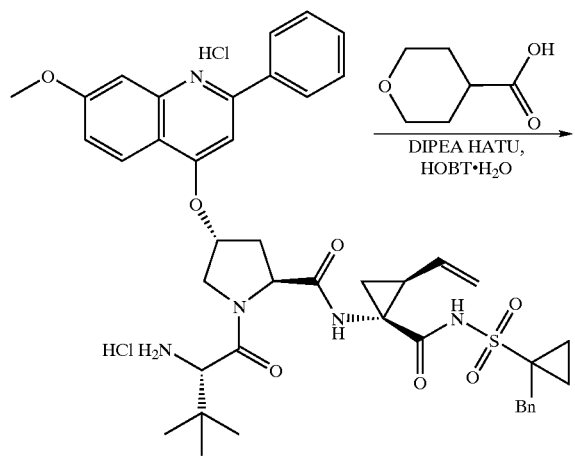

compound 55a

Step 61: Preparation of 1-[2-(3-Ethyl-ureido)-3,3-dimethyl-butyryl]-4-(7-methoxy-2-phenyl-quinolin-4-yloxy)-pyrrolidine-2-carboxylic acid [1-(1-benzyl-cyclopropanesulfonylaminocarbonyl)-2-vinyl-cyclopropyl]-amide

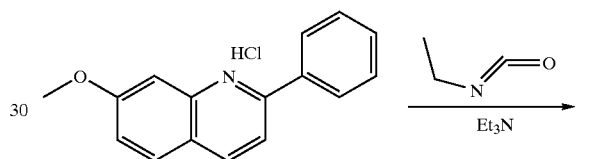

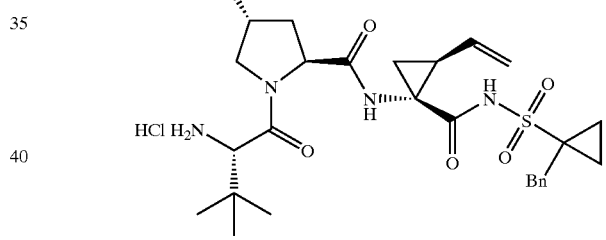

compound 55a

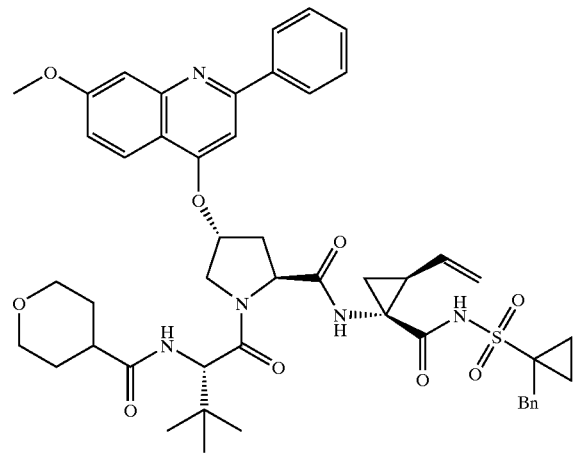

compound 60

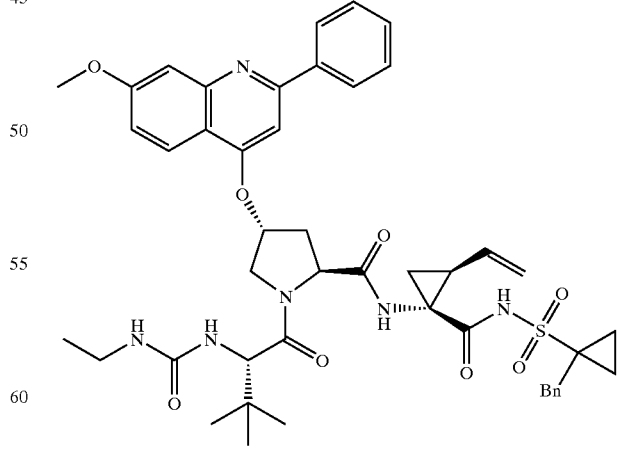

compound 61

Step 60) Compound 60 was prepared in 82% (0.084 g) yield from the bis HCl salt (0.100 g, 0.18 mmol) of Step 55a (Example 55) in analogous fashion to the procedure of step 59 (Example 59) in preparation of compound 59 except that Tetrahydro-pyran-4-carboxylic acid was used in place of cyclopropyl acetic acid: $^1$H NMR (methanol-$d_4$) ☐ ppm 4.00 (q, J=7.12 Hz, 2H), 4.04 (s, 3H), 4.13 (dd, J=12.05, 2.90 Hz, 1H), 4.25 (m, 1H), 4.60 (m, 2H), 5.18 (m, 1H), 5.34 (d, J=17.09 Hz, 1H), 5.76 (m, 2H), 7.14 (m, 2H), 7.25 (m, 3H), 7.37 (m, 1H), 7.51 (d, J=2.14 Hz, 1H), 7.53 (s, 1H), 7.70 (m, 3H), 8.05 (m, 2H), 8.33 (d, J=9.16 Hz, 1H). LC-MS (retention time: 3.06, Method J), MS m/z 893 (M$^+$+1).

Step 61) A mixture of the bis HCl salt (0.100 g, 0.117 mmol) of compound 55a of Example 55 (Step55a), ethyl isocyanate (26 μL, 0.32 mmol), and triethyl amine (82 μL, 0.585 mmol) in CH$_2$Cl$_2$ was stirred for 16 h at rt, removed the solvent in vacuo. The product was abtained by preparative HPLC (solvent B: 40 to 85%) as a white foam: $^1$H NMR (methanol-d$_4$) □ ppm 0.63 (m, 2H), 0.92 (m, 3H), 0.95 (s, 9H), 1.28 (s, 1H), 1.43 (m, 3H), 1.93 (dd, J=8.24, 5.49 Hz, 1H), 2.29 (q, J=8.85 Hz, 1H), 2.41 (m, 1H), 2.78 (m, 2H), 2.87 (m, 1H), 3.27 (d, J=13.43 Hz, 1H), 3.34 (d, J=13.42 Hz, 1H), 4.05 (s, 3H), 4.11 (dd, J=12.36, 3.20 Hz, 1H), 4.28 (s, 1H), 4.65 (m, 2H), 5.18 (dd, J=10.38, 1.53 Hz, 1H), 5.35 (d, J=17.09 Hz, 1H), 5.75 (m, 1H), 5.82 (s, 1H), 7.13 (d, J=7.02 Hz, 2H), 7.26 (m, 3H), 7.38 (dd, J=9.46, 2.44 Hz, 1H), 7.53 (d, J=2.14 Hz, 1H), 7.60 (s, 1H), 7.74 (m, 3H), 8.07 (m, 2H), 8.35 (d, J=9.16 Hz, 1H). LC-MS (retention time: 3.09, Method J), MS m/z 851 (M$^+$+1).

Compound 62 Example 62 compound 62

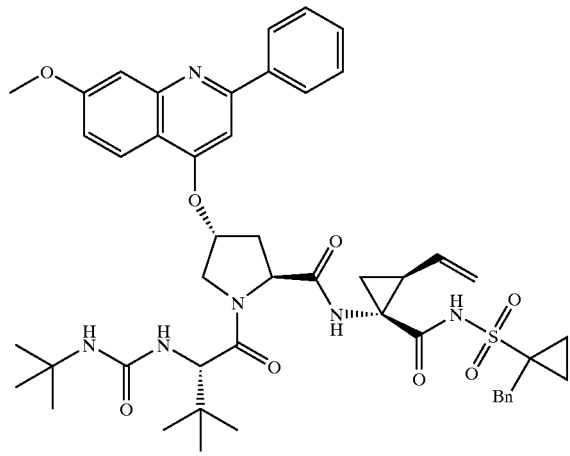

Step 62: Preparation of 1-[2-(3-tert-Butyl-ureido)-3,3-dimethyl-butyryl]-4-(7-methoxy-2-phenyl-quinolin-4-yloxy)-pyrrolidine-2-carboxylic acid [1-(1-benzylcyclopropanesulfonylaminocarbonyl)-2-vinyl-cyclopropyl]-amide

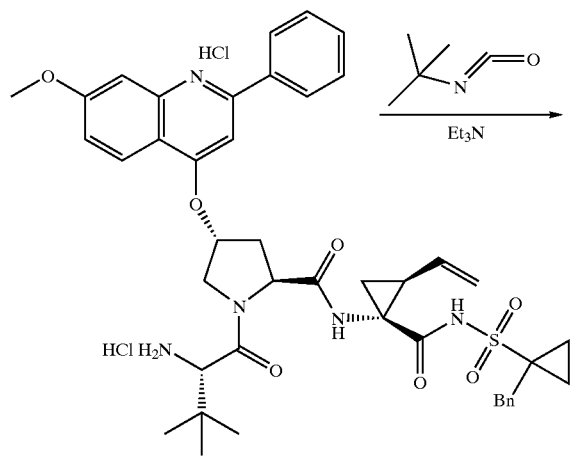

compound 55a

-continued

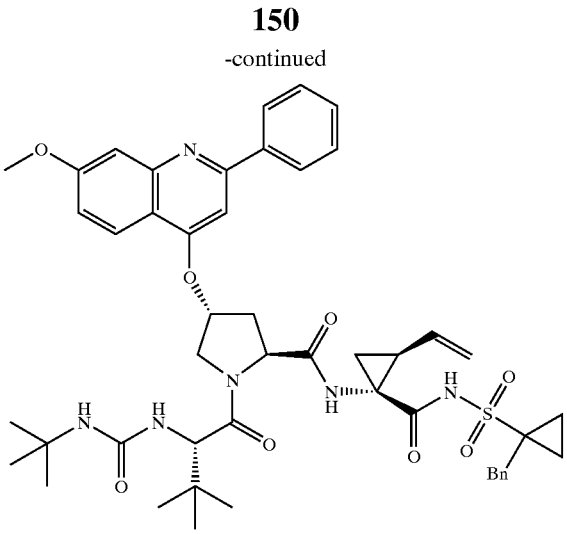

compound 62

Step 62) Compound 62 was prepared in 46% (0.072 g) yield from the bis HCl salt (0.100 g, 0.117 mmol) of Compound 55a of Step 55a (Example 55), in analogous fashion to the procedure of Example 61 step 61 in preparation of compound 48 except that tert-butyl isocyanate was used in place of ethyl isocyanate: $^1$H NMR (methanol-d$_4$) □ ppm 0.62 (m, 2H), 0.96 (s, 9H), 1.11 (s, 9H), 1.30 (m, 1H), 1.45 (m, 3H), 1.91 (dd, J=8.09, 5.34 Hz, 1H), 2.28 (q, J=8.75 Hz, 1H), 2.37 (m, 1H), 2.72 (dd, J=14.34, 6.71 Hz, 1H), 3.27 (d, J=13.43 Hz, 1H), 3.33 (d, J=13.42 Hz, 1H),4.00(s, 3H),4.10 (dd, J=12.21, 3.36 Hz, 1H), 4.26 (s, 1H), 4.59 (dd, J=10.22, 7.17 Hz, 1H), 4.65 (d, J=12.21 Hz, 1H), 5.17 (d, J=10.38 Hz, 1H), 5.33 (d, J=17.09 Hz, 1H), 5.74 (m, 2H), 7.13 (m, 2H), 7.25 (m, 4H), 7.45 (s, 1H), 7.46 (d, J=2.44 Hz, 1H), 7.64 (m, 3H), 8.06 (m, 2H), 8.26 (d, J=9.46 Hz, 1H). LC-MS (retention time: 3.26,, Method J), MS m/z 879 (M$^+$+1).

Compound 63 Example 63

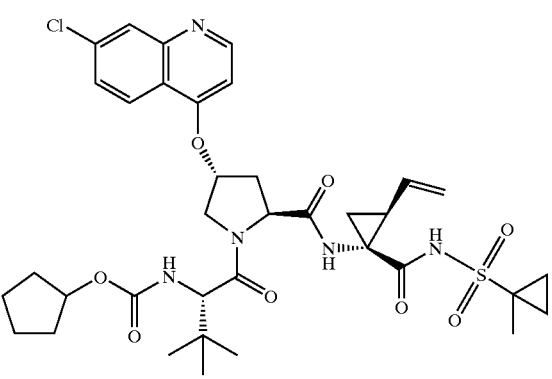

compound 63

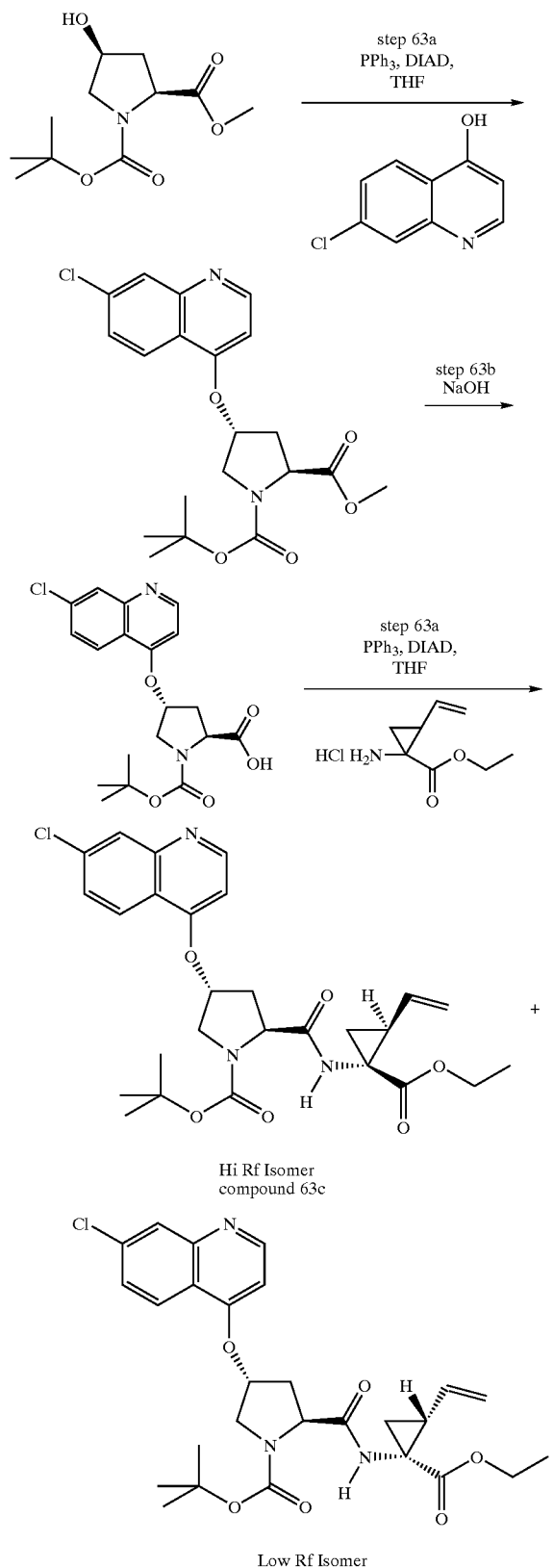

Scheme 1

Hi Rf Isomer
compound 63c

Low Rf Isomer

Step 63a: Preparation of N-Boc-4-(7-Chloro-quinolin-4-yloxy)-proline methyl ester To a suspension of N-B-Boc-cis-L-4-Hydroxyproline methyl ester (10 g, 40.7 mmol) and 7-chloroquinolin-4-ol (8.73 g, 49.0 mmol) in THF (200 mL) cooled to 0° C. was added PPh$_3$ (12.82 g, 48.9 mmol) and DIAD. (8.80 g, 42.13 mmol). The mixture was slowly allowed to warm to rt overnite, stirred at total of 30 h. The mixture was dissolved in EtOAc (800 mL), washed with 1N aqueous HCl, 5% aqueous K$_2$CO$_3$ (3×100 mL), brine (2×100 mL) and dried (MgSO$_4$), and concentrated. The residue was purified several times over a Biotage 65M (MeOH/CH$_2$Cl$_2$: 0 to 10%) to afford cumulatively 10.57 g (68%) of the desired product as a glass: $^1$H NMR (CDCl$_3$) δ 1.40 (s, 9H), 2.33–2.42 (m, 1H), 2.61–2.72 (m, 1H), 3.75 (s, 3H), 3.91 (m, 2H), 4.45–4.59 (m, 1H), 5.13 (m, 1H), 6.61–6.64 (m, 1H), 7.41 (dd, J=9, 2 Hz, 1H), 7.98 (d, J=2 Hz, 1H), 8.03 (d, J=9 Hz, 1H), 8.67–8.71 (m, 1H). LC-MS (retention time: 1.39, method D), MS m/e 407 (M$^+$+1).

Step 63b: Preparation of N—Boc-4-(7-Chloro-quinolin-4-yloxy)-proline

To a solution of the product (10.57 g, 26.0 mmol) of Step 63a of Example 63 {BOC—N—P2[(4R)-(7-chloroquinoline-4-oxo) proline methyl ester} dissolved in MeOH (800 mL) cooled to 0° C. was added an aqueous 1N NaOH solution (44.5 mL, 44.5 mmol). The mixture was warmed to rt after 6 h, stirred overnite, and the pH adjusted to pH 7 using 1.0 N aqueous HCl. The solution was concentrated until only the water layer remained, the pH adjusted to 4 using 6N aqueous HCl and the mixture was partitioned repeatedly with EtOAc (3×500 mL). The combined organic layers were dried (MgSO$_4$) and concentrated to afford 10.16 g (100%) of the as a white solid. $^1$H NMR (DMSO-d$_6$) δ 1.32, 1.34 (two s (rotamers) 9H), 2.31–2.40 (m, 1H), 2.58–2.69 (m, 1H), 3.65–3.81 (m, 2H), 4.33–4.40 (m, 1H), 5.34 (m, 1H), 7.10–7.11 (m, 1H), 7.57 (d, J=9 Hz, 1H), 7.98 (s, 1H), 8.09–8.14 (m, 1H), 8.75 (d, J=5 Hz, 1H), 12.88 (brs, 1H). $^{13}$C NMR (DMSO-d$_6$) δ 27.82, 35.84, 51.52, 57.75, 76.03, 79.33, 102.95, 119.54, 123.86, 126.34, 127.24, 134.49, 149.32, 152.88, 153.25, 159.08, 173.74. LC-MS (retention time: 1.48, method D), MS m/e 393 (M$^+$+1)

Step 63c: Preparation of BOC—NH—P2[(4R)-(7-chloroquinoline-4-oxo)-S-proline]-P1(1R,2S vinyl acca)-COOEt To a solution of the product (5.11 g, 13 mmol) of Step 63b of Example 633 {Boc-4(R)-(7-chloroquinoline-4-oxo) proline}, the HCl salt (3.48 g, 18.2 mmol) of vinyl Acca (existing as a 1:1 mixture of diastereoisomers (1R,2S/1S,2R where cyclopropyl carboxyethyl group is syn to vinyl moiety) and NMM (7.1 mL 65 mmol) in DMF (30 mL) was added HATU (6.92 g, 18.2 mmol). The mixture was stirred for 3 days. The reaction mixture was diluted with EtOAc (180 mL) and was partitioned with pH 4.0 buffer (3×100 mL). The organic layer was washed with saturated aqueous NaHCO$_3$ (2×50 mL), water (2×50 mL), and brine (2×50 mL). The organic solution was dried (MgSO$_4$) and concentrated. The residue was purified over a Biotage 40M column (EtOAc/hexanes: 50% to 100%) to afford 2.88 g of the product existing as a diastereomeric mixture. This mixture was partially separated using a Biotage 65M column (MeOH-EtOAc: 0% to 9%) to afford BOC—NH—P2[(4R)-(7-chloroquinoline-4-oxo)-S-proline]-P1(1R,2S vinyl acca P1 moiety)-COOEt as the initial eluted high Rf isomer (1.20 g, 17.4%). $^1$H NMR (CDCl$_3$/Methanol-d$_4$) δ 1.16 (t, J=7 Hz, 3H), 1.35 (s, 9H), 1.37–1.43 (m, 1H), 1.76–1.84 (m, 1H), 2.06–2.11 (m, 1H), 2.35–2.45 (m, 1H), 2.63 (m, 1H), 3.72–3.93 (m, 2H), 4.02–4.15 (m, 1H), 4.33–4.40 (m, 1H), 5.06 (d, J=9 Hz, 1H), 5.16 (m, 1H), 5.24 (d, J=17 Hz, 1H), 5.63–5.70 (m, 1H), 6.74 (m, 1H), 7.39 (dd, J=9, 2 Hz, 1H), 7.74–7.78 (m, 1H), 7.89 (d, J=2 Hz, 1H), 7.97 (d, J=9 Hz,1H), 8.60 (d, J=5 Hz, 1H). $^1$H NMR (methanol-d$_4$, 60/40 Rotomers) □ 1.24 (t, J=7 Hz, 3H), 1.39, 1.43 (2s, 9H), ratio 4:6), 1.71.–1.74 (m, 0.4H), 178–1.81 (m, 0.6H), 2.18–2.23 (m, 1H), 2.65–2.69 (m, 0.4H), 2.71–2.76 (m, 0.6H), 3.88–3.96 (m, 2H), 4.11–4.18 (m, 2H), 4.39–4.45 (m, 1H), 5.09–5.13 (m, 1H), 5.28–5.33 (m, 1H), 5.37 (m, 1H), 5.73–5.81 (m, 1H), 7.05 (d, J=5 Hz, 1H), 7.53 (d, J=8.9 Hz, 1H), 7.92 (s, 1H), 8.12 (d, J=8.9 Hz, 1H), 8.70 (d, J=5 Hz, 1H). LC-MS (retention time: 1.54, method A) MS m/z 530 (M$^+$+1). The rest of the material (~1.66 g, 24%) was mixed fractions greatly enriched in the lower Rf isomer.

Step 63d: Preparation of (L)-2-Cyclopentyloxycarbonylamino-3,3-dimethyl-butyric acid Scheme 2

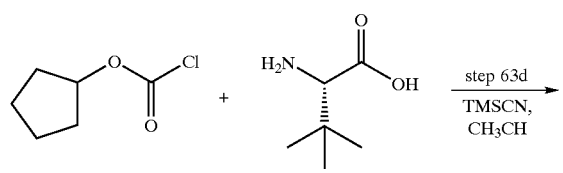

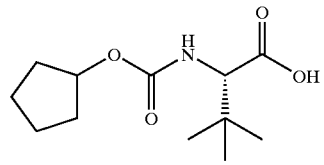

compound 63d

To a solution of L-tert-leucine (2 g, 15.25 mmol) dissolved in CH$_3$CN (50 mL) was added TMSCN (7.06 mL, 56.41 mmol) and stirred for 15 min. The reaction mixture was heated to 75° C. for 30 min. Cyclopentyl chloroformate (2.83 g, 19.06 mmol) was added to the reaction mixture and the reaction mixture was heated at 80° C. overnite, concentrated in vacuo. The residue was treated with MeOH (40 mL), stirred for 10 min, and concentrated in vacuo. The residue was adjusted pH to 8.5, and extracted with Et$_2$O (2×200 mL). The aqueous layer was acidified to pH 3 and extracted with CH$_2$Cl$_2$ (2×200 mL). The combined extract was dried (MgSO$_4$), and concentrated in vacuo. The residue was recrystallized from minimal amount of Et$_2$O/hexanes to afford the product 3.48 g (94%): $^1$H NMR (methanol-d$_4$) □ ppm 1.00 (s, 9H), 1.59 (m, 2H), 1.73 (m, 4H), 1.84 (dd, J=5.95, 3.20 Hz, 2H), 3.98 (s, 1H), 5.02 (m, 1H).

Scheme 3

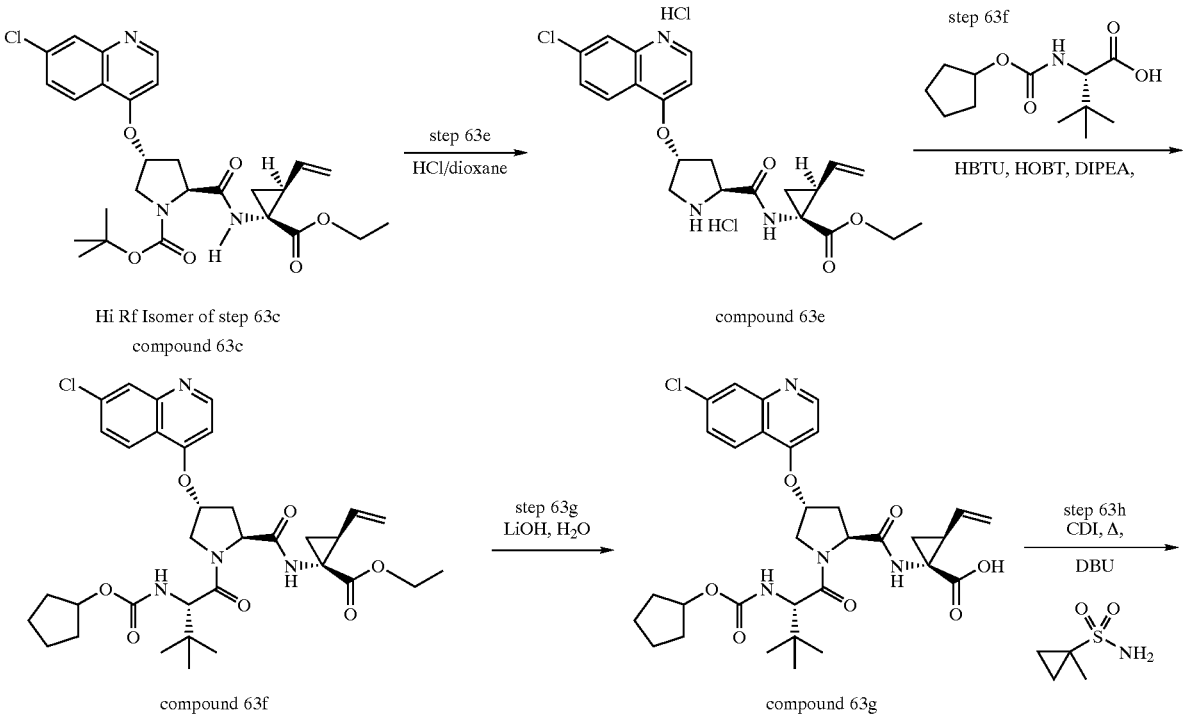

-continued

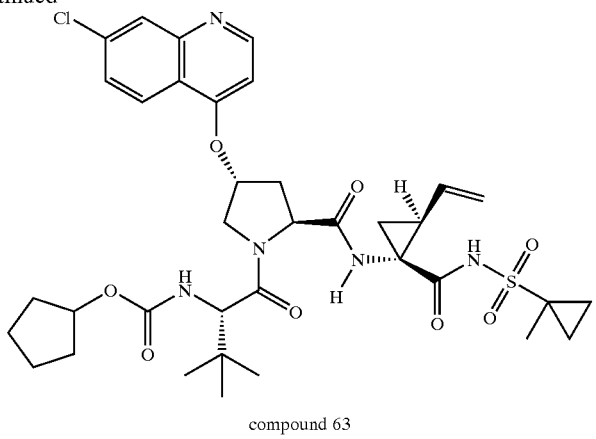

compound 63

Step 63e: Preparation of Bis HCl salt of NH₂—P2 [(4R)-(7-chloroquinoline-4-oxo)-S-proline]-P1(1R, 2S vinyl acca)-COOEt The product (0.65 g, 1.22 mmol) of step 63c of Example 63 {BOC—P2 [(4R)-(7-chloroquinoline-4-oxo)-S-proline]-P1(1R,2S Vinyl Acca-CO₂Et} was dissolved in 4N HCl/dioxane (4.5 ml, 18 mmol) and stirred for 1 h at rt. The reaction mixture was concentrated and the crude product was directly used in next step: LC-MS (retention time: 0.94, method A) LC-MS m/z 430 (M⁺+1).

Step 63f: Preparation of compound 63f, example 63f, N-Cyclopentyloxycarbonyl-NH—P3(L-val)-P2 [(4R)-(2-phenyl-7-methoxyquinoline-4-oxo)-S-proline]-P1(1R,2S Vinyl Acca)-Carboxylic acid ethyl ester or alternate designation Compound 63f, example 63f, 1-{[4-(7-Chloro-quinolin-4-yloxy)-1-(2-cyclopentyloxycarbonylamino-3,3-dimethyl-butyryl)-pyrrolidine-2-carbonyl]-amino}-2-vinyl-cyclopropanecarboxylic acid ethyl ester Step 63f) To a solution of the product (0.530 g, 1.04 mmol) of Step 63e of Example 63 {HCl salt of P2[(4R)-7-chloroquinoline-4-oxo)-S-proline]-P1(1R,2S Vinyl Acca) COOEt, the product (0.328 g, 1.35 mmol) of Step 63d of Example 63 {(L)-2-Cyclopentyloxycarbonylamino-3,3-dimethyl-butyric acid}, HOBT (0.146 g, 1.08 mmol), and diisopropylethylamine (0.755 mL, 4.32 mmol) in CH₂Cl₂ (7 mL) was added HBTU (0.512 g, 1.35 mmol). The reaction mixture was stirred for overnite and partitioned between CH₂Cl₂ and pH 4.0 buffer. The CH₂Cl₂ layer was washed with water, saturated NaHCO₃ (aq.), dried (MgSO₄), concentrated. The residue was purified over a Biotage 40M column (EtOAc/Hexanes: 35 to 100%) to afford the product 0.640 g, (92%): ¹H NMR (methanol-d₄) δ ppm 1.02 (s, 9H), 1.26 (m, 4H), 1.56 (m, 10H), 2.19 (q, J=8.75 Hz, 1H), 2.41 (m, 1H), 2.70 (dd, J=14.19, 8.09 Hz, 1H), 4.01 (dd, J=11.90, 3.05 Hz, 1H), 4.13 (m, 2H), 4.20 (s, 1H), 4.53 (m, 1H), 4.62 (m, 1H), 5.09 (d, J=10.38 Hz, 1H), 5.26 (d, J=17.09 Hz, 1H), 5.47 (m, 1 H), 5.77 (m, 1H), 7.07 (d, J=5.49 Hz, 1H), 7.47 (m, 1H), 7.94 (m, 1H), 8.20 (d, J=8.85 Hz, 1H), 8.72 (d, J=5.49 Hz, 1H). LC-MS (retention time: 1.71, Method B), MS m/z 655 (M⁺+1).

Step 63g: Preparation of Compound 63g, Example 63g, N-Cyclopentyloxycarbonyl-NH—P3(L-val)-P2 [(4R)-(2-phenyl-7-methoxyquinoline-4-oxo)-S-proline]-P1(1R,2S Vinyl Acca)-Carboxylic acid ethyl ester or alternate designation Compound 63g, example 63g, 1-{[4-(7-Chloro-quinolin-4-yloxy)-1-(2-cyclopentyloxycarbonylamino-3,3-dimethyl-butyryl)-pyrrolidine-2-carbonyl]-amino}-2-vinyl-cyclopropanecarboxylic acid Step 63g) Compound 63g was obtained in 69% (0.424 g) yield from Compound 63f (0.636 g, 0.97 mmol) in analogous fashion to the procedure of step 2e Example 2 as a white solid: ¹H NMR (methanol-d₄) □ ppm 1.02 (s, 9H), 1.57 (m, 11H), 2.14 (q, J=9.03 Hz, 1H), 2.46 (m, 1H), 2.68 (m, 1H), 4.02 (dd, J=11.89, 3.11 Hz, 1H), 4.19 (m, 1H), 4.50 (d, J=26.35 Hz, 1H), 4.64 (t, J=8.42 Hz, 1H), 5.04 (m, 1H), 5.24 (d, J=17.20 Hz, 1H), 5.44 (s, 1H), 5.87 (m, 1H), 7.05 (d, J=5.12 Hz, 1H), 7.48 (m, 1H), 7.92 (m, 1H), 8.18 (d, J=8.78 Hz, 1H), 8.71 (d, J=5.49 Hz, 1H). LC-MS (retention time: 2.32, Method A), MS m/z 627 (M⁺+1).

Step 63h: Preparation of (1-{4-(7-Chloro-quinolin-4-yloxy)-2-[1-(1-methyl-cyclopropanesulfonylaminocarbonyl)-2-vinyl-cyclopropylcarbamoyl]-pyrrolidine-1-carbonyl}-2,2-dimethyl-propyl)-carbamic acid cyclopentyl ester Step 63h) Compound 63 was prepared in 14% yield (0.0095 g) from the tripeptide acid (0.058 g, 0.13 mmol) of compound 63g of the product of Step 63g (Example 63) in analogous fashion to the procedure of Step 27c of Example 27 in the synthesis of compound 27 and purified by PTLC: ¹H NMR (DMSO-D6) δ ppm 0.77 (m, 2H), 1.02 (s, 9H), 1.52 (m, 14H), 1.85 (m, 1H), 2.15 (m, 1H), 2.46 (m, 1H), 2.67 (m, 1H), 4.06 (m, 1H), 4.21 (m, 1H), 4.55 (m, 3H), 5.04 (m, 1H), 5.23 (m, 1H), 5.47 (m, 1H), 5.85 (m, 1H), 7.08 (d, J=5.49 Hz, 1H), 7.47 (d, J=8.85 Hz, 1H), 7.93 (s, 1H), 8.20 (t, J=8.09 Hz, 1H), 8.72 (d, J=5.49 Hz, 1H). LC-MS (retention time: 1.57, Method I), MS m/z 744 (M⁺+1).

Compound 64 Example 64

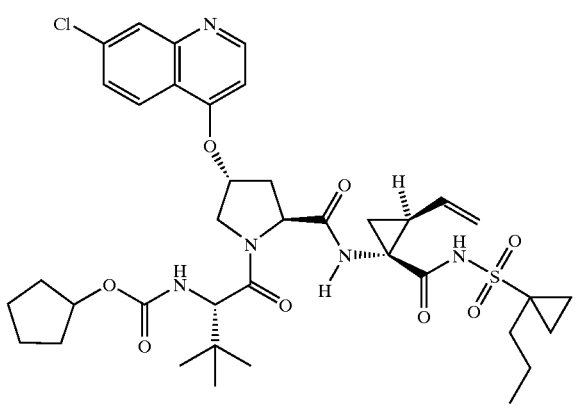

compound 64

Preparation of (1-{4-(7-Chloro-quinolin-4-yloxy)-2-[1-(1-propyl-cyclopropanesulfonylaminocarbonyl)-2-vinyl-cyclopropylcarbamoyl]-pyrrolidine-1-carbonyl}-2,2-dimethyl-propyl)-carbamic acid cyclopentyl ester

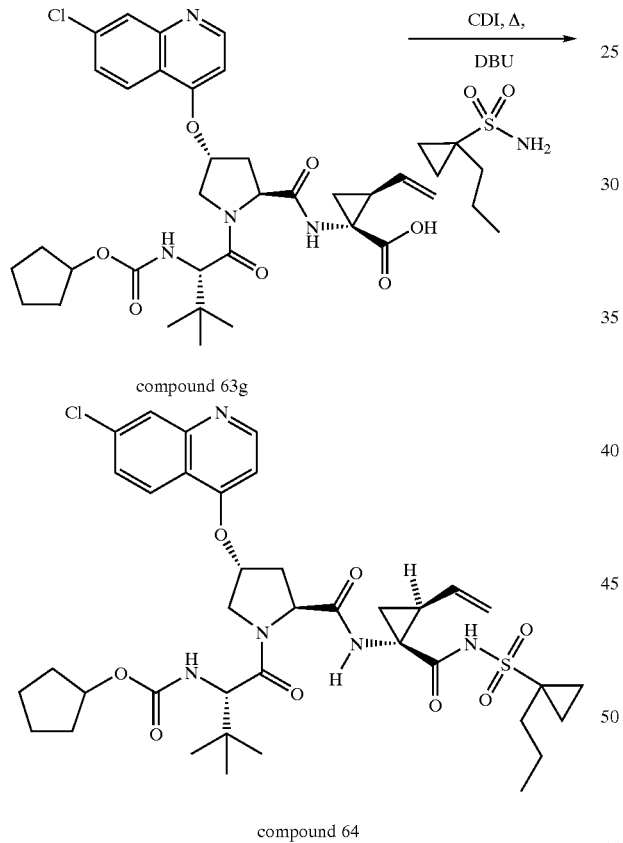

Step 64) Compound was prepared in 45% yield (0.032 g) from the chloro-P2 tripeptide acid (0.058 g, 0.13 mmol) of Compound 63g (step 63g, Example 63) in analogous fashion to the procedure of Step 27c of Example 27 in the synthesis of compound 27 and purified by PTLC: $^1$H NMR$_{(methanol-d4)}$ □ ppm 0.78 (m, 2H), 0.89 (t, J=7.02 Hz, 3H), 1.02 (s, 9H), 1.57 (m, 16H), 2.12 (m, 1H), 2.49 (m, 1H), 2.68 (dd, J=13.73, 7.02 Hz, 1H), 4.08 (m, 1H), 4.22 (s, 1H), 4.56 (m, 3H), 5.01 (dd, J=25.18, 9.61 Hz, 1H), 5.21 (d, J=17.09 Hz, 1H), 5.47 (s, 1H), 5.89 (m, 1H), 7.08 (d, J=5.19 Hz, 1H), 7.46 (d, J=7.93 Hz, 1H), 7.92 (s, 1H), 8.19 (d, J=8.24 Hz, 1H), 8.72 (d, J=5.19 Hz, 1H). LC-MS (retention time: 1.64, Method D), MS m/z 772 (M$^+$+1).

Compound 65 Example 65

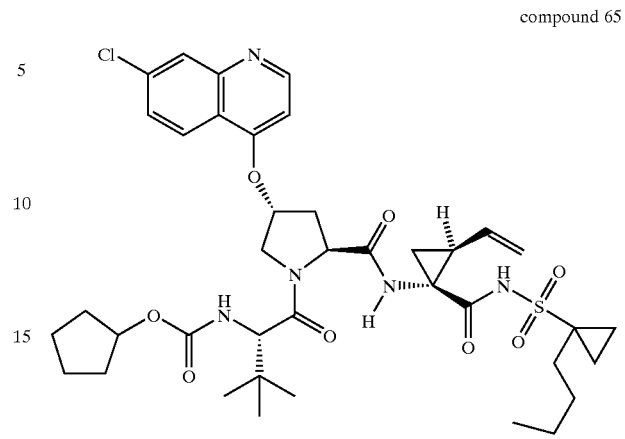

compound 65

Preparation {1-[2-[1-(1-Butyl-cyclopropanesulfonylaminocarbonyl)-2-vinyl-cyclopropylcarbamoyl]-4-(7-chloro-quinolin-4-yloxy)-pyrrolidine-1-carbonyl]-2,2-dimethyl-propyl}-carbamic acid cyclopentyl ester

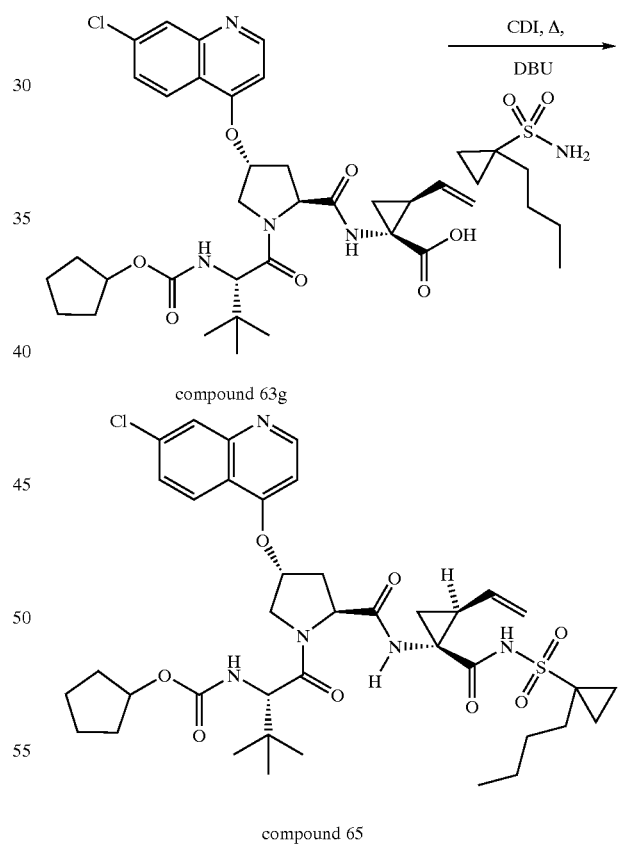

Step 65) Compound 65 was prepared in 37% yield (0.0271 g) from the chloro-P2 tripeptide acid (0.058 g, 0.13 mmol) of compound-63g (step 63g, Example 63) in analogous fashion to the procedure of Step 27c of Example 27 in the synthesis of compound 1 and purified by PTLC: $^1$H NMR (methanol-d$_4$) δ ppm 0.90 (m, 5H), 1.02 (s, 9H), 1.60 (m, 18H), 2.15 (m, 1H), 2.48 (m, 1H), 2.67 (dd, J=14.04, 7.02 Hz, 1H), 4.05 (m, 1H), 4.22 (s, 1H), 4.49 (d, J=11.90 Hz, 1H), 4.57 (m, 2H), 5.03 (m, 1H), 5.23 (d, J=17.09 Hz, 1H), 5.47 (s, 1H), 5.83 (m, 1H), 7.09 (m, 1H), 7.46 (d, J=8.85 Hz, 1H), 7.92 (s, 1H), 8.19 (m, 1H), 8.72 (d, J=5.19 Hz, 1H). LC-MS (retention time: 1.87, Method D), MS m/z 786 (M$^+$+1).

Compound 66 Example 66 compound 66

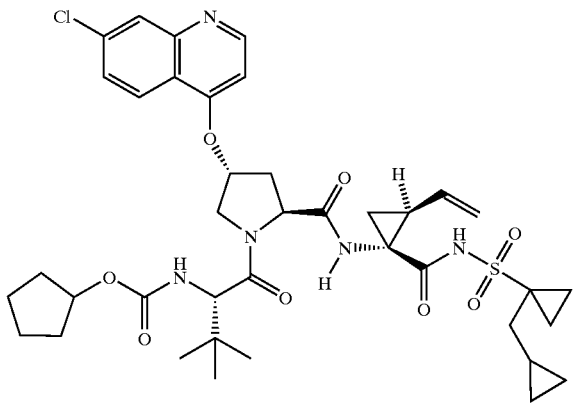

Preparation of (1-{4-(7-Chloro-quinolin-4-yloxy)-2-[1-(1-cyclopropylmethyl-cyclopropanesulfonylaminocarbonyl)-2-vinyl-cyclopropylcarbamoyl]-pyrrolidine-1-carbonyl}-2,2-dimethyl-propyl)-carbamic acid cyclopentyl ester

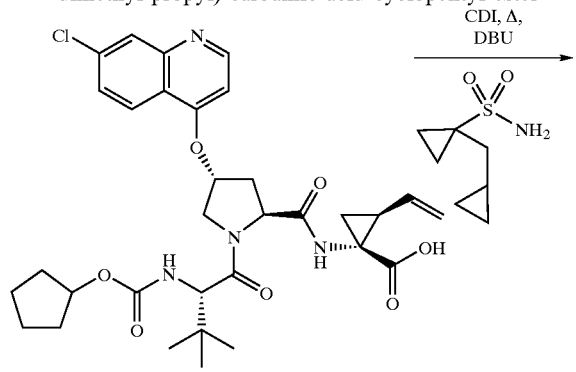

compound 63g

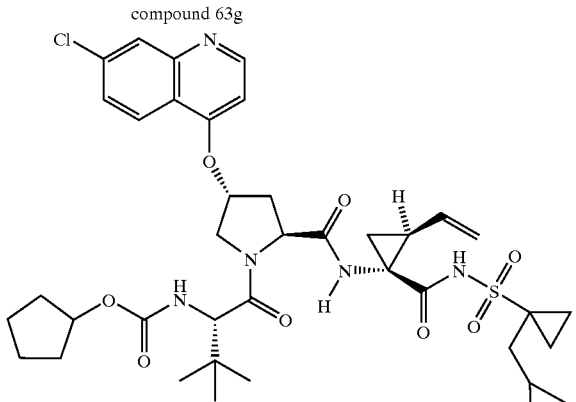

compound 66

Step 66) Compound 66 was prepared in 54% yield (0.1016 g) from the chloro-P2 tripeptide acid (0.150 g, 0.24 mmol) of compound 63g (step 63g) in analogous fashion to the procedure of Example 63 (step 63h) in the synthesis of compound 50 and purified by PTLC: $^1$H NMR (methanol-d$_4$) □ ppm 0.04 (m, 2H), 0.42 (m 2H), 0.70 (m, 1H), 1.02 (s, 9H), 1.57 (m, 16H), 2.10 (m, 1H), 2.48 (s, 1H), 2.68 (dd, J=13.73, 7.32 Hz, 1H), 4.06 (m, 1H), 4.22 (s, 1H), 4.49 (d, J=11.90 Hz, 1H), 4.57 (m, 2H), 5.00 (dd, J=23.19, 10.99 Hz, 1H), 5.20 (d, J=17.09 Hz, 1H), 5.46 (m, 1H), 5.93 (m, 1H), 7.08 (d, J=5.49 Hz, 1H), 7.46 (d, J=8.55 Hz, 1H), 7.92 (s, 1H), 8.19 (d, J=8.85 Hz, 1H), 8.72 (d, J=5.19 Hz, 1H). LC-MS (retention time: 1.76, Method I), MS m/z 784 (M$^+$+1).

Compound 67 Example 67 compound 67

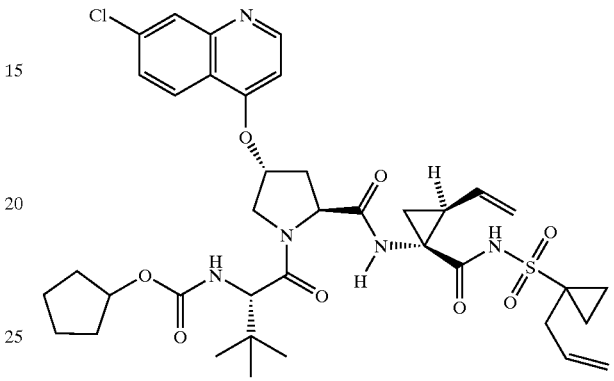

Preparation {1-[2-[1-(1-Allyl-cyclopropanesulfonylaminocarbonyl)-2-vinyl-cyclopropylcarbamoyl]-4-(7-chloro-quinolin-4-yloxy)-pyrrolidine-1-carbonyl]-2,2-dimethyl-propyl}-carbamic acid cyclopentyl ester

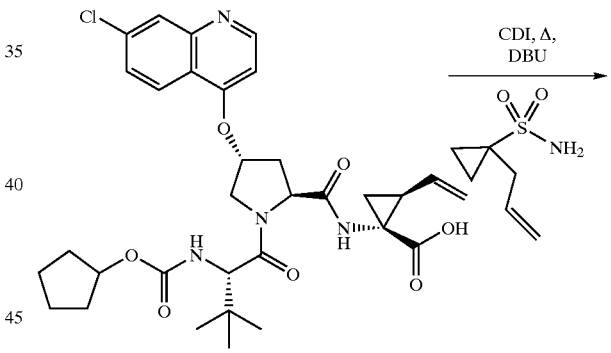

compound 63g

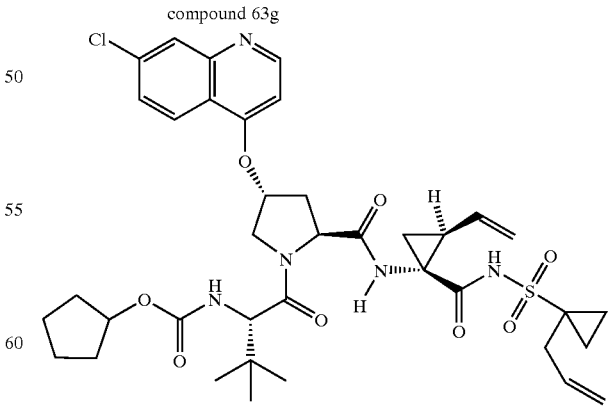

compound 67

Step 67) Compound was prepared in 16% yield (0.0051 g) from the chloro-P2 tripeptide acid (0.026 g, 0.04 mmol) of compound 63g (step 63g) in analogous fashion to the procedure of Example 63 step 63h in the synthesis of compound 63 and purified by PTLC: ¹H NMR (methanol-d₄) □ ppm 0.87 (m, 2H), 1.02 (s, 9H), 1.51 (m, 14H), 1.99 (dd, J=24.72, 15.87 Hz, 1H), 2.65 (m, 3H), 4.16 (s, 1H), 4.22 (s, 1H), 4.49 (m, 1H), 4.57 (m, 1H), 4.99 (m, 3H), 5.17 (m, 1H), 5.47 (m, 1H), 5.78 (m, 2H), 7.10 (d, J=5.49 Hz, 1H), 7.47 (m, 1H), 7.93 (m, 1H), 8.21 (m, 1H), 8.72 (d, J=5.49 Hz, 1H). LC-MS (retention time: 1.72, Method I), MS m/z 770 (M⁺+1).

Compound 68 Example 68 compound 68

Scheme 1

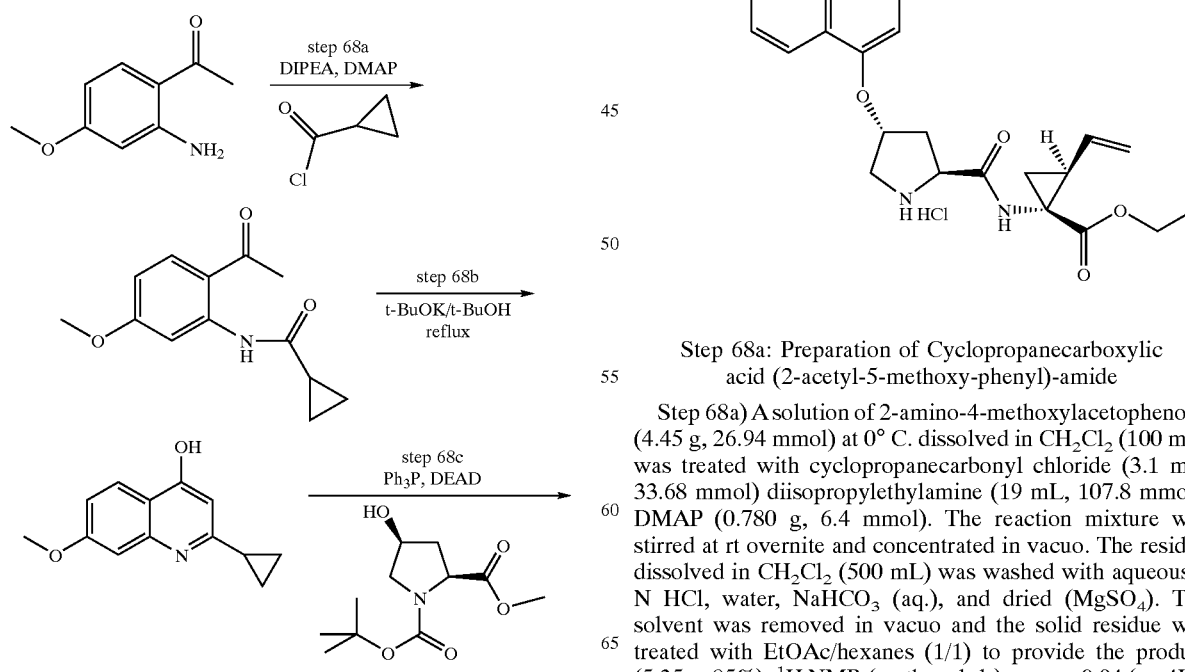

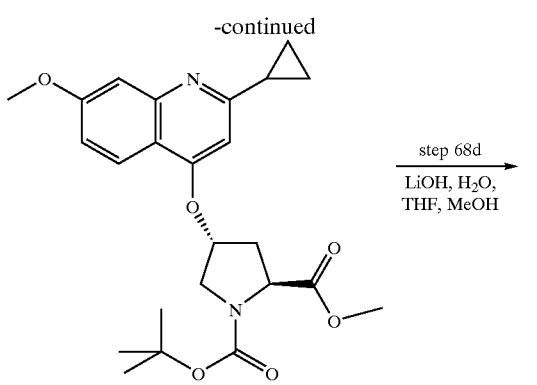

Step 68a: Preparation of Cyclopropanecarboxylic acid (2-acetyl-5-methoxy-phenyl)-amide Step 68a) A solution of 2-amino-4-methoxylacetophenone (4.45 g, 26.94 mmol) at 0° C. dissolved in CH₂Cl₂ (100 mL) was treated with cyclopropanecarbonyl chloride (3.1 mL, 33.68 mmol) diisopropylethylamine (19 mL, 107.8 mmol), DMAP (0.780 g, 6.4 mmol). The reaction mixture was stirred at rt overnite and concentrated in vacuo. The residue dissolved in CH₂Cl₂ (500 mL) was washed with aqueous 1 N HCl, water, NaHCO₃ (aq.), and dried (MgSO₄). The solvent was removed in vacuo and the solid residue was treated with EtOAc/hexanes (1/1) to provide the product (5.35 g, 85%): ¹H NMR (methanol-d₄) □ ppm 0.94 (m, 4H), 1.69 (m, J=3.97 Hz, 1H), 2.60 (s, 3H), 3.84 (s, 3H), 6.69 (d, J=7.93 Hz, 1H), 7.98 (d, J=8.85 Hz, 1H), 8.23 (s, 1H).

Step 68b: Preparation of 2-Cyclopropyl-7-methoxy-quinolin-4-ol

Step 68b) A solution of product (5.35 g, 22.72 mmol) of step 1 example 376 {cyclopropanecarboxylic acid (2-acetyl-5-methoxy-phenyl)-amide} and tert-BuOK (5.45 g, 48.6 mmol) in tert-butanol (130 g) was refluxed for 6 h. The reaction mixture was cooled, poured into ice cold buffer and adjusted to pH 7, filtered. The solid collection was recrystallized from MeOH/Et$_2$O to provide the product (1 g, 20%): $^1$H NMR (methanol-d$_4$) δ ppm 0.96 (m, 2H), 1.15 (m, 2H), 1.94 (m, 1H), 3.87 (s, 3H), 5.86 (m, 1H), 6.93 (m, 2H), 8.04 (d, J=8.85 Hz, 1H).

Step 68c: Preparation of Boc-(4R)-(2-cyclopropyl-7-methoxy-quinoline-4-oxo)-S-proline methyl ester Step 68c) To a solution of N—Boc-L-3-hydroxyproline (1.06 g, 4.32 mmol) and triphenylphosphine (2.27 g, 8.64 mmol) at 0° C. dissolved THF (25 mL) was added a solution of the product (0.93 g, 4.32 mmol) of Step 2 Example 376 {2-Cyclopropyl-7-methoxy-quinolin-4-ol} and DEAD (1.50 g, 8.64 mmol) in THF (25 mL) over 30 min. The reaction mixture was stirred overnite and concentrated. The residue was purified twice by a Biotage 40+M column (EtOAC/hexanes: 20 to 65%) to afford the product 1.74 g (90%): LC-MS (retention time: 2.56, Method J), MS m/z 443 (M$^+$+1).

Step 68d: Preparation of Boc-(4R)-(2-cyclopropyl-7-methoxy-quinoline-4-oxo)-S-proline Step 68d) To a suspension of (1.70 g, 3.86 mmol) of the product of Step 3 of Example 376 (Boc-(4R)-(2-cyclopropyl-7-methoxy-quinoline-4-oxo)-S-proline methyl ester} in THF(91 mL), CH$_3$OH (18.2 mL), and H$_2$O (27 mL) was added LiOH (0.73 g, 30 mmol). The reaction mixture was stirred for 16 h, adjusted to pH 6, the organic solvent was removed in vacuo. The residue was acidified to pH 4, and extracted with EtOAc (4×100 mL). The combined organic extract was dried (MgSO$_4$), and concentrated in vacuo to supply the product 1.64 g (100%): $^1$H NMR (methanol-d$_4$) δ ppm 1.32 (m, 13H), 2.37 (m, 2H), 2.71 (m, 1H), 3.86 (m, 1H), 3.95 (s, 3H), 4.14 (m, 1H), 4.43 (m, 1H), 5.41 (s, 1H), 6.65 (s, 1H), 7.19 (m, 1H), 7.30 (m, 1H), 8.02 (dd, J=12.63, 9.33 Hz, 1H).

Step 68e: Preparation of 4-(2-Cyclopropyl-7-methoxy-quinolin-4-yloxy)-2-(1-ethoxycarbonyl-2-vinyl-cyclopropylcarbamoyl)-pyrrolidine-1-carboxylic acid tert-butyl ester Step 68e) The product (1.61 g, 2.79 mmol) of Step 4 of Example 376 {Boc—P2{(4R)-[2-cyclopropyl-7-methoxy]quinoline-4-oxo]-S-proline}-P1 (1R,2S Vinyl Acca) COOEt} was dissolved in HCl/dioxane (15 mL; 60 mmol) and stirred for 3 h at rt. The reaction mixture was concentrated and azeotroped with dry THF to afford the product (1.58 g, 100%): LC-MS (retention time: 2.12, Method K), MS m/z 566 (M$^+$+1).

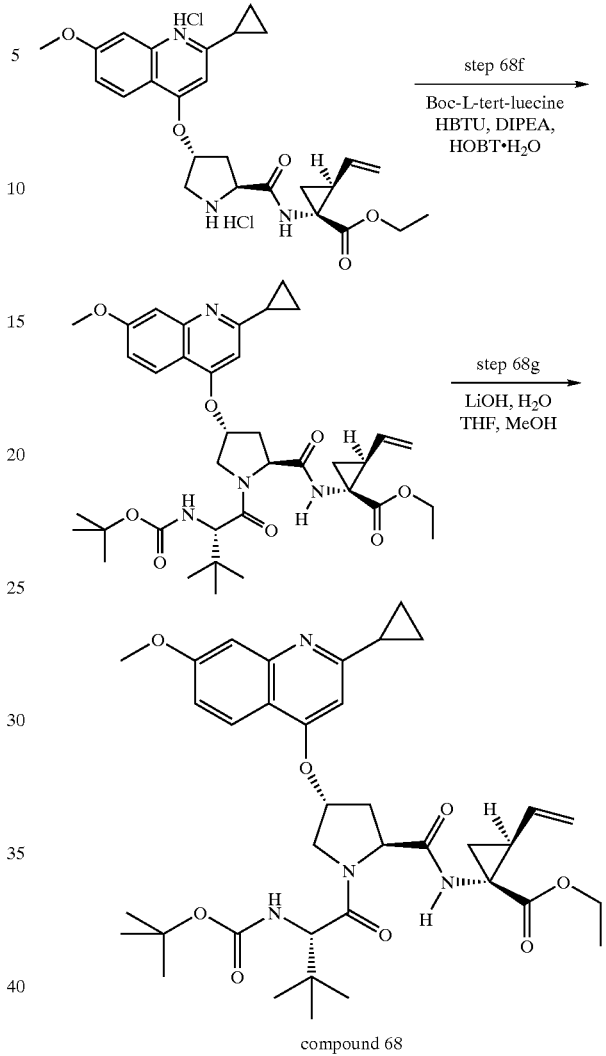

Scheme 2 compound 68

Step 68f: preparation of Bis HCl salt

Step 68f) To a suspension of the product (1.58 g, 2.79 mmol) of Step 5 of Example 376 {Bis HCl salt of P2{(4R)-[2-cyclopropyl-7-methoxylquinoline-4-oxo]-S-proline}-P1 (1R,2S Vinyl Acca) COOEt}, diisopropylethylamine (1.65 mL, 9.25 mmol), N—Boc-L-tert-leucine (0.775 g, 3.35 mmol), HOBT.H$_2$O (0.515 g, 3.36 mmol) in CH$_2$Cl$_2$ (13 mL) was added HBTU (1.28 g, 3.36 mmol). The mixture was stirred for 14 h and partitioned between EtOAc and pH 4.0 buffer. The EtOAc layer was dried (MgSO$_4$), concentrated. The residue was purified over a Biotage 40+M column (EtOAc/hexanes: 20 to 100%, followed MeOH) and further purified by PTLC (MeOH/CH$_2$Cl$_2$ 2%) to afford the product 1.4 g (63%): $^1$H NMR (methanol-d$_4$) □ ppm 1.04 (s, 9H), 1.20 (m, 5H), 1.28 (s, 9H), 1.39 (m, 2H), 1.69 (m, 1H), 2.19 (m, 2H), 2.36 (m, 1H), 2.63 (dd, J=13.54, 7.68 Hz, 1H), 3.90 (s, 3H), 4.08 (m, 4H), 4.19 (d, J=11.34 Hz, 1H), 4.47 (d, J=11.71 Hz, 1H), 4.56 (t, J=8.60 Hz, 1H), 5.08 (m, 1H), 5.24 (m, 1H), 5.39 (s, 1H), 5.78 (m, 1H), 6.56 (s, 1H), 6.96 (dd, J=9.15, 2.20 Hz, 1H), 7.21 (d, J=2.56 Hz, 1H), 7.97 (d, J=9.15 Hz, 1H). LC-MS (retention time: 2.34, Method K), MS m/z 679 (M$^+$+1).

Step 68g: preparation of 1-{[1-(2-tert-Butoxycarbonylamino-3,3-dimethyl-butyryl)-4-(2-cyclopropyl-7-methoxy-quinolin-4-yloxy)-pyrrolidine-2-carbonyl]-amino}-2-vinyl-cyclopropanecarboxylic acid ethyl ester Step 68g) To a suspension of the product of Step 6 of Example 376 (1.28 g, 1.89 mmol), Boc—NH—P3(L-tert-BuGly)-P2[(4R)-(2-cyclopropyl-7-methoxylquinoline-4-oxo)-S-proline]-P1(1R,2S Vinyl Acca)-COOEt, in THF(93 ML), CH$_3$OH (23 mL), and H$_2$O (45 mL) was added LiOH (0.491 g, 20.4 mmol). The reaction mixture was stirred for 18.5 h, adjusted to pH 4, removed the organic solvent in vacuo. The residue was extracted with EtOAc (5×100 mL). Combined organic solvents were dried (MgSO$_4$), and concentrated in vacuo to afford the desired product 1.17 g (97%): $^1$H NMR (methanol-d$_4$) δ ppm 1.04 (s, 9H), 1.24 (s, 9H), 1.27 (m, 3H), 1.42 (m, 2H), 1.68 (dd, J=8.05, 5.12 Hz, 1H), 2.17 (m, 1H), 2.33 (m, 1H), 2.47 (m, 1H), 2.66 (m, 1H), 3.95 (s, 3H), 4.09 (m, 2H), 4.51 (d, J=111.71 Hz, 1H), 4.59 (t, J=8.60 Hz, 1H), 5.07 (m, 1H), 5.26 (m, 1H), 5.52 (s, 1H), 5.85 (m, 1H), 6.69 (s, 1H), 7.10 (dd, J=9.15, 2.20 Hz, 1H), 7.27 (d, J=2.20 Hz, 1H), 8.10 (d, J=9.15 Hz, 1H). LC-MS (retention time: 2.21, Method K), MS m/z 651 (M$^+$+1).

Step 69h: Preparation of Compound 69, Example 69, BOCNH—P3(L-t-BuGly)-P2[(4R)-(2-cyclopropyl-7-methoxyquinoline-4-oxo)-S-proline]-P1(1R,2S Vinyl Acca)-CONHSO$_2$(1-benzylclopropan-1-yl) or alternate designation, Compound 69, example 69, (1-{4-(2-Cyclopropyl-7-methoxy-quinolin-4-yloxy)-2-[1-(1-phenethyl-cyclopropanesulfonylaminocarbonyl)-2-vinyl-cyclopropylcarbamoyl]-pyrrolidine-1-carbonyl}-2,2-dimethyl-propyl)-carbamic acid tert-butyl ester

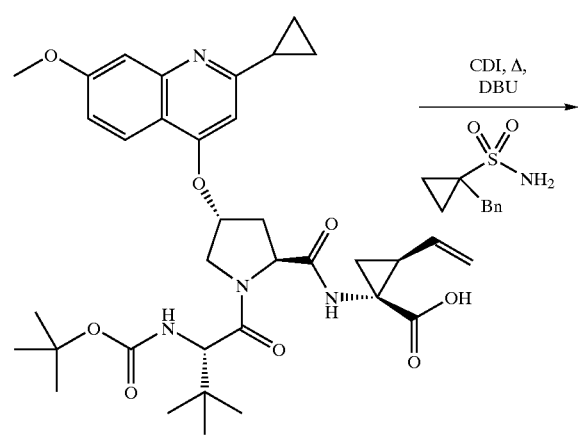

compound 69h

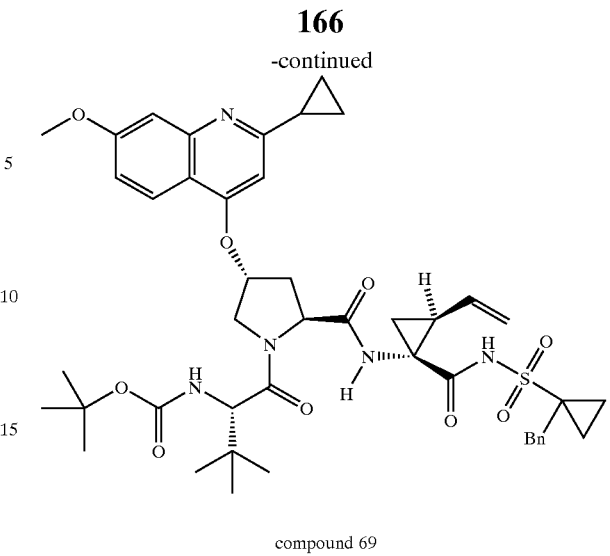

compound 69

Step 68h) Compound 69 was prepared in 41% yield (0.095 g) from the cyclopropyl-P2 tripeptide acid (0.160 g, 0.25 mmol) of the product of Step 68g (Example 68) in analogous fashion to the procedure of Step 27c (Example 27) in the synthesis of compound 27 and purified by preparative HPLC (solvent B: 45% to 85%): $^1$H NMR (methanol-d$_4$) □ ppm 0.65 (m, 2H), 0.96 (s, 9H), 1.18 (s, 9H), 1.48 (m, 6H), 1.92 (dd, J=8.05, 5.49 Hz, 1H), 2.37 (m, 3H), 2.69 (dd, J=14.09, 7.50 Hz, 1H), 3.29 (m, 2H), 4.01 (s, 3H), 4.09 (m, 2H), 4.59 (m, 2H), 5.18 (m, 1H), 5.35 (d, J=17.20 Hz, 1H), 5.67 (s, 1H), 5.77 (m, 1H), 6.83 (s, 1H), 7.14 (m, 2H), 7.31 (m, 6H), 8.23 (d, J=9.15 Hz, 1H). LC-MS (retention time: 3.73, Method K), MS m/z 844 (M$^+$+1).

Compound 69 Example 69

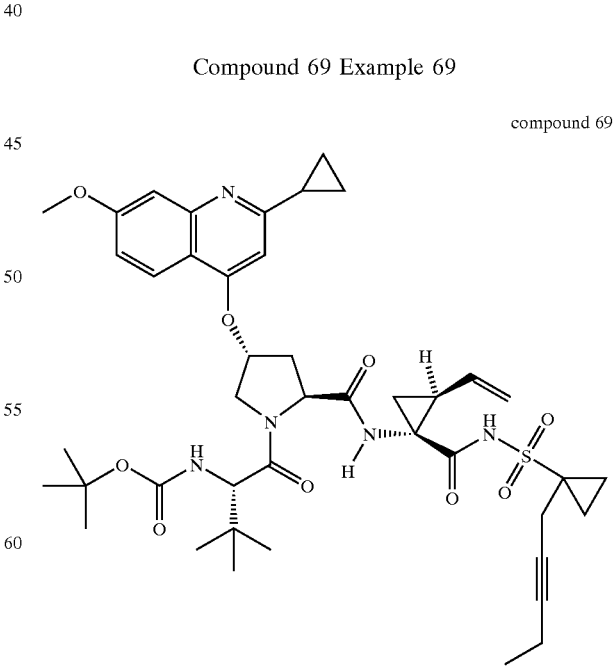

compound 69

Compound 69, Example 69, BOCNH—P3(L-t-BuGly)-P2[(4R)-(2-cyclopropyl-7-methoxyquinoline-4-oxo)-S-proline]-P1(1R,2S Vinyl Acca)-CONHSO$_2$[1-(1-pent-2-ynyl)-clopropan-1-yl) or alternate designation, Compound 69, example 69, (1-{4-(2-Cyclopropyl-7-methoxy-quinolin-4-yloxy)-2-[1-(1-pent-2-ynyl-cyclopropanesulfonylaminocarbonyl)-2-vinyl-cyclopropylcarbamoyl]-pyrrolidine-1-carbonyl}-2,2-dimethyl-propyl)-carbamic acid tert-butyl ester

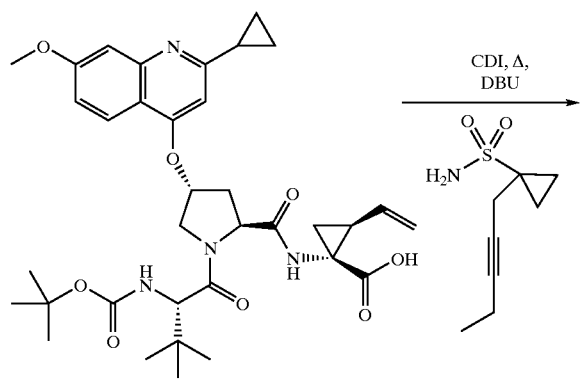

compound 68h

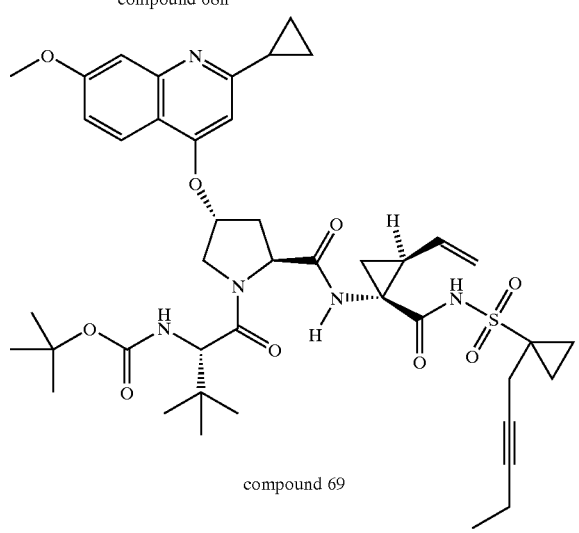

compound 69

Step 69) Compound 69 was prepared in 43% yield (0.086 g) from the cyclopropyl-P2 tripeptide acid (0.160 g, 0.25 mmol) of compound 69h of product of Step 69h (Example 69) in analogous fashion to the procedure of Example 46 in the synthesis of compound 33 and purified by preparative HPLC (solvent B: 30% to 100%): $^1$H NMR (methanol-d$_4$) □ ppm 0.91 (m, 2H), 1.01 (m, 3H), 1.04 (s, 9H), 1.15 (m, 5H), 1.26 (m, 11H), 1.80 (m, 1H), 2.08 (m, 2H), 2.22 (m, 1H), 2.45 (m, 1H), 2.99 (s, 2H), 3.34 (s, 2H), 3.90 (s, 3H), 4.08 (m, 1H), 4.23 (m, 1H), 4.45 (d, J=11.90 Hz, 1H), 4.52 (m, 1H), 5.04 (d, J=10.38 Hz, 1H), 5.20 (d, J=17.09 Hz, 1H), 5.42 (s, 1H), 5.90 (m, 1H), 6.57 (m, 1H), 6.98 (dd, J=9.00, 2.29 Hz, 1H), 7.22 (d, J=2.44 Hz, 1H), 7.99 (d, J=9.16 Hz, 1H). LC-MS (retention time: 1.98, Method H), MS m/z 820 (M$^+$+1).

Compound 70 Example 70

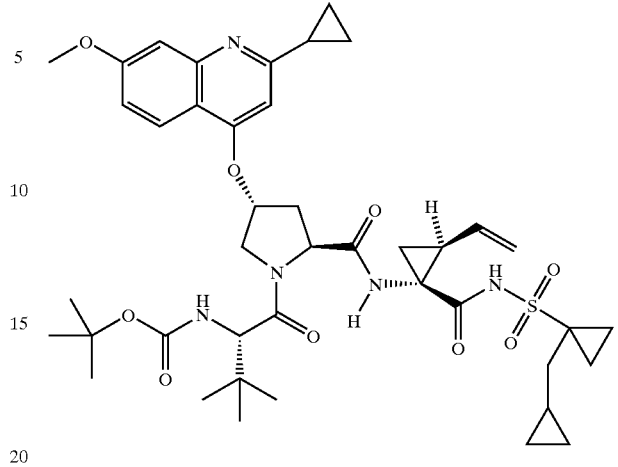

compound 70

Compound 70, Example 70, BOCNH—P3(L-t-BuGly)-P2[(4R)-(2-cyclopropyl-7-methoxyquinoline-4-oxo)-S-proline]-P1(1R,2S Vinyl Acca)-CONHSO$_2$(1-cyclopropylmethylclopropan-1-yl) or alternate designation Compound 70, Example 70, (1-{4-(2-Cyclopropyl-7-methoxy-quinolin-4-yloxy)-2-[1-(1-cyclopropylmethyl-cyclopropanesulfonylaminocarbonyl)-2-vinyl-cyclopropylcarbamoyl]-pyrrolidine-1-carbonyl}-2,2-dimethyl-propyl)-carbamic acid tert-butyl ester

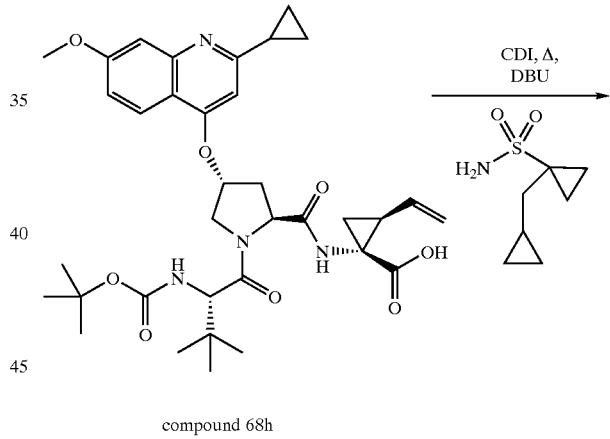

compound 68h

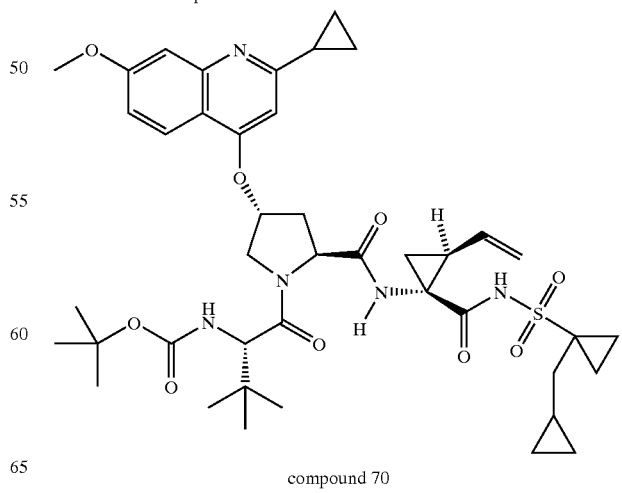

compound 70

Step 70) Compound 70 was prepared in 43% yield (0.086 g) from the cyclopropyl-P2 tripeptide acid (0.160 g, 0.25 mmol) of compound 56 h Step 69 h in analogous fashion to the procedure of Step 27c of Example 27 in the synthesis of compound 1 except that 1-cyclopropylmethylcyclopropanesulfonamide was used in place of 1-trimethylsilanyl-cyclopropanesulfonamide: and purified by preparative HPLC (solvent B: 45% to 85%): $^1$H NMR (methanol-d$_4$) □ ppm 0.06 (m, 2H), 0.45 (m, 2H), 0.67 (m, 1H), 1.04 (s, 9H), 1.28 (s, 9H), 1.43 (m, 8H), 1.87 (m, 4H), 2.25 (m, 3H), 2.60 (dd, J=12.99, 6.77 Hz, 1H), 3.91 (s, 3H), 4.07 (dd, J=12.08, 3.29 Hz, 1H), 4.24 (d, J=9.15 Hz, 1H), 4.48 (m, 2H), 5.09 (d, J=10.25 Hz, 1H), 5.26 (d, J=17.20 Hz, 1H), 5.45 (s, 1H), 5.73 (m, 1H), 6.60 (s, 1H), 7.00 (dd, J=9.15, 2.20 Hz, 1H), 7.23 (d, J=2.20 Hz, 1H), 7.99 (d, J=9.15 Hz, 1H). LC-MS LC-MS (retention time: 3.16, Method L), MS m/z 808 (M$^+$+1).

Compound 71 Example 71

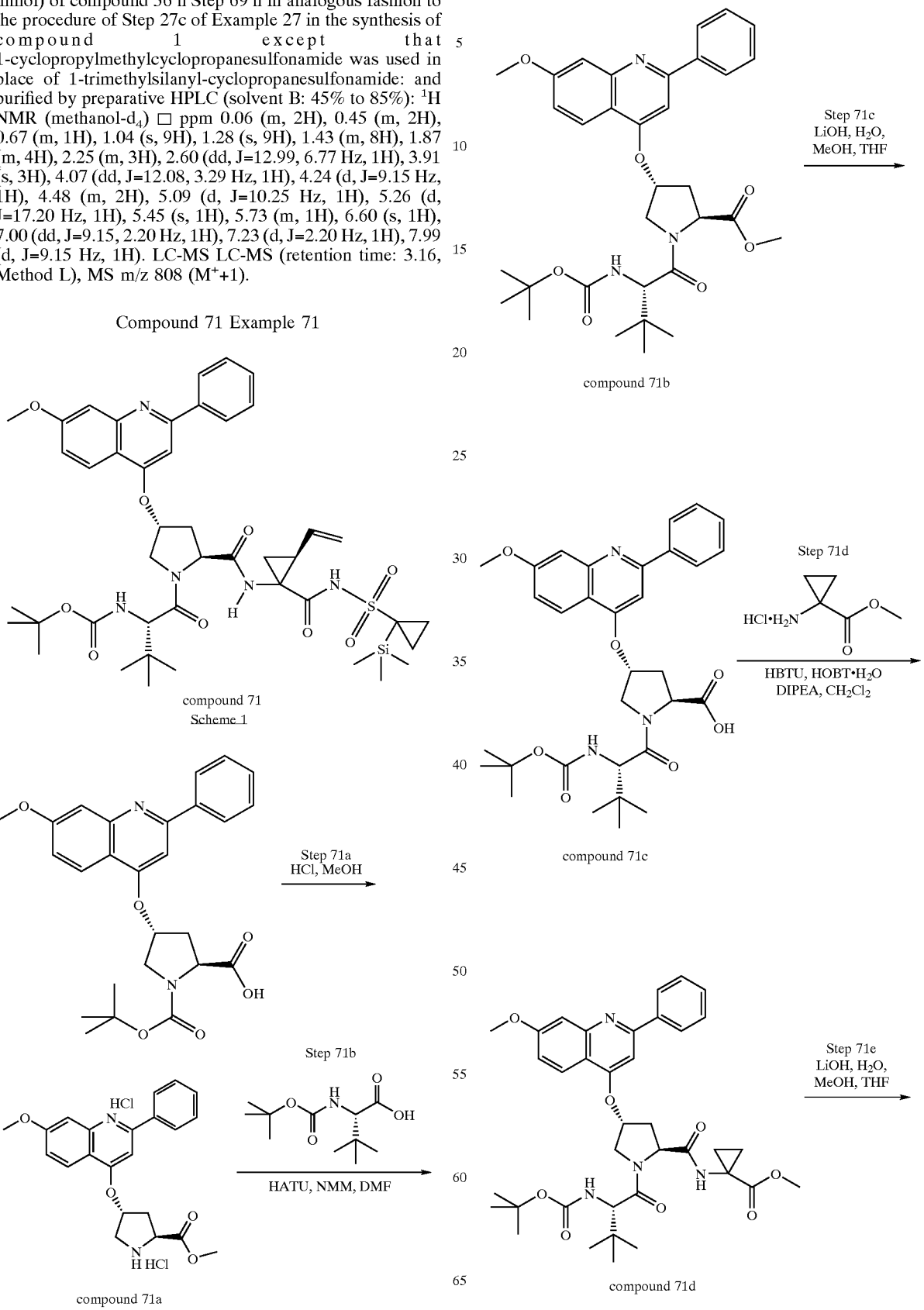

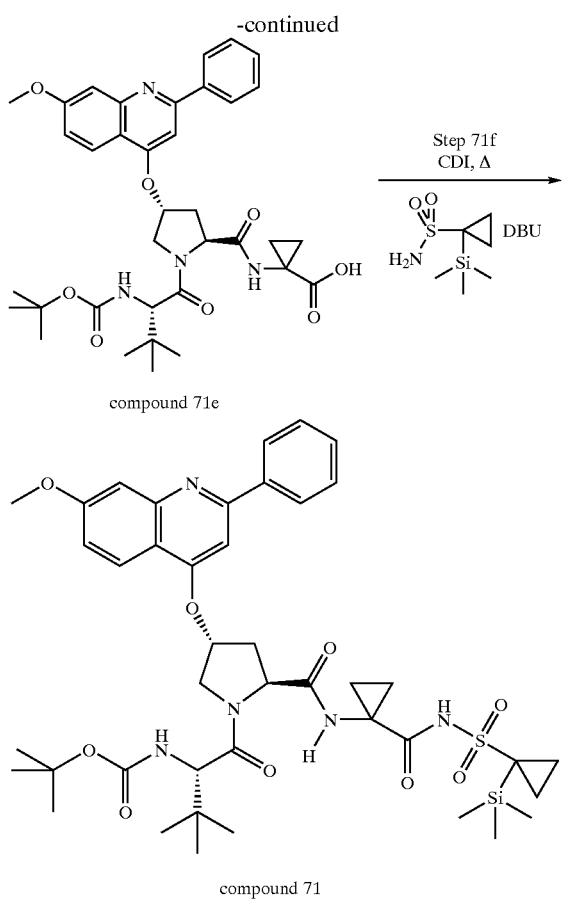

compound 71e compound 71

Step 71a: P2HN-[(4R)-(2phenyl-7-methoxyquinoline4-oxy-S-proline methyl ester dihydrochloride Step 71a) To a solution of 10 g (21.5 mmol) of N—Boc (4R)-(2-phenyl-7-methoxyquinoline-4-oxo)-S-proline, 4-oxy)-S-proline, 4-(7-Methoxy-2-phenyl-quinolin-4-yloxy)-pyrrolidine-1,2-dicarboxylic acid 1-tert-butyl ester in 500 mL of MeOH cooled to −78° C., was bubbled in gaseous HCl for 10 ml. The mixture was warmed to rt, stirred overnite and concentrated in vacuo. The residue was azeotroped repeatedly with toluene and dioxane to afford 9.71 g (100%) of the titled product as an offwhite solid. $^1$H NMR (DMSO-$d_6$) δ 2.56–2.66 (m, 1H), 2.73–2.80 (m, 1H), 3.67–3.86 (m, 2H), 3.79 (s, 3H), 3.97 (s, 3H), 4.76–4.82 (m, 1H), 5.95 (m, 1H), 7.42 (dd, J=9, 2 Hz, 1H), 7.65–7.72 (m, 4H), 8.23–8.27 (m, 2H), 8.51 (d, J=9.2 Hz, 1H), 9.68 (bs, 1H), 11.4 (bs, 1H; LC-MS (retention time: 0.94, method D), MS m/e 379 (M$^+$+1).

Step 71b: Preparation of P3N—BOC (L-t-BuGly)-P2[(4R)-(2-phenyl-7-methoxyquinoline-4-oxo)-S-proline)]-COOMe Step 71b) To suspension of the product (3.90 g, 8.60 mmol) of Step 72a (Example 72), [HN-(4R)-(2-phenyl-7-methoxyquinoline-4-oxo)-S-proline) methyl ester, bis hydrochloride], 2.65 g (11.47 mmol) of N—BOC-L-tert-leucine (L-tBuGly), 3.48 g (34.40 mmol) of NMM in DMF (20 mL) was added 3.62 g (9.52 mmol) of HATU at 0° C. The reaction mixture was slowly allowed to warm to rt overnite, was stirred for 4 days, diluted with EtOAc (200 mL), washed with pH 4.0 buffer (3×40 mL), saturated aqueous NaHCO$_3$ (40 mL), dried (MgSO$_4$), and purified by a Biotage 40 M column (eluted with 15% to 70% EtOAc in Hexanes) to supply 4.16 g (81%) of 1-(2-tert-Butoxycarbonylamino-3,3-dimethylbutyryl)-4-(7-methoxy-2-phenylquinolin-4-yloxy)-pyrrolidine-2-carboxylic acid methyl ester, which is also named P3 N—BOC (L-tBuGly)-P2 [(4R)-(2-phenyl-7-methoxyquin-oline-4-oxo)-S-proline)]-COOMe, as a foam. $^1$H NMR (CDCl$_3$) δ 1.07 (s, 9H), 1.37 (s, 9H), 2.29–2.39 (m, 1H), 2.78 (dd, J=14, 8 Hz, 1H), 3.96 (s, 3H), 4.06–4.11(m, 1H), 4.31 (d, J=10 Hz, 1H), 4.54 (d, J=11 Hz, 1H), 4.72–4.77 (m, 1H), 5.23 (d, J=10 Hz, 1H), 5.34 (m, 1H), 6.96 (s, 1H), 7.07 (dd, J=9, 2 Hz, 1H), 7.44–7.52 (m, 3H), 7.99–8.03 (m, 3H). LC-MS (retention time: 1.43, method A) MS m/e 592 (M$^+$+1).

Step 71c: Preparation of P3 N—BOC (L-t-BuGly)-P2 [(4R)-(2-phenyl-7-methoxyquinoline-4-oxo)-S-proline)]-COOH Step 71c) To a solution of 1-(2-tert-butoxycarbonyl-amino-3,3-dimethylbutyryl)-4-(7-methoxy-2-phenyl-quinolin-4-yloxy)-pyrrolidine-2-carboxylic acid methyl ester (4.179 g, 7.06 mmol) in THF (318 mL), CH$_3$OH (42 mL), and H$_2$O (170 mL) was added LiOH (1.356 g, 56.5 mmol). The reaction mixture was stirred for one day, acidified to neutral pH, and concentrated in vacuo until only the aqueous layer remained. The resulting aqueous residue was acidified to pH 4.0 by addition of 1.0 N aqueous HCl and then saturated with solid NaCl. This aqueous mixture was extracted repeatedly with 80% EtOAc/THF (4×300 mL), the combined organic solvent dried (Mg$_2$SO$_4$), filtered, and concentrated in vacuo to supply 3.69 g (91%) of the titled product as a foam. $^1$H NMR (CDCl$_3$) δ 1.03 (s, 9H), 1.27 (s, 9H), 2.36–2.43 (m, 1H), 2.78–2.83 (m, 1H), 3.94 (s, 3H), 4.05 (d, J=10 Hz, 1H), 4.24 (d, J=9 Hz, 1H), 4.54 (d, J=12 Hz, 1H), 4.63–4.67, (m, 1H), 5.52 (m, 1H), 7.09 (dd, J=9 Hz, 1H), 7.20 (s, 1H), 7.38 (s, 1H), 7.51–7.55 (m, 3H), 7.99–8.00 (m, 3H), 8.09 (d, J=9 Hz, 1H). LC-MS (retention time: 1.44, Method A), MS m/z 578 (M$^+$+1).

Step 71d: BOC P3-(L-tBuGly)-P2[(4R)-(2-phenyl-7-methoxyquinoline-4-oxo)-S-proline)]-P1-(1-aminocyclopropane-1-)COOMe Step 71d) A mixture of the product (2.0 g, 3.46 mmol) of Step 72c (Example 72), diisopropylethylamine (3 mL, 17.3 mmol), HOBT.H$_2$O (0.64 g, 4.15 mmol), and HBTU (1.58 g, 4.15 mmol) in CH$_2$Cl$_2$:(35 mL) was stirred overnite. The reaction mixture was diluted with EtOAc (300 mL), Washed with pH 4.0 buffer (3×), aqueous NaHCO$_3$(2×), brine, dried (MgSO$_4$), and concentrated. The residue was purified over Biotage 65M column (EtOAc/hexanes: 15% to 100%) to provide the product as a foam 1.97 g: $^1$H NMR $^1$H NMR (CHLOROFORM-D) □ ppm 1.02 (s, 9H), 1.29 (m, 3H), 1.29 (s, 9H), 1.57 (m, 1H), 2.40 (m, 1H), 2.67 (dd, J=13.91, 7.68 Hz, 1H), 3.65 (s, 3H), 3.89 (s, 3H), 4.04 (m, 1H), 4.21 (m, 1H), 4.48 (d, J=11.71 Hz, 1H), 4.60 (t, J=8.42 Hz, 1H), 5.41 (s, 1H), 7.00 (d, J=8.78 Hz, 1H), 7.14 (s, 1H), 7.32 (s, 1H), 7.50 (m, 3H), 8.02 (m, 3H). LC-MS (retention time: 1.49 method C), MS m/z 675 (M$^+$+1).

Step 71e: BOC P3-(L-tBuGly)-P2[(4R)-(2-phenyl-7-methoxyquinoline-4-oxo)-S-proline)]-P1-(1-aminocyclopropane-1-)COOH Step 71e) To a suspension of the product (1.97 g, 2.92 mmol) of Step 72d (Example 72), {BOC P3-(L-tBuGly)-P2 [(4R)-(2-phenyl-7-methoxyquinoline-4-oxo)-S-proline)]-

P1-(1-aminocyclopropane-1-)COOMe}, in THF(75 mL), CH₃OH (18 mL), and H₂O (60 mL) was added LiOH (0.42 g, 18 mmol). The reaction mixture was stirred overnite, adjusted to pH 7, removed the organic solvents in vacuo. The aqueous residue was acidified to pH 4, and extracted with EtOAc(3×200 mL). Combined organic solvent was dried (MgSO₄), and concentrated in vacuo to afford the desired product (Compound 80g) 1.59 g (82%): ¹H NMR (Methanol-d₄) □ ppm 1.06 (s, 9H), 1.30 (s, 9H), 1.45 (m, 2H), 1.60 (m, 1H), 1.60 (m, 1H), 2.53 (m, 1H), 2.77. (dd, J=13.43, 7.32 Hz, 1H), 3.97 (s, 3H), 4.09 (m, 1H), 4.25 (d, J=8.55 Hz, 1H), 4.57 (d, J=11.90 Hz, 1H), 4.64 (t, J=8.39 Hz, 1H), 5.57 (m, 1H), 7.10 (d, J=8.55 Hz, 1H), 7.29 (s, 1H), 7.41 (s, 1H), 7.57 (m, 3H), 8.07 (d, J=7.02 hz, 2H), 8.13 (d, J=8.85 Hz, 1H; LC-MS (retention time: 1.54, Method I), MS m/z 661 (M⁺+1).

Step 71f: Preparation ((1-{4-(7-Methoxy-2-phenyl-quinolin-4-yloxy)-2-[1-(1-trimethylsilanyl-cyclopropanesulfonylaminocarbonyl)-cyclopropylcarbamoyl]-pyrrolidine-1-carbonyl}-2,2-dimethyl-propyl)-carbamic acid tert-butyl ester Step 71f) To a solution of the tripeptide acid (0.080 g, 0.12 mmol) of (0.080 g, 0.12 mmol) of the product of Step 71e (Example 71) in THF (2 mL) was added CDI (0.039 g, 0.24 mmol), and the resulting solution was heated at 72° C. for 60 min and allowed to cool down to rt. 1-Trimethylsilanylcyclopropylsulfonamide (0.027 g, 0.14 mmol) and neat DBU (0.037 mL, 0.24 mmol) were added. The reaction mixture was stirred overnite, diluted with EtOAc (150 mL) and washed pH 4.0 buffer (2×30 mL), dried (Na₂SO₄/MgSO₄), concentrated. The residue was purified over 20×40 cM 1000 □ Analtech PTLC plates (MeOH/CH₂Cl₂: 2 to 5%) to afford the desired product (Compound 71) 0.043 g (42%) as a foam: ¹H NMR (CDCl₃) □ ppm 0.12 (s, 9H), 0.90 (m, 2H), 0.99 (s, 9H), 1.29 (d, J=18.01 Hz, 9H), 1.33 (m, 6H), 2.42 (s, 1H), 2.60 (s, 1H), 3.91 (s, 3H), 4.07 (s, 2H), 4.26 (d, J=8.85 Hz, 1H), 4.46 (d, J=11.29 Hz, 1H), 5.35 (s, 1H), 6.98 (s, 1H), 7.01 (d, J=10.68 Hz, 1H), 7.36 (s, 1H), 7.45 (m, 3H), 7.94 (d, J=7.32 Hz, 2H), 7.99 (d, J=9.16 Hz, 1H). LC-MS (retention time: 1.77, Method E), MS m/z 836 (M⁺+1).

Compound 72 Example 72 compound 72

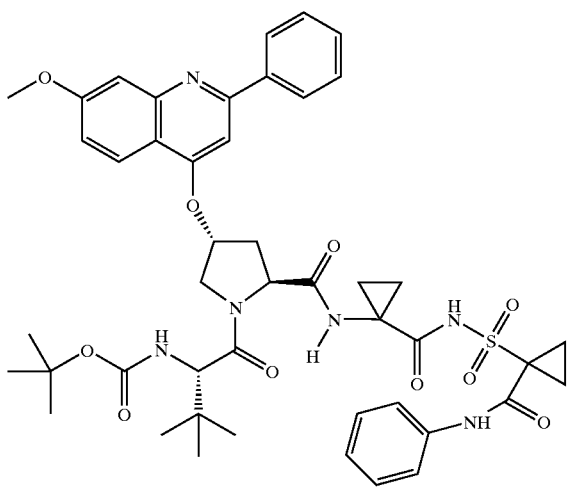

Compound 72, Example 72, BOCNH—P3(L-t-BuGly)-P2[(4R)-(2-phenyl-7-methoxyquinoline-4-oxo)-S-proline]-P1(cyclopropane)-CONHSO₂(1-phenylcarbamoyl-cyclopropan-1-yl) or Alternative Destination Compound 72, Example 72, (1-{4-(7-Methoxy-2-phenyl-quinolin-4-yloxy)-2-[1-(1-phenylcarbamoyl-cyclopropanesulfonylaminocarbonyl)-cyclopropylcarbamoyl]-pyrrolidine-1-carbonyl}-2,2-dimethyl-propyl)-carbamic acid tert-butyl ester

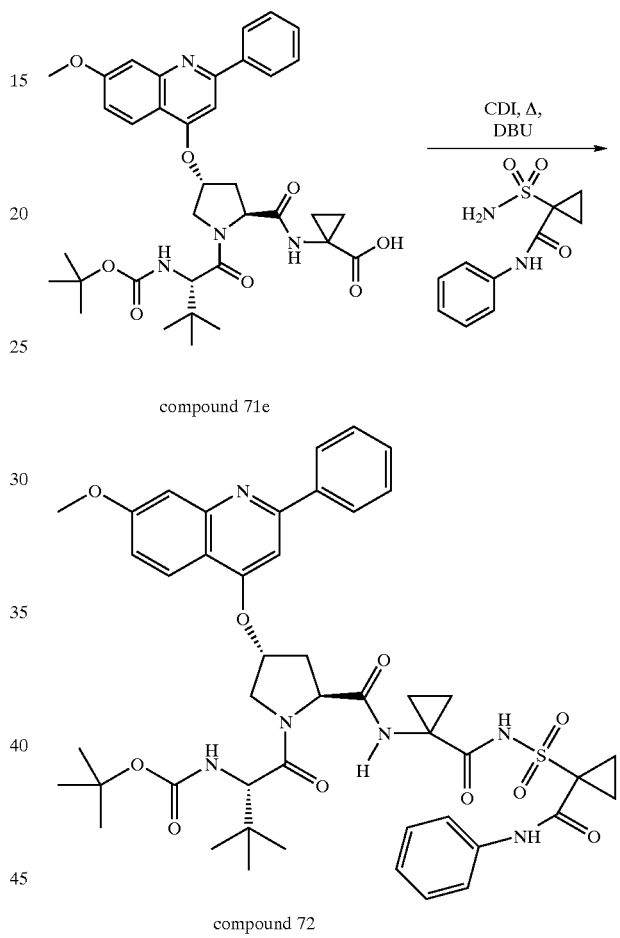

compound 71e compound 72

Step72f) Compound 72 was prepared in 73% yield (0.0785 g) from the tripeptide acid (0.080 g, 0.12 mmol) of the product of Step 71e (Example 71) in analogous fashion to the procedure of Step 71f (Example 71) in the synthesis of compound 71 except that 1-phenylcarbamoylcyclopropanesulfonamide (prepared in step 81d) was used in place of 1-trimethylsilanylcyclopropanesulfonamide: ¹H NMR (methanol-d₄) □ ppm 1.01 (s, 11H), 1.32 (s, 9H), 1.34 (m, 4H), 1.54 (m, 5H), 2.38 (m, 1H), 2.53 (m, 1H), 3.66 (d, J=9.46 Hz, 1H), 4.20 (m, 1H), 4.39 (d, J=11.90 Hz, 1H), 4.48 (t, J=8.70 Hz, 1H), 5.23 (s, 1H), 6.95 (m, 1H), 7.01 (dd, J=9.00, 1.98 Hz, 1H), 7.16 (m, 3H), 7.37 (d, J=2.14 Hz, 1H), 7.52 (m, 6H), 8.03 (d, J=9.16 Hz, 1H), 8.08 (d, J=7.93 Hz, 2H). HRMS m/z (M+H)+calcd for C₄₆H₅₅N₆SO₁₀: 83.3701 found: 883.3735. LC-MS (retention time: 1.58, Method F), MS m/z 883 (M⁺+1).

Compound 73 Example 73

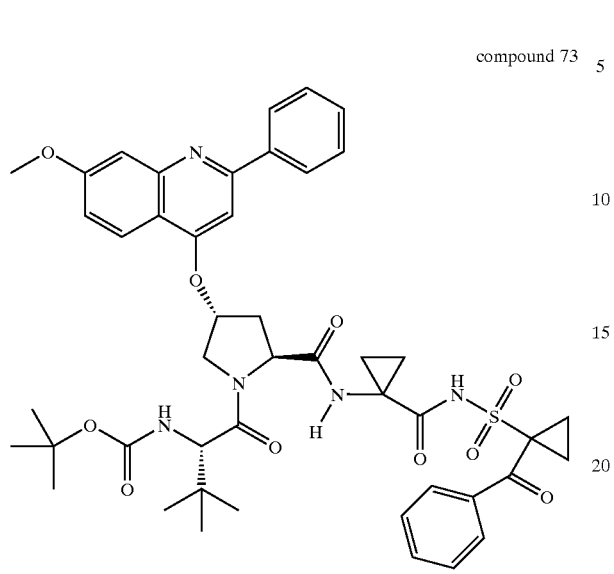

compound 73

Preparation of BOCNH—P3(L-t-BuGly)-P2[(4R)-(2-phenyl-7-methoxyquinoline-4-oxo)-S-proline]-P1 (cyclopropane)-CONHSO₂(1-benzoyl-cyclopropan-1-yl) or Alternative Destination Compound 73, Example 73, ({1-[2-[1-(1-Benzoyl-cyclopropanesulfonylaminocarbonyl)-cyclopropylcarbamoyl]-4-(7-methoxy-2-phenyl-quinolin-4-yloxy)-pyrrolidine-1-carbonyl]-2,2-dimethyl-propyl}-carbamic acid tert-butyl ester

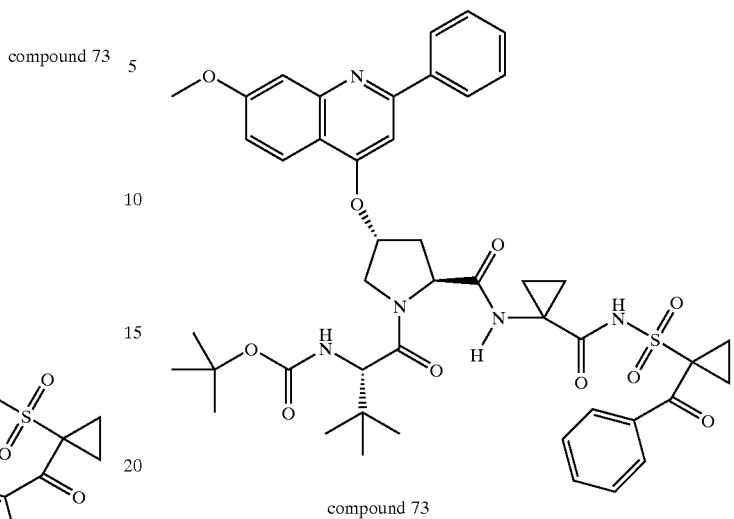

compound 73

Step 73) Compound 73 was prepared in 68% yield (0.071 g) from the cyclopropyl-P2 tripeptide acid (0.080 g, 0.12 mmol) of the product of Step 71e (Example 71) in analogous fashion to the procedure of Step 71f (Example 71) in the synthesis of compound 71 except that 1-benzoylcyclopropanesulfonamide (prepared in step 81d) was used in place of 1-trimethylsilanylcyclopropanesulfonamide: $^{1}$H NMR (methanol-$d_4$) ☐ ppm 1.00 (m, 2H), 1.04 (s, 9H), 1.32 (s, 9H), 1.34 (m, 3H), 1.71 (m, 3H), 2.53 (m, 1H), 2.71 (m, 1H), 3.95 (s, 3H), 3.99 (dd, J=11.60, 2.44 Hz, 1H), 4.27 (m, 1H), 4.52 (d, J=11.90 Hz, 1H), 4.58 (t, J=8.70 Hz, 1H), 5.46 (s, 1H), 7.07 (dd, J=9.16, 2.14 Hz, 1H), 7.24 (s, 1H), 7.38 (m, 2H), 7.51 (m, 5H), 8.09 (m, 5H). LC-MS (retention time: 1.66, Method I), MS m/z 868 (M⁺+1).

Compound 74 Example 74 compound 74

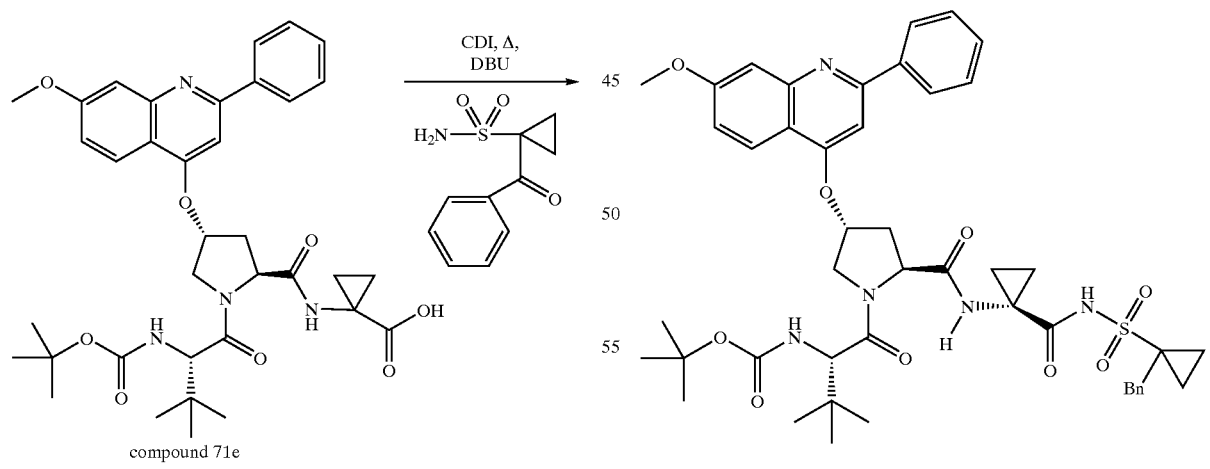

compound 71e

177

Preparation of BOCNH—P3(L-t-BuGly)-P2[(4R)-(2-phenyl-7-methoxyquinoline-4-oxo)-S-proline]-P1 (cyclopropane)-CONHSO₂(1-benzyl-cyclopropan-1-yl) or alternative destination Compound 74, Example 74, {1-[2-[1-(1-Benzyl-cyclopropanesulfonylaminocarbonyl)-cyclopropylcarbamoyl]-4-(7-methoxy-2-phenyl-quinolin-4-yloxy)-pyrrolidine-1-carbonyl]-2,2-dimethyl-propyl}-carbamic acid tert-butyl ester

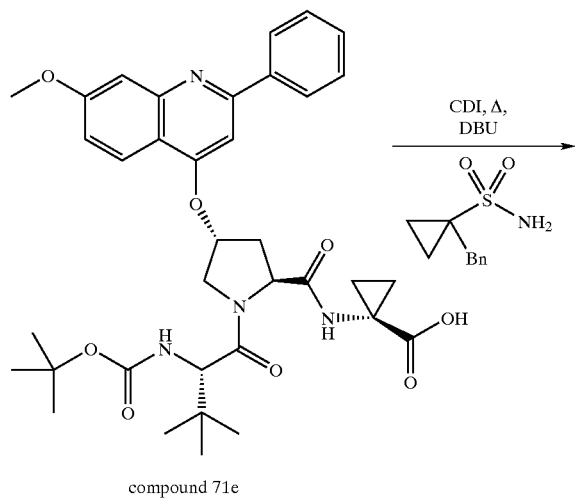

compound 71e

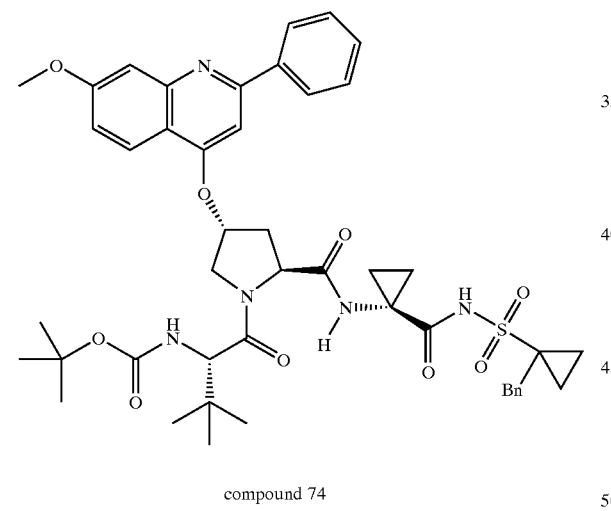

compound 74

Step 74) Compound 74 was prepared in 29% yield (0.0298 g) from the cyclopropyl-P2 tripeptide acid (0.080 g, 0.12 mmol) of the product of Step 71e (Example 71) in analogous fashion to the procedure of Step 71f (Example 71) in the synthesis of compound 71 except that 1-benzylcyclopropanesulfonamide (prepared in step 71d) was used in place of 1-trimethylsilanylcyclopropanesulfonamide: ¹H NMR (CDCl₃) ☐ ppm 0.95 (s, 9H), 1.32 (s, 9H), 1.57 (m, 6H), 2.39 (m, 2H), 2.55 (m, 1H), 2.85 (m, 1H), 3.37 (m, 2H), 3.89

178

(s, 3H), 4.03 (m, 2H), 4.22 (d, J=9.46 Hz, 1H), 4.45 (m, 1H), 5.32 (s, 1H), 6.93 (s, 1H), 6.98 (dd, J=8.85, 1.83 Hz, 1H), 7.36 (s, 1H), 7.43 (m, 5H), 7.85 (m, 1H), 7.93 (m, 4H), 8.10 (s, 1H). HRMS m/z (M+H)⁺ calcd for $C_{46}H_{56}N_5SO_9$: 854.3799 found: 854.3813. LC-MS (retention time: 1.35, Method H), MS m/z 854 (M⁺+1).

Compound 75 Example 75

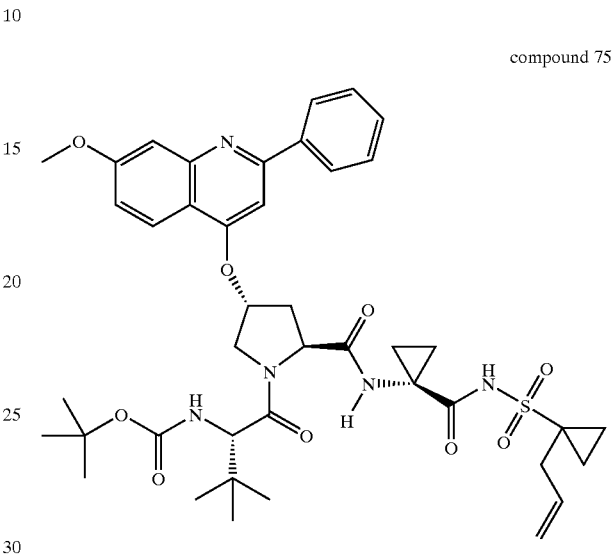

compound 75

Preparation of BOCNH—P3(L-t-BuGly)-P2[(4R)-(2-phenyl-7-methoxyquinoline-4-oxo)-S-proline]-P1 (cyclopropane)-CONHSO₂(1-allyl-cyclopropan-1-yl) or alternative destination Compound 75, Example 75, {1-[2-[1-(1-Allyl-cyclopropanesulfonylaminocarbonyl)-cyclopropylcarbamoyl]-4-(7-methoxy-2-phenyl-quinolin-4-yloxy)-pyrrolidine-1-carbonyl]-2,2-dimethyl-propyl}-carbamic acid tert-butyl ester

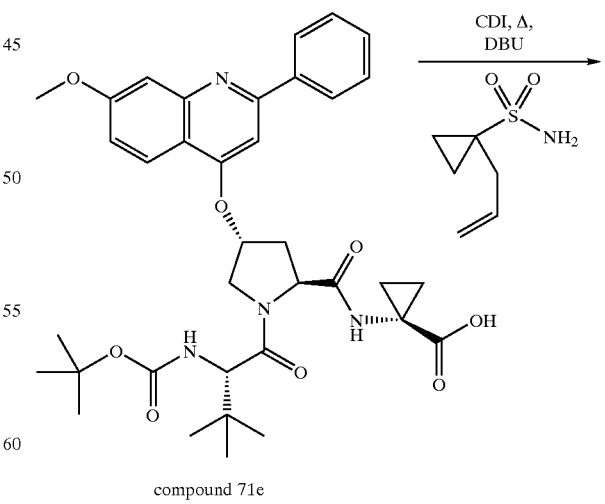

compound 71e

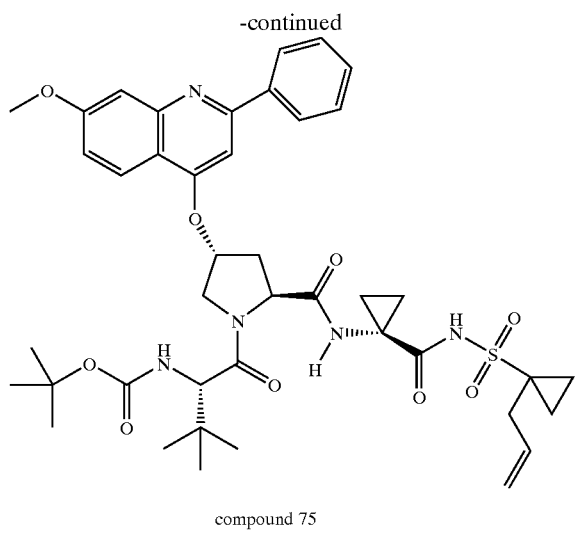

compound 75

Step 75) Compound 75 was prepared in 40% yield (0.039 g) from the cyclopropyl-P1 tripeptide acid (0.080 g, 0.12 mmol) of the product of Step 71e (Example 71) in analogous fashion to the procedure of Step 71f (Example 71) in the synthesis of compound 71 except that 1-allylcyclopropanesulfonamide (prepared in Example 4) was used in place of 1-trimethylsilanylcyclopropanesulfonamide: $^1$H NMR (CDCl$_3$) □ ppm 0.91 (m, 2H), 0.99 (s, 9H), 1.31 (s, 9H), 1.34 (m, 7H), 2.48 (s, 1H), 2.59 (m, 2H), 3.91 (s, 3H), 4.01 (m, 1H), 4.24 (s, 1H), 4.44 (d, J=11.48 Hz, 1H), 4.59 (s, 1H), 4.92 (m, 2H), 5.34 (s, 1H), 5.61 (m, 1H), 7.01 (m, 2H), 7.36 (s, 1H), 7.45 (m, 3H), 7.94 (d, J=7.02 Hz, 2H), 7.98 (d, J=8.85 Hz, 1H), LC-MS (retention time: 1.63, Method I), MS m/z 804 (M$^+$+1).

Compound 76 Example 76 compound 76

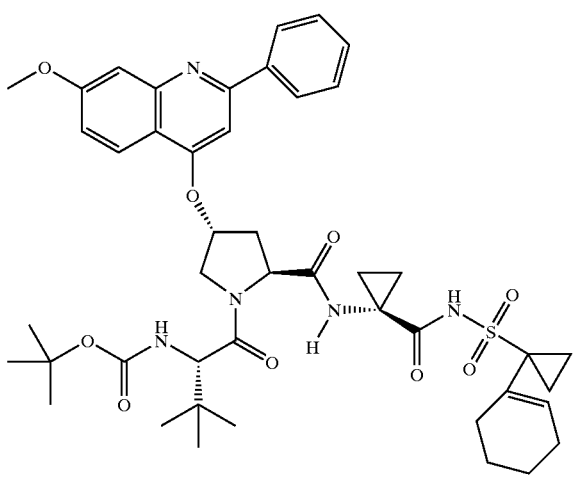

Preparation of BOCNH—P3(L-t-BuGly)-P2[(4R)-(2-phenyl-7-methoxyquinoline-4-oxo)-S-proline]-P1 (cyclopropane)-CONHSO$_2$[1-(1-cyclohexenyl)-cyclopropan-1-yl] or alternative destination Compound 76, Example 76, {1-[2-[1-(1-Cyclohex-1-enyl-cyclopropanesulfonylaminocarbonyl)-cyclopropylcarbamoyl]-4-(7-methoxy-2-phenyl-quinolin-4-yloxy)-pyrrolidine-1-carbonyl]-2,2-dimethyl-propyl}-carbamic acid tert-butyl ester

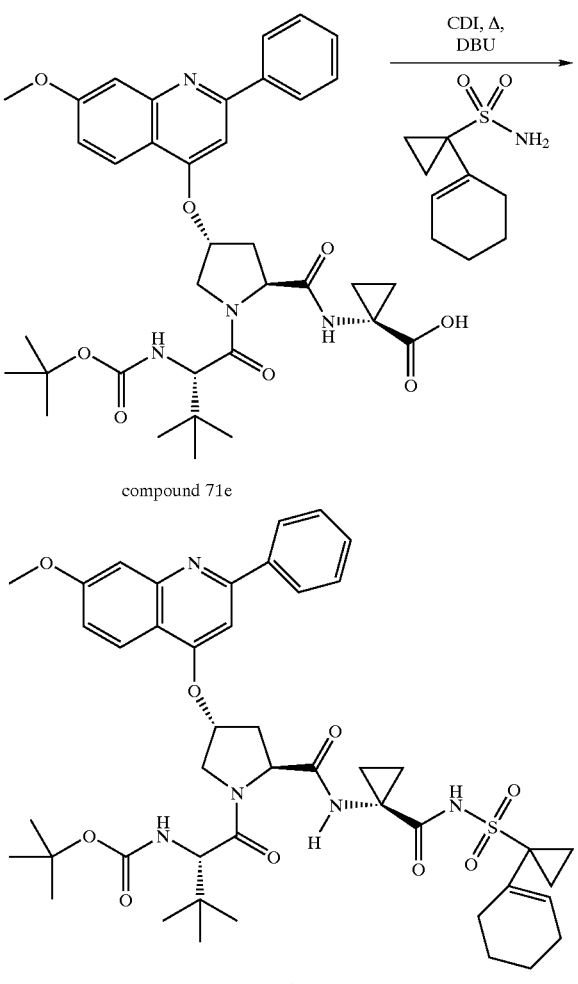

Step 76) Compound 76 was prepared in 36% yield (0.0368 g) from the cyclopropyl-P1 tripeptide acid (0.080 g, 0.12 mmol) of the product of Step 71e (Example 71) in analogous fashion to the procedure of Step 71f (Example 71) in the synthesis of compound 71 except that 1-(1-cyclohexenyl)-cyclopropanesulfonamide (prepared in Example 5) was used in place of 1-trimethylsilanylcyclopropanesulfonamide: $^1$H NMR (CDCl$_3$) □ ppm 0.92 (m, 2H), 0.99 (s, 9H), 1.00 (m, 2H), 1.32 (s, 9H), 1.46 (m, 8H), 1.96 (s, 2H), 2.13 (s, 2H), 2.43 (m, 1H), 2.59 (m, 1H), 3.91 (s, 3H), 4.01 (m, 1H), 4.26 (d, J=9.16 Hz, 1H), 4.45 (d, J=11.60 Hz, 1H), 4.55 (s, 1H), 5.36 (s, 1H), 5.85 (s, 1H), 7.03 (m, 2H), 7.36 (m, 1H), 7.45 (m, 3H), 7.94 (d, J=7.02 Hz, 2H), 7.98 (d, J=9.16 Hz, 1 H). HRMS m/z (M+H)+calcd for C$_{45}$H$_{57}$N$_5$SO$_9$: 844.3955 found: 844.3978. LC-MS (retention time: 1.66, Method F), MS m/z 844 (M$^+$+1).

Compound 77 Example 77 compound 77

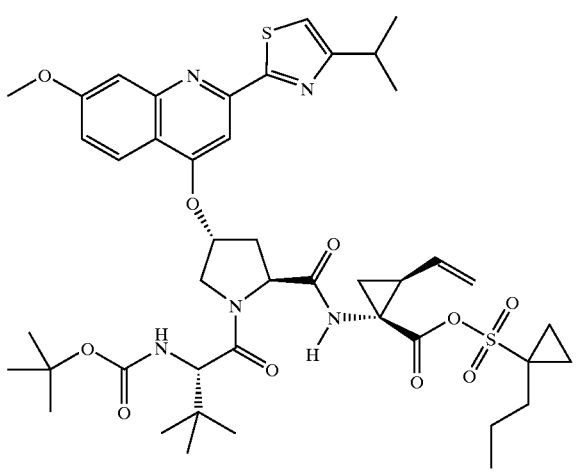

Preparation 4-[2-(4-Isopropyl-thiazol-2-yl)-7-methoxy-quinolin-4-yloxy]-pyrrolidine-1,2-dicarboxylic acid 1-tert-butyl ester Schem 1

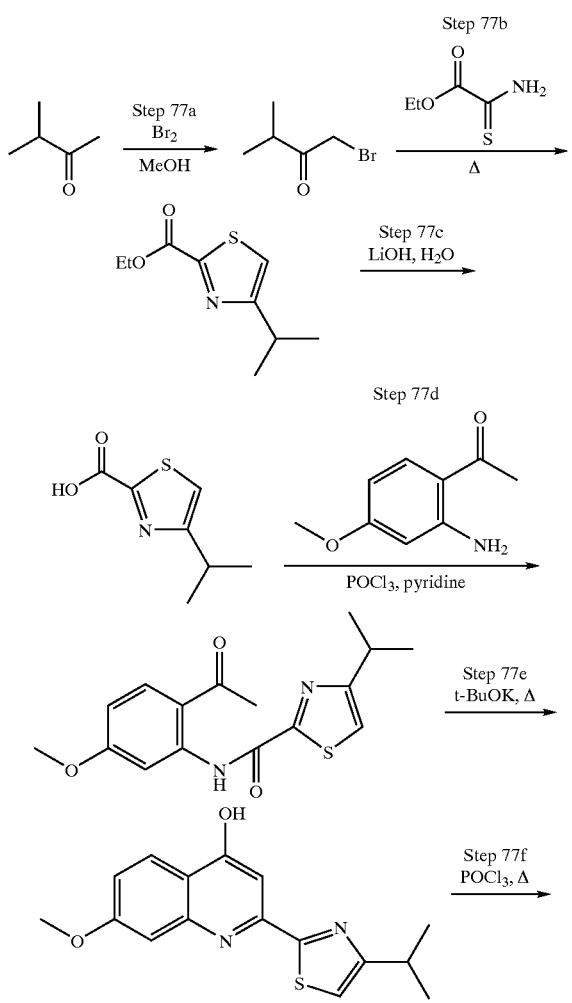

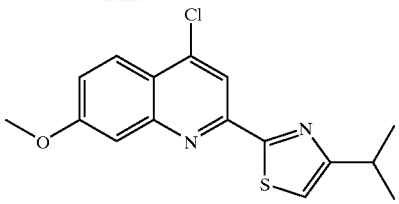

Step 77a: Preparation of 1-bromo-3-methyl-2-butanone

To a solution of 4.0 g (46.5 mmol) of 3-methyl-2-butanone (Aldrich) in 50 mL of MeOH was added dropwise a solution of 2.4 mL (46.5 mmol) of bromine over 40 min. The mixture was stirred 1.5 h, diluted with 300 mL of pentane, washed with sat. aqueous $NaHCO_3$, dried ($MgSO_4$) and concentrated to afford 5.81 g of impure 1-Bromo-3-methyl-butan-2-one which was taken directly into the step B.

Step 77b: Preparation of 4-Isopropyl-thiazole-2-carboxylic acid ethyl ester

A neat solution of 5.58 g (34 mmol) of 1-Bromo-3-methyl-butan-2-one and 4.50 g (34 mmol) of ethyl thioxamate (Aldrich) was heated at 70° C. over 18 h and then cooled to room temperature. The mixture was partitioned between sat. aqueous $NaHCO_3$ and EtOAc, the EtOAc layer dried ($MgSO_4$), concentrated and chromatographed over $SiO_2$ (eluted with 2% to 40% EtOAc/hexanes) to afford 3.4 g (48% overall) of 4-isopropylthiazole-2-carboxylic acid ethyl ester as an oil: $^1$H NMR (500 MHz, CDCl3) δ ppm 1.32 (d, J=7 Hz, 6H), 1.42 (t, J=7.2 Hz, 3H), 3.23 (m, 1H), 4.46 (q, J=7.2 Hz, 2H), 7.18 (s, 1H).

Step 77c: 4-Isopropyl-thiazole-2-carboxylic acid

To a solution of 3.12 g (15.7 mmol) of 4-isopropylthiazole-2-carboxylic acid ethyl ester in 32 mL of 75% THF/MeOH, was added 110 mg (31.3 mmol) of LiOH in 8 mL of $H_2O$. The mixture was stirred overnite, the solution adjusted to pH 5 using 1N aqueous HCl solution and concentrated in vacuo to afford 4-isopropylthiazole-2-carboxylic acid as a white solid (2.97 g including salts) which was used directly in Step E: $^1$H NMR (500 methanol-$d_4$) δ ppm 1.29 (d, J=6.7 Hz, 6H), 3.20 (m, 1H), 7.39 (m, 1H).

Step 77d: 4-Isopropyl-thiazole-2-carboxylic acid (2-acetyl-5-methoxy-phenyl)-amide To a suspension of 2.59 g (15.7 mmol) of 2-amino-4-methoxybenzophenone (product of step D) and 2.68 g (15.7 mmol) of 4-isopropylthiazole-2-carboxylic acid (product of step 77c) in 75 mL of pyridine cooled to −30° C., was added 1.93 mL (23.5 mmol) of $POCl_3$ slowly dropwise over 5 min. The mixture was stirred 3 h, warmed to room temperature and was stirred overnite. The reaction mixture was poured into ice water, and extracted several times with EtOAc. The combined EtOAc extracts were dried ($MgSO_4$), concentrated and chromatographed over $SiO_2$ (eluted with 0% to 15% MeOH/EtOAc) to afford 2.57 g (51%) of 4-Methylthiazole-2-carboxylic acid (2-acetyl-5-methoxyphenyl)amide as a yellow solid: 1H NMR (CDCl$_3$) δ ppm 1.41 (d, J=6.7 Hz, 6H), 2.64 (s, 3H), 3.24 (m, 1H), 3.91 (s, 3H), 6.67 (dd, J=9, 2.5 Hz, 1H), 7.18 (s, 1H), 7.86 (d, J=9 Hz, 1H), 8.56 (d, J=2.5 Hz, 1H), 13.48 (s, 1H).

Step 77e: 2-(4-Isopropyl-thiazol-2-yl)-7-methoxy-quinolin-4-ol

Step 77e) To a solution of 2.5 g (7.85 mmol) of 4-methylthiazole-2-carboxylic acid (2-acetyl-5-methoxyphenyl)amide (product of step E) in 50 mL of THF, was added 19 mL (19 mmol) of 1M KOtBu in THF. The mixture was heated to 70° C. for 3 h, cooled to rt and stirred overnight. The mixture was concentrated, cold water added to form a suspension. The mixture was then acidified to pH 4, filtered and dried. The resulting solid was chromatographed over $SiO_2$ (eluted with 0% to 25% MeOH in $CH_2Cl_2$) to afford 1.31 g (56%) of 2-(4-Isopropylthiazol-2-yl)-7-methoxyquinolin-4-ol as a beige solid: $^1H$ NMR (DMSO-$D_6$) δ ppm 1.32 (d, J=6.6 Hz, 6H), 3.14 (m, 1H), 3.89 (s, 3H), 7.06 (s, 1H), 7.38 (s, 1H), 7.51 (s, 1H), 7.99 (d, J=9.2 Hz, 1H), 11.77 (m, 1H). LC-MS m/e 301 (retention time: 1.53, method A).

Step 77f: 4-Chloro-2-(4-isopropyl-thiazol-2-yl)-7-methoxy-quinoline

A suspension of 1.3 g (4.3 mmol) of 2-(4-Isopropylthiazol-2-yl)-7-methoxyquinolin-4-ol, product of step F, in 60 mL of $POCl_3$ was heated to reflux for 2 h. The solvent was removed in vacuo, the residue diluted with ice cold water and the mixture adjusted to pH 9 while cooling to 0° C. This aqueous solution was extracted several times with EtOAc. The combined EtOAc extracts were washed once with brine, pH 4 buffer, dried ($MgSO_4$), and concentrated to afford 0.89 g (64%) of 4-Chloro-2-(4-isopropylthiazol-2-yl)-7-methoxyquinoline as a yellow solid: $^1H$ NMR (500 MHz, $CDCl_3$) δ ppm 1.38 (d, J=7 Hz, 6H), 3.19 (m, 1H), 3.98 (s, 3H), 7.06 (s, 1H), 7.26 (m, 1H), 7.47 (d, J=2 Hz, 1H), 8.10 (d, J=9 Hz, 1H), 8.31 (s, 1H). LC-MS m/e 319 (retention time: 2.20, method A).

Step 77g: 4-[2-(4-Isopropyl-thiazol-2-yl)-7-methoxy-quinolin-4-yloxy]-proline To a DMSO solution (10 mL) of (2S, 4R)-N—Boc-L-4-hydroxyproline (0.53 g, 2.3 mmol) was added t-BuOK (0.64 g, 5.7 mmol) portionwise. The generated mixture was stirred for 1.5 h then 4-Chloro-2-(4-isopropyl-thiazol-2-yl)-7-methoxy-quinoline (0.80 g, 2.5 mmol) from Step 77f (Example 77) was added. The reaction mixture was stirred for 1.5 day. The reaction mixture diluted with cold water and extracted with EtOAc/Ether (1/4, 2×). The aqueous layer was acidified with 1.0 N aqueous HCl to pH 4, filtered. The solid was dried in dry box to provide the product in 70% yield (0.82 g) as a pale yellow solid: LC-MS (retention time: 1.46, Method I), MS m/z 514 ($M^+$+1).

Step 77h: Preparation 4-[2-(4-Isopropyl-thiazol-2-yl)-7-methoxy-quinolin-4-yloxy]-2-[1-(1-propyl-cyclopropanesulfonylaminocarbonyl)-2-vinyl-cyclopropylcarbamoyl]-pyrrolidine-1-carboxylic acid tert-butyl ester Step 77h) A slurry of Compound 77g (Example 77) (0.200 g, 0.39 mmol), diisopropylethylamine (0.27 mL, 1.95 mmol), HCl salt of 1-propyl-cyclopropanesulfonic acid [(1R, 2S)1-amino-2-vinyl-cyclopropanecarbonyl]-amide (0.144 g, 0.47 mmol), HATU (0.192 g, 0.51 mmol), and HOBT (0.063 g, 0.39 mmol) in $CH_2Cl_2$ was stirred overnite and removed the solvent the residue was purified by preparative HPLC (solvent B: 30 to 100) to afford the product as a light yellow solid: $^1H$ NMR (methanol-$d_4$) □ ppm 0.96 (m, 5H), 1.42 (m, 6H), 1.49 (s, 9H), 1.47 (m, 5H), 1.80 (m, 1H), 1.88 (m, 2H), 2.27 (q, J=8.75 Hz, 1H), 2.42 (m, 1H), 2.66 (dd, J=14.04, 6.71 Hz, 1H), 3.22 (m, 1H), 3.96 (dd, J=14.34, 6.41 Hz, 5H), 4.44 (dd, J=9.92, 6.87 Hz, 1H), 5.14 (d, J=11.60 Hz, 1H), 5.34 (m, 1H), 5.50 (s, 1H), 5.78 (m,

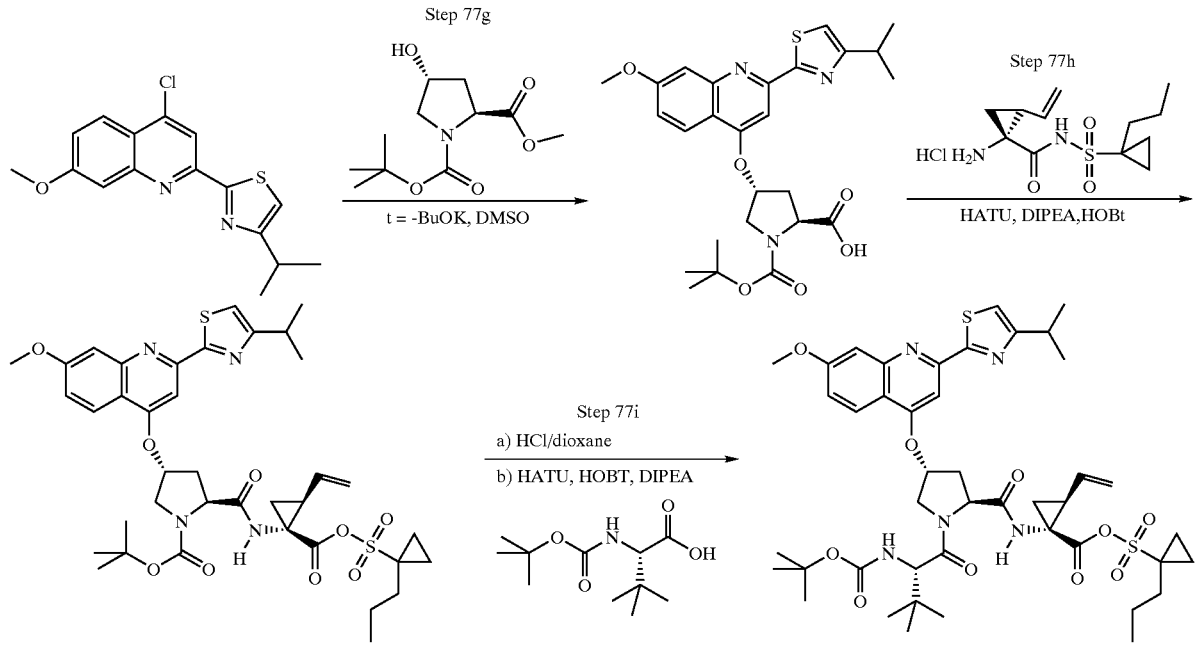

Scheme 2 compound 77h compound 77

1H), 7.20 (dd, J=9.16, 2.14 Hz, 1H), 7.36 (s, 1H), 7.41 (d, J=2.44 Hz, 1H), 7.65 (s, 1H), 8.03 (d, J=9.16 Hz, 1H).

Step 77i: Preparation of {1-[2-[1-(1-Cyclopropylmethyl-cyclopropanesulfonylaminocarbonyl)-2-vinyl-cyclopropylcarbamoyl]-4-(7-methoxy-2-phenyl-quinolin-4-yloxy)-pyrrolidine-1-carbonyl]-2-methyl-propyl}-carbamic acid tert-butyl ester Step 77i) A slurry of the compound 77 h (0.287 g, 0.3 7 mmol) in 2 mL (8 mL) of 4M HCl/dioxane solution was stirred at for 2 h. The solvent was removed in vacuo and to the residue was added CH₂Cl₂ (10 mL), diisopropylethylamine (0.26 mL), Boc-L-tert-leucine (0.104 g, 0.45 mmol), HOBt (0.061 g, 0.37 mmol), and HATU (0.185 g, 0.49 mmol). The reaction mixture was stirred overnite. Removed the solvent in vacuo and purified the residue by preparative HPLC (solvent B: 30% to 100%) to afford the product (Compund 77) as a light yellow foam: $^1$H NMR (methanol-d$_4$) □ ppm 0.85 (m, 5H), 1.04 (s, 9H), 1.31 (m, 9H), 1.33 (m, 5H), 1.38 (d, J=6.95 Hz, 6H), 1.80 (m, 3H), 2.08 (m, 1H), 2.50 (m, 1H), 2.72 (dd, J=13.54, 7.32 Hz, 1H), 3.18 (m, 1H), 3.91 (s, 3H), 4.13 (m, 1H), 4.24 (s, 1H), 4.54 (m, 2H), 5.01 (d, J=10.61 Hz, 1H), 5.19 (d, J=16.47 Hz, 1H), 5.48 (s, 1H), 5.93 (s, 1H), 7.04 (dd, J=9.15, 1.83 Hz, 1H), 7.27 (s, 1H), 7.32 (m, 1H), 7.63 (s, 1H), 8.04 (d, J=9.15 Hz, 1H).

Compound 78 Example 78

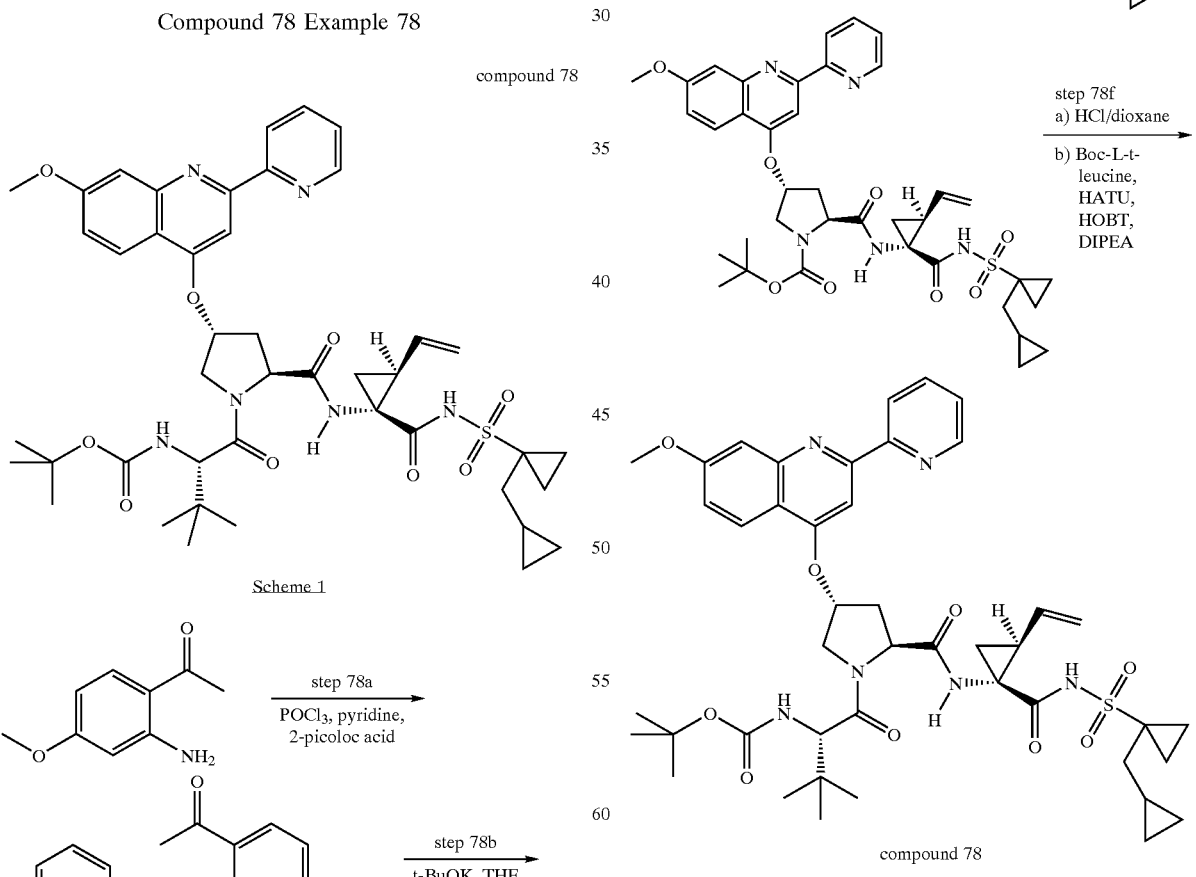

Scheme 1

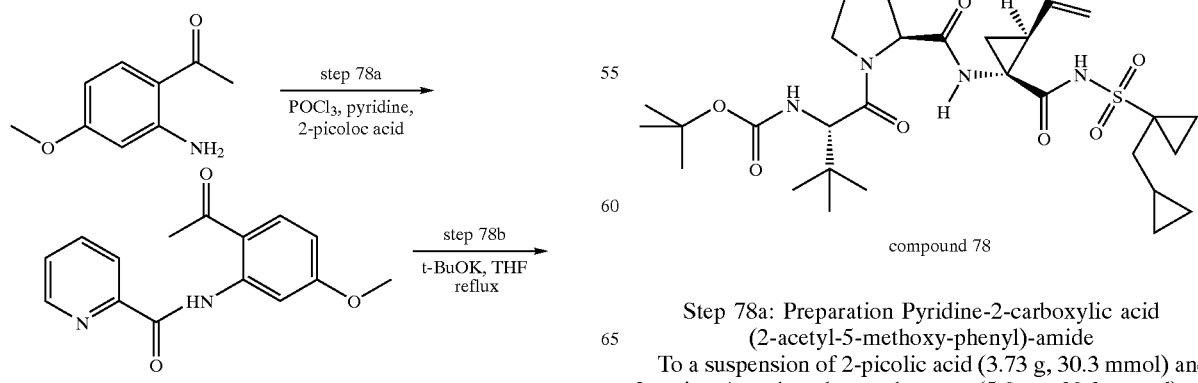

Step 78a: Preparation Pyridine-2-carboxylic acid (2-acetyl-5-methoxy-phenyl)-amide To a suspension of 2-picolic acid (3.73 g, 30.3 mmol) and 2-amino-4-methoxybenzophenone (5.0 g, 30.3 mmol) at −30° C. dissolved in pyridine (150 mL) was added POCl₃ (3.7 mL, 45.4 mmol) in 5 min. the reaction mixture was stirred for 3 hr at the temperature, and stirred at rt overnite. The reaction mixture was poured into cold water and extracted with EtOAc (3×). The combined extract was dried to provide the product (7.67 g, 93%): ¹H NMR (methanol-d₄) δ ppm 2.65 (s, 3H), 3.92 (s, 3H), 6.78 (m, 1H), 7.60 (m, 1H), 8.00 (m, 1H), 8.06 (m, 1H), 8.21 (d, J=7.63 Hz, 1H), 8.59 (t, J=2.29 Hz, 1H), 8.76 (d, J=3.97 Hz, 1H). LC-MS (retention time: 1.56, Method D), MS m/z 271 (M⁺+1).

Step 78b: 7-Methoxy-2-pyridin-2-yl-quinolin-4-ol

To a suspension suspension of Pyridine-2-carboxylic acid (2-acetyl-5-methoxy-phenyl)-amide (2.90 g, 10.7 mmol) in THF (50 mL) was added t-BuOK/THF (1M, 24 mL, 24 mmol). The reaction mixture was heated at 70° C. for 3 h and stirred overnite. The solvent was removed the in vacuo. Cold water was added to the residue and adjusted pH to 4.6 with aqueous 1.0 N HCl, filtered. The solid residue was purified over a Biotage 65M column (MeOH/CH₂Cl₂: 0 to 15%) to provide the product (2.26 g, 84%): LC-MS (retention time: 1.19, Method D), MS m/z 253 (M⁺+1).

Step 78c: 4-Chloro-7-methoxy-2-pyridin-2-yl-quinoline

A mixture of 7-Methoxy-2-pyridin-2-yl-quinolin-4-ol (2.2 g, 8.71 mmol) in POCl₃ (92 mL) was refluxed for 3 h and then removed the solvent in vacuo. Ice water was added to the residue, adjusted the pH>10 with 1.0 N NaOH, and extrated with EtOAc (2×). The combined extract was washed with water, brine, dried (MgSO₄), removed solvent to supply the product as a yellow solid (89%, 2.1 g): DMSO-D6) δ ppm 3.97 (s, 3H), 7.40 (dd, J=9.16, 2.44 Hz, 1H), 7.53 (m, 1H), 8.01 (m, 1H), 8.09 (d, J=9.16 Hz, 1H), 8.46 (s, 1H), 8.56 (d, J=7.93 Hz, 1H), 8.74 (d, J=3.97 Hz, 1H). LC-MS (retention time: 1.50, Method D), MS m/z 271 (M⁺+1).

Step 78d: Preparation of 4-(7-Methoxy-2-pyridin-2-yl-quinolin-4-yloxy)-pyrrolidine-1,2-dicarboxylic acid 1-tert-butyl ester To a solution of N—Boc-4-hydroxyproline (1.6 g, 6.7 mmol) in DMSO (20 mL) was added t-BuOK (1.9 g, 16.8 mmol). The generated mixture was stirred for 1.5 h and 4-Chloro-7-methoxy-2-pyridin-2-yl-quinoline (2.0 g, 7.4 mmol) and DMSO (10 mL) were added. The reaction mixture was stirred for 38 h, diluted with cold water and extracted with EtOAc/ether (1/4, 2×). the aqueous layer was acidified to pH 4 and extracted with EtOAc/THF (5×). the combined extract was dried (Na₂SO₄/MgSO₄), removed the solvent in vacuo and the residue was purified by preparative HPLC (0–80% solvent B) to provide the product (1.6 g, 50%): LC-MS (retention time: 1.23, Method I), MS m/z 466 (M⁺+1).

Step 78e: Preparation 2-[1-(1-Cyclopropylmethyl-cyclopropanesulfonylaminocarbonyl)-2-vinyl-cyclopropylcarbamoyl]-4-(7-methoxy-2-pyridin-2-yl-quinolin-4-yloxy)-pyrrolidine-1-carboxylic acid tert-butyl ester Step 78e) To a mixture of the acid (0.33 g, 0.71 mmol) of the product of Step 78d (Example 78), diisopropylethylamine (0.5 mL, 3.6 mmol), TFA salt (0.205 g, 0.51 mmol) of 1-Cyclopropylmethyl-cyclopropanesulfonic acid (1-amino-2-vinyl-cyclopropanecarbonyl)-amide, and HOBt (0.1 g, 0.6 mmol) in CH₂Cl₂ (8 mL) was added HATU (0.35 g, 0.92 mmol). The reaction mixture was stirred at rt overnite and diluted with EtOAc, washed with pH 4.0 buffer, dried (MgSO₄), removed the solvent in vacuo. The residue was purified by PTLC to provide the product in 59% (0.22 g) yield: ¹H NMR (methanol-d₄) □ ppm 0.64 (m, 1H), 0.96 (m, 2H), 1.33 (m, 8H), 1.39 (m, 9H), 1.90 (m, 2H), 2.18 (m, 1H), 2.54 (m, 1H), 2.81 (m, 1H), 4.01 (m, 5H), 4.44 (d, J=28.99 Hz, 1H), 5.08 (m, 1H), 5.31 (m, 1H), 5.57 (s, 1H), 6.03 (m, 1H), 6.94 (s, t H), 7.27 (d, J=8.24 Hz, 1H), 7.64 (m, 1H), 7.92 (m, 1H), 8.14 (m, 2H), 8.66 (s, 1H), 8.74 (s, 1H).

Step 78f: Preparation {1-[2-[1-(1-Cyclopropylmethyl-cyclopropanesulfonylaminocarbonyl)-2-vinyl-cyclopropylcarbamoyl]-4-(7-methoxy-2-pyridin-2-yl-quinolin-4-yloxy)-pyrrolidine-1-carbonyl]-2,2-dimethyl-propyl}-carbamic acid tert-butyl ester Step) A slurry of the compound 78e (0.220 g, 0.3 mmol) of the product of Step 78e (Example 78) in 4M HCL/dioxane (2 mL, 8 mmol) was stirred at for 2 h, removed the solvent in vacuo. To the residue was added CH₂Cl₂ (2 mL), diisopropylethylamine (0.2 mL), Boc-L-tert-leucine (0.083 g, 0.36 mmol), HOBt (0.046 g, 0.3 mmol), and HATU (0.172 g, 0.45 mmol). The reaction mixture was stirred at rt overnite and diluted with EtOAc, washed with pH 4.0 buffer, dried (MgSO₄), removed the solvent in vacuo.purification from preparative HPLC (solvent B: 30% to 100%) to afford the product in 76% (0.192 g) yield of compound 64 as a yellow foam: ¹H NMR (methanol-d₄) □ ppm 0.05 (m, 1H), 0.30 (m, 1H), 0.66 (m, 1H), 0.91 (m, 2H), 1.05 (s, 9H), 1.28 (s, 9H), 1.67 (m, 8H), 2.15 (m, 1H), 2.58 (m, 1H), 2.77 (m, 1H), 3.96 (s, 3H), 4.19 (d, J=40.25 Hz, 2H), 4.51 (d, J=16.47 Hz, 2H), 4.95 (m, 1H), 5.15 (m, 1H), 5.53 (s, 1H), 5.89 (dd, J=16.65, 9.33 Hz, 1H), 7.09 (d, J=8.42 Hz, 1H), 7.43 (d, J=1.83 Hz, 1H), 7.50 (m, 1H), 7.82 (s, 1H), 7.99 (m, 1H), 8.10 (d, J=9.15 Hz, 1H), 8.48 (d, J=7.68 Hz, 1H), 8.72 (s, 1H).

Compound 79 Example 79

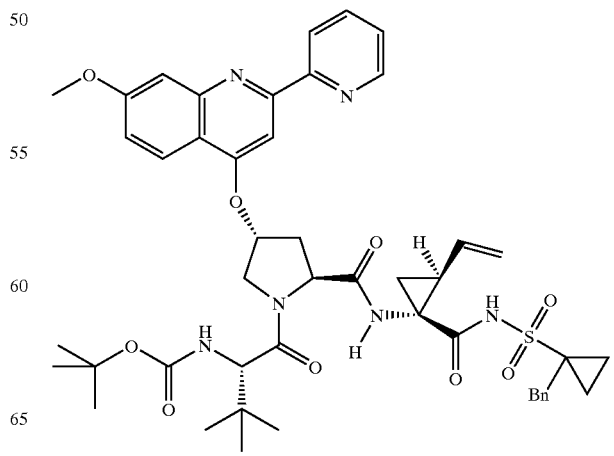

compound 79

-continued
Scheme 1

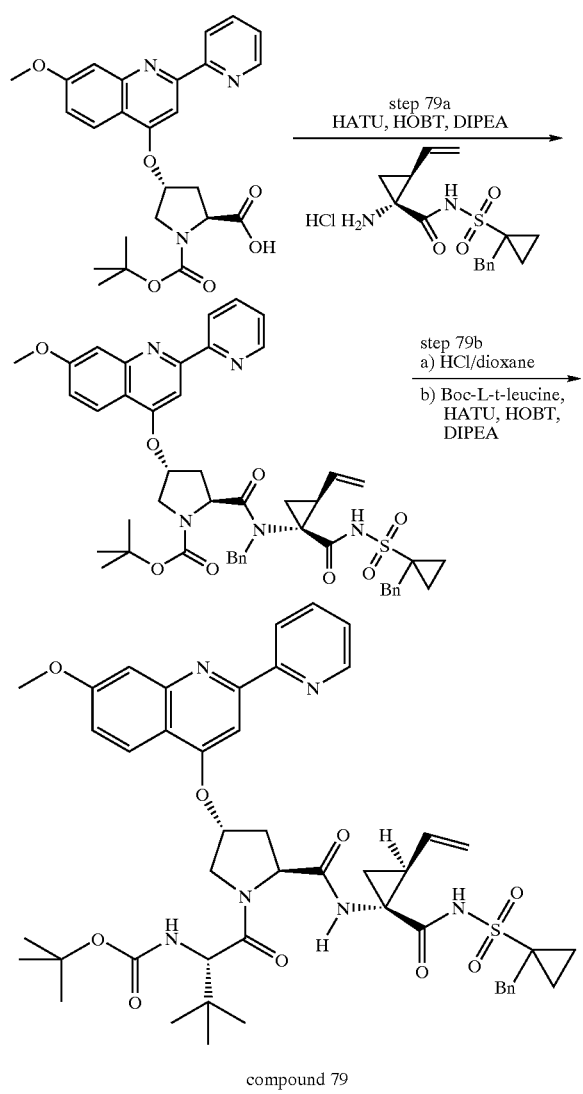

compound 79

Step 79a: Preparation 2-[1-(1-Benzyl-cyclopropanesulfonylaminocarbonyl)-2-vinyl-cyclopropylcarbamoyl]-4-(7-methoxy-2-pyridin-2-yl-quinolin-4-yloxy)-pyrrolidine-1-carboxylic acid tert-butyl ester Step 79a) Compound was prepared in 63% yield (0.207 g) from 0.20 g (0.5 mmol) of the compound 78d of the acid product of step 78d in analogous fashion to the procedure of Step 78e in the synthesis of compound 78e and purified by preparative HPLC (solvent B: 30% to 100% to afford the product:) and over 20×40 cM 1000 □ Analtech PTLC plates (MeOH/CH$_2$Cl$_2$: 0 to 7%) to afford the product in 63% (0.207 g): LC-MS (retention time: 1.75, Method H), MS m/z 768 (M$^+$+1).

Step 79b: Preparation (1-{4-(7-Methoxy-2-pyridin-2-yl-quinolin-4-yloxy)-2-[1-(1-phenethyl-cyclopropanesulfonylaminocarbonyl)-2-vinyl-cyclopropylcarbamoyl]-pyrrolidine-1-carbonyl}-2,2-dimethyl-propyl)-carbamic acid tert-butyl ester Step 79b) Compound was prepared in 14% yield (0.042 g) from 0.263 g (0.34 mmol) of the compound 79a in analogous fashion to the procedure of Example in the synthesis of compound 78 (step 78 f) and purified by preparative HPLC (solvent B: 30% to 100%) and followed by PTLC (MeOH/CH$_2$Cl$_2$; 5%): $^1$H NMR (methanol-d$_4$) □ ppm 1.00 (s, 9H), 1.26 (d, J=19.76 Hz, 9H), 1.29 (m, 5H), 1.85 (s, 1H), 2.15 (m, 1H), 2.52 (s, 1H), 2.75 (m, 1H), 3.32 (m, 2H), 3.94 (s, 3H), 4.11 (m, 1H), 4.24 (s, 1H), 4.55 (m, 2H), 5.05 (m, 1H), 5.24 (d, J=17.57 Hz, 1H), 5.50 (s, 1H), 5.89 (s, 1H), 7.10 (m, 6H), 7.43 (m, 2H), 7.77 (s, 1H), 7.96 (t, J=7.68 Hz, 1H), 8.07 (m, 1H), 8.46 (d, J=7.68 Hz, 1H), 8.66 (s, 1H); LC-MS (retention time: 1.67, Method H), MS m/z 845 (M$^+$+1).

Compound 80 Example 80

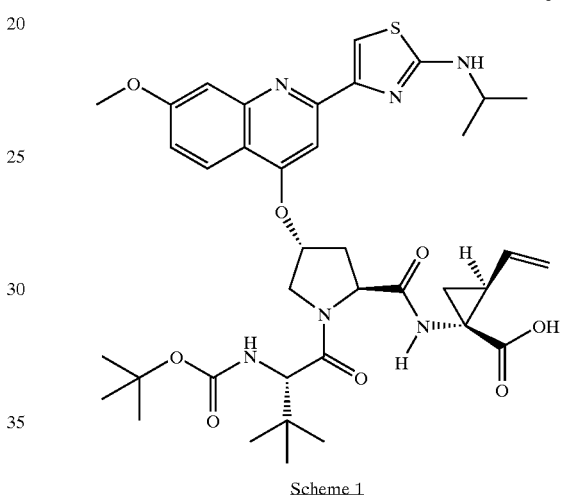

Compound 80

Scheme 1

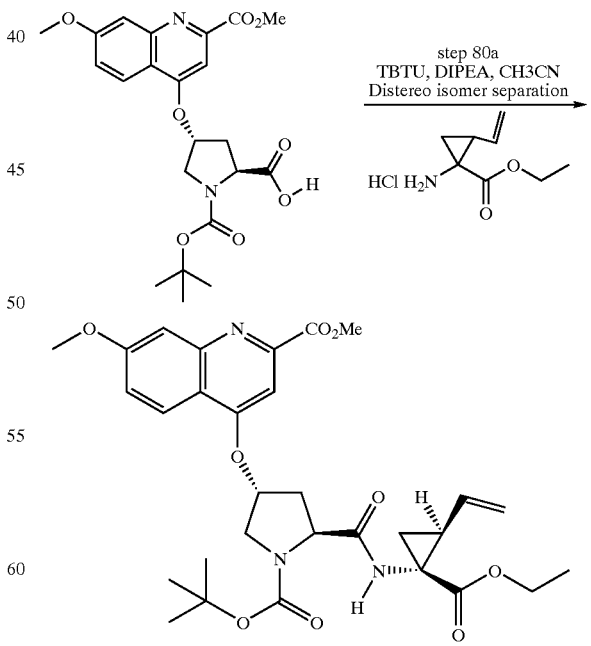

High Rf isomer used in rest of sequence

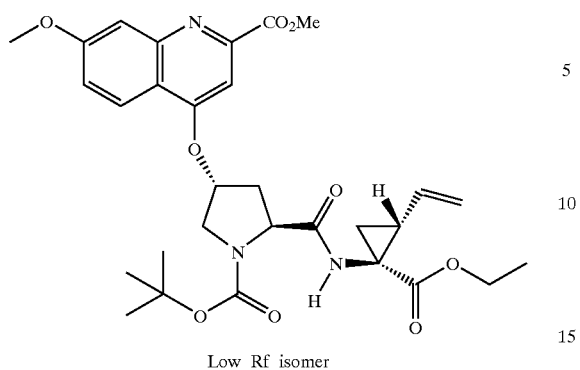

Low Rf isomer

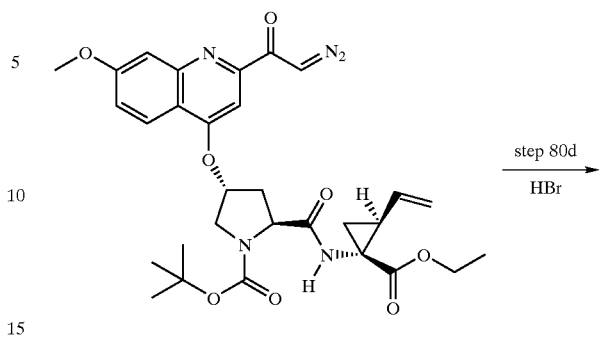

Step 80a

A solution of (1R,2S)/(1S,2R)-1-amino-2-vinylcyclopropane carboxylic acid ethyl ester hydrochloride (2.54 g, 12 mmol) in $CH_3CN$ (70 mL) was treated with a solution of diisopropylethylamine (9.5 mL, 67 mmol), [(4R)-(2-methoxycarbonyl-7-methoxylquinoline-4-oxo)-S-proline] (5.9 g, 13.2 mmol), and TBTU (3.89 g, 12.21 mmol) in $CH_3CN$ (50 mL). The reaction mixture was stirred for 14 h and concentrated. The residue dissolved in EtOAc was repeatedly washed with $NaHCO_3$ (aq.), brine, dried ($MgSO_4$), and concentrated. The residue was purified over Biotage 65M column (EtOAc/hexane: 45 to 100%) to provide the high Rf stereo isomer (Boc-P2[(4R)-(2-methoxycarbonyl-7-methoxylquinoline-4-oxo)-S-proline]-P1 (1R,2S Vinyl Acca) Acid ethyl ester 2.0 g (52%) as a white solid: $^1$H NMR (methanol-$d_4$) δ ppm 1.24 (t, J=7.02 Hz, 3H), 1.38 (m, 11H), 1.76 (m, 1H), 2.21 (m, 1H), 2.45 (m, 1H), 2.71 (m, 1H), 3.92 (m, 2H), 3.96 (s, 3H), 4.03 (s, 3H), 4.16 (q, J=7.2 Hz, 2H), 4.42 (m, 1H), 5.10 (m, 1H), 5.30 (m, 1H), 5.44 (s, 1H), 5.77 (m, 1H), 7.27 (d, J=9.16 Hz, 1H), 7.48 (s, 1H), 7.52 (s, 1H), 8.05 (s, 1H).

Scheme 2

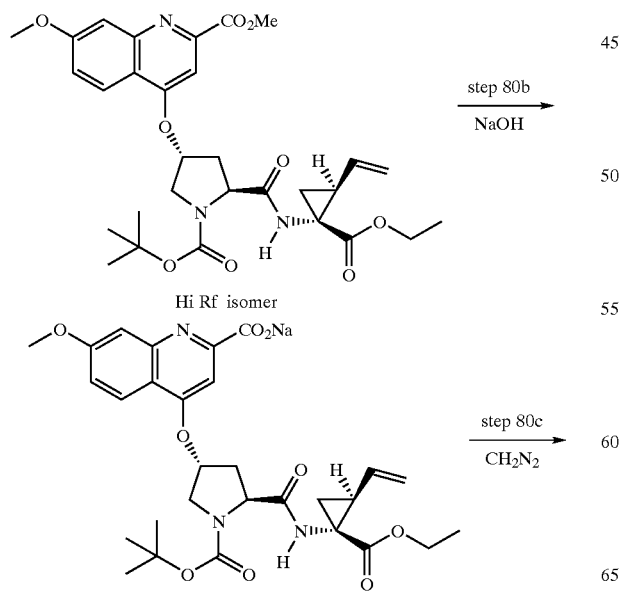

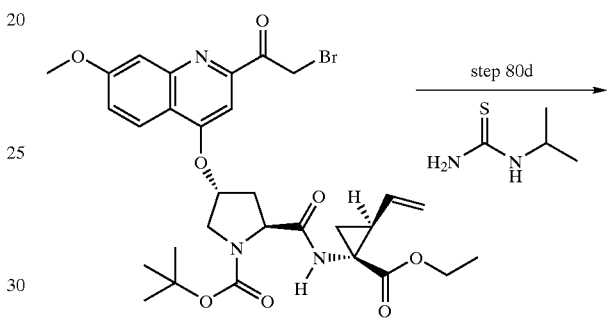

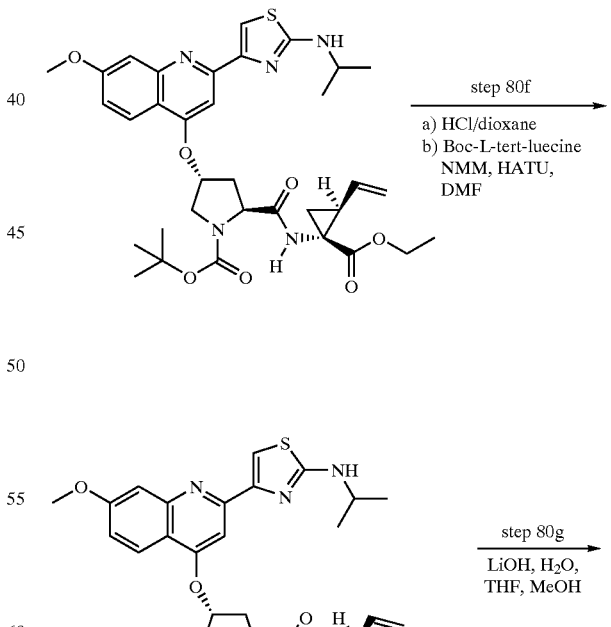

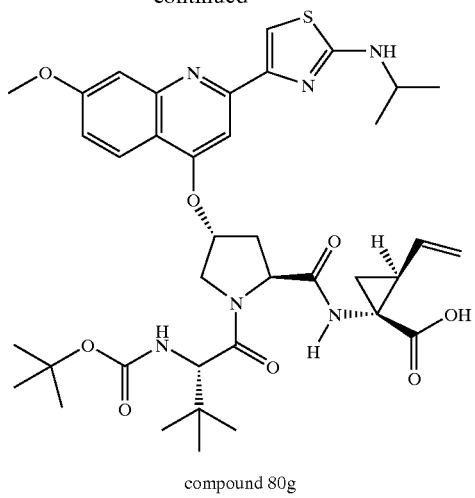

compound 80g

Step 80b

A solution of the high Rf product (3.16 g, 5.40 mmol) of Step 1 of Example 370 {Boc-P2[(4R)-(2-methoxycarbonyl-7-methoxylquinoline-4-oxo)-S-proline]-P1(1R,2S Vinyl Acca) COOEt} at 0° C. dissolved in MeOH/THF (1/1, 13.2 mL) was treated with aqueous 1.0 N NaOH (5.5 mL, 5.5 mmol), stirred for 1 h, neutralized by the addition of AcOH. The solvent was removed in vacuo. The residue was redissolved in THF/CH$_2$Cl$_2$ (1/1, 150 mL), dried (MgSO$_4$) and concentrated in vacuo to provide the product which was directly used in next step: LC-MS (retention time: 1.53 Method D), MS m/z 570 (M$^+$+1).

Step 80c

To a solution of the product (assumed at 5.4 mmol) of step 2 example 370 at 0° C. dissolved in THF (35 mL) was added a solution of fresh made CH$_2$N$_2$ (30 mmol) in Et$_2$O (80 mL). The reaction mixture was stirred at the temperature for 0.5 h, and stirred at rt for 18.5 h. After bubbling nitrogen for 1 h to the reaction mixture, the solution was removed in vacuo. The residue redissolved in EtOAc (1 L) was washed with saturated NaHCO$_3$ (aq.), (2×200 mL), brine (100 mL), and dried (MgSO$_4$). The solvent was removed in vacuo to afford the product 3.10 g (97% two steps): LC-MS (retention time: 3.06, Method J), MS m/z 594 (M$^+$+1).

Step 80d

To a solution of the product (3.03 g, 5.10 mmol) of step 3 of example 370 {Boc-P2[(4R)-(2-diazoacetyl-7-methoxylquinoline-4-oxo)-S-proline]-P1(1R,2S Vinyl Acca) COOEt} at 0° C. dissolved in THF (110 mL) was added 2 mL of 48% HBr. The mixture was stirred for 1 h, partitioned between EtOAc (500 mL) and saturated NaHCO$_3$ (aq.) (100 mL). The EtOAC layer was separated, dried (MgSO$_4$). The solvent was removed to afford the product (3.12 g, 95%): LC-MS (retention time: 1.56 Method D). MS m/z 648 (M$^+$+1), MS m/z 646 (M$^-$−1).

Step 80e

The product (1.0 g, 1.54 mmol) of step 4 of example 370 {Boc-P2[(4R)-(2-bromoacetyl-7-methoxylquinoline-4-oxo)-S-proline]-P1 (1R,2S Vinyl Acca) COOEt} was treated with isopropylthiourea (0.365 g, 3.09 mmol) in isopropyl alcohol (57 mL) for 2 h, and then the solvent was removed. The residue dissolved in aqueous 1.0 N HCl (30 mL) and EtOAC (200 mL) was adjusted pH to 7 by addition of 1.0 N NaOH (aq.). The aqueous layer was extracted with EtOAc (2×100 mL) and the combined extract was dried (MgSO$_4$), concentrated. The residue was purified by over Biotage 40+M column (EtOAc/hexanes: 30 to 100%) to afford the product 0.870 g, (84%) and ready for the next step.

Step 80f

The product (0.250 g, 0.375 mmol) of step 5 of example 370 {Boc-P2{(4R)-[2-(2-isopropylaminothiazol-4-yl)-7-methoxylquinoline-4-oxo]-S-proline}-P1 (1R,2S Vinyl Acca) COOEt} was treated with 4N HCl/dioxane (2.5 mL, 10 mmol) for 2.5 h and concentrated in vacuo. To the residue was added N-methylmorpholine (0.206 mL, 1.875 mmol) in DMF (3 mL), N-Boc-L-tert-leucine (0.117 g, 0.506 mmol), and HATU (0.192 g, 0.506 mmol). The mixture was stirred overnite and partitioned between EtOAc and pH 4.0 buffer. The EtOAc layer was washed with water, NaHCO$_3$ (aq.), dried (MgSO$_4$), concentrated. The residue was purified over a Biotage 40M column (MeOH/CH$_2$Cl$_2$:0 to 8%) to afford the product 0.289 g (99%): LC-MS (retention time: 2.53, Method K), MS m/z 779 (M$^+$+1).

Step 80 g

To a suspension of the product of Step 6 (0.274 g, 0.352 mmol) of Example 370 {BOCNH-P3(L-t-BuGly)-{[2-(2-isopropylaminothiazol-4-yl)-7-methoxylquinoline-4-oxo]-S-proline}-P1(1R,2S Vinyl Acca)-COOEt} in THF(10.6 mL), CH$_3$OH (2.6 mL), and H$_2$O (5.3 mL) was added LiOH (0.068 g, 2.86 mmol). The reaction mixture was stirred for 24, adjusted to pH 6, removed the organic solvents in vacuo. The aqueous residue was acidified to pH 4, and extracted with CH$_2$Cl$_2$ repeatedly. Combined organic solvent was dried (MgSO$_4$), and concentrated in vacuo to afford the desired product (Compound 80 g) 0.255 g (95%): LC-MS (retention time: 2.58, Method K), MS m/z 751 (M$^+$+1).

Preparation (1-{2-[1-(1-Cyclopropylmethyl-cyclopropanesulfonylaminocarbonyl)-2-vinyl-cyclopropylcarbamoyl]-4-[2-(2-isopropylamino-thiazol-4-yl)-7-methoxy-quinolin-4-yloxy]-pyrrolidine-1-carbonyl}-2,2-dimethyl-propyl)-carbamic acid tert-butyl ester

Step 80h

Scheme 3

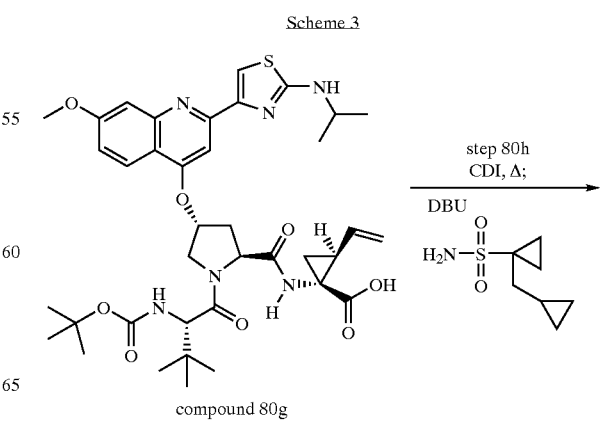

compound 80g

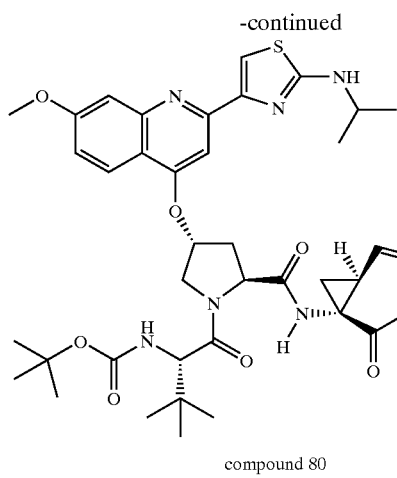

compound 80

Step 80h) The compound 80 was prepared in 2.4% yield (0.0018 g) from (0.060 g, 0.081 mmol) of the compound 67 g the product of Example 80 Step 80 g in analogous fashion to the procedure of Step 27c (Example 27) in the synthesis of compound 27 and combination purification by PTLC and Isco 35 g column: MS m/z 908 (M++t), MS m/z 906 (M⁻−1); LC-MS (retention time: 1.77, Method E), Compound 81 Example 81 compound 81

Step 81a: preparation of 1-ethoxylcarbonyl-cyclopropanyl chloroformate

Step 81) A THF solution (50 mL) of 1-hydroxy-cyclopropanecarboxylic acid ethyl ester (5 g, 38.4 mmol) and pyridine (3.3 mL, 41 mmol) was added dropwise a phosgen/toleune solution (25 mL, 47.5 mmol) at 0° C. in 5–10 min. the reaction mixture was allowed slowly warm up overnite. The solid was filtered off and the filtration was concentrated in vacuo. The residue was dissolved in hexane, refiltered, and concentrated in vacuo to afford.7.4 g (100%) the product. The product was dissolved in $CH_2Cl_2$ (100 mL)

as a stack solution: $^1$H NMR (300 MHz, CHLOROFORM-D) □ ppm 1.25 (t, J=7.14 Hz, 3H), 1.37 (m, 2H), 1.57 (m, 2H), 4.21 (q, J=6.95 Hz, 2H); (ppm) 13.97, 15.75, 62.07, 62.13, 150.54, 168.71.

Step 81b

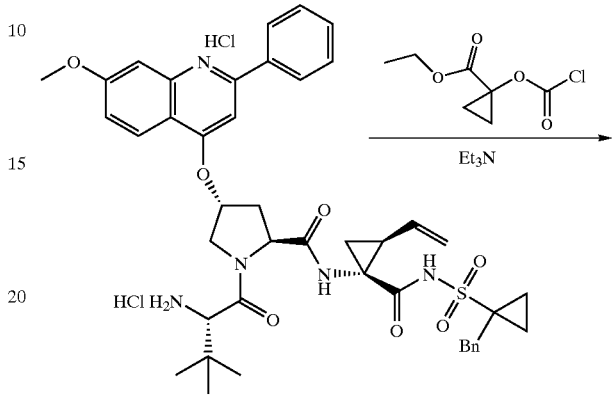

compound 55a compound 81

Step 81b) Compound 56 was prepared in 46% (0.086 g) yield from the bis HCl salt (0.100 g, 0.18 mmol) of the product of Step 55a (Example 55) in analogous fashion to the procedure of step 55b (Example 55) in preparation of Compound 55 except that 1-ethoxylcarbonyl-cyclopropanyl chloroformate was used in place of cyclopentyl chloroformate and Triethyl amine was used as the base. The product was purified by preparative HPLC (solvent B: 40% to 85%): MS m/z 934 (M⁻−1); HPLC (retention time: 3.22, Method J), $^1$H NMR (500 MHz, Solvent) δ ppm 0.90 (m, 2H), 1.03 (s, 9H), 1.14 (m, 4H), 1.30 (m, 3H), 1.48 (m, 3H), 1.95 (dd, J=8.09, 5.34 Hz, 1H), 2.32 (q, J=8.85 Hz, 1H), 2.44 (m, 1H), 2.78 (dd, J=14.04, 7.02 Hz, 1H), 3.30 (d, J=13.43 Hz, 1H), 3.37 (d, J=13.43 Hz, 1H), 4.03 (q, J=7.12 Hz, 2H), 4.07 (s, 3H), 4.16 (dd, J=12.05, 3.20 Hz, 1H), 4.28 (m, 1H), 4.64 (dd, J=10.22, 6.87 Hz, 2H), 5.21 (m, 1H), 5.37 (d, J=17.09 Hz, 1H), 5.79 (m, 2H), 7.17 (m, 2H), 7.28 (m, 3H), 7.40 (m, 1H), 7.55 (m, 2H), 7.72 (m, 3H), 8.09 (d, J=6.41 Hz, 2H), 8.36 (d, J=9.16 Hz, 1H).

Section C

Example 100

Preparation of Compound 100

Compound 100

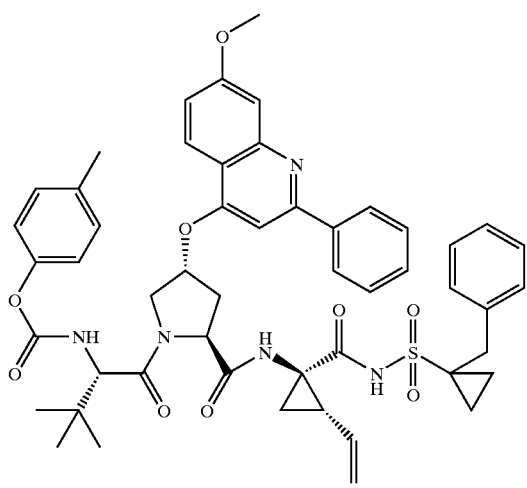

Scheme 1

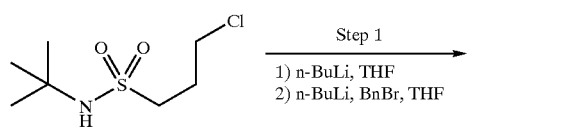

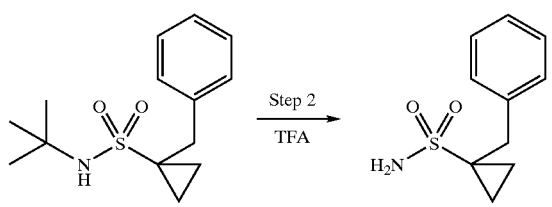

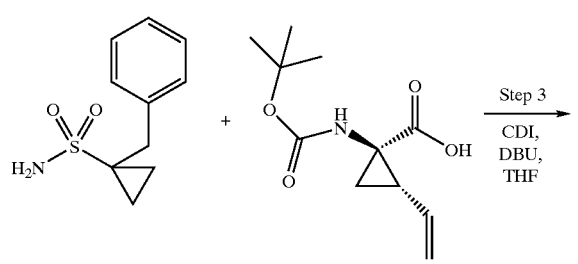

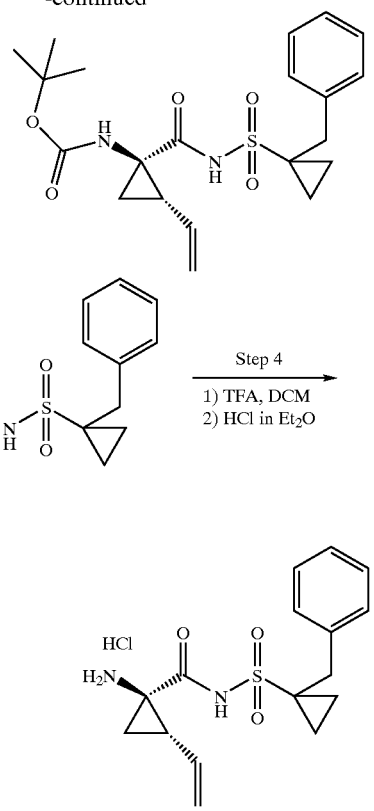

Step 1
As described above
Step 2
As described above.
Step 3
A solution of 1(R)-tert-butoxycarbonylamino-2(S)-vinyl-cyclopropanecarboxylic acid (4.45 g, 19.6 mmol) and 1,1'-carbonyldiimidazole (3.97 g, 24.5 mmol) in dry THF (60 mL) was heated to boiling under reflux for 90 min. Upon cooling to rt, the mixture was treated sequentially with the product from Example 100, Step 2 (5.17 g, 24.5 mmol) and 1,8-diazabicyclo[5.4.0]undec-7-ene (6.26 g, 41.1 mmol). The resulting mixture was stirred at rt for 72h, and was then concentrated in vacuo to a viscous brown oil. The residue was dissolved in ethyl acetate (300 mL) and was washed with 1N HCl (3×75 mL) and then with brine (75 mL). The organic was dried over anhydrous magnesium sulfate, filtered, and concentrated. Purification by flash silica gel chromatography (DCM, then 1% MeOH in DCM) gave 8.4 g (quantitative yield) of the desired product as an off-white solid: MS m/z 443 ((M+Na)+).
Step 4
The product from Example 100, Step 3 (8.4 g, 19.6 mmol) was dissolved in a mixture of TFA (75 mL) and DCM (75 mL) and the resulting solution was stirred for 2.5 h at rt. Concentration in vacuo to an oily residue, followed by addition of 1N HCl in Et$_2$O (35 mL) gave a white solid which was isolated by filtration and dried in vacuo to give 6.30 g (90.2% yield) of the desired product as an off-white powder: $^1$H NMR (CD$_3$OD) δ 0.66–0.83 (m, 2H), 1.41–1.50 (m, 1H), 1.60 (ddd, J=10.89, 6.31, 4.76 Hz, 1H), 1.71 (dd, J=10.06, 7.87 Hz, 1H), 2.17 (t, J=7.87 Hz, 1H), 2.35–2.47 (m, 1H), 3.33 (s, 2H), 5.37 (d, J=10.25 Hz, 1H), 5.48 (d, J=17.20 Hz, 1H), 5.78 (ddd, J=17.11, 10.15, 7.50 Hz, 1H), 7.13–7.20 (m, 2H), 7.24-7.35 (m, 3H); MS m/z 321 (MH+), 343 ((M+Na)+).

Scheme 2
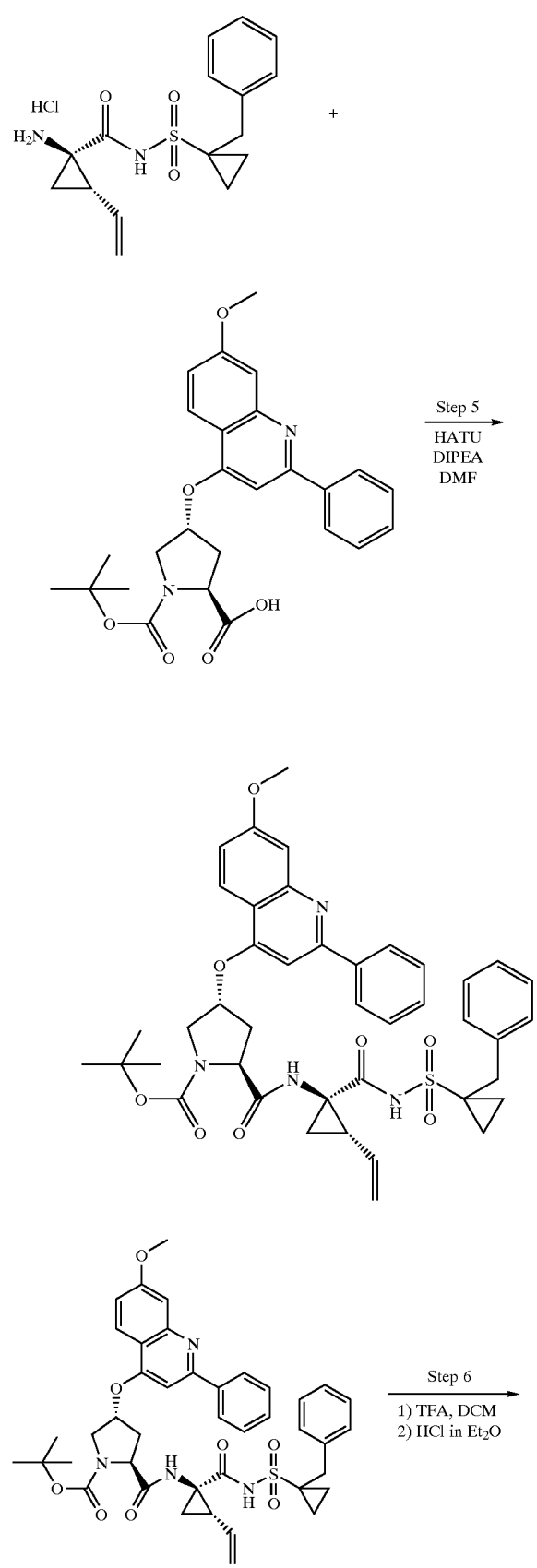
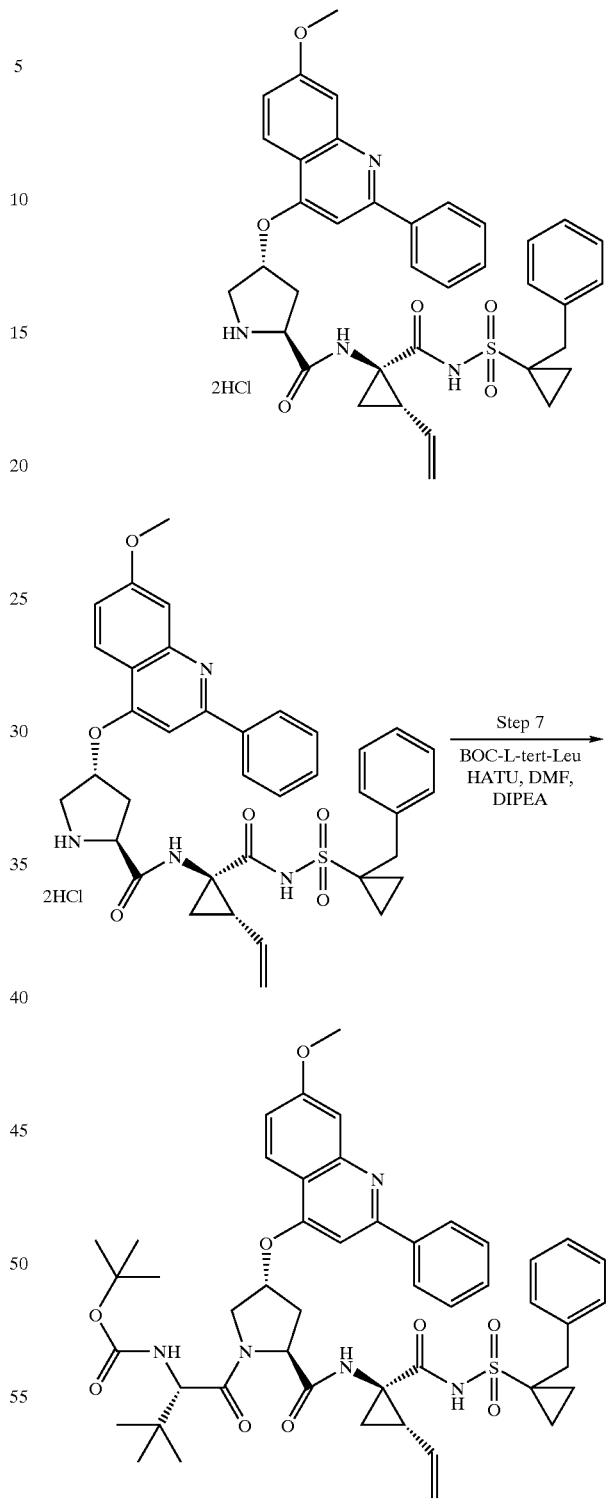
Step 5
The product of Example 100, Step 4 (3.00 g, 8.41 mmol) was combined with 4(R)-(7-Methoxy-2-phenyl-quinolin-4-yloxy)-pyrrolidine-1,2(S)-dicarboxylic acid 1-tert-butyl ester (3.90 g, 8.41 mmol), HATU (3.84 g, 10.1 mmol), DIPEA (3.26 g, 25.2 mmol) and DMF (75 mL) and the resulting solution was stirred at rt for 4.5 h. The mixture was concentrated in vacuo to a residue and was then redissolved in ethyl acetate (250 mL) and washed successively with pH=4 buffer (4×75 mL), water (50 mL) and brine (75 mL). The organic was dried over anhydrous magnesium sulfate, filtered and concentrated in vacuo. Purification by flash silica gel chromatography (step gradient: DCM, then 1% MeOH in DCM, then 2% MeOH in DCM) gave the product as 6.08 g (94.3% yield) of a beige solid: $^1$H NMR (CD$_3$OD) δ 0.57–0.64 (m, 2H), 1.41 (s, 9H), 1.44–1.54 (m, 3H), 1.90 (dd, J=7.93, 5.49 Hz, 1H), 2.36 (ddd, J=13.89, 9.77, 4.12 Hz, 1H), 2.62 (dd, J=13.89, 6.87 Hz, 1H), 2.80 (s, 2H), 3.28–3.35 (m, 1H), 3.89–3.91 (m, 2H), 3.95 (s, 3H), 4.43 (dd, J=9.61, 6.87 Hz, 1H), 5.16 (d, J=10.07 Hz, 1H), 5.34 (d, J=17.09 Hz, 1H), 5.52 (s, 1H), 5.74–5.82 (m, 1H), 7.14–7.29 (m, 8H), 7.41 (d, J=2.14 Hz, 1H), 7.52–7.57 (m, 3H), 7.97–8.06 (m, 2H); MS m/z 767 (MH+).

Step 6

The product of Example 100, Step 5 (4.50 g, 5.87 mmol) was combined with DCM (75 mL) and TFA (50 mL) and the resulting solution was stirred for 30 min at rt. Solvent was removed in vacuo to give a brown oil. The residue was dissolved in 1,2-dichloroethane and the mixture was again concentrated in vacuo to give a glassy solid. The solid was taken up in DCM (30 mL) and to the resulting solution was added 1N HCl in ether (50 mL) in dropwise fashion with rapid stirring. The slightly purple solid that precipitated from solution was isolated by filtration and dried under high vacuum. Total recovery of the desired product was 4.08 g (98.8% yield): $^1$H NMR (CD$_3$OD) δ 0.60–0.66 (m, 2H), 1.38–1.42 (m, 2H), 1.48–1.52 (m, 1H), 1.99 (dd, J=7.93, 5.49 Hz, 1H), 2.44 (q, J=8.85 Hz, 1H), 2.57 (ddd, J=14.80, 10.68, 4.43 Hz, 1H), 2.81 (s, 1H), 3.13 (dd, J=14.65, 7.32 Hz, 1H), 3.99 (d, J=2.14 Hz, 2H), 4.08 (s, 3H), 4.84–4.89 (m, 2H), 5.22 (dd, J=10.38, 1.22 Hz, 1H), 5.39 (dd, J=17.09, 1.22 Hz, 1H), 5.70 (ddd, J=17.09, 10.22, 8.70 Hz, 1H), 6.00 (s, 1H), 7.14 (d, J=7.02 Hz, 2H), 7.22–7.25 (m, 1H), 7.29 (t, J=7.32 Hz, 2H), 7.50 (dd, J=9.16, 2.44 Hz, 1H), 7.59 (d, J=2.44 Hz, 1H), 7.64 (s, 1H), 7.71–7.79 (m, 3H), 8.09–8.10 (m, 2H), 8.54 (d, J=9.16 Hz, 1H),: MS m/z 667 (MH+).

Step 7

The product of Example 100, Step 6 (2.00 g, 2.84 mmol) was combined with N—Boc-L-tert-leucine (0.658 g, 2.84 mmol), HATU (1.30 g, 3.41 mmol), DIPEA (1.11 g, 8.53 mmol) and DMF (30 mL) and the resulting solution was stirred at rt for 18 h. The mixture was concentrated in vacuo to a residue and was then redissolved in ethyl acetate (150 mL) and washed successively with pH=4 buffer (3×75 mL) and brine (50 mL). The organic was dried over anhydrous magnesium sulfate, filtered and concentrated in vacuo. Purification by flash silica gel chromatography (gradient: DCM, to 3% MeOH in DCM) gave 2.23 g (89.2% yield) of the desired product as a beige solid: $^1$H NMR (CD$_3$OD) δ 0.62–0.66 (m, 2H), 0.98 (s, 9H), 1.01–1.06 (m, 2H), 1.25 (s, 9H), 1.43–1.47 (m, 3H), 1.92 (dd, J=8.09, 5.34 Hz, 1H), 2.28 (q, J=8.85 Hz, 1H), 2.34–2.39 (m, 1H), 2.72 (dd, J=14.19, 7.17 Hz, 1H), 3.99 (s, 3H), 4.08–4.11 (m, 1H), 4.21–4.23 (m, 1H), 4.57–4.61 (m, 2H), 5.18 (d, J=10.07 Hz, 1H), 7.14–7.30 (m, 6H), 7.38 (s, 1H), 7.44 (d, J=2.14 Hz, 1H), 7.60–7.61 (m, 3H), 8.05 (dd, J=7.32, 2.14 Hz, 2H), 8.18 (d, J=9.16 Hz, 1H); MS m/z 881 (MH+).

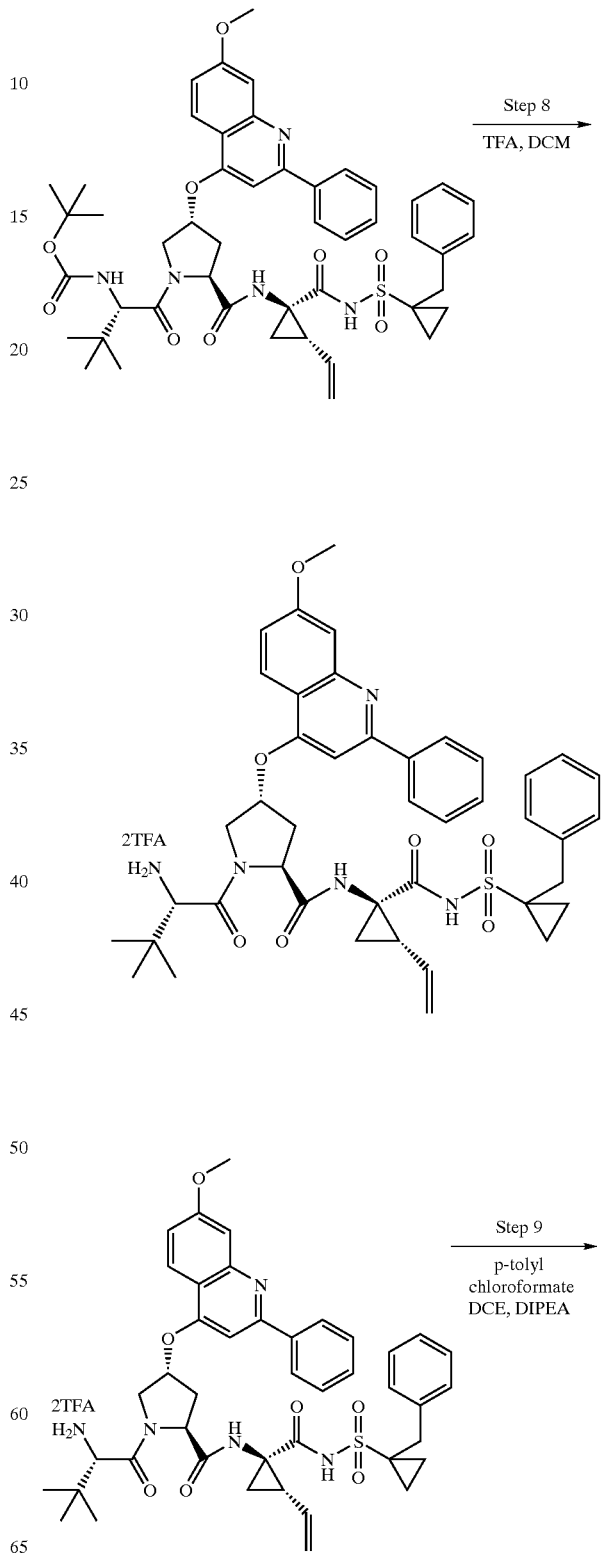

Scheme 3

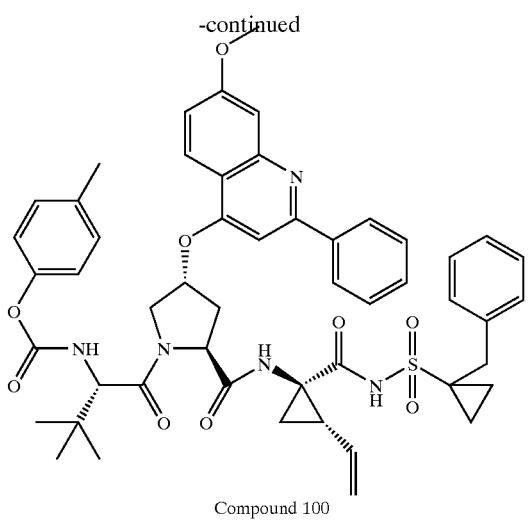

Compound 100

Step 8

A solution of the product from Example 100, Step 7 (1.50 g, 1.70 mmol) in DCM (50 mL) and trifluoroacetic acid (50 mL) was stirred for 3 h at rt. The mixture was concentrated in vacuo to a viscous residue, and was then dissolved in 1,2-dichloroethane and again concentrated in vacuo to give the desired bis-trifluoroacetic acid salt product as an off-white glassy solid (quantitative). The material was used directly in the next step without purification. $^1$H NMR (CD3OD) δ 0.64–0.72 (m, 2H), 1.12 (s, 9H), 1.42–1.56 (m, 4H), 1.94 (dd, J=8.05, 5.49 Hz, 1H), 2.33 (q, J=8.90 Hz, 1H), 2.41–2.50 (m, 1H), 2.81 (s, 2H), 4.06 (s, 3H), 4.16–4.21 (m, 2H), 4.48 (d, J=12.44 Hz, 1H), 4.75 (dd, J=10.43, 7.14 Hz, 1H), 5.21 (dd, J=10.25, 1.46 Hz, 1H), 5.33–5.39 (m, 1H), 5.77 (ddd, J=17.20, 10.25, 8.78 Hz, 1H), 5.87 (d, J=2.93 Hz, 1H), 7.14 (dd, J=7.68, 1.46 Hz, 2H), 7.24–7.30 (m, 3H), 7.46 (dd, J=9.33, 2.38 Hz, 1H), 7.57 (d, J=2.56 Hz, 1H), 7.61 (s, 1H), 7.69–7.77 (m, 3H), 8.06–8.09 (m, 2H), 8.33 (d, J=9.15 Hz, 1H), Step 9

To a solution of the product from Example 100, Step 8 (123 mg, 0.122 mmol) in 1,2-dichloroethane (3 mL) was added p-tolyl chloroformate (27.0 mg, 0.158 mmol) and N,N-diisopropylethylamine (78.7 mg, 0.609 mmol). The mixture was agitated at rt for 72 h. The reaction mixture was washed with pH=4 buffer solution (3×3 mL), and the washes were back-extracted with 1,2-dichloroethane (3 mL). The organic phases were combined and concentrated in vacuo. The crude product was then dissolved in MeOH and purified by reverse phase preparative HPLC to give Compound 100 as an off-white solid (68.1 mg, 61.2% yield): $^1$H NMR (CD$_3$OD) δ 0.61–0.67 (m, 2H), 1.06 (s, 9H), 1.42–1.50 (m, 3H), 1.91 (dd, J=7.93, 5.49 Hz, 1H), 2.24–2.36 (m, 2H), 2.33 (s, 3H), 2.68–2.72 (n, 1H), 3.95 (s, 3H), 4.09 (dd, J=11.75, 3.20 Hz, 1H), 4.37 (s, 1H), 4.52–4.59 (m, 2H), 5.17 (d, J=10.99 Hz, 1H), 5.33 (d, J=16.79 Hz, 1H), 5.54 (s, 1H), 5.77 (ddd, J=17.24, 9.61, 9.46 Hz, 1H), 6.83(d, J=8.55 Hz, 3H), 7.10(d, J=8.24 Hz, 2H), 7.15(d, J=7.02 Hz, 2H), 7.21–7.24 (m, 2H), 7.28 (t, J=7.17 Hz, 2H), 7.37 (d, J=2.44 Hz, 1H), 7.48–7.53 (m, 3H), 7.97–8.06 (m, 3H); MS m/z 914 (MH+), m/z 912 (M−1).

Example 101

Preparation of Compound 101

Compound 101

Compound 101 was prepared by following Step 9 of Example 100 except that phenyl chloroformate was used in place of p-tolyl chloroformate.

Step 9

Modifications: 25 mg (0.16 mmol) phenyl chloroformate used, 59.5 mg product obtained as a white solid (54.3% yield): $^1$H NMR (CD$_3$OD) δ 0.61–0.67 (m, 2H), 1.06 (s, 9H), 1.09–1.14 (m, 1H), 1.41–1.51 (m, 3H), 1.92 (dd, J=7.93, 5.49 Hz, 1H), 2.27 (q, J=8.85 Hz, 1H), 2.30–2.36 (m, 1H), 2.68–2.72 (m, 1H), 3.94 (s, 3H), 3.94–3.98 (m, 1H), 4.10 (dd, J=11.90, 3.05 Hz, 1H), 4.38 (s, 1H), 4.53 (d, J=11.90 Hz, 1H), 4.58 (dd, J=10.07, 7.32 Hz, 1H), 5.17 (d, J=10.99 Hz, 1H), 5.33 (d, J=17.09 Hz, 1H), 5.55 (s, 1H), 5.77 (ddd, J=17.09, 9.77, 9.46 Hz, 1H), 6.88 (dd, J=9.00, 2.29 Hz, 1H), 6.96 (d, J=7.63 Hz, 2H), 7.14–7.24 (m, 5H), 7.27–7.32 (m, 4H), 7.37 (d, J=2.14 Hz, 1H), 7.47–7.53 (m, 3H), 8.00 (d, J=6.71 Hz, 2H), 8.05 (d, J=9.16 Hz, 1H); MS m/z 900 (MH+), m/z 898 (M−1).

Example 102

Preparation of Compound 102

Compound 102

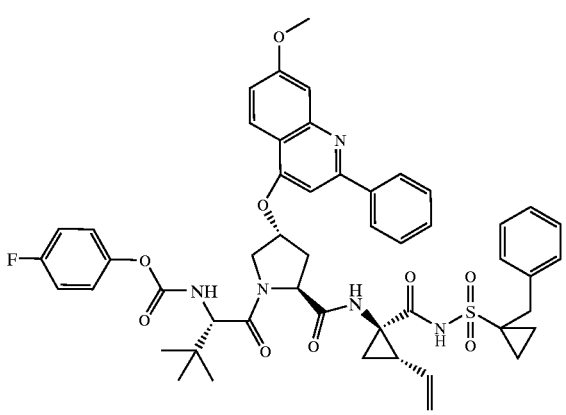

Compound 102 was prepared by following Step 9 of Example 100 except that 4-fluorophenyl chloroformate was used in place of p-tolyl chloroformate.

Step 9

Modifications: 28 mg (0.16 mmol) 4-fluorophenyl chloroformate used, 78.7 mg product obtained as an off-white solid (70.4% yield): $^1$H NMR (CD$_3$OD) δ 0.61–0.67 (m, 2H), 1.05 (s, 9H), 1.10–1.13 (m, 1H), 1.42–1.50 (m, 3H), 1.92 (dd, J=7.93, 5.49 Hz, 1H), 2.25–2.37 (m, 2H), 2.68–2.72 (m, 1H), 3.95 (s, 3H), 4.09 (dd, J=11.90, 3.05 Hz, 1H), 4.35 (s, 1H), 4.52 (d, J=11.60 Hz, 1H), 4.60 (dd, J=10.07, 7.02 Hz, 1H), 5.18 (d, J=10.68 Hz, 1H), 5.34 (d, J=17.09 Hz, 1H), 5.55 (s, 1H), 5.77 (ddd, J=17.09, 9.77, 9.46 Hz, 1H), 6.90–6.92 (m, 3H), 7.00 (t, J=8.55 Hz, 2H), 7.15 (d, J=7.02 Hz, 2H), 7.23–7.30 (m, 4H), 7.38 (d, J=2.44 Hz, 1H), 7.48–7.53 (m, 3H), 8.00–8.05 (m, 3H); MS m/z 918 (MH+), m/z 916 (M−1).

Example 103

Preparation of Compound 103

Compound 103

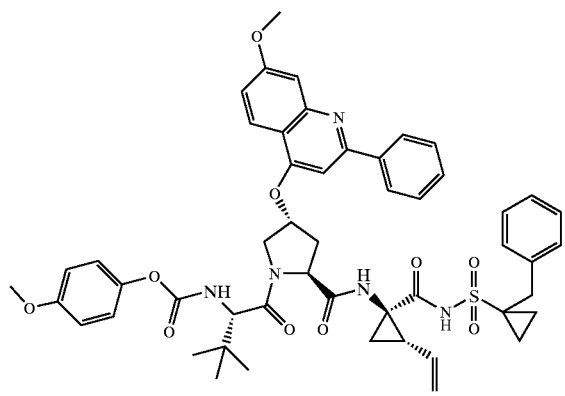

Compound 103 was prepared by following Step 9 of Example 100 except that 4-methoxyphenyl chloroformate was used in place of p-tolyl chloroformate.

Step 9

Modifications: 29 mg (0.16 mmol) 4-methoxyphenyl chloroformate used, 79.8 mg product obtained as an off-white solid (70.5% yield): $^1$H NMR (CD$_3$OD) δ 0.61–0.67 (m, 2H), 1.05 (s, 9H), 1.08–1.13 (m, 1H), 1.41–1.48 (m, 3H), 1.92 (dd, J=7.63, 5.49 Hz, 1H), 2.24–2.35 (m, 2H), 2.65–2.71 (m, 1H), 3.78 (d, J=3.05 Hz, 4H), 3.94 (s, 3H), 4.08–4.10 (m, 1H), 4.36 (s, 1H), 4.53 (d, J=12.21 Hz, 1H), 4.56–4.60 (m, 1H), 5.17 (d, J=10.38 Hz, 1H), 5.33 (d, J=17.09 Hz, 1H), 5.54 (s, 1H), 5.73–5.81 (m, 1H), 6.81–6.89 (m, 5H), 7.15 (d, J=7.32 Hz, 2H), 7.22–7.24 (m, 2H), 7.28 (t, J=7.17 Hz, 2H), 7.38 (d, J=2.44 Hz, 1H), 7.48–7.53 (m, 3H), 8.00–8.06 (m, 3H); MS m/z 930 (MH+), m/z 928 (M−1).

Example 104

Preparation of Compound 104

Compound 104

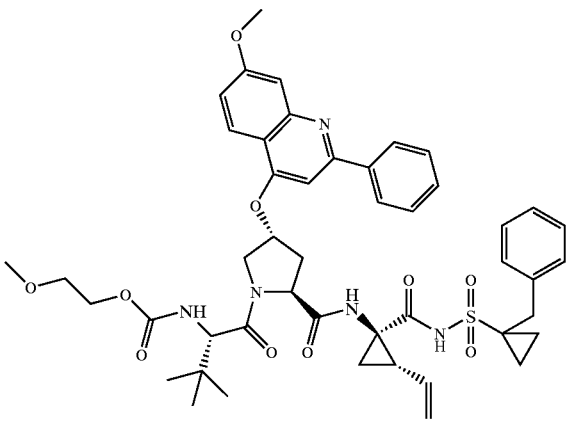

Compound 104 was prepared by following Step 9 of Example 100 except that chloroformic acid 2-methoxyethyl ester was used in place of p-tolyl chloroformate.

Step 9

Modifications: 22 mg (0.16 mmol) chloroformic acid 2-methoxyethyl ester used, 76.5 mg product obtained as an off-white solid (71.2% yield): $^1$H NMR (CD$_3$OD) δ 0.60–0.66 (m, 2H), 0.98 (s, 9H), 1.00–1.05 (m, 1H), 1.41–1.50 (m, 3H), 1.91 (dd, J=7.93, 5.49 Hz, 1H), 2.27 (q, J=8.65 Hz, 1H), 2.31–2.36 (m, 1H), 2.67–2.71 (m, 1H), 3.42–3.46 (m, 2H), 3.78 (s, 1H), 3.88–3.91 (m, 1H), 3.96 (s, 3H), 3.97–3.99 (m, 1H), 4.08 (dd, J=11.75, 2.90 Hz, 1H), 4.29–4.31 (m, 1H), 4.52 (d, J=11.90 Hz, 1H), 4.57 (dd, J=9.77, 7.32 Hz, 1H), 5.17 (d, J=10.38 Hz, 1H), 5.33 (d, J=17.09 Hz, 1H), 5.57 (s, 1H), 5.77 (dt, J=17.17, 9.58 Hz, 1H), 7.13–7.15 (m, 3H), 7.22–7.30 (m, 4H), 7.41 (d, J=2.14 Hz, 1H), 7.49–7.56 (m, 3H), 8.05–8.09 (m, 3H), MS m/z 882 (MH+), m/z 880 (M−1).

Example 105

Preparation of Compound 105

Compound 105

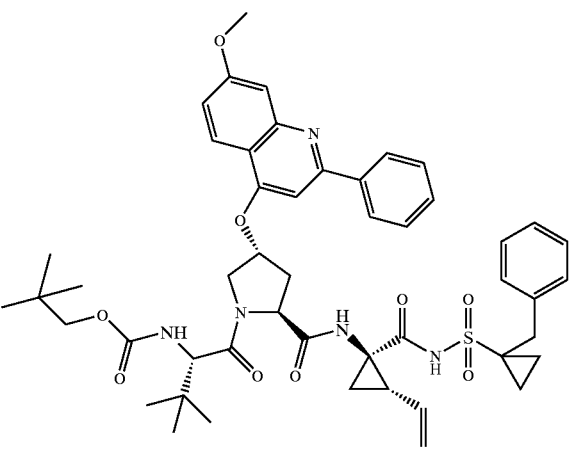

Compound 105 was prepared by following Step 9 of Example 100 except that neopentyl chloroformate was used in place of p-tolyl chloroformate.

Step 9

Modifications: 24 mg (0.16 mmol) neopentyl chloroformate used, 81.4 mg product obtained as an off-white solid (74.8% yield): $^1$H NMR (CD$_3$OD) δ 0.55 (s, 1H), 0.61–0.67 (m, 2H), 0.84 (s, 9H), 0.98 (s, 9H), 1.00–1.05 (m, 1H), 1.43–1.47 (m, 3H), 1.91 (dd, J=7.93, 5.49 Hz, 1H), 2.27 (q, J=8.85 Hz, 1H), 2.31–2.37 (m, 1H), 2.69 (dd, J=13.12, 7.63 Hz, 1H), 3.40 (d, J=10.38 Hz, 1H), 3.57 (d, J=10.38 Hz, 1H), 3.95 (s, 3H), 4.09 (dd, J=11.90, 2.44 Hz, 1H), 4.30 (s, 1H), 4.52 (d, J=11.60 Hz, 1H), 4.58 (dd, J=10.22, 7.17 Hz, 1H), 5.18 (d, J=10.68 Hz, 1H), 5.34 (d, J=17.09 Hz, 1H), 5.57 (s, 1H), 5.78 (ddd, J=17.32, 9.77, 9.54 Hz, 1H), 7.09 (dd, J=9.16, 2.14 Hz, 1H), 7.14 (d, J=6.71 Hz, 2H), 7.22–7.30 (m, 4H), 7.41 (d, J=2.14 Hz, 1H), 7.49–7.56 (m, 3H), 8.07 (t, J=8.85 Hz, 3H); MS m/z 894 (MH+), m/z 892 (M−1).

Example 106

Preparation of Compound 106

Compound 106

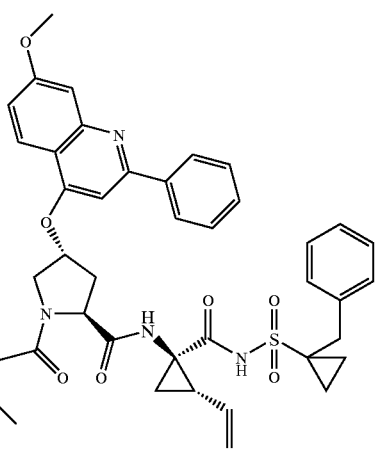

Compound 106 was prepared by following Step 9 of Example 100 except that 2-fluoroethyl chloroformate was used in place of p-tolyl chloroformate.

Step 9:

Modifications: 20 mg (0.16 mmol) 2-fluoroethyl chloroformate used, 72.3 mg product obtained as an off-white solid (68.3% yield): $^1$H NMR (CD$_3$OD) δ 0.62–0.66 (m, 2H), 0.99 (s, 9H), 1.01–1.05 (m, 1H), 1.42–1.50 (m, 3H), 1.90–1.92 (m, 1H), 2.24–2.30 (m, 1H), 2.33–2.36 (m, 1H), 2.67–2.71 (m, 1H), 3.96 (s, 3H), 4.00–4.10 (m, 3H), 4.31 (s, 1H), 4.37–4.53 (m, 3H), 4.56–4.59 (m, 1H), 5.17 (d, J=10.38 Hz, 1H), 5.33 (d, J=17.40 Hz, 1H), 5.58 (s, 1H), 5.74–5.81 (m, 1H), 7.12–7.15 (m, 3H), 7.22–7.30 (m, 4H), 7.41 (s, 1H), 7.49–7.56 (m, 3H), 8.05–8.09 (m, 3H); MS m/z 870 (MH+), m/z 868 (M−1).

Example 107

Preparation of Compound 107

Compound 107

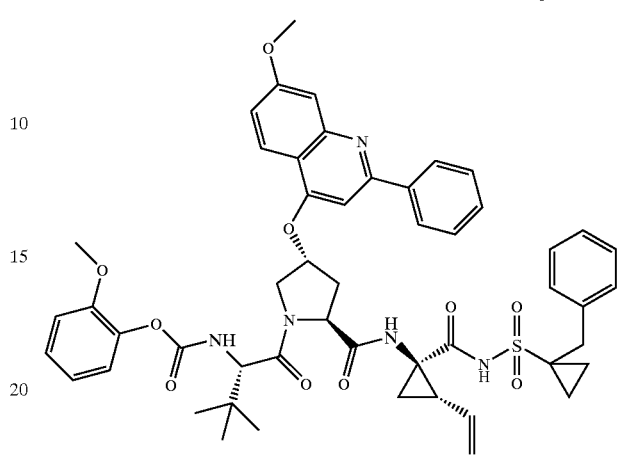

Compound 107 was prepared by following Step 9 of Example 100 except that 2-methoxyphenyl chloroformate was used in place of p-tolyl chloroformate.

Step 9:

Modifications: 29 mg (0.16 mmol) 2-methoxyphenyl chloroformate used, 82.0 mg product obtained as an off-white solid (72.4% yield): $^1$H NMR (CD$_3$OD) δ 0.64 (s, 2H), 1.07 (s, 9H), 1.14 (s, 1H), 1.42–1.50 (m, 3H), 1.90–1.93 (m, 1H), 2.26–2.36 (m, 2H), 2.65–2.71 (m, 1H), 3.68 (s, 3H), 3.95 (s, 3H), 4.12 (d, J=10.38 Hz, 1H), (s, 1H), 4.46 (d, J=11.90 Hz, 1H), 4.57–4.60 (m, 1H), 5.17 (d, J=10.07 Hz, 1H), 5.33 (d, J=17.09 Hz, 1H), 5.53 (s, 1H), 5.74–5.81 (m, 1H), 6.89–6.93 (m, 3H), 7.00 (d, J=7.93 Hz, 1H), 7.16 (t, J=7.63 Hz, 3H), 7.21–7.25 (m, 2H), 7.29 (t, J=7.02 Hz, 2H), 7.37 (s, 1H), 7.50 (d, J=7.32 Hz, 3H), 7.99–8.05 (m, 3H); MS m/z 930 (MH+), m/z 928 (M−1).

Example 108

Preparation of Compound 108

Compound 108

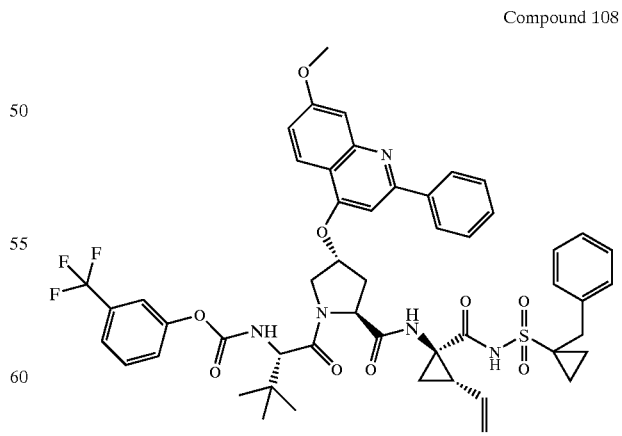

Compound 108 was prepared by following Step 9 of Example 100 except that 3-trifluoromethylphenyl chloroformate was used in place of p-tolyl chloroformate.

Step 9

Modifications: 36 mg (0.16 mmol) 3-trifluoromethylphenyl chloroformate used, 57.3 mg product obtained as an off-white solid (48.6% yield): MS m/z 968 (MH+), m/z 966 (M−1).

Example 109

Preparation of Compound 109

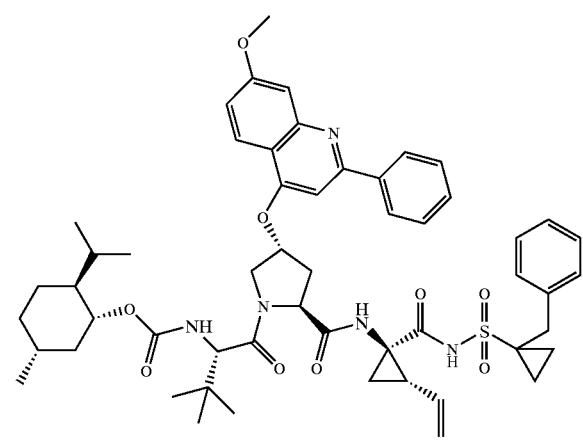

Compound 109

Compound 109 was prepared by following Step 9 of Example 100 except that 2-(−)-(1R)-menthyl chloroformate was used in place of p-tolyl chloroformate.

Step 9

Modifications: 35 mg (0.19 mmol) (−)-(1R)-menthyl chloroformate used, 79.8 mg product obtained as an off-white solid (68.1% yield): MS m/z 962 (MH$^+$), m/z 960 (M−1).

Example 110

Preparation of Compound 110

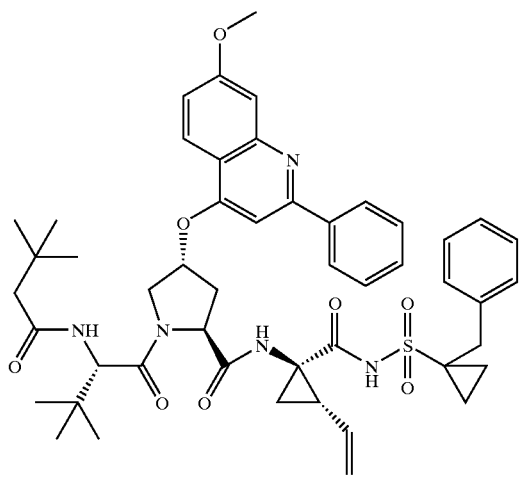

Compound 110

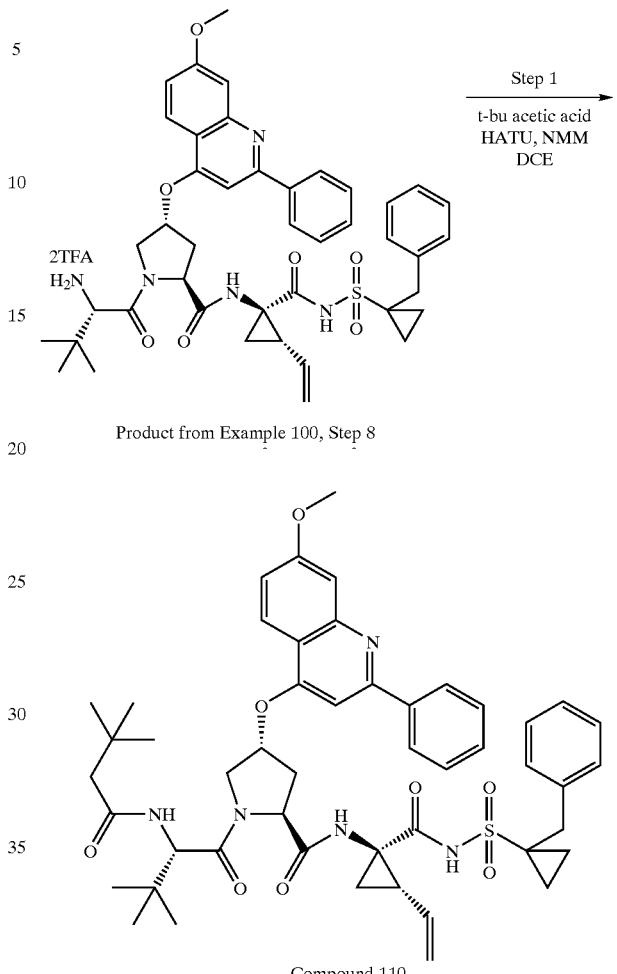

Scheme 1

Product from Example 100, Step 8

Compound 110

Step 1

A mixture of the product from Example 100, Step 8 (123 mg, 0.122 mmol), tert-butyl acetic acid (18.3 mg, 0.158 mmol), HATU (60 mg, 0.16 mmol) and N-methylmorpholine (49 mg, 0.49 mmol) in 1,2-dichloroethane was stirred for 24 h at rt. The reaction mixture was washed with pH=4 buffer solution (3×3 mL), and the washes were back-extracted with 1,2-dichloroethane (3 mL). The organic phases were combined and concentrated in vacuo. The crude product was then dissolved in MeOH and purified by reverse phase preparative HPLC to give the title compound (Compound 110) as a white solid (45.0 mg, 42.1% yield): $^1$H NMR (CD$_3$OD) δ 0.65 (s, 2H), 0.84 (s, 9H), 0.99 (s, 9H), 1.04–1.06 (m, 1H), 1.43–1.48 (m, 3H), 1.91 (dd, J=7.32, 5.80 Hz, 1H), 1.98 (s, 2H), 2.27 (q, J=8.85 Hz, 1H), 2.31–2.36 (m, 1H), 2.65–2.69 (m, 1H), 3.96 (s, 3H), 4.13 (dd, J=11.60, 2.75 Hz, 1H), 4.48 (d, J=11.90 Hz, 1H), 4.55 (dd, J=10.38, 7.02 Hz, 1H), 4.64 (d, J=9.16 Hz, 1H), 5.17 (d, J=10.38 Hz, 1H), 5.34 (d, J=17.09 Hz, 1H), 5.58 (s, 1H), 5.78 (ddd, J=17.24, 9.61, 9.46 Hz, 1H), 7.09–7.15 (m, 3H), 7.22–7.30 (m, 4H), 7.41 (d, J=1.22 Hz, 1H), 7.48–7.55 (m, 3H), 7.79 (d, J=8.55 Hz, 1H), 8.05 (d, J=8.24 Hz, 3H); MS m/z 878 (MH+), m/z 876 (M−1).

Example 111

Preparation of Compound 111

Compound 111

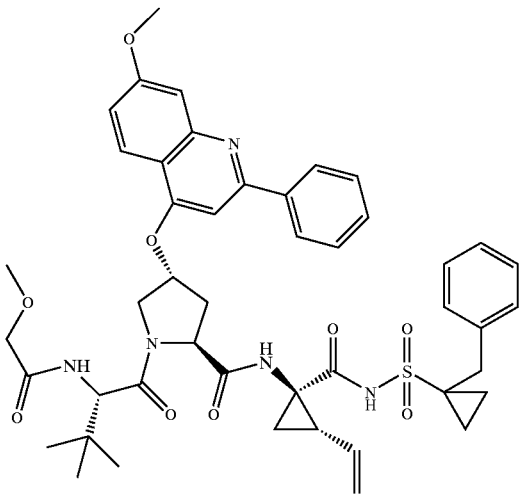

Compound 111 was prepared by following Step 1 of Example 110 except that methoxyacetic acid was used in place of tert-butyl acetic acid.

Step 1

Modifications: 14 mg (0.16 mmol) methoxyacetic acid used, 75.6 mg product obtained as an off-white solid (72.9% yield): $^1$H NMR (CD$_3$OD) δ 0.62–0.67 (m, 2H), 1.00 (s, 9H), 1.02–1.06 (m, 1H), 1.43–1.48 (m, 3H), 1.91 (dd, J=7.93, 5.49 Hz, 1 H), 3.36 (s, 3H), 3.69 (d, J=15.26 Hz, 1H), 3.84 (d, J=15.26 Hz, 1H), 3.96 (s, 3H), 4.13 (dd, J=11.90, 3.36 Hz, 1H), 4.43 (d, J=11.90 Hz, 1H), 4.58 (dd, J=10.38, 7.02 Hz, 1H), 4.65 (s, 1H), 5.18 (dd, J=10.38, 1.22 Hz, 1H), 5.34 (d, J=17.09 Hz, 1H), 5.59 (s, 1H), 5.78 (dt, J=17.09, 9.61 Hz, 1H), 7.12–7.15 (m, 3H), 7.22–7.30 (m, 4H), 7.41 (d, J=2.44 Hz, 1H), 7.49–7.56 (m, 3H), 8.02 (d, J=9.16 Hz, 1H), 8.05 (d, J=7.32 Hz, 2H); MS m/z 852 (MH$^+$), m/z 850 (M-1).

Example 112

Preparation of Compound 112

Compound 112

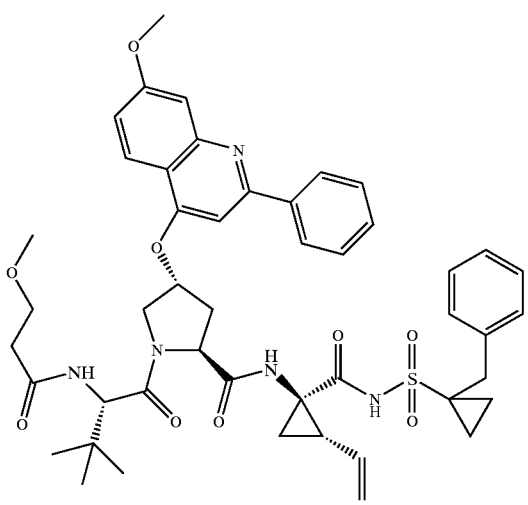

Compound 112 was prepared by following Step 1 of Example 110 except that methoxypropionic acid was used in place of tert-butyl acetic acid.

Step 1

Modifications: 17 mg (0.16 mmol) methoxypropionic acid used, 66.6 mg product obtained as an off-white solid (63.2% yield): $^1$H NMR (CD$_3$OD) δ 0.61–0.67 (m, 2H), 1.00 (s, 9H), 1.01–1.07 (m, 2H), 1.42–1.48 (m, 3H), 1.91 (dd, J=8.09, 5.34 Hz, 1H), 2.24–2.37 (m, 3H), 2.43 (ddd, J=14.95, 7.32, 5.49 Hz, 1H), 2.65–2.69 (m, 1H), 3.26 (s, 3H), 3.46–3.55 (m, 2H), 3.78 (s, 1H), 3.96 (s, 3H), 4.13 (dd, J=11.90, 3.36 Hz, 1H), 4.46 (d, J=11.60 Hz, 1H), 4.56 (dd, J=10.07, 7.02 Hz, 1H), 4.62–4.64 (m, 1H), 5.17 (dd, J=10.22, 1.68 Hz, 1H), 5.33 (dd, J=17.09, 1.22 Hz, 1H), 5.58 (s, 1H), 5.78 (ddd, J=17.09, 10.22, 9.00 Hz, 1H), 7.13–7.15 (m, 3H), 7.22–7.30 (m, 4H), 7.41 (d, J=2.14 Hz, 1H), 7.48–7.56 (m, 3H), 8.05–8.07 (m, 3H); MS m/z 866 (MH+), m/z 864 (M-1).

Example 113

Preparation of Compound 113

Compound 113

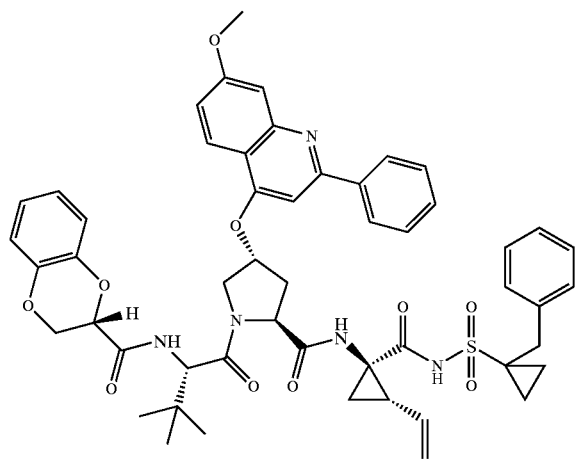

Compound 113 was prepared by following Step 1 of Example 110 except that (S)-1,4-benzodioxane-2-carboxylic acid was used in place of tert-butyl acetic acid.

Step 1

Modifications: 29 mg (0.16 mmol) (S)-1,4-benzodioxane-2-carboxylic acid used, 70.4 mg product obtained as a yellow glassy solid (61.4% yield): $^1$H NMR (CD$_3$OD) δ 0.61–0.67 (m, 2H), 0.77 (s, 9H), 0.79–0.82 (m, 1H), 1.45–1.51 (m, 3H), 1.91 (dd, J=8.09, 5.34 Hz, 1H), 2.27 (q, J=8.85 Hz, 1H), 2.35 (ddd, J=13.81, 10.45, 3.81 Hz, 1H), 2.65–2.71 (m, 1H), 3.93 (s, 3H), 4.10 (dd, J=12.21, 3.36 Hz, 1H), 4.16 (dd, J=11.60, 2.75 Hz, 1H), 4.32 (dd, J=11.44, 4.12 Hz, 1H), 4.41 (d, J=11.60 Hz, 1H), 4.51–4.52 (m, 1H), 4.58 (s, 1H), 4.61 (dd, J=10.38, 7.02 Hz, 1H), 5.18 (d, J=11.60 Hz, 1H), 5.34 (dd, J=17.24, 1.07 Hz, 1H), 5.59 (s, 1H), 5.80 (ddd, J=17.24, 9.77, 9.61 Hz, 1H), 6.80–6.90 (m, 3H), 7.03 (dd, J=7.63, 2.14 Hz, 1H), 7.13–7.15 (m, 3H), 7.21–7.29 (m, 4H), 7.40 (d, J=2.44 Hz, 1H), 7.49–7.56 (m, 3H), 8.03 (d, J=9.16 Hz, 1H), 8.06 (d, J=6.71 Hz, 2H); MS m/z 942 (MH+), m/z 940 (M-1).

Section D

Example 119

Preparation of Compound 119

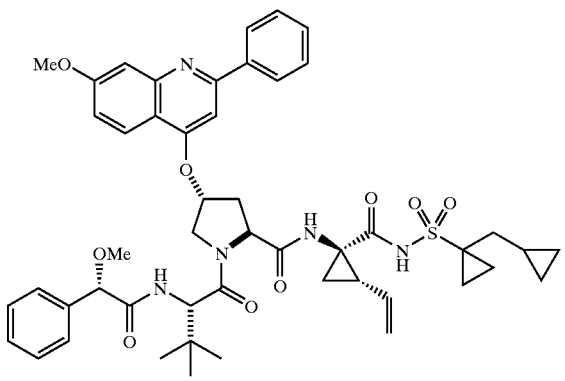

Compound 119

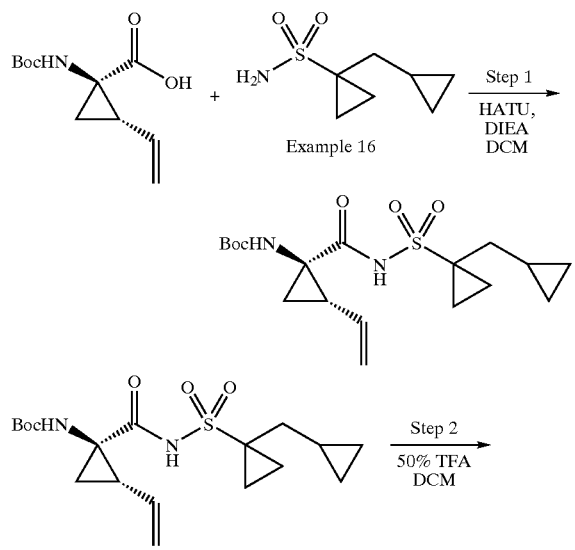

Scheme 1.

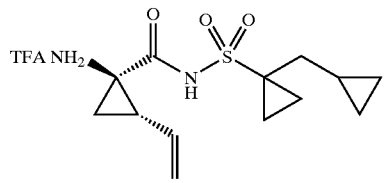

Step 1.

To a solution of 1R-tert-butoxycarbonylamino-2S-vinyl-cyclopropanecarboxylic acid (2.1 g, 9.24 mmol) in THF (26 mL) was added CDI (1.87 g, 11.6 mmol) and was heated to 78° C. for 45 min. After let cool to rt, the reaction mixture was treated with Example 16 (2.11 g, 12.01 mmol) and DBU (2.95 g, 19.4 mmol). After stirring at rt for 14 h, the reaction was diluted with EtOAc (50 mL) and washed with 4×50 mL 1N HCl. The combined aqueous layer was extracted with 3×50 mL EtOAc. The combined organic layer was with brine, dried over $MgSO_4$ and concentrated to a light brown solid product (3.48 g, 98%). The product was used as crude. $^1$H NMR (500 MHz, $CD_3OD$, 500 MHz) δ 0.07 (q, J=4.88 Hz, 2H) 0.44–0.48 (m, 2H) 0.68–0.72 (m, 1H) 1.14 (s, 2H) 1.28 (dd, J=9.46, 5.19 Hz, 1H) 1.43 (d, J=7.02 Hz, 1H) 1.46 (s, 9H) 1.49–1.53 (m, 2H) 1.81 (dd, J=7.78, 5.34 Hz, 1H) 1.86 (s, 2H) 2.16–2.20 (m, 1H) 5.08 (dd, J=10.38, 1.22 Hz, 1H) 5.27 (dd, J=17.24, 1.37 Hz, 1H) 5.51–5.55 (m, 1H).

Step 2

To a solution of the product from step 1 of Example 119 (3.75 g, 9.75 mmol) in DCM (15 mL) was added TFA (15 mL) and was stirring rt for 20 min. Solvent was concentrated under vacuum to give viscous brown oil in quantitative yield. The product was used as crude: MS m/z 285 (MH$^+$).

Scheme 2.

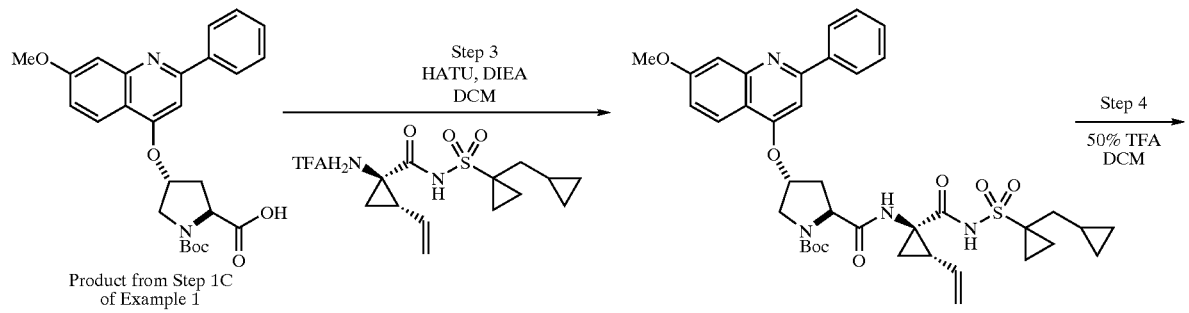

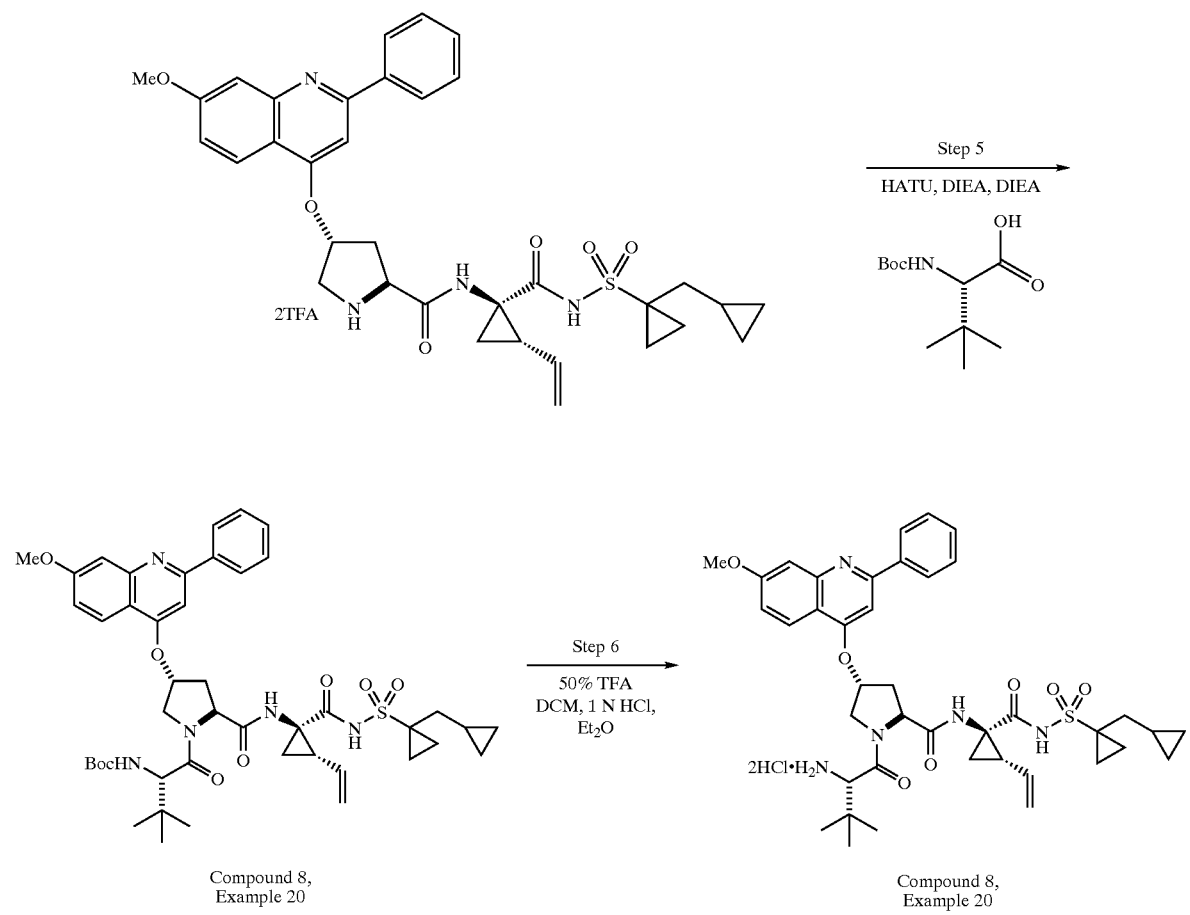

Step 3

To a solution mixture of 4R-(7-methoxy-2-phenyl-quinolin-4-yloxy)proline from step 1c of Example 1 (0.167 g, 0.359 mmol), DIEA (0.140 g, 1.08 mmol) and the product from step 2 of Example 119 (0.143 g, 0.359 mmol) in DCM (4 mL) was added HATU (0.178 g, 0.467 mmol). After stirring at rt for 14 h, the reaction was washed with 5% aqueous NaHCO$_3$ (5 mL) and the aqueous layer was extracted with 2×25 mL DCM. The combined organic layer was washed with 5% aqueous citric acid (5 mL), dried over MgSO$_4$ and concentrated. The resulting brown viscous oil was purified by flash column chromatography to give light brown viscous oil (0.215 g, 82% yield): MS m/z 731 (MH$^+$).

Step 4

To a solution of the product from step 10 of Example 119 (0.157 g, 0.215 mmol) in DCM (1.5 mL) was treated with TFA (1.5 mL) and stirred at rt for 10 mins. The reaction was concentrated and dried under vacuum to give a red viscous oil product, which was used without further purification.: MS m/z 731 (MH$^+$).

Step 5

To a solution mixture of the product from step 4 of Example 119 (1.03 g, 1.38 mmol) DIEA (0.716 g, 5.53 mmol) and Boc-L-tert Leu-OH (0.667 g, 2.07 mmol) in DCM (14 mL) was added HATU (0.789 g, 2.07 mmol). After stirring at rt for 3 h, the reaction was diluted with DCM (25 mL) washed with 5% aqueous NaHCO$_3$ (10 mL). Th aqueous layer was extracted with DCM (50 mL). The combined organic layer was washed with 5% aqueous citric acid (15 mL), dried over MgSO$_4$ and concentrated. The resulting brown viscous oil was purified by flash column chromatography (SiO2, 95:5 DCM:MeOH) to give Compound 8, Example 20 as a light brown solid (0.980 g, 84%,yield): MS m/z 844 (MH$^+$)

Step 6

The product from step 5 of Example 119 (1.1 g, 1.30 mmol) in DCM (1.5 mL) was treated with a 50% solution of TFA (5 mL) in DCM, and stirred at rt for 15 mins. The reaction was concentrated and dried under vacuum to give a brown viscous, which was redisolved in DCM (2 mL) and treated with 1N HCl (5 mL) in Et$_2$O. Solvent was concentrated and the residue was treated with 1N HCl one more time. The reaction was then concentrated and dried under vacuum to give a light brown foamy solid in quantitative yield: MS m/z 744 (MH$^+$).

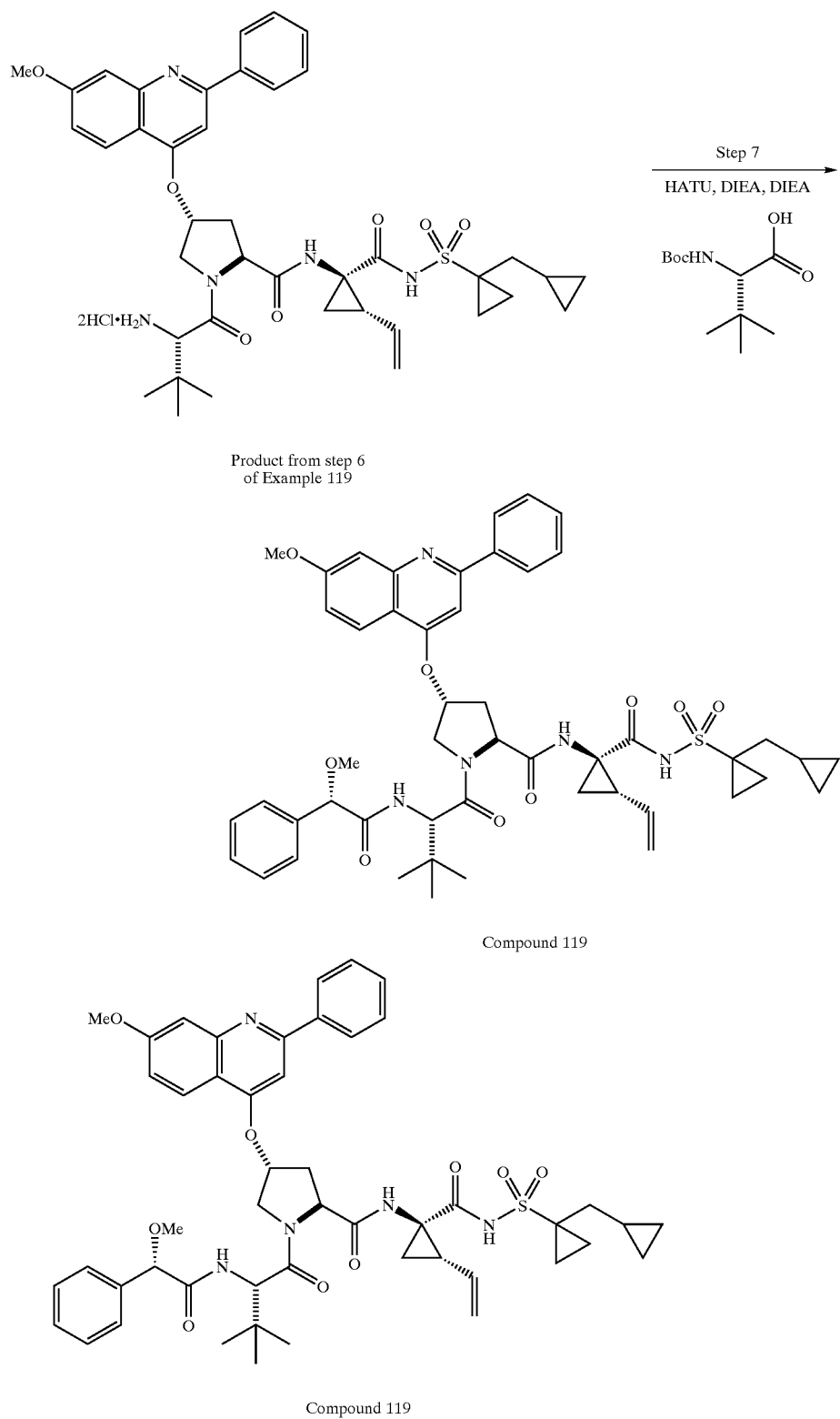
Scheme 3.
Product from step 6 of Example 119
Compound 119
Compound 119
Step 7
To a solution mixture of the product from step 6 of Example 119 (0.062 g, 0.076 mmol) DIEA (0.040 g, 0.31 mmol) and S-(+)-α-methoxy phenylacetic acid (0.019 g, 0.095 mmol) in DCM (2 mL) was added HATU (0.044 g, 0.114 mmol). After stirring at rt for 3 h, the reaction was diluted with DCM (5 mL) washed with 5% aqueous NaHCO₃ (3 mL). Th aqueous layer was extracted with DCM (5 mL). The combined organic layer was washed with 5% aqueous citric acid (3 mL), dried over MgSO₄ and concentrated. The resulting brown viscous oil was purified by flash column chromatography (SiO2, 95:5 DCM:MeOH) to give as a light brown solid (0.051 g, 75% yield): ¹H NMR (500 MHz, CD₃OD) δ 0.08–0.12 (m, 3H) 0.46–0.50 (m, 2H) 0.70–0.74 (m, 1H) 0.94 (dd, J=8.85, 4.27 Hz, 1H) 0.96–0.98 (m, 2H) 1.01 (s, 9H) 1.04 (s, 2H) 1.12–1.14 (m, 1H) 1.15–1.17 (m, 1H) 1.23–1.27 (m, 1H) 1.44 (dd, J=9.46, 5.49 Hz, 1H) 1.49–1.53 (m, 1H) 1.61 (m, 1H) 1.81 (dd, J=14.80, 7.17 Hz, 1H) 1.85 (dd, J=7.93, 2.44 Hz, 1H) 1.89 (dd, J=13.73, 6.71 Hz, 1H) 1.93 (dd, J=13.50, 6.77 Hz, 1H) 2.23 (q, J=8.95 Hz, 1H) 2.33–2.37 (m, 1H) 2.66–2.70 (m, 1H) 3.25 (s, 3H) 3.25–3.29 (m, 2H) 3.33–3.37 (m, 2H) 3.98 (s, 3H) 4.13 (dd, J=12.05, 3.51 Hz, 1H) 4.37 (s, 1H) 4.57 (d, J=10.68 Hz, 1H) 4.59 (d, J=9.77 Hz, 1H) 5.12 (dd, J=10.38, 1.53 Hz, 1H) 5.29 (dd, J=17.24, 1.37 Hz, 1H) 5.61 (s, 1H) 5.72–5.76 (m, 1H) 7.30 (d, J=9.77 Hz, 3H) 7.32 (d, J=1.83 Hz, 2H) 7.45 (d, J=2.44 Hz, 1H) 7.84 (d, J=9.46 Hz, 1H) 8.03 (d, J=9.16 Hz, 1H) 8.06 (s, 1H) 8.07 (d, J=1.53 Hz, 1H), MS m/z 892 (MH⁺).

Example 120

Preparation of Compound 120

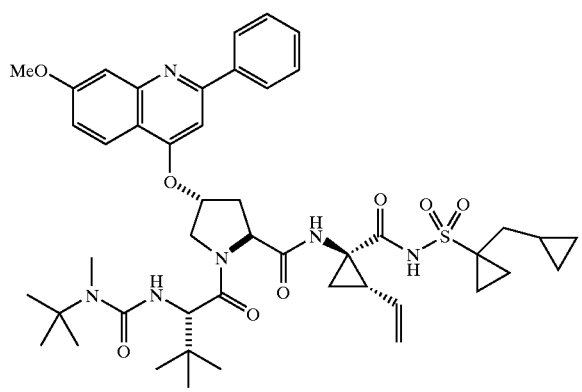

Compound 120

Scheme 1.

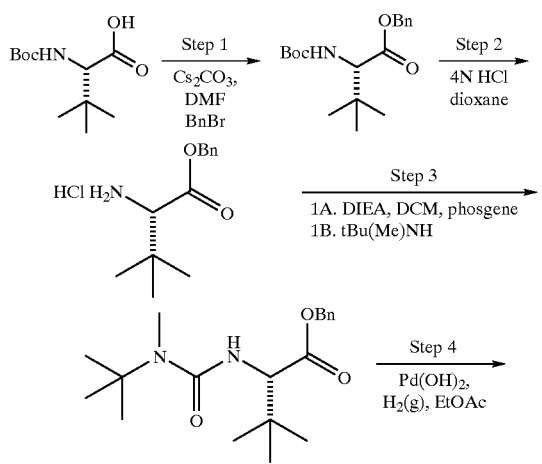

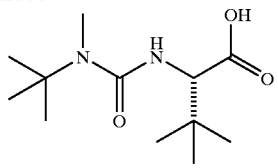

Step 1

To a solution mixture of Boc-tert-Leu-OH (20.0 g, 86.5 mmol) and K₂CO₃ (13.15 g, 95.1 mmol) in DMF (100 mL) was added benzyl bromide (15.53 g, 90.8 mmol). After stirring at rt 72 h, the reaction was diluted with EtOAc (500 mL). The resulting white precipitation was filtered and washed with EtOAc. The liquid filtrated was washed with 1×400 ml and 3×150 mL H₂c, brine (100 mL), dried over MgSO₄ and concentrated to give a quantitative yield of a clear, colorless thick oil (28.03 g): MS m1z 322 (MH⁺).

Step 2:

To a solution of the product from step 3 of Example 120 (27.8 g, 86.5 mmol) in 1,4-dioxane (100 mL) was added 4N HCl in 1,4-dioxane (215 mL) and stirred at rt for 1 h. The reaction was concentrated and dried under vacuum to give a slightly yellow waxy solid (25.62 g, 100% yield): MS m/z 222 (MH⁺).

Step 3

To a solution of phosgene (20% in Toluene, 5.2 mL, 10.0 mmol) in DCM (30 mL) was added dropwise a solution mixture of the product from step 2 of Example 120 (0.516 g, 2.0 mmol) and DIEA (0.544 g, 4.2 mmol) in DCM (10 mL). After stirring at rt for 1 h, the reaction mixture was concentrated and dried under vacuum for 1 h. The excess phosgene was slowly quenched in the roto-vap trap that contained 1N NaOH at −78° C.

The resulting solid product from above was dissolved in DCM (20 mL) and was treated N-methyl-tert-butyl amine (0.349, 4.00 mmol). After stirring at rt for 2 h, the reaction mixture was diluted with DCM (30 mL) and washed 3×25 mL with 5% aqueous citric acid, brine. The organic layer was then dried over MgSO₄ and concentrated and dried under vacuum to give a light yellow solid (0.600 g, 90%). ¹H NMR (500 MHz, CHLOROFORM-D) δ 0.98 (d, J=3.66 Hz, 6H) 1.41 (s, 9H) 1.53 (s, 1H) 2.86 (s, 3H) 4.26 (s, 1H) 5.10 (d, J=12.21 Hz, 1H) 5.21 (d, J=12.20 Hz, 1H) 7.30–7.37 (m, 5H)

Step 4

To a solution of the product from step 3 of Example 120 (0.595 g, 1.78 mmol) in MeOH (5 mL) was added Pearlman catalyst (0.120 g) and stirred at rt under a H₂ (g) atmosphere for 3 h. The catalyst was removed by vacuum filtration and washed with MeOH. It was then concentrated to give a yellow solid (0.400 g, 92% yield): MS m/z 245 (MH⁺).

Scheme 2.

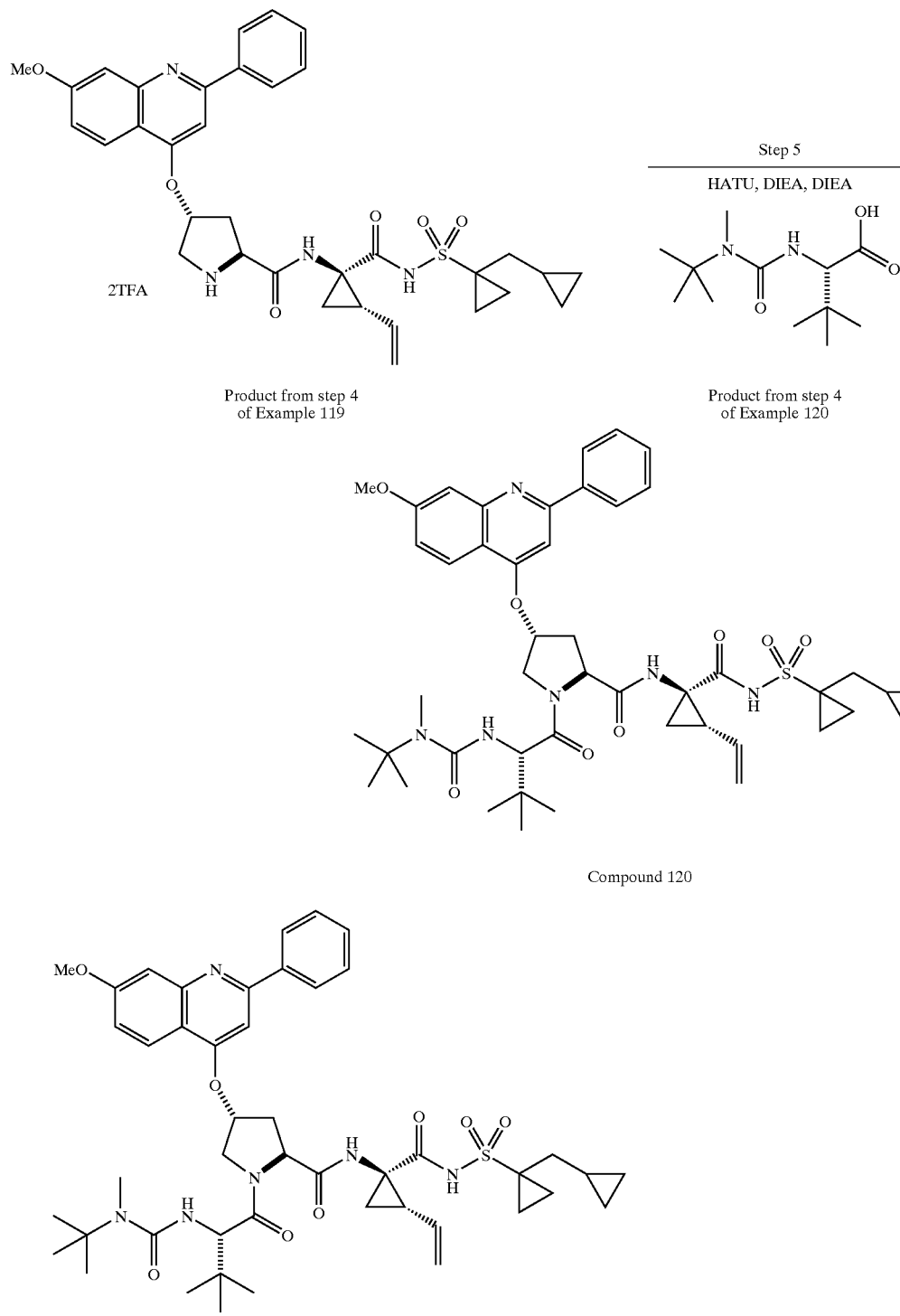

Product from step 4 of Example 119

Product from step 4 of Example 120

Compound 120

Compound 120

Step 5

To a solution mixture of the product from step 4 of Example 119 (0.106 g, 0.142 mmol), DIEA (0.074 g, 0.569 mmol) and the product from step 4 of Example 120 (0.045 g, 0.185 mmol) in DCM (2 mL) was added HATU (0.082 g, 0.213 mmol). After stirring at rt for 14 h, the reaction was diluted with DCM (15 mL) washed with 5% aqueous NaHCO$_3$ (3 mL), 5% aqueous citric acid (3 mL), brine, dried over MgSO$_4$ and concentrated. The resulting brown viscous oil was purified by flash column chromatography (SiO$_2$, 97:3 DCM:MeOH) to give a yellow solid (0.051 g, 75% yield): $^1$HNMR(CD$_3$OD, 500 MHz) δ 0.05–0.09 (m, 3H) 0.46–0.50 (m, 3H) 0.66–0.70 (m, 1H) 0.99 (s, 3H) 1.04 (t, J=4.73 Hz, 3H) 1.07 (s, 9H) 1.10–1.14 (m, 3H) 1.18–1.24

(m, 2H) 1.25 (s, 9H) 1.28–1.32 (m, 1H) 1.37 (s, 3H) 1.42–1.46 (m, 3H) 1.56–1.60 (m, 1H) 1.78 (dd, J=14.80, 7.48 Hz, 1H) 1.83 (dd, J=8.09, 5.34 Hz, 1H) 1.89 (d, J=7.02 Hz, 1H) 1.92 (dd, J=14.65, 6.41Hz, 1H) 2.19 (dd, J=17.90, 9.30 Hz, 1H) 2.32–2.36 (m, 1H) 2.64 (dd, J=13.74, 7.02 Hz, 1H) 2.87 (s, 3H) 2.93 (s, 1H) 3.70 (s, 1H) 4.14 (dd, J=11.29, 3.00 Hz, 1H) 4.42 (s, 1H) 4.53 (dd, J=10.83, 6.56 Hz, 1H) 4.57 (d, J=12.82 Hz, 1H) 5.10 (d, J=10.38 Hz, 1H) 5.27 (d, J=17.40 Hz, 1H) 5.60 (s, 1H) 5.73–5.77 (m, 1H) 7.08 (dd, J=9.16, 2.44 Hz, 1H) 7.27 (s, 1H) 7.41 (d, J=2.44 Hz, 1H) 7.50–7.54 (m, 3H) 8.05 (s, 1H) 8.07 (d, J=1.53 Hz, 1H) 8.09 (d, J=9.16 Hz, 1H); MS m/z 656 (MH$^+$).

Section E

Example 200

Preparation of Compound 200

(1-{4-(7-Methoxy-2-phenyl-quinolin-4-yloxy)-2-[1-(1-propyl-cyclopropane-sulfonylaminocarbonyl)-spiro[2.2]pent-1-ylcarbamoyl]-pyrrolidine-1-carbonyl}-2,2-dimethyl-propyl)-carbamic acid tert-butyl ester, shown below, was prepared as described in Steps 200a–c.

Compound 200

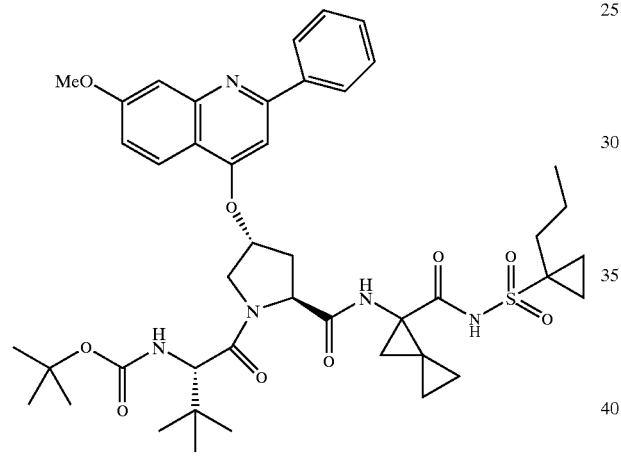

Step 200a. Preparation of spiro[2.2]pentane-1,1-dicarboxylic acid dimethyl ester, shown below.

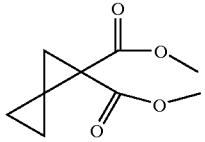

To a cooled (0° C.) mixture of methylenecyclopropane (3.89 g, 72 mmol)(prepared according to P. Binger U.S. Pat. No. 5,723,714) and Rh$_2$(OAc)$_4$ (3.18 g, 7.2 mmol) in anhydrous CH$_2$Cl$_2$ (40 mL), was added dimethyl diazomalonate (11.38 g, 72 mmol). At the top of the flask was installed a cold finger kept at −78° C. The green reaction mixture was warmed to rt at which time bubbling due to N$_2$ evolution was evident. An exotherm caused mild reflux for 15 minutes. The reaction was stirred for another 4 h. The mixture was concentrated in vacuo and purified by flash chromatography (eluting with 10:1 hexane/Et$_2$O to 5:1 hexane/Et$_2$O) to give 10.5 g (79%) of the dimethyl ester as a yellow oil. $^1$H NMR (300 MHz, CDCl$_3$) δ 3.73 (s, 6H), 1.92 (s, 2H), 1.04 (d, 4H, J=3 Hz).

Step 200b: Spiro[2.2]pentane-1,1-dicarboxylic acid methyl ester, shown below, was prepared as follows.

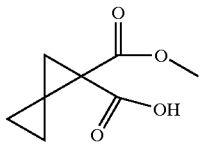

To the mixture of spiro[2.2]pentane-1,1-dicarboxylic acid dimethyl ester 800 mg (4.3 mmol) in 8 mL of MeOH and 2 mL of water was added KOH (240 mg, 4.3 mmol). This solution was stirred at rt for 2 days. It was then acidified with dilute HCl to pH 3 and extracted two times with ether. The combined organic phases were dried (MgSO$_4$) and concentrated to yield 600 mg (82%) of spiro[2.2]pentane-1,1-dicarboxylic acid methyl ester as a white solid. $^1$H NMR (300 MHz, CDCl$_3$) δ 3.82 (s, 6H), 2.35 (d, 1H, J=3 Hz), 2.26 (d, 1H, J=3 Hz), 1.20 (m, 1H), 1.15 (m, 1H), 1.11 (m, 1H), 1.05 (m, 1H). LRMS: MS m/z 169 (M$^+$−1).

Step 200c: 1-Amino-spiro[2.2]pentane-1-carboxylic acid methyl ester hydrochloride salt, shown below, was prepared as follows.

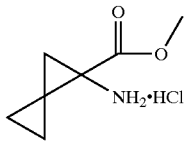

To a mixture of spiro[2.2]pentane-1,1-dicarboxylic acid methyl ester (400 mg, 2.30 mmol) in 3 mL of anhydrous t-BuOH was added 700 mg (2.50 mmol) of DPPA and 278 mg (2.70 mmol) of Et$_3$N. The mixture was heated at reflux for 21 h and then partitioned between H$_2$O and ether. The ether phase was dried over magnesium sulfate, filtered and concentrated in vacuo to yield an oil. To this oil was added 3 mL of a 4 M HCl/dioxane solution. This acidic solution was stirred at rt for 2 h and then concentrated in vacuo. The residue was triturated with ether to give 82 mg (20%) of 1-amino-spiro[2.2]pentane-1-carboxylic acid methyl ester hydrochloride salt as a white solid. $^1$H NMR (300 MHz, CDCl$_3$) δ 9.19 (br s, 3H), 3.81 (s, 3H), 2.16, (d, J=5.5 Hz, 1H), 2.01 (d, J=5.5 Hz, 1H), 1.49 (m, 1H), 1.24, (m, 1H), 1.12 (m, 2H). LRMS of free amine: MS m/z 142 (M$^+$+1)

Step 200d: 1-{[1-(2-tert-Butoxycarbonylamino-3,3-dimethyl-butyryl)-4-(7-methoxy-2-phenyl-quinolin-4-yloxy)-pyrrolidine-2-carbonyl]-amino}-spiro[2.2]pentane-1-carboxylic acid, shown below, was prepared from the product of Step 203c using the general method illustrated in Scheme I and detailed in Example 2.

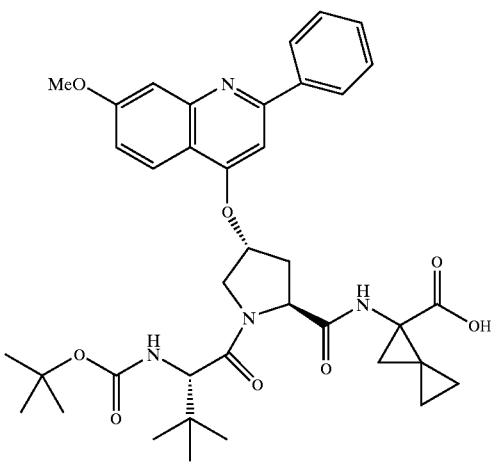

Step 200e: 1-{[1-(2-tert-Butoxycarbonylamino-3,3-dimethyl-butyryl)-4-(7-methoxy-2-phenyl-quinolin-4-yloxy)-pyrrolidine-2-carbonyl]-amino}-spiro[2.2]pentane-1-carboxylic acid (200 mg, 0.29 mmol) was slurried in 10 mL of THF. CDI (62 mg, 0.38 mmol) was added, and the mixture was refluxed for 1 h. The mixture was cooled to rt, 1-propyl-cyclopropanesulfonic acid amide (62 mg, 0.38 mmol) was added followed by DBU (58 mg, 0.38 mmol). The reaction mixture was stirred for 18 h, concentrated in vacuo, and purified by flash chromatography (hexane/ethyl acetate gradient) to give 50 mg (21%) of the titled compound, (1-{4-(7-methoxy-2-phenyl-quinolin-4-yloxy)-2-[1-(1-propyl-cyclopropane-sulfonylaminocarbonyl)-spiro[2.2]pent-1-ylcarbamoyl]-pyrrolidine-1-carbonyl}-2,2-dimethyl-propyl)-carbamic acid tert-butyl ester, as a mixture of diastereoisomers (racemic at P1).

LC-MS (retention time: 3.21, similar to the general LC/MS methods A–G: YMC Xterra MS C18 S7 3.0×50 mm, gradient time 4 min, flow rate 4 mL/min, hold time 1 min), MS m/z 832 (M$^+$+1).

Example 201

Preparation of Compound 201

{1-[2-[1-(1-Benzyl-cyclopropanesulfonylaminocarbonyl)-spiro[2.2]pent-1-ylcarbamoyl]-4-(7-methoxy-2-phenyl-quinolin-4-yloxy)-pyrrolidine-1-carbonyl]-2,2-dimethyl-propyl}-carbamic acid tert-butyl ester, Shown Below, was Prepared as Described for Example 200

Compound 201

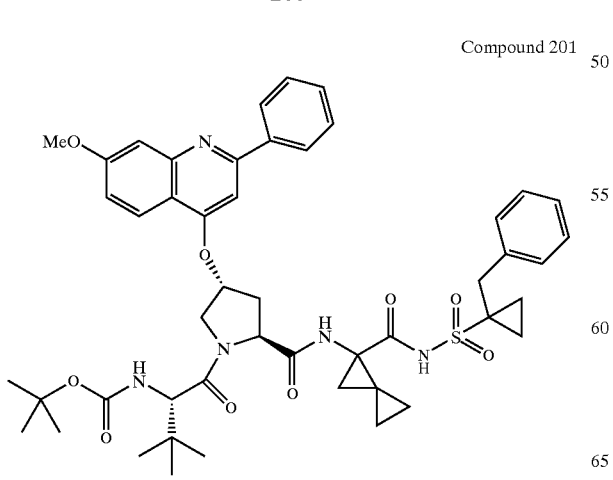

except that 1-benzyl-cyclopropanesulfonic acid amide (see example 7) was used. This procedure provided 192 mg (75%) of the titled compound as an off-white glassy foam (mixture of diastereoisomers; racemic at P1). LC-MS (retention time: 3.36, similar to the general LC/MS methods A–G: Xterra ODS S7 3.0×50 mm, gradient time 4 min, flow rate 4 mL/min, hold time 1 min), MS m/z 880 (M$^+$+1).

Example 202

Preparation of Compound 202

{1-[2-[1-(1-Cyclopropylmethyl-cyclopropanesulfonylaminocarbonyl)-spiro[2.2]pent-1-ylcarbamoyl]-4-(7-methoxy-2-phenyl-quinolin-4-yloxy)-pyrrolidine-1-carbonyl]-2,2-dimethyl-propyl}-carbamic acid tert-butyl ester, Shown Below, was Prepared as Described for Example 200

Compound 202

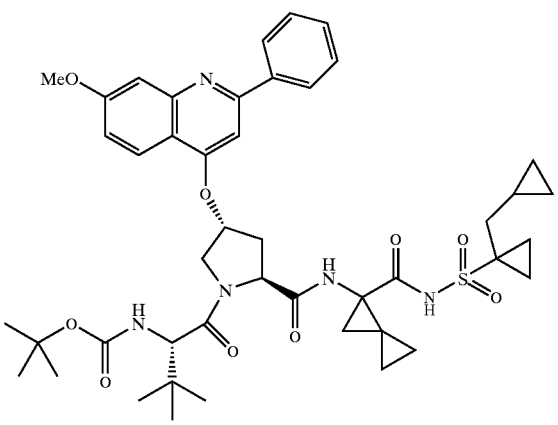

except that 1-cyclopropylmethyl-cyclopropanesulfonic acid amide was used. This procedure (0.218 mmol scale) provided 50 mg (27%) of the titled compound as an off-white solid (mixture of diastereoisomers; racemic at P1). LC-MS, MS m/z 844 (M$^+$+1).

Example 203

Preparation of Compound 203

Compound 203

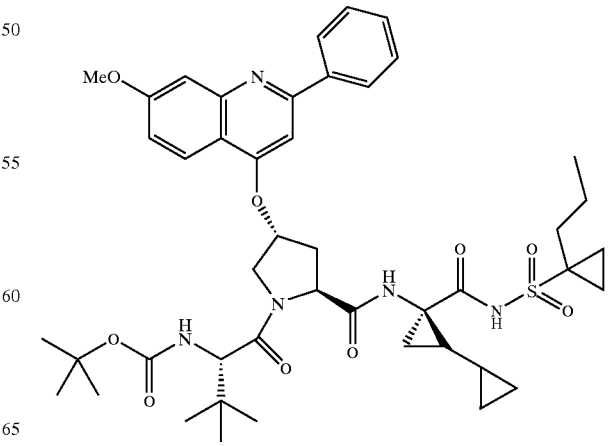

The title compound was prepared as described in Steps 203a–c.

Step 203a: Synthesis of N—Boc-(1R,2S)-1-amino-2-cyclopropylcyclopropane carboxylic acid ethyl ester

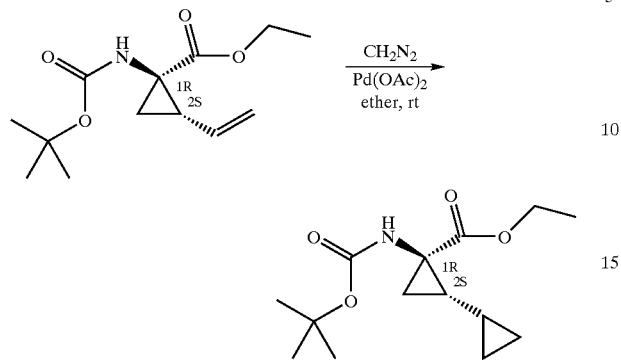

A solution of N—Boc-(1R,2S)-1-amino-2-vinylcyclopropane carboxylic acid (255 mg, 1.0 mmol) in ether (10 mL) was treated with palladium acetate (5 mg, 0.022 mmol). The orange/red solution was placed under an atmosphere of $N_2$. An excess of diazomethane in ether was added dropwise over the course of 1 h. The resulting solution was stirred at rt for 18 h. The excess diazomethane was removed using a stream of nitrogen. The resulting solution was concentrated by rotary evaporation to give the crude product. Flash chromatography (10% EtOAc/hexane) provided 210 mg (78%) of N—Boc-(1R,2S)-1-amino-2-cyclopropylcyclopropane carboxylic acid ethyl ester as a colorless oil. LC-MS (retention time: 2.13, similar to method A except: gradient time 3 min, Xterra MS C18 S7 3.0×50 mm column), MS m/e 270 ($M^+$+1).

Step 203b: The title compound was prepared from N—Boc-(1R,2S)-1-amino-2-cyclopropylcyclopropane carboxylic acid ethyl ester using methods illustrated in Scheme I and detailed in the examples above. MS (electrospray, ES+) m/z 847 ($M^+$+1).

Step 203c: Alternatively, the title compound may be prepared by cyclopropanation of the vinyl cyclopropane moiety present in (1R,2S) P1 isomer of 1-{[1-2-tert-butoxycarbonylamino-3,3-dimethyl-butyryl)-4-(7-methoxy-2-phenylquinolin-4-yloxy)p-pyrrolidine-2-carbonyl]amino}-2-vinyl-cyclopropanecarboxylic acid ethyl ester followed by conversion to the desired acylsulfonamide derivative using methods described herein.

Example 204

Preparation of Compound 204

Compound 204

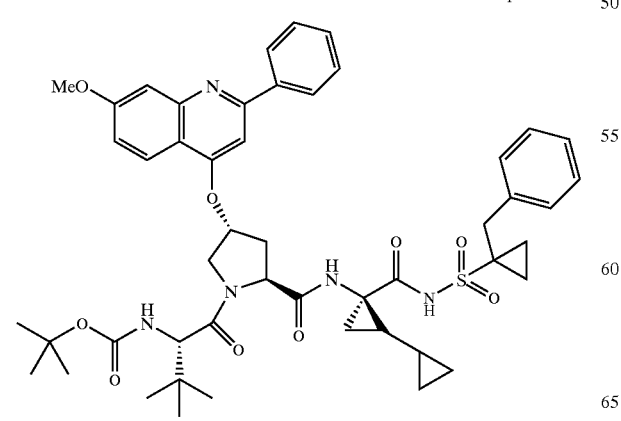

The title compound was prepared from N—Boc-(1R,2S)-1-amino-2-cyclopropylcyclopropane carboxylic acid ethyl ester using methods illustrated in Scheme I and detailed in the examples above. MS (electrospray, ES−) m/z 892 (M−H)$^-$.

Example 205

Preparation of Compound 205

Compound 205

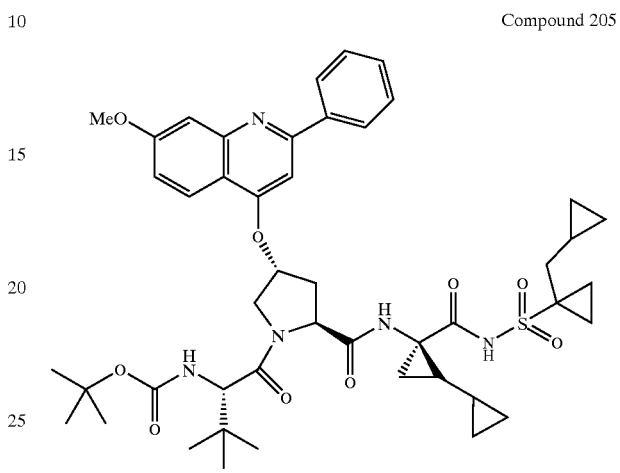

The title compound was prepared from N—Boc-(1R,2S)-1-amino-2-cyclopropylcyclopropane carboxylic acid ethyl ester using methods illustrated in Scheme I and detailed in the examples above. MS (electrospray, ES+) m/z 858 ($M^+$+1).

Example 206

Preparation of additional P1 Intermediates for incorporation in compounds of Formula I.

The P1 intermediates described in this section can be used to prepare compounds of Formula I by the methods described herein.

1. Resolution of N—Boc-(1R,2S)/(1S,2R)-1-amino-2-vinylcyclopropane carboxylic acid ethyl ester

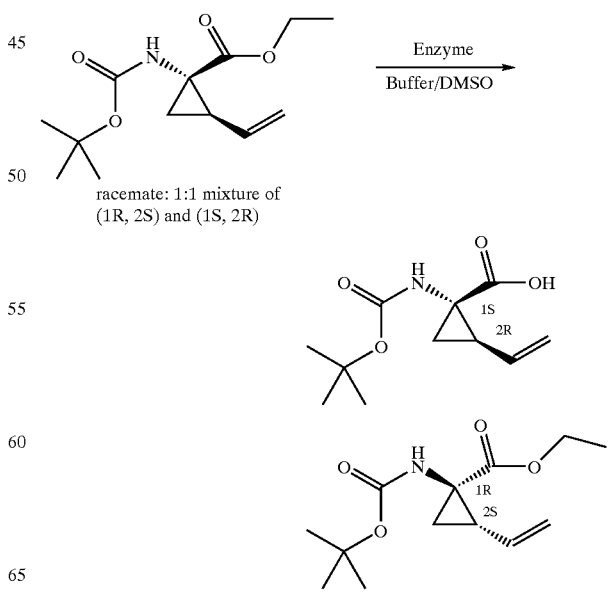

Resolution A

To an aqueous solution of sodium phosphate buffer (0.1 M, 4.25 liter ("L"), pH 8) housed in a 12 Liter jacked reactor, maintained at 39° C., and stirred at 300 rpm was added 511 grams of Acalase 2.4 L (about 425 mL) (Novozymes North America Inc.). When the temperature of the mixture reached 39° C., the pH was adjusted to 8.0 by the addition of a 50% NaOH in water. A solution of the racemic N—Boc-(1R,2S)/(1S,2R)-1-amino-2-vinylcyclopropane carboxylic acid ethyl ester (85 g) in 850 mL of DMSO was then added over a period of 40 min. The reaction temperature was then maintained at 40° C. for 24.5 h during which time the pH of the mixture was adjusted to 8.0 at the 1.5 h and 19.5 h time points using 50% NaOH in water. After 24.5 h, the enantio-excess of the ester was determined to be 97.2%, and the reaction was cooled to room temperature (26° C.) and stirred overnight (16 h) after which the enantio-excess of the ester was determined to be 100%. The pH of the reaction mixture was then adjusted to 8.5 with 50% NaOH and the resulting mixture was extracted with MTBE (2×2 L). The combined MTBE extract was then washed with 5% $NaHCO_3$ (3×100 mL), water (3×100 mL), and evaporated in vacuo to give the enantiomerically pure N—Boc-(1R,2S)/-1-amino-2-vinylcyclopropane carboxylic acid ethyl ester as light yellow solid (42.55 g; purity: 97% @ 210 nm, containing no acid; 100% enantiomeric excess ("ee")).

The aqueous layer from the extraction process was then acidified to pH 2 with 50% $H_2SO_4$ and extracted with MTBE (2×2 L). The MTBE extract was washed with water (3×100 mL) and evaporated to give the acid as light yellow solid (42.74 g; purity: 99% @ 210 nm, containing no ester).

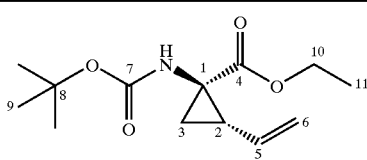

1R, 2S-ester

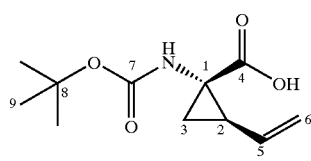

1R, 2S-acid

|  | ester | acid |
|---|---|---|
| High Resolution Mass Spec | (+) ESI, C13H22NO4, [M + H]+, cal. 256.1549, found 256.1542 | (−) ESI, C11H16NO4, [M − H]−, cal. 226.1079, found 226.1089 |

NMR observed chemical shift
Solvent: $CDCl_3$ (proton δ 7.24 ppm, C-13 δ 77.0 ppm)
Bruker DRX-500C: proton 500.032 MHz, carbon 125.746 MHz

| Position | Proton (pattern) ppm | C-13 ppm | Proton (pattern) ppm | C-13 ppm |
|---|---|---|---|---|
| 1 | — | 40.9 | — | 40.7 |
| 2 | 2.10(q, J=9.0 Hz) | 34.1 | 2.17(q, J=9.0 Hz) | 35.0 |
| 3a | 1.76(br) | 23.2 | 1.79(br) | 23.4 |
| 3b | 1.46(br) | | 1.51(br) | |
| 4 | — | 170.8 | — | 175.8 |
| 5 | 5.74(ddd, J=9.0, 10.0, 17.0 Hz) | 133.7 | 5.75(m) | 133.4 |
| 6a | 5.25(d, J=17.0 Hz) | 117.6 | 5.28(d, J=17.0 Hz) | 118.1 |
| 6b | 5.08(dd, J=10.0, 1.5 Hz) | | 5.12(d, J=10.5 Hz) | |
| 7 | — | 155.8 | — | 156.2 |
| 8 | — | 80.0 | — | 80.6 |
| 9 | 1.43(s) | 28.3 | 1.43(s) | 28.3 |
| 10 | 4.16(m) | 61.3 | — | — |
| 11 | 1.23(t, J=7.5 Hz) | 14.2 | — | — |

Resolution B

To 0.5 mL 100 mM Heps.Na buffer (pH 8.5) in a well of a 24 well plate (capacity: 10 ml/well), 0.1 mL of Savinase 16.0 L (protease from *Bacillus clausii*) (Novozymes North America Inc.) and a solution of the racemic N—Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 h, enantio-excess of the ester was determined to be 44.3% as following: 0.1 mL of the reaction mixture was removed and mixed well with 1 mL ethanol; after centrifugation, 10 microliter ("μl") of the supernatant was analyzed with the chiral HPLC. To the remaining reaction mixture, 0.1 mL of DMSO was added, and the plate was incubated for additional 3 days at 250 rpm at 40° C., after which four mL of ethanol was added to the well. After centrifugation, 10 μl of the supernatant was analyzed with the chiral HPLC and enantio-excess of the ester was determined to be 100%.

Resolution C

To 0.5 ml 100 mM Heps.Na buffer (pH 8.5) in a well of a 24 well plate (capacity: 10 mL/well), 0.1 ml of Esperase 8.0 L, (protease from *Bacillus halodurans*) (Novozymes North America Inc.) and a solution of the racemic N—Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 hour, enantio-excess of the ester was determined to be 39.6% as following: 0.1 mL of the reaction mixture was removed and mixed well with 1 mL ethanol; after cenrifugation, 10 μl of the supernatant was analyzed with the chiral HPLC. To the remaining reaction mixture, 0.1 mL of DMSO was added, and the plate was incubated for additional 3 days at 250 rpm at 40° C., after which four mL of ethanol was added to the well. After centrifugation, 10 μl of the supernatant was analyzed with the chiral HPLC and enantio-excess of the ester was determined to be 100%.

Samples analysis was carried out in the following manner:
1) Sample preparation: About 0.5 ml of the reaction mixture was mixed well with 10 volume of EtOH. After centrifugation, 10 μl of the supernatant was injected onto HPLC column.
2) Conversion determination:
Column: YMC ODS A, 4.6×50 mm, S-5 μm
Solvent: A, 1 mM HCl in water; B, MeCN
Gradient: 30% B for 1 min; 30% to 45% B over 0.5 min; 45% B for 1.5 min; 45% to 30% B over 0.5 min.
Flow rate: 2 ml/min
UV Detection: 210 nm
Retention time: acid, 1.2 min; ester, 2.8 min.
3) Enantio-excess determination for the ester:
Column: CHIRACEL OD-RH, 4.6×150 mm, S-5 μm
Mobile phase: MeCN/50 mM $HClO_4$ in water (67/33)
Flow rate: 0.75 ml/min.
UV Detection: 210 nm.
Retention time:
(1S, 2R) isomer as acid: 5.2 min;
Rcaemate: 18.5 min and 20.0 min;
(1R, 2S) isomer as ester: 18.5 min.

2. Preparation of 1-aminocyclobutanecarboxylic acid methyl ester.hydrochloride

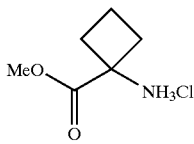

1-aminocyclobutanecarboxylic acid (100 mg, 0.869 mmol) (Tocris) was dissolved in 10 mL of MeOH, HCl gas was bubbled in for 2 h. The reaction mixture was stirred for 18 h, and then concentrated in vacuo to give 144 mg of a yellow oil. Trituration with 10 mL of ether provided 100 mg of the titled product as a white solid. $^1$H NMR (CDCl$_3$) δ 2.10–2.25 (m, 1H), 2.28–2.42 (m, 1H), 2.64–2.82 (m, 4H), 3.87 (s, 3H), 9.21 (br s, 3H).

3. Preparation of Racemic (1R,2R)/(1S,2S) 1-Amino-2-ethylcyclopropanecarboxylic acid tert-butyl ester, Shown Below

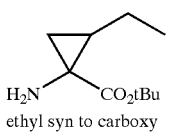
ethyl syn to carboxy

Step 1: Preparation of 2-Ethylcyclopropane-1,1-dicarboxylic acid di-tert-butyl ester, Shown Below

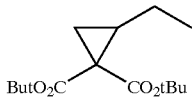

To a suspension of benzyltriethylammonium chloride (21.0 g, 92.2 mmol) in a 50% aqueous NaOH solution (92.4 g in 185 mL H$_2$O) was added 1,2-dibromobutane (30.0 g, 138.9 mmol) and di-tert-butylmalonate (20.0 g, 92.5 mmol). The reaction mixture was vigorously stirred 18 h at rt, a mixture of ice and water was then added. The crude product was extracted with CH$_2$Cl$_2$ (3×) and sequentially washed with water (3×), brine and the organic extracts combined. The organic layer was dried (MgSO$_4$), filtered and concentrated in vacuo. The resulting residue was flash chromatographed (100 g SiO$_2$, 3% Et$_2$O in hexane) to afford the titled product (18.3 g, 67.8 mmol, 73% yield) which was used directly in the next reaction.

Step 2: Preparation of Racemic 2-Ethylcyclopropane-1,1-dicarboxylic acid tert-butyl ester, Shown Below

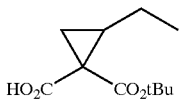

The product of Step 1 (18.3 g, 67.8 mmol) was added to a suspension of potassium tert-butoxide (33.55 g, 299.0 mmol) in dry ether (500 mL) at 0° C., followed by H$_2$O (1.35 mL, 75.0 mmol) and was vigorously stirred overnight at rt. The reaction mixture was poured in a mixture of ice and water and washed with ether (3×). The aqueous layer was acidified with a 10% aq. citric acid solution at 0° C. and extracted with EtOAc (3×). The combined organic layers were washed with water (2×), brine, dried (MgSO$_4$) and concentrated in vacuo to afford the titled product as a pale yellow oil (10 g, 46.8 mmol, 69% yield).

Step 3: Preparation of (1R,2R)/(1S,2S) 2-Ethyl-1-(2-trimethylsilanylethoxycarbonylamino)cyclopropane-carboxylic acid tert-butyl ester, Shown Below

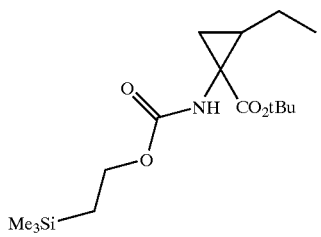

To a suspension, of the product of Step 2 (10 g, 46.8 mmol) and 3 g of freshly activated 4A molecular sieves in dry benzene (160 mL), was added Et$_3$N (7.50 mL, 53.8 mmol) and DPPA (11 mL, 10.21 mmol). The reaction mixture was refluxed for 3.5 h, 2-trimethylsilyl-ethanol (13.5 mL, 94.2 mmol) was then added, and the reaction mixture was refluxed overnite. The reaction mixture was filtered, diluted with Et$_2$O, washed with a 10% aqueous citric acid solution, water, saturated aqueous NaHCO$_3$, water (2×), brine (2×), dried (MgSO$_4$) and concentrated in vacuo. The residue was suspended with 10 g of Aldrich polyisocyanate scavenger resin in 120 mL of CH$_2$Cl$_2$, stirred at rt overnite and filtered to afford the titled product (8 g, 24.3 mmol; 52%) as a pale yellow oil: $^1$H NMR (CDCl$_3$) δ 0.03 (s, 9H), 0.97 (m, 5H), 1.20 (bm, 1H), 1.45 (s, 9H), 1.40–1.70 (m, 4H), 4.16 (m, 2H), 5.30 (bs, 1H)

Step 4: Preparation of Racemic (1R,2R)/(1S,2S) 1-Amino-2-ethylcyclopropanecarboxylic acid tert-butyl ester, Shown Below

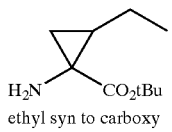
ethyl syn to carboxy

To the product of Step 3 (3 g, 9 mmol) was added a 1.0 M TBAF solution in THF (9.3 mL, 9.3 mmol) and the mixture heated to reflux for 1.5 h, cooled to rt and then diluted with 500 ml of EtOAc. The solution was successively washed with water (2×100 mL), brine (2×100 mL), dried (MgSO$_4$), concentrated in vacuo to provide the title intermediate 4. Preparation of 1-Amino-spiro[2.3]hexane-1-carboxylic acid methyl ester Hydrochloride Salt

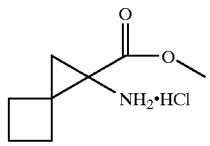

Step 1 Preparation of [2,3]hexane-1,1-dicarboxylic acid dimethyl ester, Shown Below

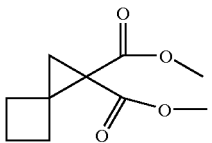

To a mixture of methylene-cyclobutane (1.5 g, 22 mmol) and Rh₂(OAc)₄ (125 mg, 0.27 mmol) in anhydrous CH₂Cl₂ (15 mL) was added 3.2 g (20 mmol) of dimethyl diazomalonate (prepared according to J. Lee et al. *Synth. Comm.,* 1995, 25, 1511–1515) at 0° C. over a period of 6 h. The reaction mixture was then warmed to rt and stirred for another 2 h. The mixture was concentrated and purified by flash chromatography (eluting with 10:1 hexane/Et₂O to 5:1 hexane/Et₂O) to give 3.2 g (72%) of [2,3]hexane-1,1-dicarboxylic acid dimethyl ester as a yellow oil. ¹H NMR (300 MHz, CDCl₃) δ 3.78 (s, 6H), 2.36 (m, 2H), 2.09 (m, 3H), 1.90 (m, 1H), 1.67 (s, 2H). LC-MS: MS m/z 199 (M⁺+1).

Step 2: Preparation of spiro[2,3]hexane-1,1-dicarboxylic acid methyl ester, Shown Below

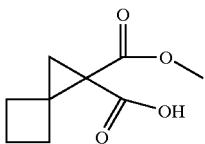

To the mixture of spiro [2,3]hexane-1,1-dicarboxylic acid dimethyl ester (200 mg, 1.0 mmol) in 2 mL of MeOH and 0.5 mL of water was added KOH (78 mg, 1.4 mmol). This solution was stirred at rt for 2 days. It was then acidified with dilute HCl and extracted two times with ether. The combined organic phases were dried (MgSO₄) and concentrated to yield 135 mg (73%) of 2 as a white solid. ¹H NMR (300 MHz, CDCl₃) δ 3.78 (s, 3H), 2.36–1.90 (m, 8H). LC-MS: MS m/z 185 (M⁺+1)

Step 3: Preparation of the Titled Product, 1-amino-spiro[2.3] hexane-1-carboxylic acid methyl ester Hydrochloride Salt To a mixture of spiro[2,3]hexane-1,1-dicarboxylic acid methyl ester (660 mg, 3.58 mmol) in 3 mL of anhydrous t-BuOH was added 1.08 g (3.92 mmol) of DPPA and 440 mg (4.35 mmol) of Et₃N. The mixture was heated at reflux for 21 h and then partitioned between H₂O and ether. The ether phase was dried over magnesium sulfate, filtered and concentrated in vacuo to yield an oil. To this oil was added 3 mL of a 4 M HCl/dioxane solution. This acidic solution was stirred at rt for 2 h and then concentrated in vacuo. The residue was triturated with ether to give 400 mg (58%) of dcsried prodict as a white solid. ¹H NMR (300 MHz, d6-DMSO) δ 8.96 (br s, 3H), 3.71 (s, 3H), 2.41 (m, 1H), 2.12 (m, 4H), 1.93 (m, 1H), 1.56 (q, 2H, J=8 Hz). LC-MS of free amine: MS m/z 156 (M⁺+1).

5. Preparation of 1-Amino-spiro[2.4]heptane-1-carboxylic acid methyl ester Hydrochloride Salt, Shown Below, was Prepared as Follows Step 1: Spiro[2.4]heptane-1,1-dicarboxylic acid dimethyl ester, Shown Below, was Prepared as Follows

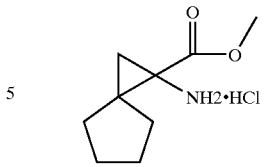

Using the same procedure described in the preparation of 1-Amino-spiro[2.3]hexane-1-carboxylic acid methyl ester hydrochloride salt 1.14 g (13.9 mmol) of methylenecyclopentane and 2.0 g (12.6 mmol) of dimethyl diazomalonate were reacted to yield 1.8 g (67%) of the dimethyl ester. ¹H NMR (300 MHz, CDCl₃) δ 3.73 (s, 6H), 1.80 (m, 2H), 1.70 (m, 4H), 1.60 (m, 4H). LC-MS: MS m/z 213 (M⁺+1).

Step 2: Preparation of Spiro[2.4]heptane-1,1-dicarboxylic acid methyl ester, Shown Below, was Prepared as Follows

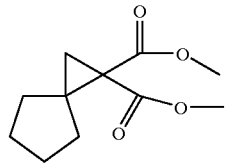

Using the same procedure described in the preparation of 1-Amino-spiro[2.3]hexane-1-carboxylic acid methyl ester hydrochloride salt 1.7 g (8.0 mmol) of the produc of Step 1 and 493 mg (8.8 mmol) of KOH gave 1.5 g (94%) of spiro[2.4]heptane-1,1-dicarboxylic acid methyl ester. ¹H NMR (300 MHz, CDCl₃) δ 3.80 (s, 3H), 2.06 (d, 1H, J=5 Hz), 1.99 (d, 1H, J=5 Hz), 1.80–1.66 (m, 8H). LC-MS: MS m/z 199 (M⁺+1).

Step 3: Preparation of 1-Amino-spiro[2.4]heptane-1-carboxylic acid methyl ester Hydrochloride Salt, Shown Below, was Prepared as Follows

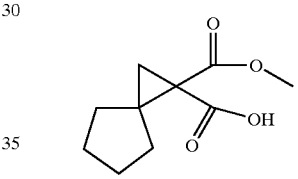

Using the same procedure described above in preparation of 1-Amino-spiro[2.3]hexane-1-carboxylic acid methyl ester hydrochloride salt, 500 mg (2.5 mmol) of the product of Step 2, 705 mg (2.5 mmol) of DPPA and 255 mg (2.5 mmol) of Et₃N gave 180 mg (35%) of this hydrochloride salt. ¹H NMR (300 MHz, d6-DMSO) δ 8.90 (br s, 3H), 3.74 (s, 3H), 1.84 (m, 1H), 1.69 (m, 4H), 1.58 (m, 4H), 1.46 (d, 1H, J=6 Hz). LC-MS of free amine: MS m/z 170 (M⁺+1).

6. Preparation of 5-Amino-spiro[2.3]hexane-5-carboxylic acid ethyl ester, Shown Below, was Prepared as Follows

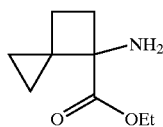

Spiro[2.3]hexan-4-one (500 mg, 5 mmol), which was prepared from bicyclopropylidene (A. Meijere et al. *Org. Syn.* 2000, 78, 142–151) according to A. Meijere et al. *J. Org. Chem.* 1988, 53, 152–161, was combined with ammonium carbamate (1.17 g, 15 mmol) and potassium cyanide (812 mg, 12.5 mmol) in 50 mL of EtOH and 50 mL of water. The mixture was heated at 55° C. for 2 days. Then NaOH (7 g, 175 mmol) was added and the solution was heated under reflux overnight. The mixture was then chilled to 0° C., acidified to pH 1 with concentrated HCl, and concentrated in vacuo. EtOH was added to the crude amino acid mixture and then concentrated to dryness (5×) so as to remove residual water. The residue dissolved in 100 mL of EtOH was cooled to 0° C. It was then treated with 1 mL of $SOCl_2$ and refluxed for 3 days. The solids were removed by filtration, and the filtrate was concentrated in vacuo to give the crude product. The crude product was partitioned between 3 N NaOH, NaCl and EtOAc. The organic phase was dried over potassium carbonate and concentrated. The residue was purified using column chromatography on C18 silica gel (eluting with $MeOH/H_2O$) to yield 180 mg (21%) of 15 as an oil. $^1H$ NMR (300 MHz, $CDCl_3$) δ 8.20 (br s, 2H), 4.27 (s, 2H), 2.80 (s, 1H), 2.54 (s, 1H), 2.34 (m, 2H), 1.31 (s, 3H), 1.02 (s, 1H), 0.66 (m, 3H). $^{13}C$ NMR (300 MHz, $CDCl_3$) δ 170.2(s), 63.0(s), 62.8 (s), 26.1 (s), 26.0 (s), 24.9 (s), 13.9 (s), 11.4 (s), 10.9 (s). LC-MS: MS m/z 170 ($M^+$+1).

Example 207

Biological Studies

Recombinant HCV NS3/4A Protease Complex FRET Peptide Assay

The purpose of this in vitro assay was to measure the inhibition of HCV NS3 protease complexes, derived from the BMS, H77C or J416S strains, as described below, by compounds of the present invention. This assay provides an indication of how effective compounds of the present invention would be in inhibiting HCV proteolytic activity.

Serum from an HCV-infected patient was obtained from Dr. T. Wright, San Francisco Hospital. An engineered full-length cDNA (compliment deoxyribonucleic acid) template of the HCV genome (BMS strain) was constructed from DNA fragments obtained by reverse transcription-PCR (RT-PCR) of serum RNA (ribonucleic acid) and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A Follett, P L Yap and H Marsden, J. Clin. Microbiol., 31(6), 1493–1503 (1993)). The amino acid sequence of the nonstructural region, NS2–5B, was shown to be >97% identical to HCV genotype 1a (II77C) and 87% identical to genotype 1b (J4L6S). The infectious clones, H77C (1a genotype) and J4L6S (1b genotype) were obtained from R. Purcell (NIH) and the sequences are published in Genbank (AAB67036, see Yanagi,M., Purcell,R. H., Emerson,S. U. and Bukh,J. Proc. Natl. Acad. Sci. U.S.A. 94(16),8738–8743 (1997); AF054247, see Yanagi,M., St Claire,M., Shapiro,M., Emerson,S. U., Purcell,R. H. and Bukh,J, Virology 244 (1), 161–172. (1998)).

The BMS, H77C and J4L6S strains were used for production of recombinant NS3/4A protease complexes. DNA encoding the recombinant HCV NS3/4A protease complex (amino acids 1027 to 1711) for these strains were manipulated as described by P. Gallinari et al. (see Gallinari P, Paolini C, Brennan D, Nardi C, Steinkuhler C, De Francesco R. Biochemistry. 38(17):5620–32, (1999)). Briefly, a three-lysine solubilizing tail was added at the 3'-end of the NS4A coding region. The cysteine in the P1 position of the NS4A–NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector (Novagen) and the NS3/4A complex was expressed in *Escherichia. coli* strain BL21 (DE3) (Invitrogen) following the protocol described by P. Gallinari et al. (see Gallinari P, Brennan D, Nardi C, Brunetti M, Tomei L, Steinkuhler C, De Francesco R., J. Virol. 72(8) :6758–69 (1998)) with modifications. Briefly, NS3/4A expression was induced with 0.5 mM Isopropyl β-D-1-thiogalactopyranoside (IPTG) for 22 hr at 20° C. A typical fermentation (10 L) yielded approximately 80 g of wet cell paste. The cells were resuspended in lysis buffer (10 mL/g) consisting of 25 mM N-(2-Hydroxyethyl)Piperazine-N'-(2-Ethane Sulfonic acid) (HEPES), pH 7.5, 20% glycerol, 500 mM Sodium Chloride (NaCl), 0.5% Triton-X100, 1 ug/ml lysozyme, 5 mM Magnesium Chloride ($MgCl_2$), 1 ug/ml DnaseI, 5 mM β-Mercaptoethanol (βME), Protease inhibitor—Ethylenediamine Tetraacetic acid (EDTA) free (Roche), homogenized and incubated for 20 mins at 4° C. The homogenate was sonicated and clarified by ultra-centrifugation at 235000 g for 1 hr at 4° C. Imidazole was added to the supernatant to a final concentration of 15 mM and the pH adjusted to 8.0. The crude protein extract was loaded on a Nickel-Nitrilotriacetic acid (Ni-NTA) column pre-equilibrated with buffer B (25 mM HEPES, pH 8.0, 20% glycerol, 500 mM NaCl, 0.5% Triton-X100, 15 mM imidazole, 5 mM βME). The sample was loaded at a flow rate of 1 mL/min. The column was washed with 15 column volumes of buffer C (same as buffer B except with 0.2% Triton-X100). The protein was eluted with 5 column volumes of buffer D (same as buffer C except with 200 mM Imidazole).

NS3/4A protease complex-containing fractions were pooled and loaded on a desalting column Superdex-S200 pre-equilibrated with buffer D (25 mM HEPES, pH7.5, 20% glycerol, 300 mM NaCl, 0.2% Triton-X100, 10 mM βME). Sample was loaded at a flow rate of 1 mL/min. NS3/4A protease complex-containing fractions were pooled and concentrated to approximately 0.5 mg/ml. The purity of the NS3/4A protease complexes, derived from the BMS, H77C and J4L6S strains, were judged to be greater than 90% by SDS-PAGE and mass spectrometry analyses.

The enzyme was stored at −80° C., thawed on ice and diluted prior to use in assay buffer. The substrate used for the NS3/4A protease assay was RET S1 (Resonance Energy Transfer Depsipeptide Substrate; AnaSpec, Inc. cat # 22991) (FRET peptide), described by Taliani et al. in Anal. Biochem. 240(2):60–67 (1996). The sequence of this peptide is loosely based on the NS4A/NS4B natural cleavage site except there is an ester linkage rather than an amide bond at the cleavage site. The peptide substrate was incubated with one of the three recombinant NS3/4A complexes, in the absence or presence of a compound of the present invention, and the formation of fluorescent reaction product was followed in real time using a Cytofluor Series 4000.

The reagents were as follow: HEPES and Glycerol (Ultrapure) were obtained from GIBCO-BRL. Dimethyl Sulfoxide (DMSO) was obtained from Sigma. β-Mercaptoethanol was obtained from Bio Rad. Assay buffer: 50 mM HEPES, pH7.5; 0.15M NaCl; 0.1% Triton; 15% Glycerol; 10 mM βME. Substrate: 2 µM final concentration (from a 2 mM stock solution in DMSO stored at −20° C.). HCV NS3/4A type 1a (1b), 2–3 nM final concentration (from a 5 µM stock solution in 25 mM HEPES, pH7.5, 20% glycerol, 300 mM NaCl, 0.2% Triton-X100, 10 mM βME). For compounds with potencies approaching the assay limit, the assay was made more sensitive by adding 50 µg/ml Bovine Serum Albumin (Sigma) to the assay buffer and reducing the end protease concentration to 300 pM.

The assay was performed in a 96-well polystyrene black plate from Falcon. Each well contained 25 µl NS3/4A protease complex in assay buffer, 50 µl of a compound of the present invention in 10% DMSO/assay buffer and 25 µl substrate in assay buffer. A control (no compound) was also prepared on the same assay plate. The enzyme complex was mixed with compound or control solution for 1 min before initiating the enzymatic reaction by the addition of substrate. The assay plate was read immediately using the Cytofluor Series 4000 (Perspective Biosystems). The instrument was set to read an emission of 340 nm and excitation of 490 nm at 25° C. Reactions were generally followed for approximately 15 minutes.

The percent inhibition was calculated with the following equation:

$$100-[(\delta F_{inh}/\delta F_{con})\times 100]$$

where δF is the change in fluorescence over the linear range of the curve. A non-linear curve fit was applied to the inhibition-concentration data, and the 50% effective concentration (IC$_{50}$) was calculated by the use of Excel Xl-fit software using the equation, $y=A+((B-A)/(1+((C/x)^\wedge D)))$.

All of the compounds tested were found to have IC50s of 1.3 µM or less. Further, compounds of the present invention, which were tested against more than one type of NS3/4A complex, were found to have similar inhibitory properties though the compounds uniformly demonstrated greater potency against the 1b strains as compared to the 1a strains.

Specificity Assays

The specificity assays were performed to demonstrate the selectivity of the compounds of the present invention in inhibiting HCV NS3/4A protease as compared to other serine or cysteine proteases.

The specificities of compounds of the present invention were determined against a variety of serine proteases: human sputum elastase (HS), porcine pancreatic elastase (PPE) and human pancreatic chymotrypsin and one cysteine protease: human liver cathepsin B. In all cases a 96-well plate format protocol using colorimetric p-nitroaniline (pNA) substrate specific for each enzyme was used as described previously (Patent WO 00/09543) with some modifications to the serine protease assays. All enzymes were purchased from Sigma while the substrates were from Bachem.

Each assay included a 2 hr enzyme-inhibitor pre-incubation at room temperature followed by addition of substrate and hydrolysis to ~30% conversion as measured on a Spectramax Pro microplate reader. Compound concentrations varied from 100 to 0.4 µM depending on their potency.

The final conditions for each assay were as follows:
50 mM Tris(hydroxymethyl)aminomethane hydrochloride (Tris-HCl) pH8, 0.5M Sodium Sulfate (Na$_2$SO$_4$), 50 mM NaCl, 0.1 mM EDTA, 3% DMSO, 0.01% Tween-20 with:

133 µM succ-AAA-pNA and 20 nM HS or 8 nM PPE; 100 µM succ-AAPF-pNA and 250 pM Chymotrypsin.

100 mM NaHPO$_4$ (Sodium Hydrogen Phosphate) pH 6, 0.1 mM EDTA, 3% DMSO, 1 mM TCEP (Tris(2-carboxyethyl)phosphine hydrochloride), 0.01% Tween-20, 30 µM Z-FR-pNA and 5 nM Cathepsin B (enzyme stock activated in buffer containing 20 mM TCEP before use).

The percentage of inhibition was calculated using the formula:

$$[1-((UV_{inh}-UV_{blank})/(UV_{ctl}-UV_{blank}))]\times 100$$

A non-linear curve fit was applied to the inhibition-concentration data, and the 50% effective concentration (IC$_{50}$) was calculated by the use of Excel Xl-fit software.

HCV Replicon Cell-based Assay

An HCV replicon whole cell system was established as described by Lohmann V, Korner F, Koch J, Herian U, Theilmann L, Bartenschlager R., Science 285(5424):110–3 (1999). This system enabled us to evaluate the effects of our HCV Protease compounds on HCV RNA replication. Briefly, using the HCV strain 1B sequence described in the Lohmann paper (Assession number: AJ238799), an HCV cDNA was generated encoding the 5' internal ribosome entry site (IRES), the neomycin resistance gene, the EMCV (encephalomyocarditis viurs)-IRES and the HCV nonstructural proteins, NS3–NS5B, and 3' non-translated region (NTR). In vitro transcripts of the cDNA were transfected into the human hepatoma cell line, Huh7. Selection for cells constitutively expressing the HCV replicon was achieved in the presence of the selectable marker, neomycin (G418). Resulting cell lines were characterized for positive and negative strand RNA production and protein production over time.

Huh7 cells, constitutively expressing the HCV replicon, were grown in Dulbecco's Modified Eagle Media (DMEM) containing 10% Fetal calf serum (FCS) and 1 mg/ml G418 (Gibco-BRL). Cells were seeded the night before (1.5×10$^4$ cells/well) in 96-well tissue-culture sterile plates. Compound and no compound controls were prepared in DMEM containing 4% FCS, 1:100 Penicillin/Streptomysin, 1:100 L-glutamine and 5% DMSO in the dilution plate (0.5% DMSO final concentration in the assay). Compound/DMSO mixes were added to the cells and incubated for 4 days at 37° C. After 4 days, plates were rinsed thoroughly with Phosphate-Buffered Saline (PBS) (3 times 150 µl). The cells were lysed with 25 µl of a lysis assay reagent containing the FRET peptide (RET S1, as described for the in vitro enzyme assay). The lysis assay reagent was made from 5× cell Luciferase cell culture lysis reagent(Promega #E153A) diluted to 1× with distilled water, NaCl added to 150 mM final, the FRET peptide diluted to 10 µM final from a 2 mM stock in 100% DMSO. The plate was then placed into the Cytofluor 4000 instrument which had been set to 340 nm excitation/490 emission, automatic mode for 21 cycles and the plate read in a kinetic mode. EC$_{50}$ determinations were carried out as described for the IC$_{50}$ determinations.

As a secondary assay, EC$_{50}$ determinations from the replicon FRET assay were confirmed in a quantitative RNA assay. Cells were lyzed using the Rneasy kit (Qiagen). Purified total RNA was normalized using RiboGreen (Jones L J, Yue S T, Cheung C Y, Singer V L, Anal. Chem., 265(2):368–74 (1998)) and relative quantitation of HCV RNA expression assessed using the Taqman procedure (Kolykhalov A A, Mihalik K, Feinstone S M, Rice C M, Journal of Virology 74, 2046–2051 (2000)) and the Platinum Quantitative RT-PCR Thermoscript One-Step kit (Invitrogen cat # 11731-015). Briefly, RNA made to a volume of 5 $\mu$l ($\leq$1 ng) was added to a 20 $\mu$l Ready-Mix containing the following: 1.25× Thermoscript reaction mix (containing Magnesium Sulfate and 2-deoxynucleoside 5'-triphosphates (dNTPs)), 3 mM dNTPs, 200 nM forward primer (sequence: 5'-gggagagccatagtggtctgc-3'), 600 nM reverse primer (5'-cccaaatctccaggcattga-3'), 100 nM probe (5'-6-FAM-cggaattgccaggacgaccgg-BHQ-1-3')(FAM: Fluorescein-aminohexyl amidite; BHQ: Black Hole Quencher), 1 $\mu$M Rox reference dye (Invitrogen cat # 12223-012) and Thermoscript Plus Platinum Taq polymerase mixture. All primers were designed with ABI Prism 7700 software and obtained from Biosearch Technologies, Novato, Calif. Samples containing known concentrations of HCV RNA: transcript were run as standards. Using the following cycling protocol (50° C., 30 min; 95° C., 5 min; 40 cycles of 95° C., 15 sec, 60° C., 1 min), HCV RNA expression was quantitated as described in the Perkin Elmer manual using the ABI Prism 7700 Sequence Detector.

The luciferase reporter assay was also used to confirm compound potency in the replicon. Utilization of a replicon luciferase reporter assay was first described by Krieger et al (Krieger N, Lohmann V, and Bartenschlager R, J. Virol. 75(10):4614–4624 (2001)). The replicon construct described for our FRET assay was modified by replacing the resistance gene neomycin with the Blasticidin-resistance gene fused to the N-terminus of the humanized form of Renilla luciferase (restriction sites Asc1/Pme1 used for the subcloning). The adaptive mutation at position 1179 (serine to isoleucine) was also introduced (Blight K J, Kolykhalov, A A, Rice, C M, Science 290(5498):1972–1974). The luciferase reporter assay was set up by seeding huh7 cells the night before at a density of 2×10$^6$ cells per T75 flask. Cells were washed the next day with 7.5 ml Opti-MEM. Following the Invitrogen protocol, 40 $\mu$l DMRIE-C was vortexed with 5 ml Opti-MEM before adding 5 $\mu$g HCV reporter replicon RNA. The mix was added to the washed huh7 cells and left for 4 hours at 37° C. In the mean time, serial compound dilutions and no compound controls were prepared in DMEM containing 10% FCS and 5% DMSO in the dilution plate (0.5% DMSO final concentration in the assay). Compound/DMSO mixes were added to each well of a 24-well plate. After 4 hours, the transfection mix was aspirated, and cells washed with 5 ml of Opti-MEM before trypsinization. Trypsinized cells were resuspended in 10% DMEM and seeded at 2×10$^4$ cells/well in the 24-well plates containing compound or no compound controls. Plates were incubated for 4 days. After 4 days, media was removed and cells washed with PBS. 100 $\mu$l 1×Renilla Luciferase Lysis Buffer (Promega) was immediately added to each well and the plates either frozen at −80° C. for later analysis, or assayed after 15 mins of lysis. Lysate (40 $\mu$l) from each well was transferred to a 96-well black plate (clear bottom) followed by 200 $\mu$l 1×Renilla Luciferase assay substrate. Plates were read immediately on a Packard TopCount NXT using a luminescence program.

The percentage inhibition was calculated using the formula below:

% control=average luciferase signal in experimental wells (+compound) average luciferase signal in DMSO control wells (−compound)

The values were graphed and analyzed using XLFit to obtain the EC$_{50}$ value.

BIOLOGICAL EXAMPLES

Representative compounds of the invention were assessed in the HCV replicon cell assay and/or in several of the outlined specificity assays. For example, Compound 1 was found to have an IC$_{50}$ of 1.8 nM against the NS3/4A BMS strain in the enzyme assay. Similar potency values were obtained with the published H77C (IC$_{50}$ of 1.2 nM) and J4L6S (IC$_{50}$ of 1.1 nM) strains. The EC$_{50}$ value in the replicon assay was 13.9 nM.

In the specificity assays, the same compound was found to have the following activity: HS=43 $\mu$M; PPE>100 $\mu$M; Chymotrypsin>100 $\mu$M; Cathepsin B>100 $\mu$M. These results indicate this family of compounds are highly specific for the NS3 protease and many of these members inhibit HCV replicon replication.

The compounds of the current invention were tested using the assays described above and found to have activities in the following ranges:

IC$_{50}$ Activity Ranges (NS3/4A BMS Strain): A is 5–50 micromolar ($\mu$M); B is 0.5–5 $\mu$M; C is 0.05–0.5 $\mu$M, D is <0.05 $\mu$M EC$_{50}$ Activity Ranges: A is 5–50 micromolar ($\mu$M); B is 0.5–5 $\mu$M; C is 0.05–0.5 $\mu$M, D is <0.05 $\mu$M The structures of compounds used in the tests can be found from the Patent compound number shown in the Actvity Table below.

In accordance with the present invention, preferred compound have a biological activity (EC$_{50}$) of 5 $\mu$M or less, more preferably 0.5 $\mu$M or less and most preferably 0.05 $\mu$M or less.

Activity Table

| Patent Cmpd # | Patent Example # | IC50 range | EC50 range |
| --- | --- | --- | --- |
| 1 | 9 | D | D |
| 2 | 10 | D | D |
| 3 | 11 | C | C |
| 4 | 12 | C | C |
| 5 | 13 | D | D |
| 6 | 14 | D | C |
| 7 | 19 | D | D |
| 8 | 20 | D | D |
| 9 | 21 | D | D |
| 10 | 22 | D | D |
| 11 | 24 | D | D |
| 12 | 25 | D | D |
| 13 | 26 | D | D |
| 27 | 27 | D | D |
| 28 | 28 | D | D |
| 29 | 29 | D | D |
| 30 | 30 | D | D |
| 31 | 31 | D | C |
| 32 | 32 | D | D |
| 33 | 33 | D | C |
| 34 | 34 | D | D |
| 35 | 35 | D | D |

Activity Table -continued

| Patent Cmpd # | Patent Example # | IC50 range | EC50 range |
|---|---|---|---|
| 36 | 36 | D | D |
| 37 | 37 | D | D |
| 38 | 38 | D | D |
| 39 | 39 | D | D |
| 40 | 40 | D | C |
| 41 | 41 | D | C |
| 42 | 42 | C | C |
| 43 | 43 | D | D |
| 44 | 44 | D | C |
| 45 | 45 | D | D |
| 46 | 46 | D | D |
| 47 | 47 | D | D |
| 48 | 48 | D | D |
| 49 | 49 | D | C |
| 50 | 50 | C | B |
| 51 | 51 | D | D |
| 52 | 52 | D | D |
| 53 | 53 | D | D |
| 54 | 54 | D | D |
| 55 | 55 | D | C |
| 56 | 56 | D | C |
| 57 | 57 | D | C |
| 58 | 58 | D | C |
| 59 | 59 | D | C |
| 60 | 60 | D | B |
| 61 | 61 | D | C |
| 62 | 62 | D | C |
| 63 | 63 | D | D |
| 64 | 64 | D | C |
| 65 | 65 | D | C |
| 66 | 66 | D | C |
| 67 | 67 | C | C |
| 68 | 68 | D | C |
| 69 | 69 | D | D |
| 70 | 70 | D | D |
| 71 | 71 | C | B |
| 72 | 72 | B | A |
| 73 | 73 | B | |
| 74 | 74 | B | A |
| 75 | 75 | D | B |
| 76 | 76 | C | B |
| 77 | 77 | D | D |
| 78 | 78 | | |
| 79 | 79 | D | C |
| 80 | 80 | D | C |
| 81 | 81 | C | C |
| 100 | 100 | C | B |
| 101 | 101 | C | B |
| 102 | 102 | C | B |
| 103 | 103 | C | C |
| 104 | 104 | C | B |
| 105 | 105 | D | C |
| 106 | 106 | D | C |
| 107 | 107 | C | B |
| 108 | 108 | C | B |
| 109 | 109 | B | |
| 110 | 110 | C | C |
| 111 | 111 | C | C |
| 112 | 112 | C | C |
| 113 | 113 | B | |
| 119 | 119 | D | C |
| 120 | 120 | D | C |
| 200 | 200 | C | B |
| 201 | 201 | B | A |
| 202 | 202 | C | B |
| 203 | 203 | D | C |
| 204 | 204 | C | C |
| 205 | 205 | D | C |

Example 208

In accord with the present invention the following compounds can be made using the methods and intermediates described herein. It should be understood that this list of compounds in no way limits the invention as described.

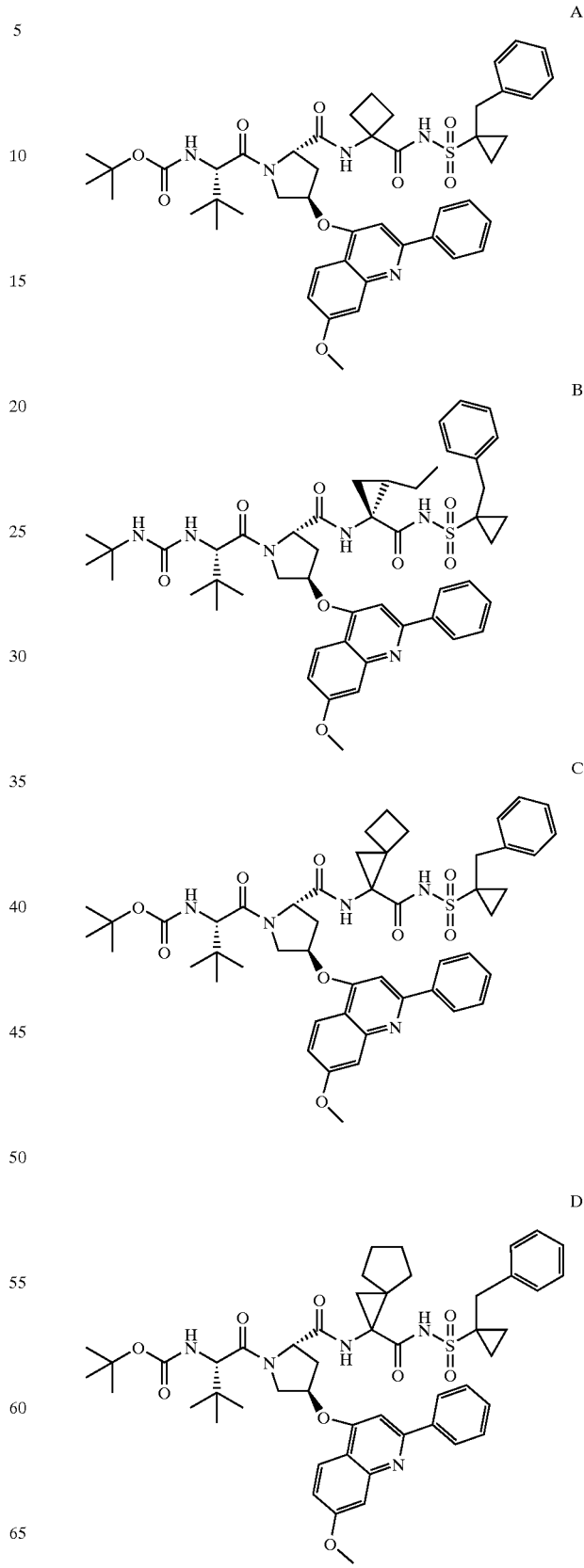

E

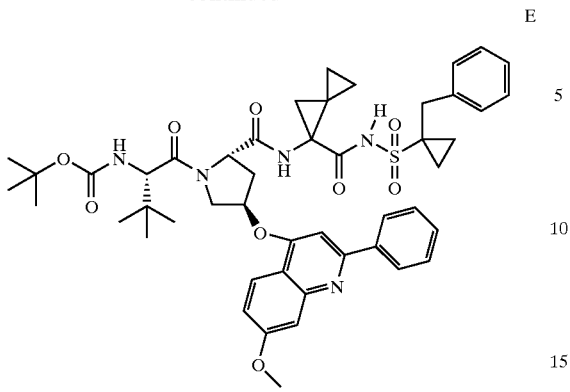

Although the invention has been described with respect to specific aspects, those skilled in the art will recognize that other aspects, not specifically described herein, are intended to be included within the scope of the claims that follow.

What is claimed is:

1. A compound having the formula:

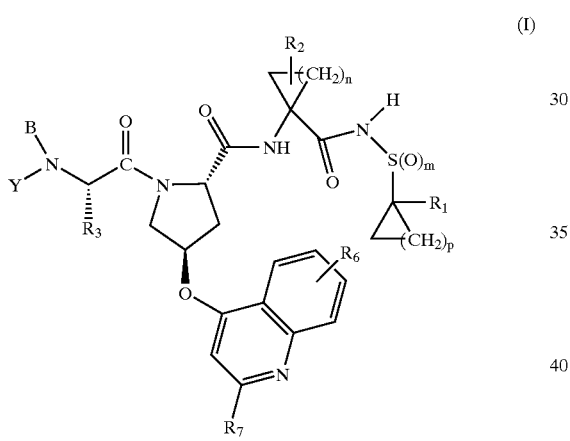

(I)

wherein:

(a) $R_1$ is trialkylsilane; halo; $C_{3-7}$ cycloalkyl, $C_{4-7}$ cycloalkenyl; $C_{6-10}$ aryl; $C_{7-14}$ alkylaryl; $C_{6-10}$ aryloxy; $C_{7-14}$ alkylaryloxy; $C_{8-15}$ alkylarylester, Het; or $C_{1-8}$ alkyl optionally substituted with $C_{1-6}$ alkoxy, hydroxy, halo, $C_{2-10}$ alkenyl, $C_{2-10}$ alkynyl, $C_{3-7}$ cycloalkyl, $C_{4-7}$ cycloalkenyl, $C_{6-10}$ aryl, $C_{7-14}$ alkylaryl, $C_{6-10}$ aryloxy, $C_{7-14}$ alkylaryloxy, $C_{8-15}$ alkylarylester or Het;

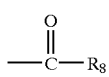

wherein $R_8$ is $C_{3-7}$ cycloalkyl, $C_{4-7}$ cycloalkenyl; $C_{6-10}$ aryl; $C_{7-14}$ alkylaryl; $C_{6-10}$ aryloxy; $C_{7-14}$ alkylaryloxy; $C_{8-15}$ alkylarylester; Het; or $C_{1-8}$ alkyl optionally substituted with $C_{1-6}$ alkoxy, hydroxy, halo, $C_{2-10}$ alkenyl, $C_{2-10}$ alkynyl, $C_{3-7}$ cycloalkyl, $C_{4-7}$ cycloalkenyl, $C_{6-10}$ aryl, $C_{7-14}$ alkylaryl, $C_{6-10}$ aryloxy, $C_{7-14}$ alkylaryloxy, $C_{8-15}$ alkylarylester or Het;

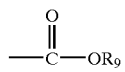

wherein $R_9$ is $C_{3-7}$ cycloalkyl, $C_{4-7}$ cycloalkenyl; $C_{6-10}$ aryl; $C_{7-14}$ alkylaryl; $C_{6-10}$ aryloxy; $C_{7-14}$ alkylaryloxy; $C_{8-15}$ alkylarylester, Het; or $C_{1-8}$ alkyl optionally substituted with $C_{1-6}$ alkoxy, hydroxy, halo, $C_{2-10}$ alkenyl, $C_{2-10}$ alkynyl, $C_{3-7}$ cycloalkyl, $C_{4-7}$ cycloalkenyl, $C_{6-10}$ aryl, $C_{7-14}$ alkylaryl, $C_{6-10}$ aryloxy, $C_{7-14}$ alkylaryloxy, $C_{8-15}$ alkylarylester or Het;

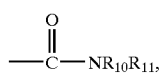

wherein $R_{10}$ and $R_{11}$ are each independently $C_{3-7}$ cycloalkyl, $C_{4-7}$ cycloalkenyl; $C_{6-10}$ aryl; $C_{7-14}$ alkylaryl; $C_{6-10}$ aryloxy; $C_{7-14}$ alkylaryloxy; $C_{8-15}$ alkylarylester; Het; or $C_{1-8}$ alkyl optionally substituted with $C_{1-6}$ alkoxy, hydroxy, halo, $C_{2-10}$ alkenyl, $C_{2-10}$ alkynyl, $C_{3-7}$ cycloalkyl, $C_{4-7}$ cycloalkenyl, $C_{6-10}$ aryl, $C_{7-14}$ alkylaryl, $C_{6-10}$ aryloxy, $C_{7-14}$ alkylaryloxy, $C_{8-15}$ alkylarylester or Het; —$SO_2R_{12}$ wherein $R_{12}$ is $C_{3-7}$ cycloalkyl, $C_{4-7}$ cycloalkenyl; $C_{6-10}$ aryl; $C_{7-14}$ alkylaryl; $C_{6-10}$ aryloxy; $C_{7-14}$ alkylaryloxy; $C_{8-15}$ alkylarylester; Het; or $C_{1-8}$ alkyl optionally substituted with $C_{1-6}$ alkoxy, hydroxy, halo, $C_{2-10}$ alkenyl, $C_{2-10}$ alkynyl, $C_{3-7}$ cycloalkyl, $C_{4-7}$ cycloalkenyl, $C_{6-10}$ aryl, $C_{7-14}$ alkylaryl, $C_{6-10}$ aryloxy, $C_{7-14}$ alkylaryloxy, $C_{8-15}$ alkylarylester or Het;

or

wherein $R_{13}$ is $C_{3-7}$ cycloalkyl, $C_{4-7}$ cycloalkenyl; $C_{6-10}$ aryl; $C_{7-14}$ alkylaryl; $C_{6-10}$ aryloxy; $C_{7-14}$ alkylaryloxy; $C_{8-15}$ alkylarylester; Het; or $C_{1-8}$ alkyl optionally substituted with $C_{1-6}$ alkoxy, hydroxy, halo, $C_{2-10}$ alkenyl, $C_{2-10}$ alkynyl, $C_{3-7}$ cycloalkyl, $C_{4-7}$ cycloalkenyl, $C_{6-10}$ aryl, $C_{7-14}$ alkylaryl, $C_{6-10}$ aryloxy, $C_{7-14}$ alkylaryloxy, $C_{8-15}$ alkylarylester or Het;

(b) $R_2$ is $C_{1-6}$ alkyl, $C_{2-6}$ alkenyl or $C_{3-7}$ cycloalkyl, each optionally substituted from one to three times with halogen; or $R_2$ is H; or $R_2$ together with the carbon to which it is attached forms a 3, 4 or 5 membered ring;

(c) $R_3$ is $C_{1-8}$ alkyl optionally substituted with halo, cyano, amino, $C_{1-6}$ dialkylamino, $C_{6-10}$ aryl, $C_{7-14}$ alkylaryl, $C_{1-6}$ alkoxy, carboxy, hydroxy, aryloxy, $C_{7-14}$ alkylaryloxy, $C_{2-6}$ alkylester, $C_{8-15}$ alkylarylester; $C_{3-12}$ alkenyl, $C_{3-7}$ cycloalkyl, or $C_{4-10}$ alkylcycloalkyl, wherein the cycloalkyl or alkylcycloalkyl are optionally substituted with hydroxy, $C_{1-6}$ alkyl, $C_{2-6}$ alkenyl or $C_{1-6}$ alkoxy; or $R_3$ together with the carbon atom to which it is attached forms a $C_{3-7}$ cycloalkyl group optionally substituted with $C_{2-6}$ alkenyl;

(d) $R_6$ is H, $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono- or or di-halo-$C_{1-6}$ alkoxy, cyano, halo, thioalkyl, hydroxy, alkanoyl, $NO_2$, SH, , amino, $C_{1-6}$ alkylamino, di ($C_{1-6}$)

alkylamino, di ($C_{1-6}$) alkylamide, carboxyl, ($C_{1-6}$) carboxyester, $C_{1-6}$ alkylsulfone, $C_{1-6}$ alkylsulfoxide, $C_{1-6}$ alkylsulfonamide or di ($C_{1-6}$) alkyl(alkoxy)amine;

(e) $R_7$ is H, $C_{1-6}$ alkyl, $C_{3-7}$ cycloalkyl, $C_{6-10}$ aryl, $C_{7-14}$ alkylaryl; $C_{6-10}$ aryloxy; $C_{7-14}$ alkylaryloxy; $C_{8-15}$ alkylarylester or Het;

(f) m is 1 or 2;

(g) n is 1 or 2;

(h) p is 1, 2 or 3;

(i) Y is H, phenyl substituted with nitro, pyridyl substituted with nitro, or $C_{1-6}$ alkyl optionally substituted with cyano, OH or $C_{3-7}$ cycloalkyl; provided that if $R_4$ or $R_5$ is H then Y is H;

(j) B is H, $C_{1-6}$ alkyl, $R_4$—(C=O)—, $R_4O(C=O)$—, $R_4$—N($R_5$)—C(=O)—, $R_4$—N($R_5$)—C(=S)—, $R_4SO_4$—, or $R_4$-N($R_5$)—SO$_2$—;

(k) $R_4$ is (i) $C_{1-10}$ alkyl optionally substituted with phenyl, carboxyl, $C_{1-6}$ alkanoyl, 1–3 halogen, hydroxy, —OC(O)$C_{1-6}$ alkyl, $C_{1-6}$ alkoxy, amino optionally substituted with $C_{1-6}$ alkyl, amido, or (lower alkyl) amido; (ii) $C_{3-7}$ cycloalkyl, $C_{3-7}$ cycloalkoxy, or $C_{4-10}$ alkylcycloalklyl, each optionally substituted with hydroxy, carboxyl, ($C_{1-6}$ alkoxy)carbonyl, amino optionally substituted with $C_{1-6}$ alkyl, amido, or (lower alkyl) amido; (iii) $C_{6-10}$ aryl or $C_{7-16}$ arylalkyl, each optionally substituted with $C_{1-6}$ alkyl, halogen, nitro, hydroxy, amido, (lower alkyl) amido, or amino optionally substituted with $C_{1-6}$ alkyl; (iv) Het; (v) bicyclo (1.1.1)pentane; or (vi) —C(O)O$C_{1-6}$ alkyl, $C_{2-6}$alkenyl or $C_{2-6}$ alkynyl; and (l) $R_5$ is H; $C_{1-6}$ alkyl optionally substituted with 1–3 halogens; or $C_{1-6}$ alkoxy provided $R_4$ is $C_{1-10}$ alkyl; or a pharmaceutically acceptable salt, solvate or prodrug thereof.

2. The compound of claim 1 wherein $R_1$ is $C_{1-8}$ alkyl optionally substituted with $C_{1-6}$ alkoxy, hydroxy, halo, $C_{2-10}$ alkenyl, $C_{2-10}$ alkynyl, $C_{3-6}$ cycloalkyl, $C_{4-7}$ cycloalkenyl, $C_{6-10}$ aryl, $C_{7-14}$ alkylaryl, $C_{6-10}$ aryloxy, $C_{7-14}$ alkylaryloxy, $C_{8-15}$ alkylarylester or Het.

3. The compound of claim 2 wherein $R_1$ is $C_{1-8}$ alkyl optionally substituted with $C_{1-6}$ alkoxy, hydroxy, halo, $C_{2-10}$ alkenyl, $C_{2-10}$ alkynyl, $C_{3-6}$ cycloalkyl, $C_{4-7}$ cycloalkenyl, $C_{6-10}$ aryl, $C_{7-14}$ alkylaryl, $C_{6-10}$ aryloxy, $C_{7-14}$ alkylaryloxy, or $C_{8-15}$ alkylarylester.

4. The compound of claim 1 wherein $R_2$ is $C_{1-6}$ alkyl, $C_{2-6}$ alkenyl or $C_{3-7}$ cycloalkyl.

5. The compound of claim 4 wherein $R_2$ is $C_{2-6}$ alkenyl.

6. The compound of claim 5 wherein $R_2$ is vinyl.

7. The compound of claim 1 wherein $R_3$ is $C_{1-8}$ alkyl optionally substituted with $C_6$aryl, $C_{1-6}$ alkoxy, carboxy, hydroxy, aryloxy, $C_{7-14}$ alkylaryloxy, $C_{2-6}$ alkylester, $C_{8-15}$ alkylarylester; $C_{3-12}$ alkenyl, $C_{3-7}$ cycloalkyl, or $C_{4-10}$ alkylcycloalkyl.

8. The compound of claim 7 wherein $R_3$ is $C_{1-8}$ alkyl optionally substituted with $C_{1-6}$ alkoxy; or $C_{3-7}$ cycloalkyl.

9. The compound of claim 8 wherein $R_3$ is t-butyl.

10. The compound of claim 1 wherein Y is H.

11. The compound of claim 1 wherein B is H, $C_{1-6}$ alkyl, $R_4$—(C=O)—, $R_4O(C=O)$—, $R_4$—N($R_5$)—C(=O)—, $R_4$—N($R_5$)—C(=S)—, $R_4SO_2$—, or $R_4$—N($R_5$)—SO$_2$—.

12. The compound of claim 11 wherein B is $R_4$—(C=O)—, $R_4O(C=O)$—, or $R_4$—N($R_5$)—C(=O)—.

13. The compound of claim 12 wherein B is $R_4O$(C=O)— and $R_4$ is $C_{1-6}$ alkyl.

14. The compound of claim 1 wherein $R_4$ is (i) $C_{1-10}$ alkyl optionally substituted with phenyl, carboxyl, $C_{1-6}$ alkanoyl, 1–3 halogen, hydroxy, $C_{1-6}$ alkoxy; (ii) $C_{3-7}$ cycloalkyl, $C_{3-7}$ cycloalkoxy, or $C_{4-10}$ alkylcycloalklyl; or (iii) $C_{6-10}$ aryl or $C_{7-16}$ arylalkyl, each optionally substituted with $C_{1-6}$ alkyl or halogen.

15. The compound of claim 14 wherein $R_4$ is (i) $C_{1-10}$ alkyl optionally substituted with 1–3 halogen or $C_{1-6}$ alkoxy; or (ii) $C_{3-7}$ cycloalkyl or $C_{4-10}$ alkylcycloalkyl.

16. The compound of claim 15 wherein $R_4$ is t-butyl.

17. The compound of claim 1 wherein $R_5$ is H or $C_{1-6}$ alkyl optionally substituted with 1–3 halogens.

18. The compound of claim 17 wherein $R_5$ is H.

19. The compound of claim 1 wherein $R_6$ is $C_{1-6}$ alkyl, $C_{3-7}$ cycloalkyl, or $C_{1-6}$ alkoxy.

20. The compound of claim 19 wherein $R_6$ is $C_{1-6}$ alkoxy.

21. The compound of claim 20 wherein $R_7$ is $C_6$ aryl or a 5–7 membered monocyclic heterocycle.

22. A method of treating an HCV infection in a patient, comprising administering to the patient a therapeutically effective amount of the compound of claim 1 or a pharmaceutically acceptable salt, solvate or prodrug thereof.

23. A method of inhibiting HCV NS3 protease comprising administering to a patient in need thereof a therapeutically effective amount of the compound of claim 1 or a pharmaceutically acceptable salt, solvate or prodrug thereof.

24. A composition comprising the compound of claim 1 or a pharmaceutically acceptable salt, solvate or prodrug thereof and a pharmaceutically acceptable carrier.

25. The composition of claim 24 further comprising an additional immunomodulatory agent.

26. The composition of claim 25 wherein the additional immunomodulatory agent is selected from the group consisting of α-, β-, and δ-interferons.

27. The composition of claim 24 further comprising an antiviral agent.

28. The composition of claim 27 wherein the antiviral agent is selected from the group consisting of ribavirin and amantadine.

29. The composition of claim 24 further comprising another inhibitor of HCV protease in combination with the compound of claim 1.

30. The composition of claim 24 further comprising an inhibitor of a target in the HCV life cycle other than HCV NS3 protease in combination with the compound of claim 1.

31. The composition of claim 30 wherein the other target is selected from the group consisting of helicase, polymerase, metalloprotease and mixtures thereof.

* * * * *

UNITED STATES PATENT AND TRADEMARK OFFICE
CERTIFICATE OF CORRECTION

PATENT NO. : 6,878,722 B2 Page 1 of 1
APPLICATION NO. : 10/441428
DATED : April 12, 2005
INVENTOR(S) : Jeffrey Allen Campbell et al.

It is certified that error appears in the above-identified patent and that said Letters Patent is hereby corrected as shown below:

Col. 244, line 65, "mono- or or" should be --mono- or --.

Col. 245, line 17, "$R_4SO_4$-," should be --$R_4SO_2$-,--.

Signed and Sealed this

Twenty-second Day of August, 2006

JON W. DUDAS
*Director of the United States Patent and Trademark Office*